(12) United States Patent
Brown et al.

(10) Patent No.: US 9,504,719 B2
(45) Date of Patent: *Nov. 29, 2016

(54) SOFT TISSUE REPAIR AND REGENERATION USING POSTPARTUM-DERIVED CELLS AND CELL PRODUCTS

(75) Inventors: Laura Brown, Hamilton Square, NJ (US); Alexander M. Harmon, Clinton, NJ (US); Anna Gosiewska, Skillman, NJ (US)

(73) Assignee: DePuy Synthes Products, Inc., Raynham, MA (US)

( * ) Notice: Subject to any disclaimer, the term of this patent is extended or adjusted under 35 U.S.C. 154(b) by 1148 days.

This patent is subject to a terminal disclaimer.

(21) Appl. No.: 11/316,104

(22) Filed: Dec. 22, 2005

(65) Prior Publication Data

US 2006/0153816 A1 Jul. 13, 2006

Related U.S. Application Data

(63) Continuation-in-part of application No. 10/877,009, filed on Jun. 25, 2004, now Pat. No. 7,560,276.

(60) Provisional application No. 60/483,264, filed on Jun. 27, 2003, provisional application No. 60/638,702, filed on Dec. 23, 2004.

(51) Int. Cl.
| | |
|---|---|
| C12N 5/073 | (2010.01) |
| A61K 35/50 | (2015.01) |
| A61K 35/51 | (2015.01) |
| C12N 5/074 | (2010.01) |
| A61K 45/06 | (2006.01) |
| A61K 35/12 | (2015.01) |

(52) U.S. Cl.
CPC .............. *A61K 35/51* (2013.01); *A61K 45/06* (2013.01); *C12N 5/0605* (2013.01); *C12N 5/0607* (2013.01); *A61K 35/12* (2013.01); *C12N 2500/32* (2013.01); *C12N 2500/34* (2013.01); *C12N 2500/44* (2013.01); *C12N 2500/90* (2013.01); *C12N 2500/95* (2013.01); *C12N 2501/12* (2013.01); *C12N 2501/21* (2013.01); *C12N 2501/23* (2013.01); *C12N 2502/02* (2013.01); *C12N 2506/02* (2013.01); *C12N 2506/03* (2013.01); *C12N 2509/00* (2013.01); *C12N 2533/50* (2013.01)

(58) Field of Classification Search
CPC ...... A61K 38/00; A61K 35/12; A61K 35/51; C12N 5/0605
See application file for complete search history.

(56) References Cited

U.S. PATENT DOCUMENTS

| | | | |
|---|---|---|---|
| 2,324,800 A | 7/1943 | Pasternack et al. | |
| 2,654,735 A | 10/1953 | Funk et al. | |
| 2,864,848 A | 12/1958 | McArthur | |
| 2,912,332 A | 11/1959 | Young et al. | |
| 3,665,061 A * | 5/1972 | Eberly, Jr. | 264/49 |
| 3,930,954 A | 1/1976 | Irie et al. | |
| 4,193,992 A | 3/1980 | Fontaine | |
| 4,216,144 A | 8/1980 | Ashmead | |
| 4,290,962 A * | 9/1981 | Tachi et al. | 552/577 |
| 4,352,883 A | 10/1982 | Lim | 435/178 |
| 4,393,240 A | 7/1983 | Stille | |
| 4,465,776 A | 8/1984 | Cidlowski et al. | |
| 4,487,865 A * | 12/1984 | Balazs et al. | 524/29 |
| 4,657,866 A | 4/1987 | Kumar | |
| 4,882,162 A | 11/1989 | Ikada et al. | 424/444 |
| 4,925,677 A * | 5/1990 | Feijen | 424/484 |
| 4,963,489 A | 10/1990 | Naughton et al. | 435/240.1 |
| 5,004,681 A | 4/1991 | Boyse et al. | 435/2 |
| 5,192,553 A | 3/1993 | Boyse et al. | 424/529 |
| 5,248,608 A | 9/1993 | Van Dooren et al. | |
| 5,286,632 A | 2/1994 | Jones | 435/91.2 |
| 5,320,962 A | 6/1994 | Stiles et al. | 435/91.2 |
| 5,342,761 A | 8/1994 | MacLeod | 435/69.1 |
| 5,437,994 A | 8/1995 | Emerson et al. | 435/373 |
| 5,443,950 A | 8/1995 | Naughton et al. | 435/1.1 |
| 5,456,835 A * | 10/1995 | Castino et al. | 210/645 |
| 5,466,233 A | 11/1995 | Weiner et al. | 604/890.1 |
| 5,474,987 A | 12/1995 | Cohen et al. | |
| 5,486,359 A | 1/1996 | Caplan et al. | 424/93.7 |
| 5,506,134 A | 4/1996 | Soule et al. | |
| 5,580,777 A | 12/1996 | Bernard et al. | |
| 5,589,376 A | 12/1996 | Anderson et al. | 435/240.2 |
| 5,670,483 A | 9/1997 | Zhang et al. | 514/14 |

(Continued)

FOREIGN PATENT DOCUMENTS

| | | |
|---|---|---|
| CN | 1407088 | 2/2003 |
| EP | 1 216 718 | 6/2002 |

(Continued)

OTHER PUBLICATIONS

Wang W. 2000. Lyophilization and development of solid protein pharmaceuticals. Int J Pharmaceutics 203: 1-60.*
Abcam. "Human Chemokine Antibody Array—Membrane (38 targets) ab169812." Available online at <http://www.abcam.com/Human-Chemokine-Antibody-Array-Membrane-38-targets-ab169812.html>. 2 pages.*
Aboody, K.S., et al., "Neural stem cells display extensive tropism for pathology in adult brain: evidence from intracranial gliomase," *PNAS*, 2000, 97(23), 12846-12851.
Age-Related Eye Disease Study Research Group, "A randomized, placebo-controlled, clinical trial of high-dose supplementation with vitamins C and E, beta carotene, and zinc for age-related macular degeneration and vision loss," AREDS Report No. 8, *Arch. Ophthalmal*, 2001, 119, 1417-1436.

(Continued)

*Primary Examiner* — Allison Fox
(74) *Attorney, Agent, or Firm* — Johnson & Johnson; Robert DeBerardine

(57) ABSTRACT

Cells derived from postpartum tissue and products thereof having the potential to support cells of and/or differentiate to cells of a soft tissue lineage, and methods of preparation and use of those postpartum tissue-derived cells, are provided by the invention. The invention also provides methods for the use of such postpartum-derived cells and products related thereto in therapies for conditions of soft tissue.

14 Claims, No Drawings

(56) References Cited

U.S. PATENT DOCUMENTS

| | | | |
|---|---|---|---|
| 5,677,181 A | 10/1997 | Parish | 435/332 |
| 5,693,332 A | 12/1997 | Hansbrough | |
| 5,698,518 A | 12/1997 | Carson et al. | 514/12 |
| 5,707,643 A | 1/1998 | Ogura et al. | 424/428 |
| 5,718,922 A | 2/1998 | Herrero-Vanrell et al. | |
| 5,736,516 A | 4/1998 | Louis | 514/12 |
| 5,811,094 A | 9/1998 | Caplan et al. | 424/93.7 |
| 5,827,735 A | 10/1998 | Young et al. | 435/325 |
| 5,834,308 A | 11/1998 | Peck et al. | 435/325 |
| 5,840,580 A | 11/1998 | Terstappen et al. | 435/372 |
| 5,842,477 A | 12/1998 | Naughton et al. | |
| 5,843,780 A | 12/1998 | Thomson | 435/363 |
| 5,855,619 A | 1/1999 | Caplan et al. | |
| 5,869,079 A | 2/1999 | Wong et al. | 424/426 |
| 5,902,598 A | 5/1999 | Chen et al. | 424/423 |
| 5,902,741 A | 5/1999 | Purchio et al. | |
| 5,906,934 A | 5/1999 | Grande et al. | 435/325 |
| 5,919,702 A | 7/1999 | Purchio et al. | 435/378 |
| 5,928,214 A | 7/1999 | Rubinstein et al. | |
| 5,942,225 A | 8/1999 | Bruder et al. | 424/93.7 |
| 5,955,343 A | 9/1999 | Holmes et al. | 435/240.1 |
| 5,962,325 A | 10/1999 | Naughton et al. | 435/395 |
| 5,994,094 A | 11/1999 | Hötten et al. | 435/69.1 |
| 6,001,647 A | 12/1999 | Peck et al. | 435/325 |
| 6,022,743 A | 2/2000 | Naughton et al. | 435/395 |
| 6,059,968 A | 5/2000 | Wolf | |
| 6,140,039 A | 10/2000 | Naughton et al. | 435/1.1 |
| 6,153,591 A * | 11/2000 | Cai et al. | 514/19 |
| 6,171,610 B1 | 1/2001 | Vacanti et al. | 424/426 |
| 6,179,872 B1 | 1/2001 | Bell et al. | |
| 6,200,606 B1 | 3/2001 | Peterson | 424/574 |
| 6,200,806 B1 | 3/2001 | Thomson | 435/366 |
| 6,214,369 B1 | 4/2001 | Grande et al. | 424/423 |
| 6,221,904 B1 * | 4/2001 | Agus et al. | 514/474 |
| 6,251,090 B1 | 6/2001 | Avery et al. | 604/9 |
| 6,261,600 B1 | 7/2001 | Kirschner et al. | |
| 6,261,841 B1 | 7/2001 | Cohen et al. | |
| 6,291,240 B1 | 9/2001 | Mansbridge et al. | |
| 6,323,188 B1 | 11/2001 | Weissman | 514/52 |
| 6,326,201 B1 | 12/2001 | Fung et al. | 435/377 |
| 6,331,313 B1 | 12/2001 | Wong et al. | 424/427 |
| 6,333,029 B1 | 12/2001 | Vyakarnam et al. | |
| 6,355,239 B1 | 3/2002 | Bruder et al. | 424/93.1 |
| 6,355,699 B1 | 3/2002 | Vyakarnam et al. | 521/61 |
| 6,358,737 B1 | 3/2002 | Bonewald et al. | |
| 6,372,494 B1 | 4/2002 | Naughton et al. | |
| 6,375,972 B1 | 4/2002 | Guo et al. | 424/423 |
| 6,387,367 B1 | 5/2002 | Davis-Sproul et al. | 424/93.1 |
| 6,391,297 B1 | 5/2002 | Halvorsen | 424/93.7 |
| 6,429,013 B1 | 8/2002 | Halvorsen et al. | 435/377 |
| 6,436,704 B1 | 8/2002 | Roberts et al. | 435/366 |
| 6,497,875 B1 | 12/2002 | Sorrell et al. | 424/93.7 |
| 6,528,245 B2 | 3/2003 | Sanchez-Ramos et al. | 435/1.1 |
| 6,534,084 B1 | 3/2003 | Vyakarnam et al. | |
| 6,555,374 B1 | 4/2003 | Gimble et al. | 435/371 |
| 6,599,323 B2 | 7/2003 | Melican et al. | 623/23.72 |
| 6,610,535 B1 | 8/2003 | Lu et al. | 435/325 |
| 6,638,765 B1 | 10/2003 | Rosenberg | 435/377 |
| 6,673,606 B1 | 1/2004 | Tennekoon et al. | 435/372 |
| 6,680,198 B1 | 1/2004 | Snyder et al. | 435/368 |
| 6,686,198 B1 | 2/2004 | Melton et al. | 435/377 |
| 6,703,017 B1 | 3/2004 | Peck et al. | 424/93.7 |
| 6,916,655 B2 | 7/2005 | Yasumoto et al. | 435/371 |
| 7,413,734 B2 | 8/2008 | Mistry et al. | |
| 7,510,873 B2 | 3/2009 | Mistry et al. | |
| 7,524,489 B2 | 4/2009 | Messina et al. | |
| 7,875,272 B2 | 1/2011 | Messina et al. | |
| 7,875,273 B2 | 1/2011 | Messina et al. | |
| 8,277,796 B2 | 10/2012 | Messina et al. | |
| 8,318,483 B2 | 11/2012 | Mistry et al. | |
| 8,658,152 B2 | 2/2014 | Messina et al. | |
| 8,703,121 B2 | 4/2014 | Harris et al. | |
| 8,790,637 B2 | 7/2014 | Mistry et al. | |
| 8,815,587 B2 | 8/2014 | Harris et al. | |
| 2001/0024824 A1 | 9/2001 | Moss et al. | 435/366 |
| 2001/0031256 A1 | 10/2001 | Edge | 424/93.7 |
| 2001/0046489 A1 | 11/2001 | Habener et al. | 424/93.21 |
| 2001/0053362 A1 | 12/2001 | Walters | |
| 2002/0022676 A1 | 2/2002 | He et al. | 523/113 |
| 2002/0028510 A1 | 3/2002 | Sanberg et al. | 435/368 |
| 2002/0062151 A1 | 5/2002 | Altman et al. | 623/13.7 |
| 2002/0081725 A1 | 6/2002 | Tsang et al. | 435/366 |
| 2002/0098584 A1 | 7/2002 | Palmer et al. | 435/366 |
| 2002/0119565 A1 | 8/2002 | Clarke et al. | 435/366 |
| 2002/0123141 A1 | 9/2002 | Hariri | 435/366 |
| 2002/0150986 A1 | 10/2002 | Lau | 435/69.1 |
| 2002/0151056 A1 | 10/2002 | Sasai et al. | 435/368 |
| 2002/0160471 A1 | 10/2002 | Kisiday et al. | 435/177 |
| 2002/0160510 A1 | 10/2002 | Hariri | 435/368 |
| 2002/0164307 A1 | 11/2002 | Habener et al. | 424/93.7 |
| 2002/0164791 A1 | 11/2002 | Van Der Kooy et al. | 435/366 |
| 2002/0168763 A1 | 11/2002 | Yan et al. | 435/325 |
| 2002/0182728 A1 | 12/2002 | Ramiya et al. | 435/366 |
| 2002/0187550 A1 | 12/2002 | Dinsmore et al. | 435/377 |
| 2002/0192816 A1 | 12/2002 | Roberts et al. | 435/366 |
| 2003/0003574 A1 | 1/2003 | Toma et al. | 435/368 |
| 2003/0007954 A1 | 1/2003 | Naughton et al. | |
| 2003/0022369 A1 | 1/2003 | Fillmore et al. | 435/371 |
| 2003/0031657 A1 | 2/2003 | Habener et al. | 424/93.21 |
| 2003/0032179 A1 | 2/2003 | Hariri et al. | |
| 2003/0032183 A1 | 2/2003 | Sheridan | 435/370 |
| 2003/0049837 A1 | 3/2003 | Weiss et al. | 435/368 |
| 2003/0059939 A1 | 3/2003 | Page et al. | 435/366 |
| 2003/0082155 A1 | 5/2003 | Habener et al. | 424/93.21 |
| 2003/0082160 A1 | 5/2003 | Yu et al. | 424/93.21 |
| 2003/0096409 A1 | 5/2003 | Yasumoto et al. | 435/371 |
| 2003/0104997 A1 | 6/2003 | Black et al. | 514/12 |
| 2003/0109036 A1 | 6/2003 | Wu | 435/366 |
| 2003/0113910 A1 | 6/2003 | Levanduski | 435/325 |
| 2003/0118566 A1 | 6/2003 | Neuman et al. | 424/93.21 |
| 2003/0124721 A1 | 7/2003 | Cheatham et al. | 435/366 |
| 2003/0138948 A1 | 7/2003 | Fisk et al. | 435/366 |
| 2003/0138951 A1 | 7/2003 | Yin | 435/370 |
| 2003/0148513 A1 | 8/2003 | Sugaya et al. | 435/368 |
| 2003/0158089 A1 | 8/2003 | Gallop et al. | |
| 2003/0161818 A1 | 8/2003 | Weiss et al. | 424/93.21 |
| 2003/0162290 A1 | 8/2003 | Inoue et al. | 435/366 |
| 2003/0170215 A1 | 9/2003 | Tsang et al. | 424/93.21 |
| 2003/0175963 A1 | 9/2003 | Rosenberg | 435/375 |
| 2003/0180269 A1 | 9/2003 | Hariri | 424/93.21 |
| 2003/0186439 A1 | 10/2003 | Nakauchi et al. | 435/370 |
| 2003/0199447 A1 | 10/2003 | Goldman et al. | 514/12 |
| 2003/0203483 A1 | 10/2003 | Seshi | 435/366 |
| 2003/0203484 A1 | 10/2003 | Black et al. | 435/368 |
| 2003/0207450 A1 | 11/2003 | Young et al. | 435/368 |
| 2003/0211087 A1 | 11/2003 | Goldman | 424/93.21 |
| 2003/0211603 A1 | 11/2003 | Earp et al. | 435/366 |
| 2003/0211605 A1 | 11/2003 | Lee et al. | 435/368 |
| 2003/0212024 A1 | 11/2003 | Keating et al. | 514/44 |
| 2003/0219894 A1 | 11/2003 | Seino et al. | 435/370 |
| 2003/0228295 A1 | 12/2003 | Svendsen | 424/93.21 |
| 2003/0235563 A1 | 12/2003 | Strom et al. | 424/93.21 |
| 2003/0235909 A1 | 12/2003 | Hariri et al. | 435/372 |
| 2004/0005704 A1 | 1/2004 | Csete et al. | 435/368 |
| 2004/0009593 A1 | 1/2004 | Keirstead et al. | 435/368 |
| 2004/0014206 A1 | 1/2004 | Robl et al. | 435/325 |
| 2004/0014210 A1 | 1/2004 | Jessell et al. | 435/368 |
| 2004/0014211 A1 | 1/2004 | Ogle et al. | 435/368 |
| 2004/0014662 A1 | 1/2004 | Lindquist et al. | 514/12 |
| 2004/0028660 A1 | 2/2004 | Hariri et al. | |
| 2004/0029269 A1 | 2/2004 | Goldman et al. | 435/368 |
| 2004/0033597 A1 | 2/2004 | Toma et al. | 435/368 |
| 2004/0037818 A1 | 2/2004 | Brand et al. | 424/93.21 |
| 2004/0048372 A1 | 3/2004 | Hariri | 435/366 |
| 2004/0058412 A1 | 3/2004 | Ho et al. | 435/69.1 |
| 2004/0063202 A1 | 4/2004 | Petersen et al. | 435/368 |
| 2004/0072344 A1 | 4/2004 | Inoue et al. | 435/366 |
| 2004/0136967 A1 | 7/2004 | Weiss et al. | 424/93.7 |
| 2004/0204387 A1 | 10/2004 | McLaurin | |
| 2004/0224401 A1 | 11/2004 | Ludwig et al. | |
| 2005/0019865 A1 | 1/2005 | Kihm et al. | 435/69.1 |
| 2005/0032209 A1 | 2/2005 | Messina et al. | 435/366 |
| 2005/0037491 A1 | 2/2005 | Mistry et al. | 435/366 |
| 2005/0054098 A1 | 3/2005 | Mistry et al. | 435/372 |

(56) References Cited

U.S. PATENT DOCUMENTS

| | | |
|---|---|---|
| 2005/0058629 A1 | 3/2005 | Harmon et al. .............. 424/93.7 |
| 2005/0058630 A1 | 3/2005 | Harris et al. ................ 424/93.7 |
| 2005/0058631 A1 | 3/2005 | Kihm et al. ................. 424/93.7 |
| 2005/0074435 A1 | 4/2005 | Casper et al. .............. 424/93.7 |
| 2005/0148074 A1 | 7/2005 | Davies et al. ................ 435/372 |
| 2005/0249731 A1 | 11/2005 | Aslan et al. ............... 424/144.1 |
| 2006/0094113 A1 | 5/2006 | Epstein et al. |
| 2006/0128014 A1 | 6/2006 | Haggblad et al. |
| 2006/0147415 A1 | 7/2006 | Mousa et al. |
| 2006/0153815 A1 | 7/2006 | Seyda et al. |
| 2006/0153816 A1 | 7/2006 | Brown et al. ............... 424/93.7 |
| 2006/0153817 A1 | 7/2006 | Kihm et al. ................. 424/93.7 |
| 2006/0153818 A1 | 7/2006 | Dhanaraj et al. ............ 424/93.7 |
| 2006/0154366 A1 | 7/2006 | Brown et al. ............... 435/366 |
| 2006/0154367 A1 | 7/2006 | Kihm et al. ................. 435/366 |
| 2006/0166361 A1 | 7/2006 | Seyda et al. |
| 2006/0171930 A1 | 8/2006 | Seyda et al. |
| 2006/0188983 A1 | 8/2006 | Harris et al. ................ 435/366 |
| 2006/0223177 A1 | 10/2006 | Harris et al. ................ 435/325 |
| 2006/0233765 A1 | 10/2006 | Messina et al. ............. 424/93.7 |
| 2006/0233766 A1 | 10/2006 | Messina et al. ............. 424/93.7 |
| 2006/0234376 A1 | 10/2006 | Mistry et al. ................ 435/366 |
| 2006/0281793 A1 | 12/2006 | Gupta et al. |
| 2007/0009494 A1 | 1/2007 | Mistry et al. ................ 424/93.7 |
| 2007/0014771 A1 | 1/2007 | Mistry et al. ................ 424/93.7 |
| 2007/0036767 A1 | 2/2007 | Mistry et al. ................ 424/93.7 |
| 2007/0141700 A1 | 6/2007 | Harmon |
| 2007/0160588 A1 | 7/2007 | Kihm et al. ............... 424/93.21 |
| 2007/0218549 A1 | 9/2007 | Mansbridge |
| 2007/0264269 A1 | 11/2007 | Harmon et al. |
| 2007/0264713 A1 | 11/2007 | Terstegge et al. |
| 2007/0275362 A1 | 11/2007 | Edinger et al. ................ 435/1.2 |
| 2008/0038782 A1 | 2/2008 | Borns |
| 2008/0112939 A1 | 5/2008 | Colter et al. |
| 2008/0145934 A1 | 6/2008 | Harris et al. |
| 2008/0159994 A1 | 7/2008 | Mantalaris et al. |
| 2008/0166328 A1 | 7/2008 | Harmon et al. |
| 2008/0226595 A1 | 9/2008 | Edinger et al. |
| 2009/0186358 A1 | 7/2009 | Melville et al. |
| 2010/0210013 A1 | 8/2010 | Mistry et al. |
| 2010/0215714 A1 | 8/2010 | Messina et al. |
| 2010/0260843 A1 | 10/2010 | Messina et al. |
| 2010/0272803 A1 | 10/2010 | Mistry et al. |
| 2012/0315251 A1 | 12/2012 | Harris et al. |
| 2013/0022585 A1 | 1/2013 | Messina et al. |
| 2014/0045263 A1 | 2/2014 | Mistry et al. |
| 2014/0154226 A1 | 6/2014 | Messina et al. |
| 2015/0064781 A1 | 3/2015 | Mistry et al. |

FOREIGN PATENT DOCUMENTS

| | | |
|---|---|---|
| EP | 1 316 322 | 6/2003 |
| EP | 0 333 328 B1 | 12/2003 |
| EP | 1 405 649 | 4/2004 |
| JP | 2003-235549 | 8/2003 |
| JP | 2004-254682 | 9/2004 |
| WO | 90/11354 A1 | 10/1990 |
| WO | 92/03917 A1 | 3/1992 |
| WO | 93/04169 A1 | 3/1993 |
| WO | 94/25584 A1 | 11/1994 |
| WO | 95/17911 A1 | 7/1995 |
| WO | WO 95/23216 | 8/1995 |
| WO | 96/01316 A1 | 1/1996 |
| WO | 96/05309 A2 | 2/1996 |
| WO | 98/17791 A1 | 4/1998 |
| WO | 98/51317 | 11/1998 |
| WO | WO 99/03973 | 1/1999 |
| WO | WO 99/28444 | 6/1999 |
| WO | 00/09666 | 2/2000 |
| WO | WO 00/38762 | 7/2000 |
| WO | WO 00/46351 | 8/2000 |
| WO | WO 00/53795 A1 | 9/2000 |
| WO | 00/73421 A3 | 12/2000 |
| WO | 01/11011 A2 | 2/2001 |
| WO | 01/19379 A3 | 3/2001 |
| WO | 01/34775 A1 | 5/2001 |
| WO | 02/29971 A1 | 4/2002 |
| WO | WO 02/36751 | 5/2002 |
| WO | 02/46373 A1 | 6/2002 |
| WO | 02/059278 A2 | 8/2002 |
| WO | 02/062969 A2 | 8/2002 |
| WO | 02/063962 A1 | 8/2002 |
| WO | 02/064748 A2 | 8/2002 |
| WO | 02/064755 A2 | 8/2002 |
| WO | WO 02/061053 | 8/2002 |
| WO | 02/086107 A2 | 10/2002 |
| WO | 03/023020 A1 | 3/2003 |
| WO | 03/025149 A2 | 3/2003 |
| WO | 03/029443 A1 | 4/2003 |
| WO | 03/029445 A1 | 4/2003 |
| WO | 03/039489 A3 | 5/2003 |
| WO | 03/042405 A2 | 5/2003 |
| WO | 03/048336 A2 | 6/2003 |
| WO | 03/055992 A2 | 7/2003 |
| WO | 03/064601 A2 | 8/2003 |
| WO | 03/066832 A2 | 8/2003 |
| WO | 03/068937 A2 | 8/2003 |
| WO | 03/070922 A1 | 8/2003 |
| WO | 03/072728 A2 | 9/2003 |
| WO | 03/080822 A1 | 10/2003 |
| WO | 03/087333 A2 | 10/2003 |
| WO | 03/087392 A2 | 10/2003 |
| WO | 03/089619 A2 | 10/2003 |
| WO | 03/010038 A1 | 12/2003 |
| WO | 03/102134 A2 | 12/2003 |
| WO | 03/102151 A2 | 12/2003 |
| WO | 03/104442 A1 | 12/2003 |
| WO | 2004/011012 A2 | 2/2004 |
| WO | 2004/011621 A2 | 2/2004 |
| WO | 2004/016747 A2 | 2/2004 |
| WO | 2004/023100 A2 | 3/2004 |
| WO | WO 2004/039248 A2 | 5/2004 |
| WO | WO 2004/072273 A1 | 8/2004 |
| WO | 2005/001076 A2 | 1/2005 |
| WO | 2005/001077 A2 | 1/2005 |
| WO | 2005/001078 A2 | 1/2005 |
| WO | 2005/001080 A2 | 1/2005 |
| WO | 2005/003334 A2 | 1/2005 |
| WO | WO 2005/001079 A2 | 1/2005 |
| WO | WO 2005/021738 | 3/2005 |
| WO | 2005/038012 A2 | 4/2005 |
| WO | WO 2005/001079 A3 | 4/2005 |
| WO | 2005/042703 A2 | 5/2005 |
| WO | WO 2005/001079 | 12/2005 |
| WO | WO 2006/027229 | 3/2006 |
| WO | WO 2006/036826 | 4/2006 |
| WO | 2006/071773 A2 | 7/2006 |
| WO | 2006/071777 A2 | 7/2006 |
| WO | 2006/071778 A2 | 7/2006 |
| WO | 2006/071794 A2 | 7/2006 |
| WO | 2006/071802 A2 | 7/2006 |
| WO | WO 2006/083394 | 8/2006 |
| WO | WO 2006/105152 | 10/2006 |
| WO | WO 2007/073552 | 6/2007 |
| WO | WO 2007/108003 | 9/2007 |
| WO | WO 2008/045498 | 4/2008 |
| WO | WO 2008/060541 | 5/2008 |

OTHER PUBLICATIONS

Allcock, H.R., et al., "Synthesis of poly[amino acid alkyl ester)phosphazenes]$^{1-3}$," *Macromolecule*, 1977, 10(4), 824-830.

Altman, G.H., et al., "Advanced bioreactor with controlled application of multi-dimensional strain for tissue engineering," *J. Biomech. Eng.*, 2002, 124, 742-749.

Altman, R.D., et al., "Radiographic assessment of progression in osteoarthritis," *Arthritis & Rheum.*, 1987, 30(11), 1214-1225.

Anseth, K.S., et al., "In situ forming degradable netrks and their application in tissue engineering and drug delivery," *J. of Control Release*, 2002, 78, 199-209.

Avital, I., et al., "Isolation, characterization, and transplantation of bone marrow-derived hepatocyte stem cells," *Biochem. & Biophys. Res. Comm.*, 2001, 288, 156-164.

(56) References Cited

OTHER PUBLICATIONS

Azizi, S.A., et al., "Engraftment and migration of human bone marrow stromal cells implanted in the brains of albino rats—similarities to astrocyte grafts," *Proc. Natl. Acad. Sci. USA*, 1998, 95, 3908-3913.
Baker, K.A., et al., "Intrastriatal and intranigral grafting of hNT neurons in the 6-OHDA rat model of Parkinson's Disease," *Exper. Neurol.*, 2000, 162, 350-360.
Balis, F., et al., "Central nervous system pharmacology of antileukemic drugs," *Am. J. of Pediatric. Hematol. Oncol.*, 1989, 11(1), 74-86.
Balkema, G.W., et al., "Impaired visual thresholds in hypopigmented animals," *Visual Neuroscience*, 1991, 6, 577-585.
Barberi, T., et al., "Neural subtype specification of fertilization and nuclear transfer embryonic stem cells and application in parkinsonian mice," *Nature Biotechnology*, 2003, 21(10), 1200-1207.
Beck, R.W., et al., "A clinical comparison of visual field testing with a new automated perimeter, the Humphrey field analyzer, and the Goldmann perimeter," *Ophthalmology*, 1985, 92(1), 77-82.
Björklund, L.M., et al., "Embryonic stem cells develop into functional dopaminergic neurons after transplantation in a Parkinson rat model," *PNAS*, 2002, 99(4), 2344-2349.
Brodsky, S.V., et al., "Coagulation, fibrinolysis and angiogenesis: new insights from knockout mice," *Exp. Nephrol.*, 2002, 10, 299-306.
Brooks, P., "Inflammation as an important feature of osteoarthritis," *Bull. rld Health Org.*, 2003, 81(9), 689-690.
Brown, J.A., et al., "Blockade of programmed death-1 ligands on dendritic cells enhances T cell activation and cytokine production," *The J. of Immunology*, 2003, 170, 1257-1266.
Burnstein, R.M., et al., "Differentiation and migration of long term expanded human neural progenitors in a partial lesion model of Parkinson's disease," *Intern. J. of Biochem. & Cell Biology*, 2004, 36, 702-713.
Caballero, S., et al., "The many possible roles of stem cells in age-related macular degeneration," *Graefe's Arch Clin. Exp. Ophthalmol*, 2004, 242, 85-90.
Campbell, I.K., et al., "Human articular cartilage and chondrocytes produce hemopoietic colony-stimulating factors in culture in response to IL-1$^1$," *J. of Immun.*, 1991, 147, 1238-1246.
Cao, Q., et al., "Stem cell repair of central nervous system injury," *J. of Neuroscience Res.*, 2002, 68, 501-510.
Caplan, A.I., et al., "Mesenchymal stem cells: building blocks for molecular medicine in the 21$^{st}$ century," *Trends in Molecular Med.*, 2001, 7(6), 259-264.
Chagracui, J., et al., "Fetal liver stroma consists of cells in epithelial-to-mesenchymal transition," *Blood*, 2003, 101, 2973-2982.
Chen, D., et al., "Differential roles for bone morphogenic protein (BMP) receptor type IB and IA in differentiation and specification of mesenchymal precursor cells to osteoblast and adipocyte lineages," *J. Cell Biol.*, 1998, 142(1), 295-305.
Cheng, A., et al., "Nitric oxide acts in a positive feedback loop with BDNF to regulate neural progenitor cell proliferation and differentiation in the mammalian brain," *Dev. Biol.*, 2003, 258, 319-333.
Coumans, B., et al., "Lymphoid cell apoptosis induced by trophoblastic cells: a model of active foeto-placental tolerance," *J. of Immunological Methods*, 1999, 224, 185-196.
D'Cruz, P.M., et al., "Mutation of the receptor tyrosine kinase gene Mertk in the retinal dystrophic RCS rat," *Hum. Mol. Genet.*, 2000, 9(4), 645-651.
Danon, D., et al., "Macrophage treatment of pressure sores in paraplegia," *J. of und Care*, 1998, 7(6), 281-283.
Danon, D., et al., "Treatment of human ulcers by application of macrophages prepared from a blood unit," *Exp. Gerontol.*, 1997, 32(6), 633-641.
Dimri, G.P., et al., "A biomarker that identifies senescent human cells in culture and in aging skin in vivo," *Proc. Natl. Acad. Sci. USA*, 1995, 92, 9363-9367.
Domb, A., et al., "Degradable polymers for site-specific drug delivery," *Polymers for Advanced Technologies*, 1992, 3, 279-292.
Doshi, S.N., et al., "Evolving role of tissue factor and its pathway inhibitor," *Critical Care Med.*, 2002, 30(5), S241-S250.
Du, Y., et al., "Functional reconstruction of rabbit corneal epithelium by human limbal cells cultured on amniotic membrane," *Molecular Vision*, 2003, 9, 635-643.
Edlund, H., "Pancreatic organogenesis—developmental mechanisms and implications for therapy," *Nat. Rev. Genet.*, 2002, 3, 524-532.
Efrat, S., et al., "Cell replacement therapy for type 1 diabetes," *TRENDS in Molecular Medicine*, 2002, 8(7), 334-339.
Ehtesham, M., et al., "Induction of glioblastoma apoptosis using neural stem cell-mediated delivery of tumor necrosis factor-related apoptosis-inducing ligand," *Cancer Res.*, 2002, 62,7170-7174.
Ehtesham, M., et al., "The use of interleukin 12-secreting neural stem cells for the treatment of intracranial glioma," *Cancer Res.*, 2002, 5657-5663.
Ende, N., et al., "Parkinson's disease mice and human umbilical cord blood," *J. Med.*, 2002, 33(1-4), 173-180, 1 page (Abstract).
Engstad, C.S., et al., "The effect of soluble β-1,3-glucan and lipopolysaccharide on cytokine production and coagulation activation in whole blood," *Int. Immunopharmacol.*, 2002, 2, 1585-1597.
Enzmann, V., et al., "Enhanced induction of RPE lineage markers in pluripotent neural stem cells engrafted into the adult rat subretinal space," *Investig. Ophthalmol. Visual Sci.*, 2003, 44, 5417-5422.
Fazeabas, A.T., et al., "Endometrial function: cell specific changes in the uterine environment," *Mol. & Cellular. Endo.*, 2002, 186, 143-147.
Fiegel, H.C., et al., "Liver-specific gene expression in cultured human hematopoietic stem cells," *Stem Cells*, 2003, 21, 98-104.
Fischer, D., et al., "Lens-injury-stimulated axonal regeneration throughout the optic pathway of adult rats," *Exp. Neurol.*, 2001, 172, 257-272.
Freed, C.R., et al., "Transplantation of embryonic dopamine neurons for severe Parkinson's disease," *N. Engl. J. Med.*, 2001, 344(10), 710-719.
Frenkel, O., et al., "Activated macrophages for treating skin ulceration: gene expression in human monocytes after hypo-osmotic shock," *Clin. Exp. Immunol.*, 2002, 128, 59-66.
Friedman, J.A., et al., "Biodegradable polymer grafts for surgical repair of the injured spinal cord," *Neurosurgery*, 2002, 51(3), 742-751.
Fukuda, K., et al., "Reprogramming of bone marrow mesenchymal stem cells into cardiomyocytes," *C.R. Biol.*, 2002, 325, 1027-1038.
Gellersen, B., et al., "Cyclic AMP and progesterone receptor crosstalk in human endometrium: a decidualizing affair," *J. of Endocrinol.*, 2003, 178, 357-372.
Gerdes, D., et al., "Cloning and tissue expression of t putative steroid membrane receptors," *Biol. Chem.*, 1998, 379, 907-911.
Gökhan, S., et al., "Basic and clinical neuroscience applications of embryonic stem cells," *Anat. Rec. (New Anat)*, 2001, 265, 142-156.
Gosiewska, A., et al., "Development of a three-dimensional transmigration assay for testing cell-polymer interactions for tissue engineering applications," *Tissue Eng.*, 2001, 7(3), 267-277.
Gottleib, D.I., "Large-scale sources of neural stem cells," *Ann. Rev. Neurosci.*, 2002, 25, 381-407.
Halvorsen, Y.D., et al., "Extracellular matrix mineralization and osteoblast gene expression by human adipose tissue-derived stromal cells," *Tissue Eng.*, 2001, 7, 729-741.
Hanahan, D., "Heritable formation of pancreatic β-cell tumours in transgenic mice expressing recombinant insulin/simian virus 40 oncogenes," *Nature*, 1985, 315, 115-122.
Haruta, M., et al., "In vitro and in vivo characterization of pigment epithelial cells differentiated from primate embryonic stem cells," *Investig. Ophthalmol. & Visual Sci.*, 2004, 45(3), 1020-1025.
Hayflick, L., "The longevity of cultured human cells," *J. Am. Geriatr. Soc.*, 1974, 22(1), 1-12.
Hayflick, L., "The strategy of senescence," *Gerontologist*, 1974, 14(1), 37-45.
Hongpaisan, J., "Inhibition of proliferation of contaminating fibroblasts by D-valine in cultures of smooth muscle cells from human myometrium," *Cell Biol. Int.*, 2000, 24, 1-7.
Hu, A., et al., "Hepatic differentiation from embryonic stem cells in vitro," *Chin. Med. J.*, 2003, 116(12), 1893-1897.

(56) References Cited

OTHER PUBLICATIONS

Hughes, G.C., et al., "Therapeutic angiogenesis in chronically ischemic porcine myocardium: comparative effects of bFGF and VEGF," *Ann. Thorac. Surg.*, 2004, 77, 812-818.

Hutmacher, D.W., "Scaffold design and fabrication technologies for engineering tissues—state of the art and future perspectives," *J. Biomater. Sci. Polymer Edn.*, 2001, 12(1), 107-124.

Isacson, O., "The production and use of cells as therapeutic agents in neurodegenerative diseases," *The Lancet (Neurology)*, 2003, 2, 417-424.

Isacson, O., et al., "Specific axon guidance factors persist in the adult brain as demonstrated by pig neuroblasts transplanted to the rat," *Neurosci.*, 1996, 75(3), 827-837.

Ito, Y., et al., "A quantitative assay using basement membrane extracts to study tumor angiogenesis in vivo," *Int. J. Cancer*, 1996, 67, 148-152.

Jackson, J.A., et al., "Regeneration of ischemic cardiac muscle and vascular endothelium by adult stem cells," *J. Clin. Invest.*, 2001, 107, 1395-1402.

Janderova, L., et al., "Human mesenchymal stem cells as an in vitro model for human adipogenesis," *Obes. Res.*, 2003, 11(1), 65-74.

Jang, Y.K., et al., "Retinoic acid-mediated induction of neurons and glial cells from human umbilical cord-derived hematopoietic stem cells," *J. of Neurosci. Res.*, 2004, 75, 573-584.

Johe, K.K., et al., "Single factors direct the differentiation of stem cells from the fetal and adult central nervous system," *Genes & Devel.*, 1996, 10, 3129-3140.

Johnstone, B., et al., "In vitro chondrogenesis of bone-marrow-derived mesenchymal stem cells," *Exp. Cell Res.*, 1998, 238, 265-272.

Jones-Villeneuve, E.M., et al., "retinoic acid-induced neural differentiation of embryonal carcinoma cells,"*Mol. & Cellu. Biol.*, 1983, 3(12), 2271-2279.

Kadiyala, S., et al., "Culture expanded canine mesenchymal stem cells possess osteochondrogenic potential in vivo and in vitro," *Cell Transplant*, 1997, 6(2), 125-134.

Kicic, A., et al., "Differentiation of marrow stromal cells into photoreceptors in the rat eye," *J. of Neurosci.*, 2003, 23(21), 7742-7749.

Kim, J.-H., et al., "Dopamine neurons derived from embryonic stem cells function in an animal model of Parkinson's disease," *Nature*, 2002, 418, 50-56.

Kim, J.Y., et al., "Ocular surface reconstruction: limbal stem cell transplantation," *Ophthal. Clin. N Am.*, 2003, 16, 67-77.

Kim, S.K., et al., "Intercellular signals regulating pancreas development and function," *Genes Dev.*, 2001, 15, 111-127.

Lang, K.J.D., et al., "Differentiation of embryonic stem cells to a neural fate: a route to re-building the nervous system," *J. of Neurosci. Res.*, 2004, 76, 184-192.

Le Belle, J.E., et al., "Stem cells for neurodegenerative disorders: where can we go from here?," *BioDrugs*, 2002, 16, 389-401.

Li, A., et al., "IL-8 directly enhanced endothelial cell survival, proliferation, and matrix metalloproteinases production and regulated angiogenesis," *J. Immunol.*, 2003, 170(6), 3369-3376.

Li, L.X., et al., "Inherited retinal dystrophy in the RCS rat: prevention of photoreceptor degeneration by pigment epithelial cell transplantation," *Exp. Eye Res.*, 1988, 47, 911-917.

Li, Y., et al., "Intracerebral transplantation of bone marrow stromal cells in a 1-methyl-4-phenyl-1,2,3,6-tetrahydropyridine mouse model of Parkinson's disease," *Neuroscience Letts.*, 2001, 315, 67-70.

Li, Y., et al., "Transplanted olfactory ensheathing cells promote regeneration of cut adult rat optic nerve axons," *J. of Neuro.*, 2003, 23(21), 7783-7788.

Liu, Y.-J., et al., "Molecular and genetic mechanisms of obesity: implications for future management," *Curr. Mol. Med.*, 2003, 3, 325-340.

Lockhart, et al., "Expression monitoring by hybridization to high-density oligonucleotide arrays," *Nat. Biotechnol.*, 1996, 14(13), 1675-1680.

Lund, R.D., et al., "Cell transplantation as a treatment for retinal disease," *Progress in Retinal and Eye Research*, 2001, 20(4), 415-449.

Lund, R.D., et al., "Subretinal transplantation of genetically modified human cell lines attenuates loss of visual function in dystrophic rats," *Proc. Natl. Acad. Sci. USA*, 2001, 98(17), 9942-9947.

Lund, R.L., et al., "Retinal transplantation: progress and problems in clinical application," *J. Leukocyte Biol.*, 2003, 74, 151-160.

Marx, W.F., et al., "Endovascular treatment of experimental aneurysms by use of biologically modified embolic devices: coil-mediated intraaneurysamal delivery of fibroblast tissue allografts," *Am. J. Neuroradiol.*, 2001, 22, 323-333.

Mason, A.J., et al., "The hypogonadal mouse: reproductive functions restored by gene therapy," *Science*, 1986, 234, 1372-1378.

Mayer-Proschel, M., et al., "Isolation of lineage-restricted neuronal precursors from multipotent neuroepithelial stem cells," *Neuron.*, 1997, 19, 773-785.

McDonald, J.A., et al., "Diminished responsiveness of male homosexual chronic hepatitis B virus carriers with HTLV-III antibodies to recombinant α-interferon," *Hepatology*, 1987, 7(4), 719-723.

Messina, D.J., et al., "Comparison of pure and mixed populations of human fetal-derived neural progenitors transplanted into intact and adult rat brain," *Exper. Neurol.*, 2003, 184, 816-829.

Mitchell, et al., "Matrix cells from Wharton's jelly form neurons and glia," *Stem Cells*, 2003, 21, 50-60.

Moll, S., et al., "Monitoring warfarin therapy in patients with lupus anticoagulants," *Ann. Intern. Med.*, 1997, 127(3), 177-185.

Mombaerts, et al., "Creation of a large genomic deletion at the T-cell antigen receptor β-subunit locus in mouse embryonic stem cells by gene targeting," *Proc. Nat. Acad. Sci. USA*, 1991, 88, 3084-3087.

Nakamura, T., et al., "Ocuar surface reconstruction using cultivated mucosal epithelial stem cells," *Cornea*, 2003, 22(Supp. 1), S75-S80.

Nicosia, R.F., et al., "Modulation of microvascular growth and morphogenesis by reconstituted basement membrane gel in three-dimensional cultures of rat aorta: a comparative study of angiogenesis in matrigal, collagen, fibrin, and plasma clot," in *Vitro Cell Dev. Biol.*, 1990, 26, 119-128.

Nishida K., et al., "Functional bioengineered corneal epithelial sheet grafts from corneal stem cells expanded ex vivo on a temperature-responsive cell culture surface," *Transplantation*, 2004, 77(3), 379-385.

Nixon, P.J., et al., "The contribution of cone responses to rat electroretinograms," *Clin. Experiment Ophthalmol.*, 2001, 29(3), 193-196.

Nusinowitz, S., et al., "Rod multifocal electroretinograms in mice," *Invest Ophthalmol Vis. Sci.*, 1999, 40(12), 2848-2858.

Oh, S.-H., et al., "Hepatocyte growth factor induces differentiation of adult rat bone marrow cells into a hepatocyte lineage in vitro," *Biochem. & Biophys. Res. Comm.*, 2000, 279, 500-504.

Okumoto, K., et al., "Differentiation of bone marrow cells into cells that express liver-specific genes in vitro: implication of the notch signals in differentiation," *Biochem. & Biophys. Res. Commun.*, 2003, 304, 691-695.

Orlic, D., et al., "Stem cells for myocardial regeneration," *Circ. Res.*, 2002, 91, 1092-1102.

Ornitz, D.M., et al., "Elastase I promoter directs expression of human growth hormone and SV40 T antigen genes to pancreatic acinar cells in transgenic mice," *Cold Spring Harbor Symp. Quant. Biol.*, 1985, vol. L, 399-409.

Osborne, N.N., et al., "Some current ideas on the pathogenesis and the role of neuroprotection in glaucomatous optic neuropathy," *Eur. J. Ophthalmol.*, 2003, 13(Supp. 3), S19-S26.

Rabbany, S.Y., et al., "Molecular pathways regulating mobilization of marrow-derived stem cells for tissue revascularization," *TRENDS in Molecular Med.*, 2003, 9(3), 109-117.

Rafii, S., et al., "Therapeutic stem and progenitor cell transplantation for organ vascularization and regeneration," *Nature Med.*, 2003, 9(6), 702-712.

Raman-Cueto, A., et al., "Functional recovery of paraplegic rats and motor axon regeneration in their spinal cords by olfactory ensheathing glia," *Neuron*, 2000, 25, 425-435.

(56) References Cited

OTHER PUBLICATIONS

Readhead, C., et al., "Expression of a myelin basic protein gene in transgenic shiverer mice: correction of the dysmyelinating phenotype," *Cell*, 1987, 48, 703-712.

Refaie, A., et al., "Experimental islet cell transplantation in rats: optimization of the transplantation site," *Trans. Proc.*, 1998, 30, 400-403.

Reubinoff, B.E., et al., "Neural progenitors from human embryonic stem cells," *Nature Biotechnology*, 2001, 19, 1134-1140.

Rickard, D.J., et al., "Induction of rapid osteoblast differentiation in rat bone marrow stromal cell cultures by dexamethasone and BMP-2," *Dev. Biol.*, 1994, 161, 218-228.

Romanov, Y.A., et al., "Searching for alternative sources of postnatal human mesenchymal stem cells,"*Stem Cells*, 2003, 21, 105-110.

Rosen, E.M., et al., "HGF/SF in angiogenesis," *Ciba Found. Symp.*, 1997, 212, 215-229.

Rutherford, A., et al., "Eyeing-up stem cell transplantation," *Trends in Molecular Medicine*, 2003, 7(1), p. 11.

Sahn, D.J., et al., "Recommendations regarding quantitation in M-Mode echocardiography: results of a survey of echocardiographic measurements," *Circulation*, 1978, 58, 1072-1083.

Sakariassen, K.S., et al., "Methods and models to evaluate shear-dependent and surface reactivity-dependent antithrombotic efficacy," *Thromb. Res.*, 2001, 104, 149-174.

Salcedo, et al., "Human endothelial cells express CCR2 and respond to MCP-1: direct role of MCP-1 in angiogenesis and tumor progression," *Blood*, 2000, 96(1), 34-40.

Sauve, Y., et al., "The relationship between full field electroretinogram and perimetry-like visual thresholds in RCS rats during photoreceptor degeneration and rescue by cell transplants," *Vision Res.*, 2004, 44(1), 9-18.

Schraermeyer, U., et al., "Subretinally transplanted embryonic stem cells rescue photoreceptor cells from degeneration in the RCS rats," *Cell Transplantation*, 2001, 10, 673-680.

Schwartz, R.E., et al., "Multipotent adult progenitor cells from bone marrow differentiate into functional hepatocyte-like cells," *J. of Clin. Invest.*, 2002, 109(10), 1291-1302.

Sebire, G., et al., "In vitro production of IL-6,IL-1 β, and tumor necrosis factor-alpha by human embryonic microglial and neural cells," *J. Immunol.*, 1993, 150, 1517-1523.

Shani, M., "Tissue-specific expression of rat myosin light-chain 2 gene in transgenic mice," *Nature*, 1985, 314, 283-286.

Shimizu, T., et al., "Cell sheet engineering for myocardial tissue reconstruction," *Biomaterials*, 2003, 24, 2309-2316.

Siminoff, R., et al., "Properties of reptilian cutaneous mechanoreceptors," *Exp. Neurol.*, 1968, 20(3), 403-414.

Sordillo, L.M., et al., "Culture of bovine mammary epithelial cells in D-valine modified medium: selective removal of contaminating fibroblasts," *Cell Biol. Int. Rep.*, 1988, 12, 355-364.

Storch, T.G., "Oxygen concentration regulates 5-azacytidine-induced myogenesis in $C_3H/10T1/2$ cultures," *Biochim. Biophys. Acta*, 1990, 1055, 126-129.

Street, C.N., et al., "Stem cells: a promising source of pancreatic islets for transplantation in type 1 diabetes," *Curr. Top Dev. Biol.*, 2003, 58, 111-136.

Svendsen, C.N., "The amazing astrocyte," *Nature*, 2002, 417, 29-32.

Svendsen, C.N., et al., "Long-term survival of human central nervous system progenitor cells transplanted into a rat model of Parkinson's disease," *Experim. Neurol.*, 1997, 148, 135-146.

Swift, G.H., et al., "Tissue-specific expression of the rat pancreatic elastase I gene in transgenic mice," *Cell*, 1984, 38, 639-646.

Tomita, M., et al., "Bone marrow-derived stem cells can differentiate into retinal cells in injured rat retina," *Stem Cells*, 2002, 20, 279-283.

Tresco, P.A., et al., "Cellular transplants as sources for therapeutic agents," *Advanced Drug Delivery Reviews*, 2000, 42, 3-27.

Tsonis, P.A., et al., "Lens and retina regeneration: transdifferentiation, stem cells and clinical applications," *Experim. Eye Res.*, 2004, 78, 161-172.

Turner, J.F., "Inherited retinal dystrophy in the RCS rat: prevention of photoreceptor degeneration by pigment epithelial cell transplantation," *Exp. Eye Res.*, 1988, 47, 911-917.

Tusher, V.G., et al., "Significance analysis of microarrays applied to the ionizing radiation response," *Proc. Natl. Acad. Sci. USA*, 2001, 98(9), 5116-5121.

Van Hoffelen, S.J., et al., "Incorporation of murine brain progenitor cells into the developing mammalian retina," *Invest. Ophthalmol. Vis. Sci.*, 2003, 44, 426-434.

Vassliopoulos, G., et al., "Transplanted bone marrow regenerates liver by cell fusion," *Nature*, 2003, 422, 901-904.

Villegas-Perez, M.P., et al., "Influences of peripheral nerve grafts on the survival and regrowth of axotomized retinal ganglion cells in adult rats," *J. of Neurosci.*, 1988, 8(1), 265-280.

Von Koskull, H., et al., "Induction of cytokeratin expression in human mesenchymal cells," *J. Cell Physiol.*, 1987, 133, 321-329.

Walboomers, X.F., et al., "Cell and tissue behavior on microgrooved surfaces," *Odontology*, 2001, 89, 2-11.

Wang, D., et al., "Synthesis and characterization of a novel degradable phosphate-containing hydrogel," *Biomaterials*, 2003, 24, 3969-3980.

Wang, X., et al., "Cell fusion is the principal source of bone-marrow-derived hepatocytes," *Nature*, 2003, 422, 897-900.

Wegman, A., et al., "Nonsteroidal anti-inflammatory drugs or acetaminophen for osteoarthritis of the hip or knee? A synstematic review of evidence and guidelines," *J. Rheumatol.*, 2004, 31, 344-354.

Weiss, M.L., et al., "Transplantation of porcine umbilical cord matrix cells into the rat brain," *Exp. Neur.*, 2003, 182, 288-299.

Wobus, A.M., et al., "Retinoic acid accelerates embryonic stem cell-derived cardiac differentiation and enhances development of ventricular cardiomyocytes," *J. Mol. Cell Cardiol.*, 1997, 29, 1525-1539.

Woodbury, D., et al., "Adult rat and human bone marrow stromal cells differentiate into neurons," *J. of Neurosci. Res.*, 2000, 61, 364-370.

Wulf, G. G. et al., "Mesengenic Progenitor Cells Derived From Human Placenta," *Tissue Engineering*, Larchmont, NY, Jul. 2004, 10(7/8), 1136-1147.

Xu, C., et al., "Characterization and enrichment of cardiomyocytes derived from human embryonic stem cells," *Circ. Res.*, 2002, 91, 501-508.

Yang, H., et al., "Region-specific differentiation of neural tube-derived neuronal restricted progenitor cells after heterotopic transplantation," *PNAS*, 2000, 97(24), 13366-13371.

Yip, H.K., et al., "Axonal regeneration of retinal ganglion cells: effect of trophic factors," *Prog. Retin Eye Res.*, 2000, 19(5), 559-575.

Yu, M., et al., "Mid-trimester fetal blood-derived adherent cells share characteristics similar to mesenchymal stem cells but full-term umbilical cord blood does not," *British J. of Haematology*, 2004, 124, 666-675.

Zangani, D., et al., "Multiple differentiation pathways of rat mammary stromal cells in vitro: acquisition of a fibroblast, adipocyte or endothelial phenotype is dependent on hormonal and extracellular matrix stimulation," *Differentiation*, 1999, 64, 91-101.

Zeng, B.Y., et al., "Regenerative and other responses to injury in the retinal stump of the optic nerve in adult albino rats: transaction of the intracranial optic nerve," *J. Anat.*, 1995, 186, 495-508.

Zhang, S.-C., et al., "In vitro differentiation of transplantable neural precursors from human embryonic stem cells," *Nature Biotechnology*, 2001, 19, 1129-1133.

Abbas, AK, Lichtman, AH Cellular and Molecular Immunology 5th Ed. (2003) Saunders, Philadelphia, p. 171.

Auda-Boucher, G., et al., "Staging of the commitment of murine cardiac cell progenitors," *Dev. Bio.*, 2000, 225(1), 214-225 (Abstract 2 pages).

Bao, Z.Z.., et al., "Regulation of chamber-specific gene expression in the developing heart by Irx4," *Science*, 1999, 283(5405), 1161-1164 (Abstract 1 page).

(56) References Cited

OTHER PUBLICATIONS

Constantini, S., et al., "The effects of methylprednisolone and the ganglioside GM1 on acute spinal cord injury in rats," *J. Neurosurg.*, 1994, 80(1), 97-111 (Abstract 2 pages).

Dawson, T.M., et al., "Neuroprotective and neurorestorative strategies for Parkinson's disease," *Nat. Neurosci.*, 2002, 5 Suppl., 1058-1061 (Abstract 1 page).

Doyle, J., "Spiraling complexity, robustness, and fragility in biology," http://www.cds.caltech.edu/~doyle/CmplxNets/Biol.pdf, available online Feb. 28, 2004.

Eagle, H., "The specific amino acid requirements of a mammalian cell (strain L) in tissue culture," *J. Biol. Chem.*, Jun. 1955, 214(2), 839-852.

Eblenkamp, M. et al., "Umbilical cord stromal cells (UCSC). Cells featuring osteogenic differentiation potential," *Der Orthopade*, Dec. 2004, 33(12), 1338-1345 (English abstract on p. 1339).

Eisenhofer, G., E., et al., "Tyrosinase: a developmentally specific major determinant of peripheral dopamine," *FASEB J.*, 2003, 1248-1255.

Foley et al., "Heart induction: embryology to cardiomyocyte regeneration," *Trends Cardiovasc Med.*, Apr. 2004, 14(3), 121-125.

Fukuchi, Y. et al., "Human Placenta-Derived Cells Have Mesenchymal Stem/Progenitor Cell Potential," *Stem Cells*, Alphamed Press, Dayton Ohio, 2004, 22(5), 649-658.

Holz et al., "Intraocular microablation of choroidal tissue by a 308 nm AIDA excimer laser for RPE-transplantation in patients with age-related macular degeneration," *BIOMED TECH* (Berlin), Apr. 2003, 48(4), 82-85.

Jikuhara et al., "Left atrial function as a reliable predictor of exercise capacity in patients with recent myocardial infarction," *Chest*, Apr. 1997, 111(4), 922-928.

Klassen et al., "Stem cells and retinal repair," *Prog. Retin. Eye Res.*, 2004, 23(2), 149-181 (Abstract 1 page).

Laface, D., et al., "Genetransfer into hematopoietic progenitor cells mediated by an aden-associated virus vector," *Virology*, 1998, 162, 483-486.

Le Bouteiller, P., et al., "Soluble HLA-G1 at the materno-foetal interface—a review," *Placenta*, 2003, 24 (Suppl. A), S10-S15.

Luyten, F. P. et al., "Skeletal tissue engineering: opportunities and challenges," *Best Pract. Res. Clin. Rheumatol*., Dec. 2001, 15(5), 759-769.

MacDonald, R.J., "Expression of the pancreatic elastase I gene in transgenic mice," *Hepatology*, 1987, 7(1), 42S-51S.

Morgenstern, J. P., et al., "Advanced mammalian gene transfer: high titre retroviral vectors with multiple drug selection markers and a complementary helper-free packaging cell line," *Nucleic Acids Res.*, 1990, 18(12), 3587-3596.

Reyes, M., et al., "Purification and ex vivo expansionof postnatal human marrow mesodernial progenitor cells," *Blood*, 2001, 98(9), 2615-2625.

Rezai, KA., et al., "Iris pigment epithelium transplantation," *Graefes Arch. Clin. Ophthalmol.*, 1997, 235, 558-562.

Rios, M., et al., "Catecholamine Synthesis is Mediated by Tyrosinase in the Absence of Tyroine Hydroxylase," *J. Neurosci.*, 1999, 3519-3526.

Salgado, A. J. et al., "Bone Tissue Engineering: State of the Art and Future Trends," *Macromol. Biosci.*, Aug. 2004, 4, 743-765.

Taylor, D. A. et al., "Cardiac chimerism as a mechanism for self-repair: does it happen and if so to what degree?" *Circulation*, Jul. 2002, 106(1), 2-4.

Xu, Y., et al., "Dopamine, in the presence of tyrosinase, covalently modifies and inactivates tyrosine hydroxylase," *J. Neurosci. Res.*, 1998, 54(5), 691-697 (Abstract, 3 pages).

Zuloff-Shani, A. et al., "Macrophage suspensions prepared from a blood unit for treatment of refractory human ulcers," *Transfus Apheresis Sci.*, 2004, 30(2), 163-167.

Agbulut, O. et al., "Comparison of Human Skeletal Myoblasts and Bone Marrow-Derived CD133+ Progenitors for the Repair of Infarcted Myocardium," *Journal of the American College of Cardiology*, 2004, 44(2), 458-463.

Aldskogius, H. et al., "Strategies for repair of the deafferented spinal cord," *Brain Res. Rev.*, 2002, 20, 301-308.

Armulik A et al., "Endothelial/Pericyte Interactions," *Circ. Res.*, 2005, 97, 512-23.

Bergers G. et al., "The role of pericytes in blood-vessel formation and maintenance," *Neuro-Oncology*, 7, 452-464.

Bhindi, R. et al., "Rat models of myocardial infarction," *Thromb Haemost*, 2006, 96, 602-610.

Daley, G. Q. et al., "Realistic Prospects for Stem Cell Therapeutics," *Hematol*., 2003, 398-418.

Edelstein, M. L. et al., "Gene therapy clinical trials worldwide 1989-2004—an overview," *J. Gene Med.*, Jun. 2004, 6(6), 597-602.

Franc, S. et al., "Microfibrillar composition of umbilical cord matrix: characterization of fibrillin, collagen VI and intact collagen V," *Placenta*, 1988, 19, 95-104.

Goodwin, H. S. et al., "Multilineage differentiation activity by cells isolated from umbilical cord blood: Expression of bone, fat and neural markers," *Biology of Blood and Marrow Transplantation*, 2001, 7, 581-588.

Hill, M. et al., "Treatment for swallowing difficulties (dysphagia) in chronic muscle disease," *Cochrane Database Syst Rev.*, 2004, (2):CD004303.

Jaffe, E. A. et al., "Culture of human endothelial cells derived from umbilical veins," *J Clin Invest*, 1973, 52, 2745-2756.

Jomura, S., et al., "Potential Treatment of Cerebral Global Ischemia with Oct-4+ Umbilical Cord Matrix Cells," *Stem Cells*, Sep. 7, 2006, AlphaMed Press, Downloaded from www.StemCells.com at Ethicon, Inc. on Sep. 11, 2006 and Supplemental Data: 2 pages.

Joussen, A. M., "Cell transplantation in age related macular degeneration: current concepts and future hopes," *Graefe's Arch. Clin. Exp. Ophthalmol.*, 2004, 242, 1-2.

Kawata, M. et al., "Transcriptional control of HLA-A,B,C antigen in human placental cytotrophoblast isolated using trophoblast- and HLA-specific monoclonal antibodies and the fluorescence-activated cell sorter," *J. Exp. Med.*, Sep. 1984, 160, 633-651.

Kirschstein, R. et al., "Can stem cells repair a damaged heart?" *Stem Cells: Scientific Progress and Future Research Directions*, 2001, 87-92.

Langeggen, H. et al., "HUVEC take up opsonized zymosan particles and secrete cytokines IL-6 and IL-8 in vitro," *FEMS Immunol. Med. Microbiol.*, 2003, 36, 55-61.

Lindvall, O. et al., "Stem cell therapy for human neurodegenerative disorders—how to make it work," *Nature Medicine*, Jul. 2004, 542-550.

Luo, D. et al., "Synthetic DNA delivery systems," *Nat. Biotechnol.*, Jan. 2000, 18(1), 33-36.

Medicetty, S. et al., "Transplantation of Human Umbilical Cord Matrix Stem Cells Alleviates Apomorphine-Induced Rotations in Parkinsonian Rats", 2003, XP-002383776, 1 page.

Medline Plus Online Medical Dictionary, definitions of "undifferentiated," "differentiate," and "differentiation." Retrieved online Mar. 6, 2007. URL:www.nlm.nih.gov/medlineplus/mplusdictionary.html.

Merx, M. W. et al., "Transplantation of human umbilical vein endothelial cells improves left ventricular function in a rat model of myocardial infarction," *Basic Res. Cardiol.*, 2005, 100, 208-216.

Moulder, J. E., "Pharmacological intervention to prevent or ameliorate chronic radiation injuries," *Semin. Radiat. Oncol.*, 2003, 13, 73-84.

Nishishita, T. et al., "A potential pro-angiogenic cell therapy with human placenta-derived mesenchymal cells," *Biochemical and Biophysical Research Communications*, 2004, 325, 24-31.

Nork, T. M. et al., "Swelling and Loss of Photoreceptors in Chronic and Experimental Glaucomas," *Arch. Ophthalmol.*, 2000, 118, 235-245.

Palu, G. et al., "In pursuit of new developments for gene therapy of human disease," J. Biotechnol., Feb. 1999, 68(1), 1-13.

Phipps, J. A. et al., "Paired-flash identification of rod and cone dysfunction in the diabetic rat," *Investigative Ophthalmology & Visual Science*, 2004, 45(12), 4592-4600.

Pittenger, M. F. et al., "Multilineage potential of adult human mesenchymal stem cells," *Science*, 1999, 284, 143-147 and seven pages of online supplementary material.

(56) References Cited

OTHER PUBLICATIONS

Pittenger, M. F. et al., "Mesenchymal Stem Cells and Their Potential as Cardiac Therapeutics," *Circ. Res.*, 2004, 95, 9-20.
Rehman, J. et al., "Secretion of Angiogenic and Antiapoptotic Factors by Human Adipose Stromal Cells," *Circulation*, 2004, 109, 1292-1298.
Roskams, A. J. et al., "Directing stem cells and progenitor cells on the stage of spinal cord injury," *Exp. Neurol.*, 2005, 193, 267-272.
Sethe, S. et al., "Aging of mesenchymal stem cells," *Ageing Research Reviews*, 2006, 5, 91-116.
Taylor, D. A. et al., "Regenerating functional myocardium: Improved performance after skeletal myoblast transplantation," *Nature Medicine*, Aug. 1998, 4(8), 929-933. Erratum in *Nature Medicine*, 4(10), 1200.
Timmermans et al., "Stem cells for the heart, are we there yet?" *Cardiology*, 2003, 100(4), 176-185.
Unigene entry for Hs.522632, *Homo sapiens* TMP metallopeptidase inhibitor 1 (TIMP1), printed from http://www.ncbi.nlm.nih.gov/UniGene on Oct. 12, 2006.
Urbich, C. et al., "Endothelial Progenitor Cells,", *Circ. Res.*, 2004, 95, 343-353.
Vajsar, J. et al., "Walker-Warburg syndrome," *Orphanet Journal of Rare Diseases*, 2006, 1, 29.
Verma, I. M. et al., "Gene therapy—promises, problems and prospects," *Nature*, Sep. 1997, 389(6648), 239-242.
Vermot-Desroches, C. et al., "Heterogeneity of antigen expression among human umbilical cord vascular endothelial cells: identification of cell subsets by co-expression of haemopoietic antigens," *Immunol. Lett.*, 1995, 48, 1-9.
Weiss, M. L. et al., "Human umbilical cord matrix stem cells: preliminary characterization and effect of transplantation in a rodent model of Parkinson's disease," *Stem Cells*, 2006, 24, 781-792.
Yang Chen et al., "Enhancement of neovascularization with cord blood CD133+ cell-derived endothelial progenitor cell transplantation," *Thrombosis and Haemostasis*, Jun. 2004, 91(6), 1202-1212.
Yokoo, T. et al., "Stem cell gene therapy for chronic renal failure," *Curr Gene Ther.*, 2003, 3, 387-394.
Zimmermann, S. et al., "Lack of telomerase activity in human mesenchymal stem cells," *Leukemia*, 2003, 17, 1146-1149.
Blakemore, W. F. et al., "Modelling Large Areas of Demyelination in the Rat Reveals the Potential and Possible Limitations of Transplanted Glial Cells for Remyelination in the CNS," *GLIA*, 2002, 38, 155-168.
Mackay et al., "Chondrogenic differentiation of cultured human mesenchymal stem cells from marrow," Tissue Engineering, 1998, 4(4), 415-428.
Jackson, K.A. et al., "Regeneration of Ischemic Cardiac Muscle and Vascular Enothelium by Adult Stem Cells", *Journal of Clinical Investigation*, 2001, 107(11), 1395-1402, XP-002976368.
Lodie, T.A. et al., "Systematic Analysis of Reportedly Distinct Populations of Multipotent Bone Marrow-Derived Stem Cells Reveals a Lack of Distinction", *Tissue Engineering*, 2002, 8(5), 739-751, XP-002306489.
Mitchell, K.E. et al., "Matrix Cells from Wharton's Jelly Form Neurons and Glia", *Stem Cells*, 2003, 21(1), 50-60, XP-002281007.
Ishii, M. et al., "Molecular Markers istinguish Bone Marrow Mesenchymal Stem Cells from Fibroblasts", *Biochemical and Biophysical Research Communications*, 2005, 332(1), 297-303.
Qian, Y. et al., "Recovery of Placental-Derived Adherent Cells with Mesenchymal Stem Cell Characteristics", 2001, 98(11), 147B, XP-009026843.
Tremain, N. et al., "MicroSAGE Analysis of 2,353 Expressed Genes in a Single Cell-Derived Colony of Undifferentiated Human Mesenchymal Stem Cells Reveals mRNAs of Multiple Cell Lineages", *Stem Cells*, 2001, 19, 408-418.
Abbas, A.K. et al., *Cellular and Molecular Immunology*, 5th Ed. (2003) Saunders, Philadelphia, p. 171.
Aggarwal et al., "Human Mesenchymal Stem Cells Modulate Allogeneic Immune Cell Responses," *Blood*, 2005; 105(4):1815-1822.

Aston, J. E., et al., "Repair of Articular Surfaces by Allografts of Articular and Growth-Plate Cartilage," *Journal of Bone and Joint Surgery*, 1986; 68-B(1):29-35.
Bai, M., et al, "Dimerization of the Extracellular Calcium-sensing Receptor (CaR) on the Cell Surface of CaR-Transfected HEK293 Cells," *J. Biol Chem.*, 1998; 273(36): 23605-23610.
Bussolati et al., "Isolation of Renal Progenitor Cells from Adult Human Kidney," *American Journal of Pathology*, 2005; 166(2):545-555.
Carter, D. et al., "Characterization of MSC Potential to Treat GVHD Using Molecular Markers Linked to MSC-Mediated Immunosuppression in Vitro," *Blood*, 2005; 106(11) part 2, Abstract No. 4322, 160B.
"Cell Lysis, p. 2" http://www.piercenet.com/obiects/view.cfm?type=Page&ID=1904ED25-8FA4-475C-8068-C2EB13D5F4E7; assessed Aug. 7, 2008.
Chen, J. et al., "Therapeutic Benefit of Intravenous Administration of Bone Marrow Stromal Cells after Cerebral Ischemia in Rats," *Stroke*, 2001; 32(4):1005-1011.
Del Monte, F. et al., "Improvement in Survival and Cardiac Metabolism After Gene Transfer of Sarcoplasmic Reticulum $Ca^{2+}$-ATPase in a Rat Model of Heart Failure," *Circulation*, 2001;104:1424-1429.
Dickinson, A.M. et al., "Non-HLA Immunogenetics in Hematopoietic Stem Cell Transplantation," *Curr. Opin. Immunol.*, 2005; 17(5):517-525.
Fernandes;A.M. et al., "Mouse Embryonic Stem Cell Expansion in a Microcarrier-based Stirred Culture System," *Journal of Biotechnology*, 2007; 132(2): 227-236.
Gröhn, P. et al., "Collagen-Coated $BA^{2+}$-Alginate Microcarriers for the Culture of Anchorage-Dependent Mammalian Cells," *Bio Techniques*, 1997; 22(5): 970-975.
Gupta, S. et al., "Isolation and Characterization of Kidney-Derived Stem Cells," *J. of Am. Soci. of Nephrol.*, 2006; 17(11):3028-3040.
Herrera, M.B. et al., "Mesenchymal Stem Cells Contribute to the Renal Repair of Acute Tubular Epithelial Injury," *Int. J. Mol. Med.*, 2004; 14(6):1035-1041.
Hishikawa, K. et al., "Musculin/MyoR is Expressed in Kidney Side Population Cells and Can Regulate Their Function," *Journal of Cell Biology*, 2005; 169(6):921-928.
Hoynowski, S.M. et al., "Characterization and Differentiation of Equine Umbilical Cord-Derived Matrix Cells," *Biochemical and Biophysical Research Communications*, 2007; 362:347-353.
In't Anker, P., et al., "Isolation of Mesenchymal Stem Cells of Fetal or Maternal Origin from Human Placenta," *Stem Cells*, 2004; 22:1338-1345.
Jones, J. et al., "Insulin-Like Growth Factors and their Binding Proteins: Biological Actions," *Endocrine Review*, 1995; 16(1):3-34.
Jørgensen, N.R. et al., "Intercellular Calcium Signaling Occurs Between Human Osteoblasts and Osteoclasts and Requires Activation of Osteoclast P2X7 Receptors," *The Journal of Biological Chemistry*, (2002); 277(9): 7574-7580.
Kisiday, J. et al., "Self-Assembling Peptide Hydrogel Fosters Chondrocyte Extracellular Matrix Production and Cell Division: Implications for Cartilage Tissue Repair," *PNAS*, 2002; 99(15):9996 10001.
Kitamura, S. et al., "Establishment and Characterization of Renal Progenitor Like Cells from S3 Segment of Nephron in Rat Adult Kidney," *The FASEB Journal: Official Publication of The Federation of American Societies for Experimental Biology*, 2005; 19(13):1789-1797.
Klahr, S et al., "Obstructive Nephropathy and Renal Fibrosis," *Am. J. Physiol. Renal. Physiol.*, 2002; 283(5):F861-875.
Kurtz, A. et al., "Activity in Fetal Bovine Serum that Stimulates Erythroid Colony Formation in Fetal Mouse Livers is Insulinlike Growth Factor I," *J. Clin. Invest.*, 1985; 76;1643-1648.
Li, C.D. et al, "Mesenchymal Stem Cells Derived From Human Placenta Suppress Allogeneic Umbilical Cord Blood Lymphocyte Proliferation," *Cell Research*, 2005; 15(7):539-547.
Li, Y. et al., "Intact, Injured, Necrotic and Apoptotic Cells after Focal Cerebral Ischemia in the Rat," *J. Neural. Sci.*, 1998; 156(2):119-132.

(56) References Cited

OTHER PUBLICATIONS

Li, Y. et al., "Ultrastructural and Light Microscopic Evidence of Apoptosis after Middle Cerebral Arte Occlusion in the Rat," *Am. J. Pathol.*, 1995; 146(5):1045-1051.

Lindenlaub, T. et al., "Partial Sciatic Nerve Transection as a Model of Neuropathic Pain: A Qualitative and Quantitative Study," *PAIN*, 2000; 89(1): 97-106.

Ma, L. et al , "Human Umbilical Cord Wharton's Jelly-Derived Mesenchymal Stem Cells Differentiation into Nerve-Like Cells," *Chinese Med. Jour.*, 2005; 118(23):1987-1993.

Ma, P.X . et al., "Synthetic Nano-Scale Fibrous Extracellular Matrix ," *J. Biomed Mater Res.*, 1999; 46(1):60-72.

Maeshima, A. et al., "Adult Kidney Tubular Cell Population Showing Phenotypic Plasticity, Tubulogenic Capacity, and Integration Capability into Developing Kidney," *Journal of American Society of Nephrology*, 2006; 17(1):188-198.

Melero-Martin, J. et al., "Optimal In-Vitro Expansion of Chondroprogenitor Cells in Monolayer Culture," *Biotechnology and Bioengineering*, 2006; 93(3):519-533.

Merriam-Webster Medline Plus Online Medical Dictionary, definitions of "iliac", "ilium" ileal/ileac and "ileum". [online] [retrieved on Feb. 12, 2008]. Retrieved from the Internet: URL://www.nlm.nih.gov/medlineplus/mplusdictionary.html.

Merriam-Webster Online Dictionary 10th Edition, Definition of "Scaffold" [retrieved on Sep. 12, 2008].

Moore, A.E. et al., "Parkinsonian Motor Deficits are Reflected by Proportional A9/A10 Dopamine Neuron Degeneration in the Rat," *Exp. Neurol.*, 2001; 172(2) :363-376.

Morigi, M. et al., "Mesenchymal Stem Cells are Renotropic, Helping to Repair the Kidney and Improve Function in Acute Renal Failure," *J. Am. Soc. Nephrol.*, 2004; 15(7):1794-1804.

Morishima, Y. et al., "The Clinical Significance of Human Leukocyte Antigen (HLA) Allele Compatibility in Patients Receiving a Marrow Transplant from Serologically HLA-A, HLA-B, and HLA-DR Matched Unrelated Donors," *Blood*, 2002; 99(11):4200-4206.

Ninichuk, V. et al., "Multipotent Mesenchymal Stem Cells Reduce Interstitial Fibrosis But Do Not Delay Progression of Chronic Kidney Disease in Collagen4A3-Deficient Mice," *Kidney Int.*, 2006; 70(1):121-29.

Oliver, J.A. et al., "The Renal Papilla is a Niche for Adult Kidney Stem Cells," *J. Clin Invest.*, 2004, 114(6):795-804.

Panepucci, R.A. et al, "Comparison of Gene Expression of Umbilical Cord Vein and Bone Marrow-Derived Mesenchymal Stem Cells," *Stem Cells*, 2004; 22(7):1263-1278.

Pera, M.F. et al., "Human Embryonic Stem Cells", *J. Cell Science*, 2000; 113:5-10.

Pisharodi, M. et al., "An Animal Model for Neuron-Specific Spinal Cord Lesions by the Microinjection of N-Methylaspartate, Kainic Acid, and Quisqualic Acid," 1985; *Appl. Neurophysiology*, 48:226-233.

Plaia, T., et al., "Characterization of a New Nih-Registered Variant Human Embryonic Stem Cell Line, BG01V: A Tool for Human Embryonic Stem Cell Research," *Stem Cells*, 2006: 24(3): 531-546.

Pountos, I. et al., "Mesenchymal Stem Cell Tissue Engineering: Techniques for Isolation, Expansion and Application," *Injury*, 2007; 38(Supp. 4):S23-33.

Quaini, F. et al., "Chimerism of the Transplanted Heart," *NEJM*, 2002; 346:5-15.

Russo, E., "Cultivating Policy from Cell Types," *The Scientist*, 2001; 15(11):6.

Sagrinati, C. et al., "Isolation and Characterization of Multipotent Progenitor Cells from the Bowman's Capsule of Adult Human Kidney," *Journal of American Society of Nephrology*, 2006; 17(9)2443-56.

Schallert, T. et al., "Use-Dependent Structural Events in Recovery of Function," *Brain Plasticity, Adv. Neurol.*, 1997; 73:229-38.

Schouten, J.W. et al., "A Review and Rationale for the Use of Cellular Transplantation as a Therapeutic Strategy for Traumatic Brain Injury," *Journal of Neurotrauma*, 2004; 21(11):1501-1538.

Schreuder, G.M. et al., "The HLA Dictionary 1999: A Summary of HLA-A, -B, -C, -DRB1/3/4/5, -DQB1 Alleles and Their Association with Serologically Defined HLA-A, -B, -C, -DR and -DQ Antigens," *Tissue Antigens*, 1999; 54(4):409-37.

Shuto, T. et al., "Dexamethasone Stimulates Osteoclast-Like Cell Formation by Inhibiting Granulocyte-Macrophage Colony-Stimulating Factor Production in Mouse Bone Marrow Cultures," *Endocrinology*, 1994; 134(3):1121-26.

Song, H. et al., "Astroglia Induce Neurogenesis From Adult Neural Stem Cells," *Nature*, 2002; 417(6884):39-44.

Tao, W., "Application of Encapsulated Cell Technology for Retinal Degenerative Disease", *Expert. Opin. Biol. Ther.*, 2006; 6(7): 717-726.

Toma, C. et al., "Human Mesenchymal Stem Cells Differentiate to a Cardiomyocyte Phenotype in the Adult Murine Heart," *Circulation*, 2002; 105:93-98.

Turner, D., "The Human Leucocyte Antigen (HLA) System," *Vox Sang.*, 2004; 87(Suppl 1):S87-S90.

Ujike, H. et al., "Gene Expression Related to Synaptogenesis, Neuritogenesis, and MAP Kinase in Behavioral Sensitization to Psychostimulants," *Ann. N.Y. Acad. Sci.*, 2002; 965:55-67.

Ulloa-Montoya, F. et al., "Culture Systems for Pluripotent Stem Cells," *Journal of Bioscience and Bioengineering*, 2005; 100(1):12-27.

Webster, T.J. et al., "Nanoceramic Surface Roughness Enhances Osteoblast and Osteoclast Functions for Improved Orthopaedic/Dental Implant Efficacy," *Scripta Materialia*, 2001; 44(8/9):1639-1642.

Wenning, G.K. et al., "Neural Transplantation in Animal Models of Multiple System Atrophy: A Review," *J. Nueral Transm.*, 1999; Suppl.(55):103-13.

Wikipedia, Definition of "Iliac crest" provided by Wikipedia, the free encyclopedia; retrieved from the Internet at URL: http://en.wikipedia.org/wiki/Iliac_crest; downloaded on Dec. 18, 2007.

Williams, J.T. et al., "Cells Isolated From Adult Human Skeletal Muscle Capable of Differentiating Into Multiple Mesodermal Phenotypes," *Am. Surg.*, Jan. 1999:65(I):22-6.

Wolford, L.M. et al., "Considerations in Nerve Repair," *BUMC Proceedings*, 2003; 16:152-156.

Xu, A. et al.,"Soft, Porous Poly(D,L lactide-co-glycotide) Microcarriers Designed for Ex Vivo Studies and for Transplantation of Adherent Cell Types including Progenitors," *Annals of the New York Academy of Sciences*, 2001; 944:144-159.

Yamashima, T., "Implication of Cysteine Proteases Calpain, Cathepsin and Caspase in Ischemic Neuronal Death of Primates," *Progress in Neurobiology*, 2000; 62:273-295.

Zhang, L. et al., "A Test for Detecting Long-Term Sensorimotor Dysfunction in the Mouse after Focal Cerebral Ischemia," *J. Neurosci. Methods*, 2002; 117(2):207-14.

Zhang, X. et al., "Efficient Adeno-Associated Virus-Mediated Gene Expression in Human Placenta-Derived Mesenchymal Cells," *Microbiol. Immunol.*, 2003; 47(1):109-16.

Zhang, Y. et al., "Comparison of Mesenchymal Stem Cells from Human Placenta and Bone Marrow," *Chinese Medical Journal*, 2004; 117(6):882-87.

Zhang, Z.G. et al., "Correlation of VEGF and Angiopoietin Expression with D- ISRuption of Blood-Brain Barrier and Angiogenesis after Focal Cerebral Ischemia," *J. Cereb. Blood Flow Metab.*, 2002; 22(4):379-92.

In the U.S. Patent and Trademark Office, Non-Final Office Action in re: U.S. Appl. No. 10/877,012, dated Sep. 24, 2007, 18 pages.

In the U.S. Patent and Trademark Office, Final Office Action in re: U.S. Appl. No. 10/877,012, dated Mar. 15, 2007, 13 pages.

In the U.S. Patent and Trademark Office, Non-Final Office Action in re: U.S. Appl. No. 10/877,012, dated Jul. 18, 2006, 26 pages.

In the U.S. Patent and Trademark Office, Non-Final Office Action in re: U.S. Appl. No. 11/315,897, dated Jun. 13, 2008, 12 pages.

In the U.S. Patent and Trademark Office, Non-Final Office Action in re: U.S. Appl. No. 10/877,446, dated Feb. 28, 2008, 19 pages.

In the U.S. Patent and Trademark Office, Final Office Action in re: U.S. Appl. No. 10/877,446, dated Jun. 27, 2007, 24 pages.

In the U.S. Patent and Trademark Office, Non-Final Office Action in re: U.S. Appl. No. 10/877,446, dated Nov. 20, 2006, 24 pages.

(56) References Cited

OTHER PUBLICATIONS

In the U.S. Patent and Trademark Office, Non-Final Office Action in re: U.S. Appl. No. 10/877,269, dated Jan. 17, 2008, 10 pages.
In the U.S. Patent and Trademark Office, Final Office Action in re: U.S. Appl. No. 10/877,269, dated Aug. 14, 2007, 6 pages.
In the U.S. Patent and Trademark Office, Non-Final Office Action in re: U.S. Appl. No. 10/877,269, dated May 3, 2007, 12 pages.
In the U.S. Patent and Trademark Office, Non-Final Office Action in re: U.S. Appl. No. 11/315,898, dated Feb. 13, 2008, 12 pages.
In the U.S. Patent and Trademark Office, Final Office Action in re: U.S. Appl. No. 11/315,943, dated Aug. 20, 2008, 7 pages.
In the U.S. Patent and Trademark Office, Non-Final Office Action in re: U.S. Appl. No. 11/315,943, dated Feb. 12, 2008, 11 pages.
In the U.S. Patent and Trademark Office, Non-Final Office Action in re: U.S. Appl. No. 10/877,445, dated Jul. 11, 2008, 12 pages.
In the U.S. Patent and Trademark Office, Non-Final Office Action in re: U.S. Appl. No. 10/877,445, dated Mar. 19, 2008, 12 pages.
In the U.S. Patent and Trademark Office, Final Office Action in re: U.S. Appl. No. 10/877,445, dated Nov. 5, 2007, 17 pages.
In the U.S. Patent and Trademark Office, Non-Final Office Action in re: U.S. Appl. No. 10/877,445, dated May 17, 2007, 20 pages.
In the U.S. Patent and Trademark Office, Final Office Action in re: U.S. Appl. No. 10/877,445, dated Sep. 11, 2006, 30 pages.
In the U.S. Patent and Trademark Office, Non-Final Office Action in re: U.S. Appl. No. 10/877,445, dated Nov. 21, 2005, 17 pages.
In the U.S. Patent and Trademark Office, Non-Final Office Action in re: U.S. Appl. No. 11/322,372, dated Sep. 3, 2008, 13 pages.
In the U.S. Patent and Trademark Office, Non-Final Office Action in re: U.S. Appl. No. 10/877,541, dated Jul 25, 2007, 13 pages.
In the U.S. Patent and Trademark Office, Advisory Office Action in re: U.S. Appl. No. 10/877,541, dated Apr. 18, 2007, 4 pages.
In the U.S. Patent and Trademark Office, Final Office Action in re: U.S. Appl. No. 10/877,541, dated Jan. 10, 2007, 19 pages.
In the U.S. Patent and Trademark Office, Non-Final Office Action in re: U.S. Appl. No. 10/877,541, dated Feb. 22, 2006, 13 pages.
In the U.S. Patent and Trademark Office, Advisory Office Action in re: U.S. Appl. No. 11/317,574, dated Jun. 4, 2008, 3 pages.
In the U.S. Patent and Trademark Office, Final Office Action in re: U.S. Appl. No. 11/317,574, dated Mar. 5, 2008, 10 pages.
In the U.S. Patent and Trademark Office, Final Office Action in re: U.S. Appl. No. 11/317,574, dated Aug. 10, 2007, 14 pages.
In the U.S. Patent and Trademark Office, Non-Final Office Action in re: U.S. Appl. No. 10/877,009 dated Jan. 9, 2008, 12 pages.
In the U.S. Patent and Trademark Office, Final Office Action in re: U.S. Appl. No. 10/877,009, dated Jul. 25, 2007, 17 pages.
In the U.S. Patent and Trademark Office, Non-Final Office Action in re: U.S. Appl. No. 10/877,009, dated Nov. 21, 2006, 15 pages.
In the U.S. Patent and Trademark Office, Non-Final Office Action in re: U.S. Appl. No. 10/876,998, dated Jun. 25, 2008, 9 pages.
In the U.S. Patent and Trademark Office, Final Office Action in re: U.S. Appl. No. 10/876,998, dated Feb. 27, 2008, 18 pages.
In the U.S. Patent and Trademark Office, Non-Final Office Action in re: U.S. Appl. No. 10/876,998, dated Jul. 13, 2007, 30 pages.
In the U.S. Patent and Trademark Office, Final Office Action in re: U.S. Appl. No. 10/876,998, dated Oct. 18, 2006, 29 pages.
In the U.S. Patent and Trademark Office, Non-Final Office Action in re: U.S. Appl. No. 10/876,998, dated Mar. 30, 2006, 24 pages.
In the U.S. Patent and Trademark Office, Non-Final Office Action in re: U.S. Appl. No. 11/321,863, dated Aug. 19, 2008, 15 pages.
In the U.S. Patent and Trademark Office, Non-Final Office Action in re: U.S. Appl. No. 11/322,003, dated Jun. 2, 2008, 14 pages.
In the U.S. Patent and Trademark Office, Non-Final Office Action in re: U.S. Appl. No. 11/321,864, dated Apr. 21, 2008, 7 pages.
In the U.S. Patent and Trademark Office, Final Office Action in re: U.S. Appl. No. 11/315,969, dated May 19, 2008, 9 pages.
In the U.S. Patent and Trademark Office, Non-Final Office Action in re: U.S. Appl. No. 11/315,969, dated Nov. 1, 2007, 12 pages.
In the U.S. Patent and Trademark Office, Final Office Action in re: U.S. Appl. No. 11/297,778, dated Apr. 11, 2008, 9 pages.
In the U.S. Patent and Trademark Office, Non-Final Office Action in re: U.S. Appl. No. 11/297,778, dated Feb. 22, 2007, 8 pages.
In the U.S. Patent and Trademark Office, Final Office Action in re: U.S. Appl. No. 11/304,091, dated Apr. 11, 2008, 11 pages.
In the U.S. Patent and Trademark Office, Non-Final Office Action in re: U.S. Appl. No. 11/304,091, dated Feb. 23, 2007, 9 pages.
In the United States Patent and Trademark Office, Final Office Action in re: U.S. Appl. No. 11/315,898, dated Sep. 16, 2008, 13 pages.
In the United States Patent and Trademark Office, Non-Final Office Action in re: U.S. Appl. No. 11/323,372, dated Sep. 3, 2008, 45 pages.
In the United States Patent and Trademark Office, Non-Final Office Action, in re: U.S. Appl. No. 11/297,156, dated Oct. 10, 2008, 36 pages.
In the United States Patent and Trademark Office, Non-Final Office Action in re: U.S. Appl. No. 11/317,574, dated Sep. 30, 2008, 28 pages.
In the U. S. Patent and Trademark Office, Advisory Action in re: U.S. Appl. No. 11/315,969 dated Sep. 29, 2009, 8 pages.
In the U. S. Patent and Trademark Office, Advisory Action in re: U.S. Appl. No. 11/322,372 dated May 12, 2009, 10 pages.
In the U. S. Patent and Trademark Office, Final Office Action in re: U.S. Appl. No. 11/315,969 dated May 13, 2009, 11 pages.
In the U. S. Patent and Trademark Office, Final Office Action in re: U.S. Appl. No. 10/877,445 dated Jul. 8, 2010, 20 pages.
In the U. S. Patent and Trademark Office, Non-Final Office Action in re: U.S. Appl. No. 11/315,969, dated Dec. 23, 2008, 18 pages.
In the U. S. Patent and Trademark Office, Non-Final Office Action in re: U.S. Appl. No. 11/321,864, dated Jan. 8, 2009, 18 pages.
In the U. S. Patent and Trademark Office, Final Office Action in re: U.S. Appl. No. 11/321,863, dated Feb. 12, 2009, 24 pages.
In the U. S. Patent and Trademark Office, Non-Final Office Action in re: U.S. Appl. No. 11/315,943, dated Feb. 20, 2009, 17 pages.
In the U. S. Patent and Trademark Office, Non-Final Office Action in re: U.S. Appl. No. 10/877,445, dated Mar. 19, 2009, 23 pages.
In the U. S. Patent and Trademark Office, Non-Final Office Action in re: U.S. Appl. No. 11/481,481, dated Mar. 20, 2009, 48 pages.
In the U. S. Patent and Trademark Office, Final Office Action in re: U.S. Appl. No. 11/315,897, dated Mar. 20, 2009, 21 pages.
In the U. S. Patent and Trademark Office, Non-Final Office Action in re: U.S. Appl. No. 11/481,480, dated Mar. 20, 2009, 50 pages.
In the U. S. Patent and Trademark Office, Final Office Action in re: U.S. Appl. No. 11/322,003 dated Feb. 13, 2009, 24 pages.
In the U. S. Patent and Trademark Office, Final Office Action in re: U.S. Appl. No. 10/876,998 dated Feb. 13, 2009, 17 pages.
In the U. S. Patent and Trademark Office, Final Office Action in re: U.S. Appl. No. 11/322,372 dated Feb. 13, 2009, 22 pages.
In the U. S. Patent and Trademark Office, Non-Final Office Action in re: U.S. Appl. No. 11/315,898 dated Feb. 20, 2009, 18 pages.
In the U. S. Patent and Trademark Office, Non-Final Office Action in re: U.S. Appl. No. 11/481,456 dated Apr. 16, 2009, 50 pages.
In the U. S. Patent and Trademark Office, Non-Final Office Action in re: U.S. Appl. No. 11/317,574 dated Apr. 29, 2009, 29 pages.
In the U. S. Patent and Trademark Office, Non-Final Office Action in re: U.S. Appl. No. 10/877,446 dated Jun. 12, 2009, 16 pages.
In the U. S. Patent and Trademark Office, Final Office Action in re: U.S. Appl. No. 11/322,372 dated Aug. 6, 2009, 13 pages.
In the U. S. Patent and Trademark Office, Final Office Action in re: U.S. Appl. No. 11/481,456 dated Oct. 9, 2009, 18 pages.
In the U. S. Patent and Trademark Office, Final Office Action in re: U.S. Appl. No. 11/321,864 dated Aug. 17, 2009, 16 pages.
In the U. S. Patent and Trademark Office, Non-Final Office Action in re: U.S. Appl. No. 11/317,574 dated Dec. 28, 2009, 26 pages.
In the U. S. Patent and Trademark Office, Non-Final Office Action in re: U.S. Appl. No. 11/321,863 dated Jan. 7, 2010, 16 pages.
In the U. S. Patent and Trademark Office, Non-Final Office Action in re: U.S. Appl. No. 11/321,864 dated Jan. 27, 2010, 17 pages.
In the U. S. Patent and Trademark Office, Non-Final Office Action in re: U.S. Appl. No. 11/315,969 dated Jan. 27, 2010, 14 pages.
In the U. S. Patent and Trademark Office, Non-Final Office Action in re: U.S. Appl. No. 11/315,943 dated Feb. 19, 2010, 16 pages.

(56) References Cited

OTHER PUBLICATIONS

In the U. S. Patent and Trademark Office, Non-Final Office Action in re: U.S. Appl. No. 11/481,456 dated May 14, 2010, 9 pages.
In the U. S. Patent and Trademark Office, Non-Final Office Action in re: U.S. Appl. No. 11/481,481 dated May 13, 2010, 9 pages.
In the U. S. Patent and Trademark Office, Non-Final Office Action in re: U.S. Appl. No. 11/315,897 dated May 14, 2010, 13 pages.
In the U. S. Patent and Trademark Office, Non-Final Office Action in re: U.S. Appl. No. 11/481,480 dated May 17, 2010, 10 pages.
Bruder, S. P., et al., "Mesenchymal Stem Cell Surface Antigen SB-10 Corresponds to Activated Leukocyte Cell Adhesion Molecule and Is Involved in Osteogenic Differentiation," *Journal of Bone and Mineral Research*, 1998; 13(4):655-663.
In the U. S. Patent and Trademark Office, Non-Final Office Action in re: U.S. Appl. No. 10/876,998 dated Aug. 3, 2010, 14 pages.
In the U. S. Patent and Trademark Office, Final Office Action in re: U.S. Appl. No. 11/321,863 dated Aug. 17, 2010, 15 pages.
In the U. S. Patent and Trademark Office, Non-Final Action in re: U.S. Appl. No. 11/315,897 dated Sep. 2, 2009, 12 pages.
In the U. S. Patent and Trademark Office, Final Action in re: U.S. Appl. No. 11/481,480 dated Sep. 17, 2009, 12 pages.
In the U. S. Patent and Trademark Office, Final Action in re: U.S. Appl. No. 10/877,446 dated Jun. 4, 2010, 17 pages.
In the U. S. Patent and Trademark Office, Final Action in re: U.S. Appl. No. 10/876,998 dated May 27, 2009, 14 pages.
In the U. S. Patent and Trademark Office, Non-Final Action in re: U.S. Appl. No. 10/876,998 dated Nov. 24, 2009, 7 pages.
In the U. S. Patent and Trademark Office, Final Action in re: U.S. Appl. No. 11/322,003 dated Feb. 13, 2009, 17 pages.
Diegelmann et al., "Inhibition of Collagen Secretion from Bone and Cultured Fibroblasts by Microtubular Disruptive Drugs," Proc., Nat. Acad. Sci., 1972; 69(4):892-896.
In the U. S. Patent and Trademark Office, Final Office Action in re: U.S. Appl. No. 11/321,864 dated Aug. 31, 2010, 7 pages.
In the U. S. Patent and Trademark Office, Final Office Action in re: U.S. Appl. No. 11/315,969 dated Aug. 31, 2010, 6 pages.
In the U. S. Patent and Trademark Office, Final Office Action in re: U.S. Appl. No. 11/322,372 dated Aug. 31, 2010, 11 pages.
In the U. S. Patent and Trademark Office, Final Office Action in re: U.S. Appl. No. 11/317,574 dated Oct. 6, 2010, 16 pages.
In the U. S. Patent and Trademark Office, Non-Final Office Action in re: U.S. Appl. No. 12/054,718 dated Sep. 29, 2010, 18 pages.
In the U. S. Patent and Trademark Office, Non-Final Office Action in re: U.S. Appl. No. 11/322,372 dated Jan. 21, 2010, 10 pages.
In the U. S. Patent and Trademark Office, Final Office Action in re: U.S. Appl. No. 11/481,481 dated Sep. 18, 2009, 11 pages.
In the U. S. Patent and Trademark Office, Advisory Action in re: U.S. Appl. No. 11/315,897 dated Jun. 30, 2009, 3 pages.
In the U. S. Patent and Trademark Office, Non-Final Office Action in re: U.S. Appl. No. 11/315,897 dated Sep. 2, 2009, 12 pages.
In the U. S. Patent and Trademark Office, Final Office Action in re: U.S. Appl. No. 11/481,480 dated Sep. 17, 2009, 12 pages.
In the U. S. Patent and Trademark Office, Final Office Action in re: U.S. Appl. No. 10/877,446 dated Jun. 4, 2010, 17 pages.
In the U. S. Patent and Trademark Office, Final Office Action in re: U.S. Appl. No. 10/876,998 dated May 27, 2009, 14 pages.
In the U. S. Patent and Trademark Office, Non-Final Office Action in re: U.S. Appl. No. 10/876,998 dated Nov. 24, 2009, 7 pages.
In the U. S. Patent and Trademark Office, Final Office Action in re: U.S. Appl. No. 11/322,003 dated Feb. 13, 2009, 17 pages.
In the U. S. Patent and Trademark Office, Non-Final Office Action in re: U.S. Appl. No. 10/876,998 dated Feb. 1, 2011, 11 pages.
In the U. S. Patent and Trademark Office, Non-Final Office Action in re: U.S. Appl. No. 11/481,456 dated Feb. 3, 2011, 10 pages.
In the U. S. Patent and Trademark Office, Non-Final Office Action in re: U.S. Appl. No. 11/481,481 dated Feb. 3, 2011, 10 pages.
In the U. S. Patent and Trademark Office, Non-Final Office Action in re: U.S. Appl. No. 12/389,305 dated Feb. 8, 2011, 14 pages.
In the U. S. Patent and Trademark Office, Non-Final Office Action in re: U.S. Appl. No. 11/481,480 dated Feb. 3, 2011, 10 pages.
In the U.S. Patent and Trademark Office, Final Office Action in re: U.S. Appl. No. 10/877,446 dated Nov. 2, 2011, 12 pages.
In the U.S. Patent and Trademark Office, Final Office Action in re: U.S. Appl. No. 12/389,305 dated Oct. 12, 2011, 12 pages.
In the U.S. Patent and Trademark Office, Final Office Action in re: U.S. Appl. No. 12/429,849 dated Mar. 20, 2012, 9 pages.
In the U. S. Patent and Trademark Office, Final Office Action in re: U.S. Appl. No. 11/481,456 dated Oct. 11, 2011, 6 pages.
In the U. S. Patent and Trademark Office, Final Office Action in re: U.S. Appl. No. 10/877,446 dated Nov. 2, 2011, 12 pages.
In the U.S. Patent and Trademark Office, Non-Final Office Action in re: U.S. Appl. No. 12/697,081 dated Apr. 2, 2012, 8 pages.
In the U.S. Patent and Trademark Office, Non-Final Office Action in re: U.S. Appl. No. 13/605,716 dated Feb. 13, 2013, 13 pages.
Bakhshi, et al. "Mesenchymal stem cells from the Wharton's jelly of umbilical cord segments provide stromal support for the maintenance of cord blood hematopoietic stem cells during long-term ex vivo culture", *Transfusion*, 2008; 48: 2638-2644.
Cell Isolation Theory, in Tissue Dissociation Guide, Worthington Biochemical, accessible at http://www.tissuedissociation.com, accessed Aug. 8, 2007.
Diao et al, "Human Umbilical Cord Mesenchymal Stem Cells: Osteogenesis In Vivo as Seed Cells for Bone Tissue Engineering," *J. BioMed Mater Res.*, 2009; 91A:123-131.
Draper et al., "Surface Antigens of Human Embryonic Stem Cells: Changes Upon Differentiation in Culture," J. Anat., 2002; 200:249-258.
Fukuchi, Y. et al., "Human Placenta-Derived Cells Have Mesenchymal Stem/Progenitor Cell Potential," *Stem Cells*, 2004; 22:649-658.
Haynesworth et al., "Cell Surface Antigens on Human Marrow-Derived Mesenchymal Cells are Detected by Monoclonal Antibodies," Bone, 1992; 13:69-80.
Igura et al. "Human Placental Derived Stem Cells Differentiate into Neural Cells," Blood , 2002; 100(11): 517A (Abstract 2021).
Kusama et al., "Growth and morphogenesis of mouse prostate epithelial cells in collagen gel matrix culture" Cell Biol Int Rep, 1989; 13:569-575.
Makino et al., "Cardiomyocytes can be generated from marrow stromal cells in vitro," J. Clin. Invest., 1999; 103:697-705.
Naughton et al., "Cells isolated from Wharton's jelly of the human umbilical cord develop a cartilage phenotype when treated with TGF-b in vitro," 1997; FASEB J 11:A19 (Abstract 108).
Seaver et al. "The chick oviduct in tissue culture. I. Initial characterization of growing primary oviduct tissue cultures," Exp. Cell Res., 1984; 155: 241-251.
Seiji, T. et al., Possibility of Regenerative Medicine Using Human Amniotic Cells, Regenerative Medicine, 2002; 1(2):79-85.
Shake et al., "Mesenchymal stem cell implantation in a swine myocardial infarct model: engraftment and functional effects," Ann Thorac Surg, 2002; 73:1919-1926.
Wang, Y. et al., "Enhanced Recovery of Hematopoietic Progenitor and Stem Cells from Cultivated, Postpartum Human Placenta," Blood, 2001; 98(11): 183a (Abstract 769 ).
Zhang, J, et al., "Differentiation potential of bone marrow mesenchymal stem cells into retina in normal and laser-injured rat eye", Science in China Ser. C Life Science, 2004; 47:241-250.
In the U.S. Patent and Trademark Office, Non-Final Office Action in re: U.S. Appl. No. 11/317,574 dated Jul. 11, 2013, 29 pages.
In the U.S. Patent and Trademark Office, Non-Final Office Action in re: Application No. 11/322,372 dated Jan. 16, 2014, 20 pages.
In the U.S. Patent and Trademark Office, Non-Final Office Action in re: U.S. Appl. No. 11/321,864 dated Jan. 29, 2014, 9 pages.
In the U.S. Patent and Trademark Office, Non- Final Office Action in re: U.S. Appl. No. 11/321,863 dated Jan. 31, 2014, 17 pages.
In the U.S. Patent and Trademark Office, Final Office Action in re: U.S. Appl. No. 11/317,574 dated Feb. 3, 2014, 16 pges.
In the U.S. Patent and Trademark Office, Non-Final Office Action in re: U.S. Appl. No. 10/876,998 dated Feb. 11, 2014, 14 pages.
In the U.S. Patent and Trademark Office, Non-Final Office Action in re: U.S. Appl. No. 12/389,305 dated Mar. 6, 2014, 38 pages.
In the U.S. Patent and Trademark Office, Non-Final Office Action in re: U.S. Appl. No. 12/389,305 dated Mar. 21, 2014, 47 pages.

(56) References Cited

OTHER PUBLICATIONS

In the U.S. Patent and Trademark Office, Non-Final Office Action in re: U.S. Appl. No. 10/877,446 dated Mar. 21, 2014, 22 pages.
In the U.S. Patent and Trademark Office, Non-Final Office Action in re: U.S. Appl. No. 11/315,969 dated Mar. 21,2014, 17 pages.
Baksh, D. et al., "Comparison of proliferative and multilineage differentiation potential of human mesenchymal stem cells derived from umbilical cord and bone marrow." *Stem Cells*, 2007; 25: 1384-1392.
Bhatia, R. et al., "A clinically suitable ex vivo expansion culture system for LTC-IC and CFC using stroma-conditioned medium," *Exp Hematol*, 1997; 25(9): 980-91 (Abstract only).
Ciavarella, S. et al., "Umbilical Cord Mesenchymal Stem Cells: Role of Regulatory Genes in Their Differentiation to Osteoblasts," *Stem Cells and Development*, 2009; 18:1211-1220.
Covas, D.T. et al., "Isolation and culture of umbilical vein mesenchymal stem cells." *Brazilian Journal of Medical and Biological Research*, 2003; 36: 1179-1183.
Deans, R.J. et al., "Mesenchymal stem cells: Biology and potential clinical uses," *Experimental Hematology*, 2000; 28: 875-884.
"Dulbecco's Modified Eagle's Medium (DME) Formulation." Sigma-Aldrich, available online at <http://www.sigmaaldrich.com/life-science/cell-culture/learning-center/media-formulations/dme.printerview.html>. Accessed Mar. 17, 2014.
Henderson, G.I. et al., "Inhibition of placental valine uptake after acute and chronic maternal ethanol consumption." *J Pharmacol Exp Therap*, 1981; 216: 465-472.
Kestendjieva, S. et al., "Characterization of mesenchymal stem cells isolated from the human umbilical cord." *Cell Biology International*, 2008; 32: 724-732.
Kocher, A. A. et al., "Neovascularization of ischemic myocardium by human bone-marrow-derived angioblasts prevents cardiomyocyte apoptosis, reduces remodeling and improves cardiac function," *Nature Medicine*, 2001; 7:430-6.
Lonza (Cambrex), hMSC Human Mesenchymal Stem Cells, Lonza, 2014, http://www.lonza.com/products-services/bio-research/primary-and-stem-cells/adult-stem-cells-and-media/hmsc-mesenchymal-stem-cells.aspx; accessed Jan. 31, 2014.
Voet D and Voet JG, Biochemistry (2d Ed., John Wiley & Sons), 1995; Chapter 4. Amino Acids: B. The Fischer Convention, p. 64.
In the U.S. Patent and Trademark Office, Final Office Action in re: U.S. Appl. No. 12/389,305 dated Aug. 6, 2014, 57 pages.
In the U.S. Patent and Trademark Office, Final Office Action in re: U.S. Appl. No. 10/877,446 dated Aug. 6, 2014, 35 pages.
In the U.S. Patent and Trademark Office, Final Office Action in re: U.S. Appl. No. 11/321,864 dated Nov. 3, 2014, 10 pages.
"11885—DMEM, low glucose, pyruvate." Life Technologies. Available online at <http://www.lifetechnolgies.com/us/en/home/technical-resources/media-formulation.48.html>. Accessed Jul. 31, 2014. 2 pages.
Secco, M. et al., "Multipotent Stem Cells from Umbilical Cord: Cord is Richer than Blood!" Stem Cells, 2008; 26:146-150.
Troyer, D. L. et al., "Concise Review: Wharton's Jelly-Derived Cells Are a Primitive Stromal Cell Population," Stem Cells, 2008; 26:591-599.
In the U.S. Patent and Trademark Office Final Office Action in re: U.S. Appl. No. 11/317,574 dated Feb. 3, 2014, 12 pages.
In the U.S. Patent and Trademark Office, Final Office Action in re: U.S. Appl. No. 10/876,998 dated Dec. 16, 2014, 19 pages.
In the U.S. Patent and Trademark Office, Non-Final Office Action in re: U.S. Appl. No. 11/322,372 dated Nov. 25, 2014, 24 pages.
In the U.S. Patent and Trademark Office, Final Office Action in re: U.S. Appl. No. 11/315,969 dated Dec. 18, 2014, 30 pages.
In the U.S. Patent and Trademark Office, Final Office Action in re: U.S. Appl. No. 11/321,863 dated Jan. 31, 2014, 17 pages.
In the U.S. Patent and Trademark Office, Non-Final Office Action in re: U.S. Appl. No. 14/152,649 dated Feb. 26, 2015, 9 pages.
In the U.S. Patent and Trademark Office, Non-Final Office Action in re: U.S. Appl. No. 14/444,689 dated Mar. 24, 2015, 9 pages.
In the U.S. Patent and Trademark Office, Final Office Action in re: U.S. Appl. No. 11/317,574 dated Apr. 1, 2015, 12 pages.
In the U.S. Patent and Trademark Office, Final Office Action in re: U.S. Appl. No. 13/471,095 dated Jun. 12, 2015, 10 pages.
In the U.S. Patent and Trademark Office, Final Office Action in re: U.S. Appl. No. 14/152,649 dated Jul. 10, 2015, 7 pages.
In the U.S. Patent and Trademark Office, Final Office Action in re: U.S. Appl. No. 13/111,933 dated Jul. 15, 2015, 31 pages.
In the U.S. Patent and Trademark Office, Final Office Action in re: U.S. Appl. No. 12/339,872 dated Aug. 3, 2015, 14 pages.
In the U.S. Patent and Trademark Office, Non-Final Office Action in re: U.S. Appl. No. 10/877,446 dated Sep. 3, 2015, 82 pages.
In the U.S. Patent and Trademark Office, Non-Final Office Action in re: U.S. Appl. No. 11/321,864 dated Sep. 2, 2015, 11 pages.
In the U.S. Patent and Trademark Office, Non-Final Office Action in re: U.S. Appl. No. 12/389,305 dated Sep. 4, 2015, 63 pages.
In the U.S. Patent and Trademark Office, Non-Final Office Action in re: U.S. Appl. No. 14/152,649 dated Oct. 27, 2015, 7 pages.
Broxmeyer, H.E. et al., "Growth characteristics and expansion of human umbilical cord blood and estimation of its potential for transplantation in adults," *PNAS*, 1992; 89(9): 4109-4113.
Chen, K. et al., "Human umbilical cord mesenchymal stem cells hUC-MSCs exert immunosuppressive activities through a PGE2-dependent mechanism,"*Clinical Immunology*, 2010, 135; 448-458.
Hass, R. et al., "Different populations and sources of human mesenchymal stem cells (MSC): A comparison of adult and neonatal tissue-derived MSC," *Cell Communication and Signaling*, 2011; 9:12, p. 1-14.
Ho, A.D. et al., "Heterogeneity of mesenchymal stromal cell preparations," *Cytotherapy*, 2008;10(4):320-30.
Kern, S. et al., "Comparative analysis of mesenchymal stem cells from bone marrow, umbilical cord blood, or adipose tissue," *Stem Cells*, 2006; 24(5):1294-301.
Otsuka, A. et al. "Lipopolysaccharide augments HLA-A,B,C molecule expression but inhibits interferon-gamma-induced HLA-DR molecule expression on cultured human endothelial cells," *Immunology*, 1991; 73; 428-432.
Park, B-G et al., "Development of high density mammalian cell culture system for the production of tissue-type plasminogen activator," *Biotechnology and Bioprocess Engineering*, 2000; 5:123-129.
Pittenger, M.F. et al.; "Human mesenchymal stem cells: progenitor cells for cartilage, bone, fat and stroma," *Current Topics in Microbiology and Immunology*, 2000; 251:3-11.
Rachakatla, R. S. et al., "Development of Human Umbilical Cord Matrix Stem Cell-Based Gene Therapy for Experimental Lung Tumors," *Cancer Gene Therapy*, 2007; 14:828-835.
Solomon, D. E., "An in vitro examination of extracellular matrix scaffold for use in wound healing," *Int. J. Path*, 2002, 93: 209-216.
Xu, Y et al., "Umbilical Cord-Derived Mesenchymal Stem Cells Isolated by a Novel Explantation Technique Can Differentiate into Functional Endothelial Cells and Promote Revascularization," *Stem Cells and Development*, 2010, 19(10): 1511-1522.
Zhao, Q.H. et al., "Biological characteristics of human umbilical cord-derived mesenchymal stem cells and their differentiation into chondrogenic and osteogenic cells," *Zhonghua Yi Xue Za Zhi.*, 2011;91(5):317-21 (Abstract only).
In the U.S. Patent and Trademark Office Non-Final Office Action in re: U.S. Appl. No. 12/389,305 dated Mar. 21, 2014, 47 pages.
In the U.S. Patent and Trademark Office, Final Office Action in re: U.S. Appl. No. 10/876,998 dated Dec. 22, 2015, 21 pages.
In the U.S. Patent and Trademark Office, Final Office Action in re: U.S. Appl. No. 11/321,864 dated Dec. 22, 2015, 15 pages.
In the U.S. Patent and Trademark Office, Non-Final Office Action in re: U.S. Appl. No. 11/317,574 dated Jan. 6, 2015, 11 pages.
In the U.S. Patent and Trademark Office, Final Office Action in re: U.S. Appl. No. 11/322,372 dated Jan. 6, 2015, 27 pages.
In the U. S. Patent and Trademark Office, Final Office Action in re: U.S. Appl. No. 12/337,439 dated Mar. 17, 2016, 29 pages.
In the U. S. Patent and Trademark Office, Final Office Action in re: U.S. Appl. No. 11/315,969 dated Apr. 21, 2016, 20 pages.
In the U. S. Patent and Trademark Office, Final Rejection in re: U.S. Appl. No. 10/876,998 dated May 20, 2016, 21 pages.

(56) References Cited

OTHER PUBLICATIONS

In the U. S. Patent and Trademark Office, Final Office Action in re: U.S. Appl. No. 12/389,305 dated May 24, 2016, 21 pages.
In the U. S. Patent and Trademark Office, Non-Final Office Action in re: U.S. Appl. No. 10/877,446 dated May 24, 2016 36 pages.
In the U.S. Patent and Trademark Office, Non-Final Office Action in re: U.S. Appl. No. 11/322,372 dated May 31, 2016, 29 pages.
In the U.S. Patent and Trademark Office, Final Office Action in re: U.S. Appl. No. 11/317,574 dated May 31, 2016, 18 pages.
In the U.S. Patent and Trademark Office, Final Office Action in re: U.S. Appl. No. 14/152,649 dated Jun. 14, 2016, 6 pages.
In the U.S. Patent and Trademark Office, Final Office Action in re: U.S. Appl. No. 11/317,574 dated Jul. 7, 2016, 9 pages.
Baksh, D. et al., "Adult mesenchymal stem cells: characterization, differentiation, and application in cell and gene therapy", *J Cell Mol Med.*, 2004; 8(3):301-16.
Bertram H. et al., "Matrix-assisted cell transfer for intervertebral disc cell therapy", *Biochem Biophys Res Commun*, 2005; 331(4):1185-92.
Lu, L.L. et al., "Isolation and characterization of human umbilical cord mesenchymal stem cells with hematopoiesis-supportive function and other potentials," *Haematologica*, 2006; 91(8):1017-26.
Mankikar, S.D., "Stem Cells: A New Paradigm in Medical Therapeutics," *Journal of Long-Term Effects of Medical Implants*, 2010; 20:219-250.
Naughton, B.A. et al., "Hematopoiesis on nylon mesh templates. I. Long-term culture of rat bone marrow cells," *Journal of Medicine*, 1987; 18(3-4):219-50.
Wakitani, S. et al., "Mesenchymal cell-based repair of large, full-thickness defects of articular cartilage", *J Bone Joint Surg Am*, 1994; 76(4): 579-592.
Weiss, M.L. et al., "Stem Cells in the Umbilical Cord," *Stem Cell Rev.*, 2006; 2(2):155-162.

\* cited by examiner

SOFT TISSUE REPAIR AND REGENERATION USING POSTPARTUM-DERIVED CELLS AND CELL PRODUCTS

CROSS-REFERENCE TO RELATED APPLICATIONS

This is a continuation-in-part of U.S. application Ser. No. 10/877,009, filed Jun. 25, 2004, now U.S. Pat. No. 7,560,276, issued Jul. 14, 2009, which itself claims benefit of U.S. Provisional Application No. 60/483,264, filed Jun. 27, 2003, the entire contents of each of which are incorporated by reference herein. This also claims benefit of U.S. Provisional Application 60/638,702, filed Dec. 23, 2004, the entire contents of which are incorporated by reference herein.

FIELD OF THE INVENTION

This invention relates to the field of mammalian cell biology and cell culture. In particular, the invention relates to cultured cells derived from postpartum tissue having the potential to support cells of and/or differentiate to cells of a soft tissue lineage, and methods of preparation and use of those postpartum tissue-derived cells. The invention also relates to methods for the use of such postpartum-derived cells in the regeneration and repair of soft tissue, and in cell-based therapies for conditions of soft tissue.

BACKGROUND OF THE INVENTION

Injuries to soft tissue, for example, vascular, skin, or musculoskeletal tissue, are quite common. One example of a fairly common soft tissue injury is damage to the pelvic floor. This is a potentially serious medical condition that may occur during childbirth or from complications thereof which can lead to damage to the vesicovaginal fascia. Such an injury can result in a cystocele, which is a herniation of the bladder. Similar medical conditions include rectoceles (a herniation of the rectum), enteroceles (a protrusion of the intestine through the rectovaginal or vesicovaginal pouch), and enterocystoceles (a double hernia in which both the bladder and intestine protrude).

The basic manifestation of a hernia is a protrusion of an organ into a defect within the fascia. Surgical approaches toward hernia repair have focused on reducing the presence of the hernial contents in the peritoneal cavity and generating a firm closure of the fascial defect either by using prosthetic, allogeneic, or autologous materials. A number of techniques have been used to produce this closure including the movement of autologous tissues and the use of synthetic mesh products. Drawbacks to these current products and procedures include hernia recurrence upon weakening of the closure.

As another example of a soft tissue condition, ligaments and tendons are viscoelastic structures that mediate normal joint movement and stability and are subject to tear and brittleness with age or injury. These structures are complex, relatively static collagenous structures with functional links to the bone, muscle, menisci, and other nearby tendons and ligaments.

Soft tissue conditions further include, for example, conditions of skin (e.g., ischemic wounds, diabetic wounds, scar revision or the treatment of traumatic wounds, severe burns, skin ulcers (e.g., decubitus (pressure) ulcers, venous ulcers, and diabetic ulcers), and surgical wounds such as those associated with the excision of skin cancers); vascular conditions (e.g., vascular disease such as peripheral arterial disease, abdominal aortic aneurysm, carotid disease, and venous disease; vascular injury; and improper vascular development); conditions affecting vocal cords; cosmetic conditions (e.g., those involving repair, augmentation, or beautification); muscle diseases (e.g., congenital myopathies; myasthenia gravis; inflammatory, neurogenic, and myogenic muscle diseases; and muscular dystrophies such as Duchenne muscular dystrophy, Becker muscular dystrophy, myotonic dystrophy, limb-girdle-muscular dystrophy, facioscapulohumeral muscular dystrophy, congenital muscular dystrophies, oculopharyngeal muscular dystrophy, distal muscular dystrophy, and Emery-Dreifuss muscular dystrophy); conditions of connective tissues such as tendons and ligaments, including but not limited to a periodontal ligament and anterior cruciate ligament; and conditions of organs and/or fascia (e.g., the bladder, intestine, pelvic floor).

Surgical approaches to correct soft tissue conditions or defects in the body generally involve the implantation of structures made of biocompatible, inert materials that attempt to replace or substitute for the defective function. Implantation of non-biodegradable materials results in permanent structures that remain in the body as a foreign object. Implants that are made of resorbable materials are suggested for use as temporary replacements where the object is to allow the healing process to replace the resorbed material. However, these approaches have met with limited success for the long-term correction of structures in the body.

Thus, novel therapeutic regimens for conditions related to soft tissue are of great clinical significance.

SUMMARY OF THE INVENTION

The invention is generally directed to postpartum-derived cells which are derived from postpartum tissue which is substantially free of blood and which is capable of self-renewal and expansion in culture and having the potential to differentiate into or provide trophic support to a cell of a mesodermal or ectodermal lineage, for example, a soft tissue cell phenotype.

In some embodiments, the present invention provides cells derived from human postpartum tissue substantially free of blood, capable of self-renewal and expansion in culture, having the ability to differentiate to or provide trophic support to cells of a soft tissue phenotype or to differentiate to cells of a soft tissue phenotype; requiring L-valine for growth; capable of growth in about 5% to about 20% oxygen; and further having at least one of the following characteristics:

production of at least one of GCP-2, tissue factor, vimentin, and alpha-smooth muscle actin;

lack of production of at least one of lack of production of at least one of NOGO-A, GRO-alpha or oxidized low density lipoprotein receptor, as detected by flow cytometry;

production of at least one of CD10, CD13, CD44, CD73, CD90, PDGFr-alpha, PD-L2 and HLA-A,B,C;

lack of production of at least one of CD31, CD34, CD45, CD80, CD86, CD117, CD141, CD178, B7-H2, HLA-G, and HLA-DR,DP,DQ, as detected by flow cytometry;

expression, which relative to a human cell that is a fibroblast, a mesenchymal stem cell, or an iliac crest bone marrow cell, is increased for at least one of interleukin 8; reticulon 1; chemokine (C-X-C motif) ligand 1 (melanoma growth stimulating activity, alpha); chemokine (C-X-C motif) ligand 6 (granulocyte chemotactic protein 2); chemokine (C-X-C motif) ligand 3; and tumor necrosis factor, alpha-induced protein 3 or expression, which relative to a human cell that is a fibroblast, a mesenchymal stem cell, or an iliac crest bone marrow cell, is increased for at least one of: C-type lectin superfamily member A2, Wilms tumor 1, aldehyde dehydrogenase 1 family member A2, renin, oxidized low density lipoprotein receptor 1, protein kinase C zeta, clone IMAGE:4179671, hypothetical protein DKFZp564F013, downregulated in ovarian cancer 1, and clone DKFZp547K1113;

expression, which relative to a human cell that is a fibroblast, a mesenchymal stem cell, or an iliac crest bone marrow cell, is reduced for at least one of: short stature homeobox 2; heat shock 27 kDa protein 2; chemokine (C-X-C motif) ligand 12 (stromal cell-derived factor 1); elastin; cDNA DKFZp586M2022 (from clone DKFZp586M2022); mesenchyme homeobox 2; sine oculis homeobox homolog 1; crystallin, alpha B; dishevelled associated activator of morphogenesis 2; DKFZP586B2420 protein; similar to neuralin 1; tetranectin; src homology three (SH3) and cysteine rich domain; B-cell translocation gene 1, anti-proliferative; cholesterol 25-hydroxylase; runt-related transcription factor 3; hypothetical protein FLJ23191; interleukin 11 receptor, alpha; procollagen C-endopeptidase enhancer; frizzled homolog 7; hypothetical gene BC008967; collagen, type VIII, alpha 1; tenascin C; iroquois homeobox protein 5; hephaestin; integrin, beta 8; synaptic vesicle glycoprotein 2; cDNA FLJ12280 fis, clone MAMMA1001744; cytokine receptor-like factor 1; potassium intermediate/small conductance calcium-activated channel, subfamily N, member 4; integrin, alpha 7; DKFZP586L151 protein; transcriptional co-activator with PDZ-binding motif (TAZ); sine oculis homeobox homolog 2; KIAA1034 protein; early growth response 3; distal-less homeobox 5; hypothetical protein FLJ20373; aldo-keto reductase family 1, member C3 (3-alpha hydroxysteroid dehydrogenase, type II); biglycan; fibronectin 1; proenkephalin; integrin, beta-like 1 (with EGF-like repeat domains); cDNA clone EUROIMAGE 1968422; EphA3; KIAA0367 protein; natriuretic peptide receptor C/guanylate cyclase C (atrionatriuretic peptide receptor C); hypothetical protein FLJ14054; cDNA DKFZp564B222 (from clone DKFZp564B222); vesicle-associated membrane protein 5; EGF-containing fibulin-like extracellular matrix protein 1; BCL2/adenovirus E1B 19 kDa interacting protein 3-like; AE binding protein 1; cytochrome c oxidase subunit VIIa polypeptide 1 (muscle); neuroblastoma, suppression of tumorigenicity 1; and insulin-like growth factor binding protein 2, 36 kDa;

secretion of at least one of MCP-1, IL-6, IL-8, GCP-2, HGF, KGF, FGF, HB-EGF, BDNF, TPO, MIP1a, RANTES, and TIMP1;

lack of secretion of at least one of TGF-beta2, ANG2, PDGFbb, MIP1b, I309, MDC, and VEGF, as detected by ELISA; and the ability to undergo at least 40 population doublings in culture.

In certain embodiments, the postpartum-derived cell is an umbilicus-derived cell. In other embodiments, it is a placenta-derived cell. In specific embodiments, the cell has all identifying features of any one of: cell type PLA 071003 (P8) (ATCC Accession No. PTA-6074); cell type PLA 071003 (P11) (ATCC Accession No. PTA-6075); cell type PLA 071003 (P16) (ATCC Accession No. PTA-6079); cell type UMB 022803 (P7) (ATCC Accession No. PTA-6067); or cell type UMB 022803 (P17) (ATCC Accession No. PTA-6068). The postpartum-derived cells of the invention are preferably human cells. The cells may provide trophic support to cells of a soft tissue phenotype, for example, that of fascia, epithelium, endothelium, skin, vasculature, muscles, tendons, and ligaments. The cells themselves may be induced to differentiate to a soft tissue phenotype.

Populations of PPDCs are provided by the invention. In some embodiments, a population of postpartum-derived cells is mixed with another population of cells. In some embodiments, the cell population is heterogeneous. A heterogeneous cell population of the invention may comprise at least about 5%, 10%, 20%, 30%, 40%, 50%, 60%, 70%, 80%, 90%, or 95% undifferentiated or differentiation-induced PPDCs of the invention. The heterogeneous cell populations of the invention may further comprise, for example, stem cells, epithelial cells (e.g., mucosal cells, for example, cells of oral mucosa; gastrointestinal tract; nasal epithelium; respiratory tract epithelium; vaginal epithelium; corneal epithelium), bone marrow cells, adipocytes, stem cells, keratinocytes, vascular endothelial cells (e.g., aortic endothelial cells, coronary artery endothelial cells, pulmonary artery endothelial cells, iliac artery endothelial cells, microvascular endothelial cells, umbilical artery endothelial cells, umbilical vein endothelial cells, and endothelial progenitors (e.g., CD34+, CD34+/CD117+ cells)), smooth muscle cells, myoblasts, myocytes, stromal cells, bladder urothelial cells, cells of the larynx, esophageal cells, and cells of the gastrointestinal tract, and other soft tissue cells or progenitor cells, and mixtures thereof. Cell populations of the invention may be substantially homogeneous, i.e., comprise substantially only PPDCs (preferably at least about 96%, 97%, 98%, 99% or more PPDCs). Homogeneous cell populations of the invention may comprise umbilicus- or placenta-derived cells. Homogeneous populations of placenta-derived cells may be of neonatal or maternal lineage. Homogeneity of a cell population may be achieved by any method known in the art, for example, by cell sorting (e.g., flow cytometry), bead separation, or by clonal expansion.

The invention also provides heterogeneous and homogeneous cell cultures containing undifferentiated or differentiation-induced postpartum-derived cells of the invention.

Some embodiments of the invention provide a matrix for administration to a patient. In some embodiments, the matrix is seeded with a population of postpartum-derived cells (PPDCs) of the invention. In some embodiments, the matrix is pretreated with a population of postpartum-derived cells of the invention. The PPDCs may be differentiation-induced or undifferentiated. The population of PPDCs may be substantially homogeneous or heterogeneous. For example, the matrix may be inoculated with PPDCs and cells of at least one other desired cell type, for example but not by way of limitation, epithelial cells (e.g., cells of oral mucosa, gastrointestinal tract, nasal epithelium, respiratory tract epithelium, vaginal epithelium, corneal epithelium), bone marrow cells, adipocytes, stem cells, keratinocytes, melanocytes, dermal fibroblasts, vascular endothelial cells (e.g., aortic endothelial cells, coronary artery endothelial cells, pulmonary artery endothelial cells, iliac artery endothelial cells, microvascular endothelial cells, umbilical artery endothelial cells, umbilical vein endothelial cells, and endothelial progenitors (e.g., CD34+, CD34+/CD117+ cells)), myoblasts, myocytes, stromal cells, and other soft tissue cells or progenitor cells. The matrix may contain or be pre-treated with one or more bioactive factors including, for example, drugs, anti-inflammatory agents, antiapoptotic agents, and growth factors. The seeded or pre-treated matrices can be introduced into a patient's body in any way known in the art, including but not limited to implantation, injection, surgical attachment, transplantation with other tissue, and the like. The matrices of the invention may be configured in vitro or in vivo to a desired shape and/or size, for example, to the shape and/or size of a tissue or organ in vivo. The scaffolds of the invention may be flat or tubular or may comprise sections thereof. The scaffolds of the invention may be multilayered.

Also encompassed within the scope of the invention are PPDC products including extracellular matrix (ECM) of PPDCs, cell fractions (e.g., soluble cell fractions; insoluble cell fractions; cell lysate, supernates of cell fractions; cell membrane-containing fractions) of PPDCs, and PPDC-conditioned medium. Matrices of the invention may comprise or be pre-treated with any one of the foregoing PPDC-products.

In some embodiments the invention provides compositions of PPDCs or a PPDC product and one or more bioactive factors, for example, but not limited to growth factors, anti-apoptotic agents, anti-inflammatory agents, and/or differentiation-inducing factors. Some compositions of the invention comprise PPDCs and one or more other cell types, for example, epithelial cells (e.g., cells of oral mucosa, gastrointestinal tract, nasal epithelium, respiratory tract epithelium, vaginal epithelium, corneal epithelium), bone marrow cells, adipocytes, stem cells, keratinocytes, melanocytes, dermal fibroblasts, vascular endothelial cells (e.g., aortic endothelial cells, coronary artery endothelial cells, pulmonary artery endothelial cells, iliac artery endothelial cells, microvascular endothelial cells, umbilical artery endothelial cells, umbilical vein endothelial cells, and endothelial progenitors (e.g., CD34+, CD34+/CD117+ cells)), myoblasts, myocytes, stromal cells, and other soft tissue cells or progenitor cells.

In some embodiments of the inventions, PPDCs provide trophic support to a soft tissue cell. Examples of soft tissue cells offered trophic support by PPDCs include cells of cartilage tissue, meniscal tissue, ligament tissue, tendon tissue, intervertebral disc tissue, periodontal tissue, skin tissue, vascular tissue, muscle tissue, fascia tissue, periosteal tissue, ocular tissue, pericardial tissue, lung tissue, synovial tissue, nerve tissue, kidney tissue, bone marrow, urogenital tissue, intestinal tissue, liver tissue, pancreas tissue, spleen tissue, or adipose tissue.

In some embodiments of the invention, PPDCs are induced to differentiate to a cell of a soft tissue phenotype, for example but not limited to, a phenotype of a cell of cartilage tissue, meniscal tissue, ligament tissue, tendon tissue, intervertebral disc tissue, periodontal tissue, skin tissue, vascular tissue, muscle tissue, fascia tissue, periosteal tissue, ocular tissue, pericardial tissue, lung tissue, synovial tissue, nerve tissue, kidney tissue, bone marrow, urogenital tissue, intestinal tissue, liver tissue, pancreas tissue, spleen tissue, or adipose tissue.

Pharmaceutical compositions of the postpartum-derived cells, extracellular matrix produced thereby, cell fractions, and PPDC-conditioned medium are included within the scope of the invention. The pharmaceutical compositions preferably include a pharmaceutically acceptable carrier or excipient.

In some embodiments, methods of regenerating soft tissue in a patient in need thereof by administering PPDCs, PPDC products, PPDC compositions, or matrices of the invention to a patient are provided.

Further provided by the invention are methods for treating a soft tissue condition in a patient by administering one or more postpartum-derived cell, PPDC population, or PPDC products of the invention (e.g., ECM, matrix, cell fraction, conditioned medium, or composition of the invention). Treatment of a soft tissue condition according to the invention includes but is not limited to trophic support of soft tissue, tissue repair, tissue reconstruction, tissue bulking, cosmetic treatment, therapeutic treatment, tissue augmentation, and tissue sealing. The PPDCs and PPDC products of the invention may be used in the treatment of, for example but not by way of limitation, a hernia, damage to the pelvic floor, a burn, cancer, traumatic injury, scars, skin ulcers (e.g., decubitus (pressure) ulcers, venous ulcers, and diabetic ulcers), ischemic wounds, surgical wounds such as those associated with the excision of skin cancers; vascular disease such as peripheral arterial disease, abdominal aortic aneurysm, carotid disease, and venous disease; muscle disease (e.g., congenital myopathies; myasthenia gravis; inflammatory, neurogenic, and myogenic muscle diseases; and muscular dystrophies such as Duchenne muscular dystrophy, Becker muscular dystrophy, myotonic dystrophy, limb-girdle-muscular dystrophy, facioscapulohumeral muscular dystrophy, congenital muscular dystrophies, oculopharyngeal muscular dystrophy, distal muscular dystrophy, and Emery-Dreifuss muscular dystrophy); and replacement and repair of connective tissues such as tendons and ligaments (e.g., anterior cruciate ligament, rotator cuff, periodontal ligament).

The invention further provides methods of providing trophic support to cells such as soft tissue cells by exposing or contacting a cell to a postpartum-derived cell of the invention or a PPDC-product. Examples of soft tissue cells for which PPDCs may provide trophic support according to the invention include a stem cell, a myocyte, a myoblast, a keratinocyte, a melanocyte, a dermal fibroblast, a bone marrow cell, an adipocyte, an epithelial cell, a stromal cell, and an endothelial cell (e.g., aortic endothelial cells, coronary artery endothelial cells, pulmonary artery endothelial cells, iliac artery endothelial cells, microvascular endothelial cells, umbilical artery endothelial cells, umbilical vein endothelial cells, and endothelial progenitors (e.g., CD34+, CD34+/CD117+ cells). Such exposure of the soft tissue cell may stimulate angiogenesis. Methods of the invention further include methods of inducing angiogenesis by exposing a soft tissue cell to a PPDC or PPDC product. Examples of soft tissue cells that form endothelial networks in accordance with the methods of the invention include aortic endothelial cells, coronary artery endothelial cells, pulmonary artery endothelial cells, iliac artery endothelial cells, microvascular endothelial cells, umbilical artery endothelial cells, umbilical vein endothelial cells, and endothelial progenitors (e.g., CD34+, CD34+/CD117+ cells). Methods of providing trophic support or stimulating angiogenesis of the invention may be effected in vitro or in vivo.

Methods of the invention also include methods of treating a patient in need of angiogenic factors by administering to a patient a PPDC or PPDC product of the invention.

Also provided by the invention are methods of producing a vascular network. In some embodiments, the methods of producing a vascular network involve exposing or contacting a population of soft tissue cells to a PPDC cell population or PPDC product. The population of soft tissue cells preferably contains at least one soft tissue cell of an aortic endothelial cell, coronary artery endothelial cell, pulmonary artery endothelial cell, iliac artery endothelial cell, microvascular endothelial cell, umbilical artery endothelial cell, and umbilical vein endothelial cell. The method of producing a vascular network may be performed in vitro or in vivo. The invention also encompasses the vascular networks produced by the methods of the invention. Methods of treating a condition such as a soft tissue condition in a patient by administering the vascular networks also are provided. In some embodiments, the soft tissue condition is a vascular condition, such as a vascular disease or injury or improper vascular development. In some aspects of the invention, the vascular network is administered by transplantation to the patient.

Further provided by the invention are kits of the PPDCs and/or PPDC products. The kits of the invention preferably include at least one component of a matrix, a hydrating agent, a cell culture substrate, a bioactive factor, a second cell type, a differentiation-inducing agent, cell culture media, and instructions, for example, for culture of the cells or administration of the cells and/or cell products.

In some embodiments, the invention provides methods for identifying compounds that modulate growth and/or differentiation of a postpartum-derived cell comprising contacting a cell of the invention with a compound and monitoring the cell for growth or a marker of differentiation. Also provided are methods for identifying compounds toxic to a postpartum-derived cell of the invention by contacting the cell with a compound and monitoring survival of the cell.

Other features and advantages of the invention will be apparent from the detailed description and examples that follow.

DETAILED DESCRIPTION OF ILLUSTRATIVE EMBODIMENTS

Definitions

Various terms used throughout the specification and claims are defined as set forth below.

Stem cells are undifferentiated cells defined by their ability at the single cell level to both self-renew and differentiate to produce progeny cells, including self-renewing progenitors, non-renewing progenitors and terminally differentiated cells. Stem cells are also characterized by their ability to differentiate in vitro into functional cells of various cell lineages from multiple germ layers (endoderm, mesoderm and ectoderm), as well as to give rise to tissues of multiple germ layers following transplantation and to contribute substantially to most, if not all, tissues following injection into blastocysts.

Stem cells are classified by their developmental potential as: (1) totipotent—able to give rise to all embryonic and extraembryonic cell types; (2) pluripotent—able to give rise to all embryonic cell types; (3) multipotent—able to give rise to a subset of cell lineages, but all within a particular tissue, organ, or physiological system (for example, hematopoietic stem cells (HSC) can produce progeny that include HSC (self-renewal), blood cell-restricted oligopotent progenitors, and all cell types and elements (e.g., platelets) that are normal components of the blood); (4) oligopotent—able to give rise to a more restricted subset of cell lineages than multipotent stem cells; and (5) unipotent—able to give rise to a single cell lineage (e.g., spermatogenic stem cells).

Stem cells are also categorized on the basis of the source from which they may be obtained. An adult stem cell is generally a multipotent undifferentiated cell found in tissue comprising multiple differentiated cell types. The adult stem cell can renew itself and, under normal circumstances, differentiate to yield the specialized cell types of the tissue from which it originated, and possibly other tissue types. An embryonic stem cell is a pluripotent cell from the inner cell mass of a blastocyst-stage embryo. A fetal stem cell is one that originates from fetal tissues or membranes. A postpartum stem cell is a multipotent or pluripotent cell that originates substantially from extraembryonic tissue available after birth, namely, the placenta and the umbilicus. These cells have been found to possess features characteristic of pluripotent stem cells, including rapid proliferation and the potential for differentiation into many cell lineages. Postpartum stem cells may be blood-derived (e.g., as are those obtained from umbilical cord blood) or non-blood-derived (e.g., as obtained from the non-blood tissues of the umbilical cord and placenta).

Embryonic tissue is typically defined as tissue originating from the embryo (which in humans refers to the period from fertilization to about six weeks of development. Fetal tissue refers to tissue originating from the fetus, which in humans refers to the period from about six weeks of development to parturition. Extraembryonic tissue is tissue associated with, but not originating from, the embryo or fetus. Extraembryonic tissues include extraembryonic membranes (chorion, amnion, yolk sac and allantois), umbilical cord and placenta (which itself forms from the chorion and the maternal decidua basalis).

Differentiation is the process by which an unspecialized ("uncommitted") or less specialized cell acquires the features of a specialized cell, such as a nerve cell or a muscle cell, for example. A differentiated or differentiation-induced cell is one that has taken on a more specialized ("committed") position within the lineage of a cell. The term committed, when applied to the process of differentiation, refers to a cell that has proceeded in the differentiation pathway to a point where, under normal circumstances, it will continue to differentiate into a specific cell type or subset of cell types, and cannot, under normal circumstances, differentiate into a different cell type or revert to a less differentiated cell type. De-differentiation refers to the process by which a cell reverts to a less specialized (or committed) position within the lineage of a cell. As used herein, the lineage of a cell defines the heredity of the cell, i.e., which cells it came from and what cells it can give rise to. The lineage of a cell places the cell within a hereditary scheme of development and differentiation. A lineage-specific marker refers to a characteristic specifically associated with the phenotype of cells of a lineage of interest and can be used to assess the differentiation of an uncommitted cell to the lineage of interest.

In a broad sense, a progenitor cell is a cell that has the capacity to create progeny that are more differentiated than itself and yet retains the capacity to replenish the pool of progenitors. By that definition, stem cells themselves are also progenitor cells, as are the more immediate precursors to terminally differentiated cells. When referring to the cells of the present invention, as described in greater detail below, this broad definition of progenitor cell may be used. In a narrower sense, a progenitor cell is often defined as a cell that is intermediate in the differentiation pathway, i.e., it arises from a stem cell and is intermediate in the production of a mature cell type or subset of cell types. This type of progenitor cell is generally not able to self-renew. Accordingly, if this type of cell is referred to herein, it will be referred to as a non-renewing progenitor cell or as an intermediate progenitor or precursor cell.

As used herein, the phrase differentiates into a mesodermal, ectodermal or endodermal lineage refers to a cell that becomes committed to a specific mesodermal, ectodermal or endodermal lineage, respectively. Examples of cells that differentiate into a mesodermal lineage or give rise to specific mesodermal cells include, but are not limited to, cells that are adipogenic, chondrogenic, cardiogenic, dermatogenic, hematopoietic, endothelial, myogenic, nephrogenic, urogenitogenic, osteogenic, pericardiogenic, or stromal. Examples of cells that differentiate into ectodermal lineage include, but are not limited to epithelial cells, neurogenic cells, and neurogliagenic cells. Examples of cells that differentiate into endodermal lineage include, but are not limited to pleurigenic cells, and hepatogenic cells, cells that give rise to the lining of the intestine, and cells that give rise to pancreogenic and splanchogenic cells.

The cells of the invention are referred to herein as postpartum-derived cells or postpartum cells (PPDCs). Subsets of the cells of the present invention are referred to as placenta-derived cells (PDCs) or umbilicus-derived cells (UDCs). In addition, the cells may be described as being stem or progenitor cells, the latter term being used in the broad sense. The term derived is used to indicate that the cells have been obtained from their biological source and grown or otherwise manipulated in vitro (e.g., cultured in a growth medium to expand the population and/or to produce a cell line). The in vitro manipulations of postpartum-derived cells and the unique features of the postpartum-derived cells of the present invention are described in detail below.

Various terms are used to describe cells in culture. Cell culture refers generally to cells taken from a living organism and grown under controlled conditions ("in culture"). A primary cell culture is a culture of cells, tissues or organs taken directly from organisms and before the first subculture. Cells are expanded in culture when they are placed in a growth medium under conditions that facilitate cell growth and/or division, resulting in a larger population of the cells. When cells are expanded in culture, the rate of cell proliferation is sometimes measured by the amount of time needed for the cells to double in number. This is referred to as doubling time.

A cell line is a population of cells formed by one or more subcultivations of a primary cell culture. Each round of subculturing is referred to as a passage. When cells are subcultured, they are referred to as having been passaged. A specific population of cells, or a cell line, is sometimes referred to or characterized by the number of times it has been passaged. For example, a cultured cell population that has been passaged ten times may be referred to as a P10 culture. The primary culture, i.e., the first culture following the isolation of cells from tissue, is designated P0. Following the first subculture, the cells are described as a secondary culture (P1 or passage 1). After the second subculture, the cells become a tertiary culture (P2 or passage 2), and so on. It will be understood by those of skill in the art that there may be many population doublings during the period of passaging; therefore the number of population doublings of a culture is greater than the passage number. The expansion of cells (i.e., the number of population doublings) during the period between passaging depends on many factors, including but not limited to the seeding density, substrate, medium, and time between passaging.

A conditioned medium is a medium in which a specific cell or population of cells has been cultured, and then removed. While the cells are cultured in the medium, they secrete cellular factors that can provide trophic support to other cells. Such trophic factors include, but are not limited to hormones, cytokines, extracellular matrix (ECM), proteins, vesicles, antibodies, and granules. The medium containing the cellular factors is the conditioned medium.

Generally, a trophic factor is defined as a substance that promotes survival, growth, proliferation, maturation, differentiation, and/or maintenance of a cell, or stimulates increased activity of a cell. Trophic support is used herein to refer to the ability to promote survival, growth, proliferation, maturation, differentiation, and/or maintenance of a cell, or to stimulate increased activity of a cell.

When referring to cultured vertebrate cells, the term senescence (also replicative senescence or cellular senescence) refers to a property attributable to finite cell cultures; namely, their inability to grow beyond a finite number of population doublings (sometimes referred to as Hayflick's limit). Although cellular senescence was first described using fibroblast-like cells, most normal human cell types that can be grown successfully in culture undergo cellular senescence. The in vitro lifespan of different cell types varies, but the maximum lifespan is typically fewer than 100 population doublings (this is the number of doublings for all the cells in the culture to become senescent and thus render the culture unable to divide). Senescence does not depend on chronological time, but rather is measured by the number of cell divisions, or population doublings, the culture has undergone. Thus, cells made quiescent by removing essential growth factors are able to resume growth and division when the growth factors are re-introduced, and thereafter carry out the same number of doublings as equivalent cells grown continuously. Similarly, when cells are frozen in liquid nitrogen after various numbers of population doublings and then thawed and cultured, they undergo substantially the same number of doublings as cells maintained unfrozen in culture. Senescent cells are not dead or dying cells; they are actually resistant to programmed cell death (apoptosis), and have been maintained in their nondividing state for as long as three years. These cells are very much alive and metabolically active, but they do not divide. The nondividing state of senescent cells has not yet been found to be reversible by any biological, chemical, or viral agent.

As used herein, the term Growth medium refers to a culture medium sufficient for expansion of postpartum-derived cells. Growth medium preferably contains Dulbecco's Modified Essential Media (DMEM). More preferably, Growth medium contains glucose. Growth medium preferably contains DMEM-low glucose (DMEM-LG) (Invitrogen, Carlsbad, Calif.). Growth medium preferably contains about 15% (v/v) serum (e.g., fetal bovine serum, defined bovine serum). Growth medium preferably contains at least one antibiotic agent and/or antimycotic agent (e.g., penicillin, streptomycin, amphotericin B, gentamicin, nystatin; preferably, 50 units/milliliter penicillin G sodium and 50 micrograms/milliliter streptomycin sulfate). Growth medium preferably contains 2-mercaptoethanol (Sigma, St. Louis Mo.). Most preferably, Growth medium contains DMEM-low glucose, serum, 2-mercaptoethanol, and an antibiotic agent.

As used herein, standard growth conditions refers to standard atmospheric conditions comprising about 5% $CO_2$, a temperature of about 35-39° C., more preferably 37° C., and a relative humidity of about 100%.

The term isolated refers to a cell, cellular component, or a molecule that has been removed from its native environment.

The term about refers to an approximation of a stated value within a range of ±10%.

Soft tissue, as used herein, refers generally to extraskeletal structures found throughout the body and includes but is not limited to cartilage tissue, meniscal tissue, ligament tissue, tendon tissue, intervertebral disc tissue, periodontal tissue, skin tissue, vascular tissue, muscle tissue, fascia tissue, periosteal tissue, ocular tissue, pericardial tissue, lung tissue, synovial tissue, nerve tissue, kidney tissue, bone marrow, urogenital tissue, intestinal tissue, liver tissue, pancreas tissue, spleen tissue, or adipose tissue, and combinations thereof.

Soft tissue condition (or injury or disease) is an inclusive term encompassing acute and chronic conditions, disorders or diseases of soft tissue. For example, the term encompasses conditions caused by disease or trauma or failure of the tissue to develop normally. Examples of soft tissue conditions include but are not limited to hernias, damage to the pelvic floor, tear or rupture of a tendon or ligament, skin wounds (e.g., scars, traumatic wounds, ischemic wounds, diabetic wounds, severe burns, skin ulcers (e.g., decubitus (pressure) ulcers, venous ulcers, and diabetic ulcers), and surgical wounds such as those associated with the excision of skin cancers); vascular conditions (e.g., vascular disease such as peripheral arterial disease, abdominal aortic aneurysm, carotid disease, and venous disease; vascular injury, improper vascular development); and muscle diseases (e.g., congenital myopathies; myasthenia gravis; inflammatory, neurogenic, and myogenic muscle diseases; and muscular dystrophies such as Duchenne muscular dystrophy, Becker muscular dystrophy, myotonic dystrophy, limb-girdle-muscular dystrophy, facioscapulohumeral muscular dystrophy, congenital muscular dystrophies, oculopharyngeal muscular dystrophy, distal muscular dystrophy, and Emery-Dreifuss muscular dystrophy).

The term treating (or treatment of) a soft tissue condition refers to ameliorating the effects of, or delaying, halting or reversing the progress of, or delaying or preventing the onset of, a soft tissue condition as defined herein and includes trophic support of soft tissue, soft tissue repair, reconstruction (e.g., breast reconstruction), bulking, cosmetic treatment, therapeutic treatment, tissue augmentation (e.g., bladder augmentation), and tissue sealing.

The term effective amount refers to a concentration of a reagent or pharmaceutical composition, such as a growth factor, differentiation agent, trophic factor, cell population or other agent, that is effective for producing an intended result, including cell growth and/or differentiation in vitro or in vivo, or treatment of a soft tissue condition as described herein. With respect to growth factors, an effective amount may range from about 1 nanogram/milliliter to about 1 microgram/milliliter. With respect to PPDCs as administered to a patient in vivo, an effective amount may range from as few as several hundred or fewer to as many as several million or more. In specific embodiments, an effective amount of PPDCs may range from $10^3$-$10^{11}$. It will be appreciated that the number of cells to be administered will vary depending on the specifics of the condition to be treated, including but not limited to size or total volume/surface area to be treated, as well as proximity of the site of administration to the location of the region to be treated, among other factors familiar to the medicinal biologist.

The terms effective period (or time) and effective conditions refer to a period of time or other controllable conditions (e.g., temperature, humidity for in vitro methods), necessary or preferred for an agent or pharmaceutical composition to achieve its intended result.

The term patient or subject refers to animals, including mammals, preferably humans, who are treated with the pharmaceutical compositions or in accordance with the methods described herein.

The term pharmaceutically acceptable carrier (or medium), which may be used interchangeably with the term biologically compatible carrier or medium, refers to reagents, cells, compounds, materials (including, for example, matrices), compositions, and/or dosage forms which are, within the scope of sound medical judgment, suitable for use in contact with the tissues of human beings and animals without excessive toxicity, irritation, allergic response, or other complication commensurate with a reasonable benefit/risk ratio. As described in greater detail herein, pharmaceutically acceptable carriers suitable for use in the present invention include liquids, semi-solid (e.g., gels) and solid materials (e.g., scaffolds). As used herein, the term biodegradable describes the ability of a material to be broken down (e.g., degraded, eroded, dissolved) in vivo. The term includes degradation in vivo with or without elimination (e.g., by resorption) from the body. The semi-solid and solid materials may be designed to resist degradation within the body (non-biodegradable) or they may be designed to degrade within the body (biodegradable, bioerodable). A biodegradable material may further be bioresorbable or bioabsorbable, i.e., it may be dissolved and absorbed into bodily fluids (water-soluble implants are one example), or degraded and ultimately eliminated from the body, either by conversion into other materials or breakdown and elimination through natural pathways. Examples include, but are not limited to, hyaluronic acid and saline.

Several terms are used herein with respect to cell replacement therapy. The terms autologous transfer, autologous transplantation, autograft and the like refer to treatments wherein the cell donor is also the recipient of the cell replacement therapy. The terms allogeneic transfer, allogeneic transplantation, allograft and the like refer to treatments wherein the cell donor is of the same species as the recipient of the cell replacement therapy, but is not the same individual. A cell transfer in which the donor's cells have been histocompatibly matched with a recipient is sometimes referred to as a syngeneic transfer. The terms xenogeneic transfer, xenogeneic transplantation, xenograft and the like refer to treatments wherein the cell donor is of a different species than the recipient of the cell replacement therapy.

The term matrix as used herein refers to a support for the PPDCs or PPDC product of the invention, for example, a scaffold (e.g., VNW scaffold, foams such as PCL/PGA, or self-assembling peptides such as RAD16) or supporting medium (e.g., hydrogel or a biomaterial such as Collagen/oxidized regenerated cellulose).

The following abbreviations are used herein:
ANG2 (or Ang2) for angiopoietin 2;
APC for antigen-presenting cells;
BDNF for brain-derived neurotrophic factor;
bFGF for basic fibroblast growth factor;
bid (BID) for "bis in die" (twice per day);
BSP for bone sialoprotein;
CK18 for cytokeratin 18;
CXC ligand 3 for chemokine receptor ligand 3;
DAPI for 4'-6-Diamidino-2-phenylindole-2HCl;
DMEM for Dulbecco's Modified (or Minimal) Essential Medium;
DMEM:lg (or DMEM:Lg, DMEM:LG) for DMEM with low glucose;
EDTA for ethylene diamine tetraacetic acid;
EGF (or E) for epidermal growth factor;
EPO for erythropoietin;
FACS for fluorescent activated cell sorting;
FBS for fetal bovine serum;
FGF (or F) for fibroblast growth factor;
GCP-2 for granulocyte chemotactic protein-2;
GDF-5 for growth and differentiation factor 5;
GFAP for glial fibrillary acidic protein;
HB-EGF for heparin-binding epidermal growth factor;
HCAEC for Human coronary artery endothelial cells;

HGF for hepatocyte growth factor;
hMSC for Human mesenchymal stem cells;
HNF-1 alpha for hepatocyte-specific transcription factor;
HUVEC for Human umbilical vein endothelial cells;
I309 for a chemokine and the ligand for the CCR8, receptor and is responsible for chemoattraction of TH2 type T-cells;
IGF for insulin-like growth factor;
IL-6 for interleukin-6;
IL-8 for interleukin 8;
K19 for keratin 19;
K8 for keratin 8;
KGF for keratinocyte growth factor;
MCP-1 for monocyte chemotactic protein 1;
MDC for macrophage-derived chemokine;
MIP1alpha for macrophage inflammatory protein 1alpha;
MIP1beta for macrophage inflammatory protein 1beta;
MMP for matrix metalloprotease (MMP);
MSC for mesenchymal stem cells;
NHDF for Normal Human Dermal Fibroblasts;
NPE for Neural Progenitor Expansion media;
OxLDLR for oxidized low density lipoprotein receptor;
PBMC for peripheral blood mononuclear cell;
PBS for phosphate buffered saline;
PDC for placenta-derived cell;
PDGFbb for platelet derived growth factor;
PDGFr-alpha for platelet derived growth factor receptor alpha;
PD-L2 for programmed—death ligand 2;
PE for phycoerythrin;
PO for "per os" (by mouth);
PPDC for postpartum-derived cell;
Rantes (or RANTES) for regulated on activation, normal T cell expressed and secreted;
rb for rabbit;
rh for recombinant human;
SC for subcutaneously;
SCID for severe combined immunodeficiency;
SDF-1alpha for stromal-derived factor 1alpha;
SHH for sonic hedgehog;
SMA for smooth muscle actin;
SOP for standard operating procedure;
TARC for thymus and activation-regulated chemokine;
TCP for tissue culture plastic;
TGFbeta2 for transforming growth factor beta2;
TGFbeta-3 for transforming growth factor beta-3;
TIMP1 for tissue inhibitor of matrix metalloproteinase 1;
TPO for thrombopoietin;
TuJ1 for BIII Tubulin;
UDC for umbilicus-derived cell;
VEGF for vascular endothelial growth factor;
vWF for von Willebrand factor; and
alphaFP for alpha-fetoprotein.
Description Various patents and other publications are cited herein and throughout the specification, each of which is incorporated by reference herein in its entirety.

In one aspect, the invention provides postpartum-derived cells (PPDCs) derived from postpartum tissue substantially free of blood. The PPDCs may be derived from placenta of a mammal including but not limited to human. The cells are capable of self-renewal and expansion in culture. The postpartum-derived cells have the potential to differentiate into cells of other phenotypes. The invention provides, in one of its several aspects, cells that are derived from umbilicus, as opposed to umbilical cord blood. The invention also provides, in one of its several aspects, cells that are derived from placental tissue.

The cells have been characterized as to several of their cellular, genetic, immunological, and biochemical properties. For example, the cells have been characterized by their growth, by their cell surface markers, by their gene expression, by their ability to produce certain biochemical trophic factors, and by their immunological properties.

Derivation and Expansion of Postpartum-Derived Cells (PPDCs)

According to the methods described herein, a mammalian placenta and umbilicus are recovered upon or shortly after termination of either a full-term or pre-term pregnancy, for example, after expulsion after birth. Postpartum tissue can be obtained from any completed pregnancy, full-term or less than full-term, whether delivered vaginally, or through other means, for example, cesarean section. The postpartum tissue may be transported from the birth site to a laboratory in a sterile container such as a flask, beaker, culture dish, or bag. The container may have a solution or medium, including but not limited to a salt solution, such as, for example, Dulbecco's Modified Eagle's Medium (DMEM) or phosphate buffered saline (PBS), or any solution used for transportation of organs used for transplantation, such as University of Wisconsin solution or perfluorochemical solution. One or more antibiotic and/or antimycotic agents, such as but not limited to penicillin, streptomycin, amphotericin B, gentamicin, and nystatin, may be added to the medium or buffer. The postpartum tissue may be rinsed with an anticoagulant solution such as heparin-containing solution. It is preferable to keep the tissue at about 4-10° C. prior to extraction of PPDCs. It is even more preferable that the tissue not be frozen prior to extraction of PPDCs.

Isolation of PPDCs preferably occurs in an aseptic environment. Blood and debris are preferably removed from the postpartum tissue prior to isolation of PPDCs. For example, the postpartum tissue may be washed with buffer solution, such as but not limited to phosphate buffered saline. The wash buffer also may comprise one or more antimycotic and/or antibiotic agents, such as but not limited to penicillin, streptomycin, amphotericin B, gentamicin, and nystatin.

In some aspects of the invention, the different cell types present in postpartum tissue are fractionated into subpopulations from which the PPDCs can be isolated. This may be accomplished using techniques for cell separation including, but not limited to, enzymatic treatment to dissociate postpartum tissue into its component cells, followed by cloning and selection of specific cell types, for example but not limited to selection based on morphological and/or biochemical markers; selective growth of desired cells (positive selection), selective destruction of unwanted cells (negative selection); separation based upon differential cell agglutinability in the mixed population as, for example, with soybean agglutinin; freeze-thaw procedures; differential adherence properties of the cells in the mixed population; filtration; conventional and zonal centrifugation; centrifugal elutriation (counter-streaming centrifugation); unit gravity separation; countercurrent distribution; electrophoresis; and flow cytometry, for example, fluorescence activated cell sorting (FACS).

In a preferred embodiment, postpartum tissue comprising a whole placenta or a fragment or section thereof is disaggregated by ultrasonic disruption, mechanical force (mincing or shear forces), enzymatic digestion with single or combinatorial proteolytic enzymes, such as a matrix metalloprotease and/or neutral protease, for example, collagenase, trypsin, dispase, LIBERASE (Boehringer Mannheim Corp., Indianapolis, Ind.), hyaluronidase, and/or pepsin, or a combination of mechanical and enzymatic methods. For example, the cellular component of the postpartum tissue may be disaggregated by methods using collagenase-mediated dissociation. Enzymatic digestion methods preferably employ a combination of enzymes, such as a combination of a matrix metalloprotease and a neutral protease. The matrix metalloprotease is preferably a collagenase. The neutral protease is preferably thermolysin or dispase, and most preferably is dispase. More preferably, enzymatic digestion of postpartum tissue uses a combination of a matrix metalloprotease, a neutral protease, and a mucolytic enzyme for digestion of hyaluronic acid, such as a combination of collagenase, dispase, and hyaluronidase or a combination of LIBERASE (Boehringer Mannheim Corp., Indianapolis, Ind.) and hyaluronidase. Collagenase may be type 1, 2, 3, or 4. Other enzymes known in the art for cell isolation include papain, deoxyribonucleases, serine proteases, such as trypsin, chymotrypsin, or elastase, that may be used either on their own or in combination with other enzymes such as matrix metalloproteases, mucolytic enzymes, and neutral proteases. Serine proteases are preferably used consecutively following use of other enzymes. The temperature and period of time tissues or cells are in contact with serine proteases is particularly important. Serine proteases may be inhibited by alpha 2 microglobulin in serum and therefore the medium used for digestion is usually serum-free. EDTA and DNAse are commonly used in enzyme digestion procedures to increase the efficiency of cell recovery. The degree of dilution of the digestion may also greatly affect the cell yield as cells may be trapped within the viscous digest. The LIBERASE (Boehringer Mannheim Corp., Indianapolis, Ind.) Blendzyme (Roche) series of enzyme combinations are very useful and may be used in the instant methods. Other sources of enzymes are known, and the skilled artisan may also obtain such enzymes directly from their natural sources. The skilled artisan is also well-equipped to assess new, or additional enzymes or enzyme combinations for their utility in isolating the cells of the invention. Preferred enzyme treatments are 0.5, 1, 1.5, or 2 hours long or longer. In more preferred embodiments, the tissue is incubated at 37° C. during the enzyme treatment of the disintegration step.

Postpartum tissue comprising the umbilicus and placenta may be used without separation. Alternatively, the umbilicus may be separated from the placenta by any means known in the art. In some embodiments of the invention, postpartum tissue is separated into two or more sections, such as umbilicus and placenta. In some embodiments of the invention, placental tissue is separated into two or more sections, each section consisting of predominantly of either neonatal, neonatal and maternal, or maternal aspect. The separated sections then are dissociated by mechanical and/or enzymatic dissociation according to the methods described herein. Cells of neonatal or maternal lineage may be identified by any means known in the art, for example, by karyotype analysis or in situ hybridization for the Y-chromosome. Karyotype analysis also may be used to identify cells of normal karyotype.

Isolated cells or postpartum tissue from which PPDCs grow out may be used to initiate, or seed, cell cultures. Cells are transferred to sterile tissue culture vessels either uncoated or coated with extracellular matrix or ligands such as laminin, collagen, gelatin, fibronectin, ornithine, vitronectin, and extracellular membrane protein (e.g., MATRIGEL (BD Discovery Labware, Bedford, Mass.)). PPDCs are cultured in any culture medium capable of sustaining growth of the cells such as, but not limited to, DMEM (high or low glucose), Eagle's basal medium, Ham's F10 medium (F10), Ham's F-12 medium (F12), Iscove's modified Dulbecco's medium, Mesenchymal Stem Cell Growth Medium (MSCGM), DMEM/F12, RPMI 1640, advanced DMEM (Gibco), DMEM/MCDB201 (Sigma), and CELL-GRO FREE. The culture medium may be supplemented with one or more components including, for example, serum (e.g., fetal bovine serum (FBS), preferably about 2-15% (v/v); equine serum (ES); human serum(HS)); beta-mercaptoethanol (BME), preferably about 0.001% (v/v); one or more growth factors, for example, platelet-derived growth factor (PDGF), insulin-like growth factor-1 (IGF-1), leukemia inhibitory factor (LIF), epidermal growth factor (EGF), fibroblast growth factor (FGF), vascular endothelial growth factor (VEGF), and erythropoietin (EPO); amino acids, including L-valine; and one or more antibiotic and/or antimycotic agents to control microbial contamination, such as, for example, penicillin G, streptomycin sulfate, amphotericin B, gentamicin, and nystatin, either alone or in combination. The culture medium preferably comprises Growth medium (DMEM-low glucose, serum, BME, an antimycotic agent, and an antibiotic agent).

The cells are seeded in culture vessels at a density to allow cell growth. In a preferred embodiment, the cells are cultured at about 0 to about 5 percent by volume $CO_2$ in air. In some preferred embodiments, the cells are cultured at about 2 to about 25 percent $O_2$ in air, preferably about 5 to about 20 percent $O_2$ in air. The cells preferably are cultured at about 25 to about 40° C., more preferably about 35° C. to about 39° C., and more preferably are cultured at 37° C. The cells are preferably cultured in an incubator. The medium in the culture vessel can be static or agitated, for example, using a bioreactor. PPDCs preferably are grown under low oxidative stress (e.g., with addition of glutathione, ascorbic acid, catalase, tocopherol, N-acetylcysteine). "Low oxidative stress", as used herein, refers to conditions of no or minimal free radical damage to the cultured cells.

Methods for the selection of the most appropriate culture medium, medium preparation, and cell culture techniques are well known in the art and are described in a variety of sources, including Doyle et al., (eds.), 1995, CELL & TISSUE CULTURE: LABORATORY PROCEDURES, John Wiley & Sons, Chichester; and Ho and Wang (eds.), 1991, ANIMAL CELL BIOREACTORS, Butterworth-Heinemann, Boston, which are incorporated herein by reference.

The culture medium is changed as necessary, for example, by carefully aspirating the medium from the dish, for example, with a pipette, and replenishing with fresh medium. Incubation is continued until a sufficient number or density of cells accumulate in the dish. The original explanted tissue sections may be removed and the remaining cells trypsinized using standard techniques or using a cell scraper. After trypsinization, the cells are collected, removed to fresh medium and incubated as above. In some embodiments, the medium is changed at least once at approximately 24 hours post-trypsinization to remove any floating cells. The cells remaining in culture are considered to be PPDCs.

After culturing the isolated cells or tissue fragments for a sufficient period of time, PPDCs will have grown out, either as a result of migration from the postpartum tissue or cell division, or both. In some embodiments of the invention, PPDCs are passaged, or removed to a separate culture vessel containing fresh medium of the same or a different type as that used initially, where the population of cells can be mitotically expanded. PPDCs are preferably passaged up to about 100% confluence, more preferably about 70 to about 85% confluence. The lower limit of confluence for passage is understood by one skilled in the art. The PPDCs of the invention may be utilized from the first subculture (passage 0) to senescence. The preferable number of passages is that which yields a cell number sufficient for a given application. In certain embodiments, the cells are passaged 2 to 25 times, preferably 4 to 20 times, more preferably 8 to 15 times, more preferably 10 or 11 times, and most preferably 11 times. Cloning and/or subcloning may be performed to confirm that a clonal population of cells has been isolated.

Cells of the invention may be cryopreserved and/or stored prior to use.

Characterization of PPDCs

PPDCs may be characterized, for example, by growth characteristics (e.g., population doubling capability, doubling time, passages to senescence), karyotype analysis (e.g., normal karyotype; maternal or neonatal lineage), flow cytometry (e.g., FACS analysis), immunohistochemistry and/or immunocytochemistry (e.g., for detection of epitopes including but not limited to vimentin, desmin, alpha-smooth muscle actin, cytokeratin 18, von Willebrand factor, CD34, GROalpha, GCP-2, oxidized low density lipoprotein receptor 1, and NOGO-A), gene expression profiling (e.g., gene chip arrays; polymerase chain reaction (for example, reverse transcriptase PCR, real time PCR, and conventional PCR)), protein arrays, protein secretion (e.g., by plasma clotting assay or analysis of PPDC-conditioned medium, for example, by Enzyme Linked ImmunoSorbent Assay (ELISA)), antibody analysis (e.g., ELISA; antibody staining for cell surface markers including but not limited to CD10, CD13, CD31, CD34, CD44, CD45, CD73, CD80, CD86, CD90, CD117, CD141, CD178, platelet-derived growth factor receptor alpha (PDGFr-alpha), HLA class I antigens (HLA-A, HLA-B, HLA-C), HLA class II antigens (HLA-DP, HLA-DQ, HLA-DR), B7-H2, and PD-L2), mixed lymphocyte reaction (e.g., as measure of stimulation of allogeneic PBMCs), and/or other methods known in the art.

PPDCs can undergo at least 40 population doublings in culture. Population doubling may be calculated as [ln (cell final/cell initial)/ln 2]. Doubling time may be calculated as (time in culture (h)/population doubling).

Undifferentiated PPDCs preferably produce at least one of NOGO-A, GCP-2, tissue factor, vimentin, and alpha-smooth muscle actin; more preferred are cells which produce each of GCP-2, tissue factor, vimentin, and alpha-smooth muscle actin. In some embodiments, two, three, four, or five of these factors are produced by the PPDCs.

In some embodiments, PPDCs lack production of at least one of NOGO-A, GRO-alpha, or oxidized low density lipoprotein receptor, as detected by flow cytometry. In some embodiments, PPDCs lack production of at least two or three of these factors.

PPDCs may comprise at least one cell surface marker of CD10, CD13, CD44, CD73, CD90, PDGFr-alpha, PD-L2 and HLA-A,B,C. PPDCs preferably produce each of these surface markers. PPDCs may be characterized in their lack of production of at least one of CD31, CD34, CD45, CD80, CD86, CD117, CD141, CD178, B7-H2, HLA-G, and HLA-DR,DP,DQ, as detected by flow cytometry. PPDCs preferably lack production of each of these surface markers. In some embodiments, PPDCs exhibit expression, which relative to a human cell that is a fibroblast, a mesenchymal stem cell, or an iliac crest bone marrow cell, is increased for at least one of interleukin 8; reticulon 1; chemokine (C-X-C motif) ligand 1 (melanoma growth stimulating activity, alpha); chemokine (C-X-C motif) ligand 6 (granulocyte chemotactic protein 2); chemokine (C-X-C motif) ligand 3; and tumor necrosis factor, alpha-induced protein 3; or at least one of C-type lectin superfamily member A2, Wilms tumor 1, aldehyde dehydrogenase 1 family member A2, renin, oxidized low density lipoprotein receptor 1, protein kinase C zeta, clone IMAGE:4179671, hypothetical protein DKFZp564F013, downregulated in ovarian cancer 1, and clone DKFZp547K1113. Preferred PPDCs express, relative to a human cell that is a fibroblast, a mesenchymal stem cell, or an iliac crest bone marrow cell, increased levels of interleukin 8; reticulon 1; chemokine (C-X-C motif) ligand 1 (melanoma growth stimulating activity, alpha); chemokine (C-X-C motif) ligand 6 (granulocyte chemotactic protein 2); chemokine (C-X-C motif) ligand 3; and tumor necrosis factor, alpha-induced protein 3; or increased levels of C-type lectin superfamily member A2, Wilms tumor 1, aldehyde dehydrogenase 1 family member A2, renin, oxidized low density lipoprotein receptor 1, protein kinase C zeta, clone IMAGE:4179671, hypothetical protein DKFZp564F013, downregulated in ovarian cancer 1, and clone DKFZp547K1113. In PPDCs wherein expression, relative to a human cell that is a fibroblast, a mesenchymal stem cell, or an iliac crest bone marrow cell, is increased for at least one of interleukin 8; reticulon 1; chemokine (C-X-C motif) ligand 1 (melanoma growth stimulating activity, alpha); chemokine (C-X-C motif) ligand 6 (granulocyte chemotactic protein 2); chemokine (C-X-C motif) ligand 3; and tumor necrosis factor, alpha-induced protein 3, increased relative levels of at least one of C-type lectin superfamily member A2, Wilms tumor 1, aldehyde dehydrogenase 1 family member A2, renin, oxidized low density lipoprotein receptor 1, protein kinase C zeta, clone IMAGE:4179671, hypothetical protein DKFZp564F013, downregulated in ovarian cancer 1, and clone DKFZp547K1113 are preferably not present. In PPDCs wherein expression, relative to a human cell that is a fibroblast, a mesenchymal stem cell, or an iliac crest bone marrow cell, is increased for at least one of C-type lectin superfamily member A2, Wilms tumor 1, aldehyde dehydrogenase 1 family member A2, renin, oxidized low density lipoprotein receptor 1, protein kinase C zeta, clone IMAGE:4179671, hypothetical protein DKFZp564F013, downregulated in ovarian cancer 1, and clone DKFZp547K1113, increased relative levels of at least one of interleukin 8; reticulon 1; chemokine (C-X-C motif) ligand 1 (melanoma growth stimulating activity, alpha); chemokine (C-X-C motif) ligand 6 (granulocyte chemotactic protein 2); chemokine (C-X-C motif) ligand 3; and tumor necrosis factor, alpha-induced protein 3 are preferably not present.

PPDCs may have expression, which relative to a human cell that is a fibroblast, a mesenchymal stem cell, or an iliac crest bone marrow cell, is reduced for at least one of: short stature homeobox 2; heat shock 27 kDa protein 2; chemokine (C-X-C motif) ligand 12 (stromal cell-derived factor 1); elastin; cDNA DKFZp586M2022 (from clone DKFZp586M2022); mesenchyme homeobox 2; sine oculis homeobox homolog 1; crystallin, alpha B; dishevelled associated activator of morphogenesis 2; DKFZP586B2420 protein; similar to neuralin 1; tetranectin; src homology three (SH3) and cysteine rich domain; B-cell translocation gene 1, anti-proliferative; cholesterol 25-hydroxylase; runt-related transcription factor 3; hypothetical protein FLJ23191; interleukin 11 receptor, alpha; procollagen C-endopeptidase enhancer; frizzled homolog 7; hypothetical gene BC008967; collagen, type VIII, alpha 1; tenascin C; iroquois homeobox protein 5; hephaestin; integrin, beta 8; synaptic vesicle glycoprotein 2; cDNA FLJ12280 fis, clone MAMMA1001744; cytokine receptor-like factor 1; potassium intermediate/small conductance calcium-activated channel, subfamily N, member 4; integrin, alpha 7; DKFZP586L151 protein; transcriptional co-activator with PDZ-binding motif (TAZ); sine oculis homeobox homolog 2; KIAA1034 protein; early growth response 3; distal-less homeobox 5; hypothetical protein FLJ20373; aldo-keto reductase family 1, member C3 (3-alpha hydroxysteroid dehydrogenase, type II); biglycan; fibronectin 1; proenkephalin; integrin, beta-like 1 (with EGF-like repeat domains); cDNA clone EUROIMAGE 1968422; EphA3; KIAA0367 protein; natriuretic peptide receptor C/guanylate cyclase C (atrionatriuretic peptide receptor C); hypothetical protein FLJ14054; cDNA DKFZp564B222 (from clone DKFZp564B222); vesicle-associated membrane protein 5; EGF-containing fibulin-like extracellular matrix protein 1; BCL2/adenovirus E1B 19 kDa interacting protein 3-like; AE binding protein 1; cytochrome c oxidase subunit VIIa polypeptide 1 (muscle); neuroblastoma, suppression of tumorigenicity 1; and insulin-like growth factor binding protein 2, 36 kDa; the skilled artisan will appreciate that the expression of a wide variety of genes is conveniently characterized on a gene array, for example on an AFFYMETRIX GENECHIP.

PPDCs may secrete a variety of biochemically active factors, such as growth factors, chemokines, cytokines and the like. Preferred cells secrete at least one of MCP-1, IL-6, IL-8, GCP-2, HGF, KGF, FGF, HB-EGF, BDNF, TPO, MIP1a, RANTES, and TIMP1. PPDCs may be characterized in their lack of secretion of at least one of TGF-beta2, ANG2, PDGFbb, MIP1b, I309, MDC, and VEGF, as detected by ELISA. These and other characteristics are available to identify and characterize the cells, and distinguish the cells of the invention from others known in the art.

In preferred embodiments, the cell comprises two or more of the foregoing characteristics. More preferred are those cells comprising, three, four, or five or more of the characteristics. Still more preferred are those postpartum-derived cells comprising six, seven, or eight or more of the characteristics. Still more preferred presently are those cells comprising all nine of the claimed characteristics.

Also presently preferred are cells that produce at least two of GCP-2, NOGO-A, tissue factor, vimentin, and alpha-smooth muscle actin. More preferred are those cells producing three, four, or five of these proteins.

The skilled artisan will appreciate that cell markers are subject to vary somewhat under vastly different growth conditions, and that generally herein described are characterizations in Growth Medium, or variations thereof. Postpartum-derived cells that produce at least one, two, three, or four of CD10, CD13, CD44, CD73, CD90, PDGFr-alpha, PD-L2 and HLA-A, B, C are preferred. More preferred are those cells producing five, six, or seven of these cell surface markers. Still more preferred are postpartum-derived cells that can produce eight, nine, or ten of the foregoing cell surface marker proteins.

PPDCs that lack production of at least one, two, three, or four of the proteins CD31, CD34, CD45, CD80, CD86, CD117, CD141, CD178, B7-H2, HLA-G, and HLA-DR, DP, DQ, as detected by flow cytometry are preferred. PPDCs lacking production of at least five, six, seven, or eight or more of these markers are preferred. More preferred are cells which lack production of at least nine or ten of the cell surface markers. Most highly preferred are those cells lacking production of eleven, twelve, or thirteen of the foregoing identifying proteins.

Presently preferred cells produce each of CD10, CD13, CD44, CD73, CD90, PDGFr-alpha, and HLA-A, B, C, and do not produce any of CD31, CD34, CD45, CD117, CD141, or HLA-DR, DP, DQ, as detected by flow cytometry.

It is preferred that postpartum-derived cells exhibit expression, which relative to a human cell that is a fibroblast, a mesenchymal stem cell, or an iliac crest bone marrow cell, is increased for at least one of at least one, two, or three of interleukin 8; reticulon 1; chemokine (C-X-C motif) ligand 1 (melanoma growth stimulating activity, alpha); chemokine (C-X-C motif) ligand 6 (granulocyte chemotactic protein 2); chemokine (C-X-C motif) ligand 3; and tumor necrosis factor, alpha-induced protein 3; or at least one, two, or three of C-type lectin superfamily member A2, Wilms tumor 1, aldehyde dehydrogenase 1 family member A2, renin, oxidized low density lipoprotein receptor 1, protein kinase C zeta, clone IMAGE:4179671, hypothetical protein DKFZp564F013, downregulated in ovarian cancer 1, and clone DKFZp547K1113. More preferred are those cells which exhibit elevated relative expression of four or five, and still more preferred are cells capable of increased relative expression of six, seven, or eight of the foregoing genes of the respective gene sets. Most preferably, the cells exhibit expression, which relative to a human cell that is a fibroblast, a mesenchymal stem cell, or an iliac crest bone marrow cell, is increased for a combination of interleukin 8; reticulon 1; chemokine (C-X-C motif) ligand 1 (melanoma growth stimulating activity, alpha); chemokine (C-X-C motif) ligand 6 (granulocyte chemotactic protein 2); chemokine (C-X-C motif) ligand 3; tumor necrosis factor, alpha-induced protein 3 or a combination of C-type lectin superfamily member A2, Wilms tumor 1, aldehyde dehydrogenase 1 family member A2, renin, oxidized low density lipoprotein receptor 1, protein kinase C zeta, clone IMAGE: 4179671, hypothetical protein DKFZp564F013, downregulated in ovarian cancer 1, and clone DKFZp547K1113.

For some embodiments, preferred are cells, which relative to a human cell that is a fibroblast, a mesenchymal stem cell, or an iliac crest bone marrow cell, have reduced expression for at least one of the genes corresponding to: short stature homeobox 2; heat shock 27 kDa protein 2; chemokine (C-X-C motif) ligand 12 (stromal cell-derived factor 1); elastin; cDNA DKFZp586M2022 (from clone DKFZp586M2022); mesenchyme homeobox 2; sine oculis homeobox homolog 1; crystallin, alpha B; dishevelled associated activator of morphogenesis 2; DKFZP586B2420 protein; similar to neuralin 1; tetranectin; src homology three (SH3) and cysteine rich domain; B-cell translocation gene 1, anti-proliferative; cholesterol 25-hydroxylase; runt-related transcription factor 3; hypothetical protein FLJ23191; interleukin 11 receptor, alpha; procollagen C-endopeptidase enhancer; frizzled homolog 7; hypothetical gene BC008967; collagen, type VIII, alpha 1; tenascin C; iroquois homeobox protein 5; hephaestin; integrin, beta 8; synaptic vesicle glycoprotein 2; cDNA FLJ12280 fis, clone MAMMA1001744; cytokine receptor-like factor 1; potassium intermediate/small conductance calcium-activated channel, subfamily N, member 4; integrin, alpha 7; DKFZP586L151 protein; transcriptional co-activator with PDZ-binding motif (TAZ); sine oculis homeobox homolog 2; KIAA1034 protein; early growth response 3; distal-less homeobox 5; hypothetical protein FLJ20373; aldo-keto reductase family 1, member C3 (3-alpha hydroxysteroid dehydrogenase, type II); biglycan; fibronectin 1; proenkephalin; integrin, beta-like 1 (with EGF-like repeat domains); cDNA clone EUROIMAGE 1968422; EphA3; KIAA0367 protein; natriuretic peptide receptor C/guanylate cyclase C (atrionatriuretic peptide receptor C); hypothetical protein FLJ14054; cDNA DKFZp564B222 (from clone DKFZp564B222); vesicle-associated membrane protein 5; EGF-containing fibulin-like extracellular matrix protein 1; BCL2/adenovirus E1B 19 kDa interacting protein 3-like; AE binding protein 1; cytochrome c oxidase subunit VIIa polypeptide 1 (muscle); neuroblastoma, suppression of tumorigenicity 1; and insulin-like growth factor binding protein 2, 36 kDa. More preferred are cells that have, relative to human fibroblasts, mesenchymal stem cells, or iliac crest bone marrow cells, reduced expression of at least 5, 10, 15 or 20 genes corresponding to those listed above. Presently more preferred are cell with reduced expression of at least 25, 30, or 35 of the genes corresponding to the listed sequences. Also more preferred are those postpartum-derived cells having expression that is reduced, relative to that of a human fibroblast, a mesenchymal stem cell, or an iliac crest bone marrow cell, of genes corresponding to 35 or more, 40 or more, or even all of the sequences listed.

Secretion of certain growth factors and other cellular proteins can make cells of the invention particularly useful. Preferred postpartum-derived cells secrete at least one, two, three or four of MCP-1, IL-6, IL-8, GCP-2, HGF, KGF, FGF, HB-EGF, BDNF, TPO, MIP1a, RANTES, and TIMP1. Cells which secrete five, six, seven or eight of the listed proteins are also preferred. Cells which can secrete at least nine, ten, eleven or more of the factors are more preferred, as are cells which can secrete twelve or more, or even all thirteen of the proteins in the foregoing list.

While secretion of such factors is useful, PPDCs can also be characterized by their lack of secretion of factors into the medium. Postpartum-derived cells that lack secretion of at least one, two, three or four of TGF-beta2, ANG2, PDGFbb, MIP1b, I309, MDC, and VEGF, as detected by ELISA, are presently preferred for use. Cells that are characterized in their lack secretion of five or six of the foregoing proteins are more preferred. Cells which lack secretion of all seven of the factors listed above are also preferred.

Examples of placenta-derived cells of the invention were deposited with the American Type Culture Collection (ATCC, Manassas, Va.) and assigned ATCC Accession Numbers as follows: (1) strain designation PLA 071003 (P8) was deposited Jun. 15, 2004 and assigned Accession No. PTA-6074; (2) strain designation PLA 071003 (P11) was deposited Jun. 15, 2004 and assigned Accession No. PTA-6075; and (3) strain designation PLA 071003 (P16) was deposited Jun. 16, 2004 and assigned Accession No. PTA-6079.

Examples of umbilicus-derived cells of the invention were deposited with the American Type Culture Collection (ATCC, Manassas, Va.) on Jun. 10, 2004, and assigned ATCC Accession Numbers as follows: (1) strain designation UMB 022803 (P7) was assigned Accession No. PTA-6067; and (2) strain designation UMB 022803 (P17) was assigned Accession No. PTA-6068.

PPDCs can be isolated. The invention also provides compositions of PPDCs, including populations of PPDCs. In some embodiments, the cell population is heterogeneous. A heterogeneous cell population of the invention may comprise at least about 5%, 10%, 20%, 30%, 40%, 50%, 60%, 70%, 80%, 90%, or 95% PPDCs of the invention. The heterogeneous cell populations of the invention may further comprise epithelial cells (e.g., mucosal cells, for example, cells of oral mucosa; gastrointestinal tract; nasal epithelium; respiratory tract epithelium; vaginal epithelium; corneal epithelium), bone marrow cells, adipocytes, stem cells, keratinocytes, vascular endothelial cells (e.g., aortic endothelial cells, coronary artery endothelial cells, pulmonary artery endothelial cells, iliac artery endothelial cells, microvascular endothelial cells, umbilical artery endothelial cells, umbilical vein endothelial cells, and endothelial progenitors (e.g., CD34+, CD34+/CD117+ cells)), smooth muscle cells, myoblasts, myocytes, stromal cells, bladder urothelial cells, cells of the larynx, esophageal cells, and cells of the gastrointestinal tract, and other soft tissue cells or progenitor cells. For example, cell populations of the invention may include PPDCs and at least one cell type of bone marrow cells, adipocytes, stem cells, keratinocytes, vascular endothelial cells, myoblasts, myocytes, stromal cells, and other soft tissue progenitor cells. In some embodiments, the cell population is substantially homogeneous, i.e., comprises substantially only PPDCs (preferably at least about 96%, 97%, 98%, 99% or more PPDCs). The homogeneous cell population of the invention may comprise umbilicus- or placenta-derived cells. Homogeneous populations of umbilicus-derived cells may be free of cells of maternal lineage. Homogeneous populations of placenta-derived cells may be of neonatal or maternal lineage. Homogeneity of a cell population may be achieved by any method known in the art, for example, by cell sorting (e.g., flow cytometry), bead separation, or by clonal expansion.

Methods of the invention further include methods for producing a population of postpartum-derived cells by expanding a cell of the invention in culture. The postpartum-derived cells of the invention preferably expand in the presence of from about 5% to about 20% oxygen. The postpartum-derived cells of the invention preferably are expanded in culture medium such as but not limited to Dulbecco's modified Eagle's medium (DMEM), mesenchymal stem cell growth medium, advanced DMEM (Gibco), DMEM/MCDB201 (Sigma), RPMI1640, CELL-GRO FREE, advanced DMEM (Gibco), DMEM/MCDB201 (Sigma), Ham's F10 medium, Ham's F12 medium, DMEM/F12, Iscove's modified Dulbecco's medium, or Eagle's basal medium. The culture medium preferably contains low or high glucose, about 2%-15% (v/v) serum, betamercaptoethanol, and an antibiotic agent. The culture medium may contain at least one of fibroblast growth factor, platelet-derived growth factor, vascular endothelial growth factor, and epidermal growth factor. The cells of the invention may be grown on an uncoated or coated surface. Surfaces for growth of the cells may be coated for example with gelatin, collagen (e.g., native or denatured), fibronectin, laminin, ornithine, vitronectin, or extracellular membrane protein (e.g., MATRIGEL). In some embodiments, a population of postpartum-derived cells is mixed with another population of cells.

The cells of the invention can be induced to differentiate to an ectodermal, endodermal, or mesodermal lineage, preferably a mesodermal or ectodermal lineage. For example, PPDCs may be induced to differentiate into a given lineage by subjecting them to differentiation-inducing cell culture conditions. Also provided herein are populations of cells incubated in the presence of one or more factors, or under conditions, that stimulate cell differentiation along a desired pathway (e.g., toward a soft tissue phenotype such as a muscular, endothelial, or epithelial phenotype).

Methods to characterize differentiation-induced cells of the invention, include, but are not limited to, histological, morphological, biochemical and immunohistochemical methods, or using cell surface markers, or genetically or molecularly, or by identifying factors secreted by the differentiation-induced cell, and by the inductive qualities of the differentiation-induced PPDCs.

Methods of Using PPDCs or PPDC Products

Genetic Engineering of PPDCs

The cells of the invention can be engineered using any of a variety of vectors including, but not limited to, integrating viral vectors, e.g., retrovirus vector or adeno-associated viral vectors; non-integrating replicating vectors, e.g., papilloma virus vectors, SV40 vectors, adenoviral vectors; or replication-defective viral vectors. Other methods of introducing DNA into cells include the use of liposomes, electroporation, a particle gun, or by direct DNA injection.

Hosts cells are preferably transformed or transfected with a nucleic acid of interest controlled by or in operative association with, one or more appropriate expression control elements such as promoter or enhancer sequences, internal ribosomal entry sites (IREs), transcription terminators, polyadenylation sites, among others, and a selectable marker.

Following the introduction of the nucleic acid of interest, engineered cells may be allowed to grow in enriched media and then switched to selective media. A selectable marker in the nucleic acid of interest may confer resistance to a selection agent or allow cells to grow in the absence of an otherwise required factor. Cells may stably integrate the DNA of interest into their chromosomes. Cells expressing the DNA of interest may be cloned and expanded into cell lines.

This method can be advantageously used to engineer cell lines which express the DNA of interest.

Any promoter may be used to drive the expression of the DNA of interest. For example, viral promoters include, but are not limited to, the CMV promoter/enhancer, SV40, papillomavirus, Epstein-Barr virus or elastin gene promoter. Preferably, the control elements used to control expression of the gene of interest allow for the regulated expression of the gene so that the product is synthesized only when desired in vivo. If transient expression is desired, constitutive promoters are preferably used in a non-integrating and/or replication-defective vector. Alternatively, inducible promoters could be used to drive the expression of the gene of interest when necessary.

Inducible promoters include, but are not limited to, those associated with metallothionein and heat shock proteins.

An expression control element may be tissue-specific. An example of a transcriptional control region that exhibits tissue specificity is the myosin light chain-2 gene control region, which is active in skeletal muscle (Shani, 1985, *Nature* 314:283).

The cells of the invention may be genetically engineered to "knock out" or "knock down" expression of factors that promote inflammation or rejection at the implant site. Negative modulatory techniques for the reduction of target gene expression levels or target gene product activity levels are discussed below. "Negative modulation," as used herein, refers to a reduction in the level and/or activity of target gene product relative to the level and/or activity of the target gene product in the absence of the modulatory treatment. The expression of a native gene can be reduced or knocked out using a number of techniques including, for example, inhibition of expression by inactivating the gene completely (commonly termed "knockout"), for example using the homologous recombination technique. Usually, an exon encoding an important region of the protein (or an exon 5' to that region) is interrupted by a positive selectable marker, e.g., neo, preventing the production of normal mRNA from the target gene and resulting in inactivation of the gene. A gene may also be inactivated by creating a deletion in part of a gene or by deleting the entire gene. By using a construct with two regions of homology to the target gene, for example, the intervening sequence can be deleted (Mombaerts et al., 1991, *Proc. Nat. Acad. Sci. U.S.A.* 88:3084-3087).

Antisense, small interfering RNA, DNAzymes, and ribozyme molecules which inhibit expression of the target gene can also be used in accordance with the invention to reduce the level of target gene activity. For example, antisense RNA molecules which inhibit the expression of major histocompatibility gene complexes (HLA) have been shown to be most versatile with respect to immune responses. Still further, triple helix molecules can be utilized in reducing the level of target gene activity.

These techniques are described in detail by L. G. Davis et al. (eds), 1994, BASIC METHODS IN MOLECULAR BIOLOGY, 2nd ed., Appleton & Lange, Norwalk, Conn., which is incorporated herein by reference.

Using any of the foregoing techniques, for example, the expression of IL-1 can be knocked out or knocked down in the cells of the invention to reduce the production of inflammatory mediators by the cells of the invention. Likewise, the expression of MHC class II molecules can be knocked out or knocked down in order to reduce the risk of rejection of the implanted tissue.

Once the cells of the invention have been genetically engineered, they may be administered to a patient to allow for the treatment of a soft tissue condition or to produce an anti-inflammatory gene product such as, for example, peptides or polypeptides corresponding to the idiotype of neutralizing antibodies for GM-CSF, TNF, IL-1, IL-2, or other inflammatory cytokines.

Alternatively, the genetically engineered cells may be used to produce new tissue in vitro, which is then administered to a subject, as described herein.

Secretion of Trophic Factors

The secretion of growth factors by PPDCs may provide trophic support for a second cell type in vitro or in vivo. PPDCs may secrete, for example, at least one of monocyte chemotactic protein 1 (MCP-1), interleukin-6 (IL6), interleukin 8 (IL-8), GCP-2, hepatocyte growth factor (HGF), keratinocyte growth factor (KGF), fibroblast growth factor (FGF), heparin binding epidermal growth factor (HB-EGF), brain-derived neurotrophic factor (BDNF), thrombopoietin (TPO), macrophage inflammatory protein 1 alpha (MIP1a), RANTES, and tissue inhibitor of matrix metalloproteinase 1 (TIMP1), which can be augmented by a variety of techniques, including ex vivo cultivation of the cells in chemically defined medium.

As demonstrated by Example 14 herein, PPDCs have the ability to support survival, growth, and differentiation of other cell types in co-culture. The methods of the invention thus also include methods of providing trophic support to a soft tissue cell. The methods may include a step of exposing a soft tissue cell to a PPDC or PPDC product, such as PPDC conditioned medium. Examples of cells which may be supported by PPDCs or PPDC products include but are not limited to stem cells, myocytes, myoblasts, keratinocytes, melanocytes, dermal fibroblasts, bone marrow cells, adipocytes, epithelial cells, endothelial cells, stromal cells, and endothelial cells (e.g., aortic endothelial cells, coronary artery endothelial cells, pulmonary artery endothelial cells, iliac artery endothelial cells, microvascular endothelial cells, umbilical artery endothelial cells, umbilical vein endothelial cells, and endothelial progenitors). Exposure to or co-culture of PPDC or PPDC products with endothelial cells may stimulate angiogenesis by the endothelial cells.

PPDCs or PPDC products are co-cultured or exposed in vitro or are administered in vivo to provide trophic support to another cell type, including but not limited to epithelial cells (e.g., mucosal cells, for example, cells of oral mucosa; gastrointestinal tract; nasal epithelium; respiratory tract epithelium; vaginal epithelium; corneal epithelium), bone marrow cells, adipocytes, stem cells, keratinocytes, vascular endothelial cells (e.g., aortic endothelial cells, coronary artery endothelial cells, pulmonary artery endothelial cells, iliac artery endothelial cells, microvascular endothelial cells, umbilical artery endothelial cells, umbilical vein endothelial cells, and endothelial progenitors (e.g., CD34+, CD34+/CD117+ cells)), smooth muscle cells, myoblasts, myocytes, stromal cells, bladder urothelial cells, cells of the larynx, esophageal cells, and cells of the gastrointestinal tract, stem cells, and other soft tissue cells or progenitor cells, and mixtures thereof. For co-culture, it may be desirable for the PPDCs and the desired other cells to be co-cultured under conditions in which the two cell types are in contact. This can be achieved, for example, by seeding the cells as a heterogeneous population of cells in culture medium or onto a suitable culture substrate. Alternatively, the PPDCs can first be grown to confluence and employed as a substrate for the second desired cell type in culture. In this latter embodiment, the cells may further be physically separated, e.g., by a membrane or similar device, such that the other cell type may be removed and used separately following the co-culture period. In other embodiments, the desired other cells are cultured in contact with a PPDC product, such as conditioned medium, extracellular matrix, and/or a cell fraction of PPDCs. In other embodiments, matrices comprising PPDCs or PPDC products are administered to provide trophic support to another cell type. Use of PPDCs or PPDC products to promote expansion and/or differentiation of other cell types may find applicability in research and in clinical/therapeutic areas. For instance, such methods may be utilized to facilitate growth and/or differentiation of cells of a given phenotype in culture (e.g., cells of a soft tissue phenotype) for basic research purposes or for use in drug screening assays. The methods may also be utilized for in vitro expansion of cells of a soft tissue phenotype for later administration for therapeutic purposes. For example, cells may be harvested from an individual, expanded in vitro in co-culture with PPDCs or a PPDC product, then returned to that individual (autologous transfer) or another individual (syngeneic, allogeneic, or xenogeneic transfer). In these embodiments, it will be appreciated that, following in vitro expansion, the population of cells comprising the PPDCs or PPDC products could be administered to a patient in need of treatment, for example, of a soft tissue condition as described herein. Alternatively, in situations where autologous transfer is appropriate or desirable, the cultured cell populations may be physically separated in culture, enabling removal of the autologous cells for administration to the patient.

In some embodiments, the culturing methods are performed in vivo. For example, PPDCs or a PPDC product may be administered to a patient to provide trophic support to another cell type, including but not limited to epithelial cells (e.g., mucosal cells, for example, cells of oral mucosa; gastrointestinal tract; nasal epithelium; respiratory tract epithelium; vaginal epithelium; corneal epithelium), bone marrow cells, adipocytes, stem cells, keratinocytes, vascular endothelial cells (e.g., aortic endothelial cells, coronary artery endothelial cells, pulmonary artery endothelial cells, iliac artery endothelial cells, microvascular endothelial cells, umbilical artery endothelial cells, umbilical vein endothelial cells, and endothelial progenitors (e.g., CD34+, CD34+/CD117+ cells)), smooth muscle cells, myoblasts, myocytes, stromal cells, bladder urothelial cells, cells of the larynx, esophageal cells, and cells of the gastrointestinal tract, and other soft tissue cells or progenitor cells, and mixtures thereof.

In some embodiments, PPDCs or PPDC products induce angiogenesis in co-culture with cells such as but not limited to epithelial cells (e.g., mucosal cells, for example, cells of oral mucosa; gastrointestinal tract; nasal epithelium; respiratory tract epithelium; vaginal epithelium; corneal epithelium), bone marrow cells, adipocytes, stem cells, keratinocytes, vascular endothelial cells (e.g., aortic endothelial cells, coronary artery endothelial cells, pulmonary artery endothelial cells, iliac artery endothelial cells, microvascular endothelial cells, umbilical artery endothelial cells, umbilical vein endothelial cells, and endothelial progenitors (e.g., CD34+, CD34+/CD117+ cells)), smooth muscle cells, myoblasts, myocytes, stromal cells, bladder urothelial cells, cells of the larynx, esophageal cells, and cells of the gastrointestinal tract, and other soft tissue cells or progenitor cells. For example, angiogenic factors, including but not limited to EPO, TIMP1, ANG2, PDGF-bb, TPO, KGF, HGF, FGF, VEGF, and HBEGF, are released by PPDCs. In some embodiments, methods of inducing angiogenesis according to the invention include exposing a soft tissue cell or population thereof to a PPDC or PPDC product in vitro or in vivo. Examples of soft tissue cells that form endothelial networks in accordance with the methods of the invention include aortic endothelial cells, coronary artery endothelial cells, pulmonary artery endothelial cells, iliac artery endothelial cells, microvascular endothelial cells, umbilical artery endothelial cells, umbilical vein endothelial cells, and endothelial progenitors (e.g., CD34+, CD34+/CD117+ cells). Where the method is performed in vivo, PPDCs or PPDC products may be administered to a patient as described herein. For example, a PPDC population or product may be administered to a patient to provide needed angiogenic factors.

PPDCs and PPDC products of the invention may be used to produce a vascular network, as demonstrated in Example 14. Methods of producing a vascular network involve exposing (e.g., contacting) a population of soft tissue cells to PPDCs or a PPDC product such as a cell fraction (e.g., lysate or soluble cell fraction thereof), extracellular matrix, or conditioned medium. The population of soft tissue cells preferably contains at least one soft tissue cell of an aortic endothelial cell, coronary artery endothelial cell, pulmonary artery endothelial cell, iliac artery endothelial cell, microvascular endothelial cell, umbilical artery endothelial cell, and umbilical vein endothelial cell. The method of producing a vascular network may be performed in vitro or in vivo. Also included within the scope of the invention are the vascular networks so produced. The vascular networks of the invention may be administered to a patient as a therapeutic regimen. In some preferred embodiments, the vascular networks are administered as treatment of a soft tissue condition, for example but not by way of limitation, a vascular condition, such as a vascular disease or injury or improper vascular development. In some aspects of the invention, the vascular network is administered by transplantation to the patient. In preferred embodiments, damaged or diseased vasculature is removed prior to administration of the vascular network of the invention.

Conditioned Medium of PPDCs

Another embodiment of the invention features use of differentiation-induced or undifferentiated PPDCs for production of conditioned medium. Such conditioned media are contemplated for use in in vitro culture of cells, for example, stem or soft tissue progenitor cells, or cells of a soft tissue phenotype, including but not limited to epithelial cells (e.g., cells of oral mucosa, gastrointestinal tract, nasal epithelium, respiratory tract epithelium, vaginal epithelium, corneal epithelium), bone marrow cells, adipocytes, keratinocytes, vascular endothelial cells (e.g., aortic endothelial cells, coronary artery endothelial cells, pulmonary artery endothelial cells, iliac artery endothelial cells, microvascular endothelial cells, umbilical artery endothelial cells, umbilical vein endothelial cells, and endothelial progenitors (e.g., CD34+, CD34+/CD117+ cells)), myoblasts, myocytes, stromal cells, and other soft tissue cells or progenitor cells, and mixtures thereof, or in vivo to support transplanted cells comprising homogeneous or heterogeneous populations of PPDCs or stem or progenitor cells, and/or cells of a soft tissue phenotype, epithelial cells (e.g., cells of oral mucosa, gastrointestinal tract, nasal epithelium, respiratory tract epithelium, vaginal epithelium, corneal epithelium), bone marrow cells, adipocytes, keratinocytes, vascular endothelial cells (e.g., aortic endothelial cells, coronary artery endothelial cells, pulmonary artery endothelial cells, iliac artery endothelial cells, microvascular endothelial cells, umbilical artery endothelial cells, umbilical vein endothelial cells, and endothelial progenitors (e.g., CD34+, CD34+/CD117+ cells)), myoblasts, myocytes, stromal cells, and other soft tissue cells or progenitor cells, and mixtures thereof, for example. PPDC conditioned medium also may be administered in vivo to support the growth, maintenance, and/or differentiation of endogenous cells.

Therapeutic Applications of PPDCs and PPDC Products

PPDCs and PPDC products of the invention may be used to treat patients having a soft tissue condition, for example but not limited to patients requiring the repair or replacement of soft tissue resulting from disease or trauma or failure of the tissue to develop normally, or to provide a cosmetic function, such as to augment features of the body. The treatment may comprise at least one of soft tissue repair, reconstruction, bulking, cosmetic treatment, therapeutic treatment, tissue augmentation, and tissue sealing. Provided herein are methods of treating soft tissue conditions in a patient by administering to the patient PPDCs and/or PPDC products of the invention. Therapeutic applications of the PPDCs and PPDC products of the invention include but are not limited to treatment of hernias, congenital defects, damage to the pelvic floor, tear or rupture of a tendon or ligament, a traumatic wound, skin repair and regeneration (e.g., scar revision or the treatment of traumatic wounds, burns, skin ulcers (e.g., decubitus (pressure) ulcers, venous ulcers, and diabetic ulcers), and surgical wounds such as those associated with the excision of skin cancers; treatment of vascular conditions (e.g., vascular disease such as peripheral arterial disease, abdominal aortic aneurysm, carotid disease, and venous disease; vascular injury; improper vascular development); and muscle diseases (e.g., congenital myopathies; myasthenia gravis; inflammatory, neurogenic, and myogenic muscle diseases; and muscular dystrophies such as Duchenne muscular dystrophy, Becker muscular dystrophy, myotonic dystrophy, limb-girdle-muscular dystrophy, facioscapulohumeral muscular dystrophy, congenital muscular dystrophies, oculopharyngeal muscular dystrophy, distal muscular dystrophy, and Emery-Dreifuss muscular dystrophy), breast reconstruction, and bladder augmentation.

Also provided by the invention are methods of treating a patient in need of angiogenic factors comprising administering to the patient the PPDCs or PPDC products (e.g., conditioned medium) of the invention.

The PPDCs and PPDC products of the invention may be administered alone or as admixtures with other cells. For example, the PPDCs and PPDC products may be administered by way of a matrix. A matrix of the invention may comprise a three-dimensional scaffold. Scaffolds of the invention may be particulate, flat, tubular, single-layered, or multilayered. The PPDCs and PPDC products may be administered with conventional pharmaceutically acceptable carriers. Where PPDCs are to be administered with other cells, the PPDCs may be administered simultaneously or sequentially with the other cells. Where cells are to be administered sequentially with other cell types, the PPDCs may be administered before or after the cells of a second phenotype. Cells which may be administered in conjunction with PPDCs include epithelial cells (e.g., cells of oral mucosa, gastrointestinal tract, nasal epithelium, respiratory tract epithelium, vaginal epithelium, corneal epithelium), bone marrow cells, adipocytes, stem cells, keratinocytes, vascular endothelial cells (e.g., aortic endothelial cells, coronary artery endothelial cells, pulmonary artery endothelial cells, iliac artery endothelial cells, microvascular endothelial cells, umbilical artery endothelial cells, umbilical vein endothelial cells, and endothelial progenitors (e.g., CD34+, CD34+/CD117+ cells)), myoblasts, myocytes, stromal cells, bladder urothelial cells, smooth muscle cells, gastrointestinal cells, esophageal cells, larynx cells, mucosal cells, and other soft tissue cells or progenitor cells.

The PPDCs and PPDC products may be administered with other beneficial drugs or biological molecules (e.g., growth factors, trophic factors). The pharmaceutical compositions of the invention comprise PPDCs and/or PPDC products and a pharmaceutically acceptable carrier. In preferred embodiments, the pharmaceutical compositions comprise PPDCs and/or PPDC products in an effective amount to treat a soft tissue condition. When administered with other agents, the PPDCs and/or PPDC products may be administered together in a single pharmaceutical composition, or in separate pharmaceutical compositions, simultaneously or sequentially with the other bioactive factor (either before or after administration of the other agents). Bioactive factors which may be co-administered include anti-apoptotic agents (e.g., EPO, EPO mimetibody, TPO, IGF-I and IGF-II, HGF, caspase inhibitors); anti-inflammatory agents (e.g., p38 MAPK inhibitors, TGF-beta inhibitors, statins, IL-6 and IL-1 inhibitors, pemirolast, tranilast, REMICADE, and NSAIDs (non-steroidal anti-inflammatory drugs; e.g., tepoxalin, tolmetin, suprofen); immunosupressive/immunomodulatory agents (e.g., calcineurin inhibitors, such as cyclosporine, tacrolimus; mTOR inhibitors (e.g., sirolimus, everolimus); anti-proliferatives (e.g., azathioprine, mycophenolate mofetil); corticosteroids (e.g., prednisolone, hydrocortisone); antibodies such as monoclonal anti-IL-2Ralpha receptor antibodies (e.g., basiliximab, daclizumab), polyclonal anti-T-cell antibodies (e.g., anti-thymocyte globulin (ATG); anti-lymphocyte globulin (ALG); monoclonal anti-T cell antibody OKT3)); anti-thrombogenic agents (e.g., heparin, heparin derivatives, urokinase, PPack (dextrophenylalanine proline arginine chloromethylketone), antithrombin compounds, platelet receptor antagonists, antithrombin antibodies, anti-platelet receptor antibodies, aspirin, dipyridamole, protamine, hirudin, prostaglandin inhibitors, and platelet inhibitors); and anti-oxidants (e.g., probucol, vitamin A, ascorbic acid, tocopherol, coenzyme Q-10, glutathione, L-cysteine, N-acetylcysteine), as well as local anesthetics. As another example, the cells may be co-administered with scar inhibitory factor as described in U.S. Pat. No. 5,827,735, incorporated herein by reference.

Pharmaceutical compositions of the invention may comprise, in addition to the PPDC or PPDC product, at least one other cell type. For example, pharmaceutical compositions of the invention may comprise a soft tissue cell. Examples of the at least one other cell type to be included in the pharmaceutical compositions of PPDCs and/or PPDC products of the invention include stem cells, epithelial cells, dermal fibroblasts, melanocytes, keratinocytes, and other epithelial progenitor cells, myocytes, myoblasts, and muscle cells (e.g., smooth muscle cells), endothelial cells, and stromal cells.

In some embodiments, PPDCs are administered as undifferentiated cells, i.e., as cultured in Growth medium.

The PPDCs and related products of the invention may be surgically implanted, injected, engrafted, delivered (e.g., by way of a catheter or syringe), or otherwise administered directly or indirectly to the site in need of repair or augmentation. PPDCs and PPDC products may be administered by way of a matrix (e.g., a three-dimensional scaffold), or via injectable viscoelastic supplements such as hyaluronic acid, alginates, self-assembling peptides, hydrogels and collagen. PPDCs and PPDC products may be administered with conventional pharmaceutically acceptable carriers. Routes of administration of PPDCs and PPDC products include intramuscular, intravenous, intraarterial, intraperitoneal, subcutaneous, oral, and nasal administration. Preferable routes of in vivo administration include transplantation, implantation, injection, delivery via a catheter, microcatheter, suture, stent, microparticle, pump, or any other means known in the art.

When PPDCs or PPDC products are administered in semi-solid or solid devices, surgical implantation into a precise location in the body is typically a suitable means of administration. Liquid or fluid pharmaceutical compositions may be administered to a more general location (e.g., throughout a diffusely affected area, for example), from which PPDCs or PPDC products migrate to a particular location, e.g., by responding to chemical signals.

Dosage forms and regimes for administering PPDCs or PPDC products described herein are developed in accordance with good medical practice, taking into account the condition of the individual patient, e.g., nature and extent of the condition being treated, age, sex, body weight and general medical condition, and other factors known to medical practitioners. Thus, the effective amount of a pharmaceutical composition to be administered to a patient is determined by these considerations as known in the art.

In some embodiments of the invention, it may not be necessary or desirable to immunosuppress a patient prior to initiation of PPDC- or PPDC product-based therapy. PPDCs have been shown not to stimulate allogeneic PBMCs in a mixed lymphocyte reaction. Accordingly, transplantation with allogeneic, or even xenogeneic, PPDCs may be tolerated.

It may be desirable to pharmacologically immunosuppress a patient prior to initiating PPDC- or PPDC product-based therapy. This may be accomplished through the use of systemic or local immunosuppressive agents, or it may be accomplished by delivering the PPDCs in an encapsulated device. PPDCs may be encapsulated in a capsule that is permeable to nutrients and oxygen required by the cell and therapeutic factors the cell is yet impermeable to immune humoral factors and cells. Preferably the encapsulant is hypoallergenic, is easily and stably situated in a target tissue, and provides added protection to the implanted structure. PPDCs also may be genetically modified to reduce their immunogenicity.

Survival of transplanted PPDCs in a living patient can be determined through the use of a variety of scanning techniques, e.g., computerized axial tomography (CAT or CT) scan, magnetic resonance imaging (MRI) or positron emission tomography (PET) scans. Determination of transplant survival can also be done by removing a section of the target tissue and examining it, for example, visually or through a microscope. Alternatively, cells can be treated with stains that are specific for cells of a given lineage. Transplanted cells can also be identified by prior incorporation of tracer dyes such as rhodamine- or fluorescein-labeled microspheres, fast blue, bisbenzamide, ferric microparticles, or genetically introduced reporter gene products, such as beta-galactosidase or beta-glucuronidase.

Functional integration of transplanted PPDCs into a subject can be assessed by examining restoration of the function that was damaged or diseased, for example, restoration of joint function, blood flow, muscle contraction, etc., or augmentation of function.

Compositions and Pharmaceutical Compositions

Compositions of PPDCs and related products (e.g., extracellular matrix, cell fraction, secreted factors, conditioned medium), including for example pharmaceutical compositions, are included within the scope of the invention. Compositions of the invention may include one or more bioactive factors, for example but not limited to, a growth factor, a differentiation-inducing factor, a cell survival factor such as caspase inhibitor, an anti-inflammatory agent such as p38 kinase inhibitor, or an angiogenic factor such as VEGF or bFGF. Some examples of bioactive factors include PDGF-bb, EGF, bFGF, IGF-1, and LIF. In some embodiments, undifferentiated or differentiation-induced PDPCs are cultured in contact with the bioactive factor. In some embodiments, undifferentiated PPDCs remain undifferentiated upon contact with the bioactive factor. In other embodiments, the bioactive factor induces differentiation of the PPDCs.

Pharmaceutical compositions of the invention may comprise homogeneous or heterogeneous populations of differentiated and/or undifferentiated PPDCs or PPDC products in a pharmaceutically acceptable carrier.

Pharmaceutically acceptable carriers include organic or inorganic carrier substances suitable which do not deleteriously react with the cells of the invention or related products. To the extent they are biocompatible, suitable pharmaceutically acceptable carriers include water, salt solution (such as Ringer's solution), alcohols, oils, gelatins, and carbohydrates, such as lactose, amylose, or starch, fatty acid esters, hydroxymethylcellulose, hyaluronic acid, and polyvinyl pyrolidine. Such preparations can be sterilized, and if desired, mixed with auxiliary agents such as lubricants, preservatives, stabilizers, wetting agents, emulsifiers, salts for influencing osmotic pressure, buffers, and coloring. Pharmaceutical carriers suitable for use in the present invention are known in the art and are described, for example, in Pharmaceutical Sciences ($17^{th}$ Ed., Mack Pub. Co., Easton, Pa.) and WO 96/05309, each of which are incorporated by reference herein.

The compositions may be delivered in the form of a spray, suspension, solution, dry powder, cream, ointment, or gel.

The dosage (e.g., the number of cells to be administered) and frequency of administration of the pharmaceutical compositions will depend upon a number of factors, including but not limited to, the nature of the condition to be treated, the extent of the symptoms of the condition, characteristics of the patient (e.g., age, size, gender, health).

For example but not by way of limitation, PPDCs, extracellular matrices or cell fractions thereof, conditioned medium, matrices, vascular networks, and compositions produced according to the invention may be used to repair or replace underdeveloped, damaged, or destroyed soft tissue, to augment existing soft tissue, to introduce new or altered tissue, to modify artificial prostheses, or to join biological tissues or structures. For example, some embodiments of the invention include (i) hernia closures with replacement soft tissue constructs grown in three-dimensional cultures; (ii) skin grafts with soft tissue constructs; (iii) prostheses; (iv) blood vessel grafts; and (v) tendon or ligament reconstruction. Examples of such conditions that can be treated according to the methods of the invention include congenital anomalies such as hemifacial microsomia, malar and zygomatic hypoplasia, unilateral mammary hypoplasia, pectus excavatum, pectoralis agenesis (Poland's anomaly) and velopharyngeal incompetence secondary to cleft palate repair or submucous cleft palate (as a retropharyngeal implant); acquired defects (post-traumatic, post-surgical, post-infectious) such as scars, subcutaneous atrophy (e.g., secondary to discoid lupus erythematosus), keratotic lesions, acne pitting of the face, linear scleroderma with subcutaneous atrophy, saddle-nose deformity, Romberg's disease, and unilateral vocal cord paralysis; cosmetic defects such as glabellar frown lines, deep nasolabial creases, circum-oral geographical wrinkles, sunken cheeks and mammary hypoplasia; hernias; tears or ruptures of a tendon or ligament; severe burns, skin ulcers (e.g., decubitus (pressure) ulcers, venous ulcers, and diabetic ulcers), and surgical wounds such as those associated with the excision of skin cancers; vascular diseases such as peripheral arterial disease, abdominal aortic aneurysm, carotid disease, and venous disease; muscle diseases (e.g., congenital myopathies; myasthenia gravis; inflammatory, neurogenic, and myogenic muscle diseases; and muscular dystrophies such as Duchenne muscular dystrophy, Becker muscular dystrophy, myotonic dystrophy, limb-girdle-muscular dystrophy, facioscapulohumeral muscular dystrophy, congenital muscular dystrophies, oculopharyngeal muscular dystrophy, distal muscular dystrophy, and Emery-Dreifuss muscular dystrophy); and replacement and repair of connective tissues such as tendons and ligaments.

The successful repair or replacement of damaged tissue can be enhanced if the implanted cells and/or tissue can be fixed in place at the site of repair. Post-implantation movement may cause the new cells or tissue to become dislodged from the site if a pro-active fixation technique is not employed. Various methods can be used to fix the new cells and/or tissue in place, including: patches derived from biocompatible tissues, which can be placed over the site; biodegradable sutures, hollow sutures, porous sutures, or other fasteners, e.g., pins, staples, tacks, screws and anchors; non-absorbable fixation devices, e.g., sutures, pins, screws and anchors; adhesives; and the use of interference fit geometries.

The PPDCs and PPDC products of the invention may be administered alone, in a pharmaceutically acceptable carrier, through a catheter or microcatheter, via a pump or spray, or on or in a matrix as described herein.

Use of PPDCs or PPDC Products for Transplantation

The treatment methods of the subject invention involve the implantation of PPDCs, PPDC products, or trans-differentiated cells into individuals in need thereof. PPDCs or PPDC products of the present invention may be delivered to the site of therapeutic need or "home" to the site.

The cells of the present invention may be differentiated in vitro prior to implantation in a patient. In vitro differentiation allows for controlled application of bioactive factors. Alternatively, the cells of the present invention may differentiate in situ or provide trophic support to endogenous cells. The appropriate cell implantation dosage in humans can be determined from existing information relating to, e.g., the activity of the cells. From in vitro culture and in vivo animal experiments, the amount of factors produced can be quantitated. This information is also useful in calculating an appropriate dosage of implanted material. Additionally, the patient can be monitored to determine if additional implantation can be made or implanted material reduced accordingly.

To enhance vascularization and survival of the transplanted cells, angiogenic factors such as VEGF, PDGF or bFGF can be added either alone or in combination with endothelial cells or their progenitors, including CD34+, CD34+/CD117+ cells.

One or more other components may be co-administered, including selected extracellular matrix components, such as one or more types of collagen known in the art, and/or growth factors, platelet-rich plasma, and drugs. Alternatively, the cells of the invention may be genetically engineered to express and produce growth factors. Bioactive factors which may be usefully incorporated into the cell formulation include anti-apoptotic agents (e.g., EPO, EPO mimetibody, TPO, IGF-I and IGF-II, HGF, caspase inhibitors); anti-inflammatory agents (e.g., p38 MAPK inhibitors, TGF-beta inhibitors, statins, IL-6 and IL-1 inhibitors, pemirolast, tranilast, REMICADE, and NSAIDs (non-steroidal anti-inflammatory drugs; e.g., tepoxalin, tolmetin, suprofen); immunosupressive/immunomodulatory agents (e.g., calcineurin inhibitors, such as cyclosporine, tacrolimus; mTOR inhibitors (e.g., sirolimus, everolimus); anti-proliferatives (e.g., azathioprine, mycophenolate mofetil); corticosteroids (e.g., prednisolone, hydrocortisone); antibodies such as monoclonal anti-IL-2Ralpha receptor antibodies (e.g., basiliximab, daclizumab), polyclonal anti-T-cell antibodies (e.g., anti-thymocyte globulin (ATG); anti-lymphocyte globulin (ALG); monoclonal anti-T cell antibody OKT3)); anti-thrombogenic agents (e.g., heparin, heparin derivatives, urokinase, PPack (dextrophenylalanine proline arginine chloromethylketone), antithrombin compounds, platelet receptor antagonists, anti-thrombin antibodies, anti-platelet receptor antibodies, aspirin, dipyridamole, protamine, hirudin, prostaglandin inhibitors, and platelet inhibitors); and anti-oxidants (e.g., probucol, vitamin A, ascorbic acid, tocopherol, coenzyme Q-10, glutathione, L-cysteine, N-acetylcysteine) as well as local anesthetics. As another example, the cells may be co-administered with scar inhibitory factor as described in U.S. Pat. No. 5,827,735, incorporated herein by reference.

In a non-limiting embodiment, a formulation comprising PPDCs or PPDC products of the invention is prepared for administration directly to the site where the new soft tissue is desired. In some embodiments, the support for the PPDCs or PPDC products of the invention is biodegradable. As an example of a formulation of the invention, and not by way of limitation, PPDCs or PPDC products of the invention may be suspended in a hydrogel solution for injection. Examples of suitable hydrogels for use in the invention include self-assembling peptides, such as RAD16. Alternatively, the hydrogel solution may be allowed to harden, for instance in a mold, to form a matrix having PPDCs or PPDC products dispersed therein prior to implantation. Or, once the matrix has hardened, the cell formulations may be cultured so that the cells are mitotically expanded prior to implantation. Hydrogels are organic polymers (natural or synthetic) which are cross-linked via covalent, ionic, or hydrogen bonds to create a three-dimensional open-lattice structure which entraps water molecules to form a gel. Examples of materials which can be used to form a hydrogel include polysaccharides such as alginate and salts thereof, peptides, polyphosphazines, and polyacrylates, which are crosslinked ionically, carboxymethyl cellulose (CMC), oxidized regenerated cellulose (ORC), or block polymers such as polyethylene oxide-polypropylene glycol block copolymers which are crosslinked by temperature or pH, respectively. In some embodiments of the invention, the formulation comprises an in situ polymerizable gel, as described, for example, in U.S. Patent Application Publication 2002/0022676; Anseth et al., *J. Control Release,* 78(1-3): 199-209 (2002); Wang et al., *Biomaterials,* 24(22):3969-80 (2003). Methods of synthesis of the hydrogel materials, as well as methods for preparing such hydrogels, are known in the art.

Other components may also be included in the formulation, including but not limited to any of the following: (1) buffers to provide appropriate pH and isotonicity; (2) lubricants; (3) viscous materials to retain the cells at or near the site of administration, including, for example, alginates, agars and plant gums; and (4) other cell types that may produce a desired effect at the site of administration, such as, for example, enhancement or modification of the formation of tissue or its physicochemical characteristics, or as support for the viability of the cells, or inhibition of inflammation or rejection. The cells may be covered by an appropriate wound covering to prevent cells from leaving the site. Such wound coverings are known to those of skill in the art.

Bioactive factors which may be usefully incorporated into the formulations of the invention include anti-apoptotic agents (e.g., EPO, EPO mimetibody, TPO, IGF-I and IGF-II, HGF, caspase inhibitors); anti-inflammatory agents (e.g., p38 MAPK inhibitors, TGF-beta inhibitors, statins, IL-6 and IL-1 inhibitors, pemirolast, tranilast, REMICADE, and NSAIDs (non-steroidal anti-inflammatory drugs; e.g., tepoxalin, tolmetin, suprofen); immunosupressive/immunomodulatory agents (e.g., calcineurin inhibitors, such as cyclosporine, tacrolimus; mTOR inhibitors (e.g., sirolimus, everolimus); anti-proliferatives (e.g., azathioprine, mycophenolate mofetil); corticosteroids (e.g., prednisolone, hydrocortisone); antibodies such as monoclonal anti-IL-2Ralpha receptor antibodies (e.g., basiliximab, daclizumab), polyclonal anti-T-cell antibodies (e.g., anti-thymocyte globulin (ATG); anti-lymphocyte globulin (ALG); monoclonal anti-T cell antibody OKT3)); anti-thrombogenic agents (e.g., heparin, heparin derivatives, urokinase, PPack (dextrophenylalanine proline arginine chloromethylketone), antithrombin compounds, platelet receptor antagonists, anti-thrombin antibodies, anti-platelet receptor antibodies, aspirin, dipyridamole, protamine, hirudin, prostaglandin inhibitors, and platelet inhibitors); and anti-oxidants (e.g., probucol, vitamin A, ascorbic acid, tocopherol, coenzyme Q-10, glutathione, L-cysteine, N-acetylcysteine) as well as local anesthetics. As another example, the cells may be co-administered with scar inhibitory factor as described in U.S. Pat. No. 5,827,735, incorporated herein by reference.

Formulation of a Soft Tissue Patch

Cultures or co-cultures of PPDCs in a pre-shaped well enables the manufacture of a soft tissue patch of pre-determined thickness and volume. The volume of the resulting tissue patch is dependent upon the volume of the well and upon the number of PPDCs in the well. Tissue of optimal pre-determined volume may be prepared by routine experimentation by altering either or both of the aforementioned parameters.

The cell contacting surface of the well may be coated with a molecule that discourages adhesion of PPDCs to the cell contacting surface. Preferred coating reagents include silicon based reagents i.e., dichlorodimethylsilane or polytetrafluoroethylene based reagents, i.e., TEFLON. Procedures for coating materials with silicon based reagents, specifically dichlorodimethylsilane, are well known in the art. See for example, Sambrook et al. (1989) "Molecular Cloning A Laboratory Manual", Cold Spring Harbor Laboratory Press, the disclosure of which is incorporated by reference herein. It is appreciated that other biocompatible reagents that prevent the attachment of cells to the surface of the well may be useful in the practice of the instant invention.

Alternatively, the well may be cast from a pliable or moldable biocompatible material that does not permit attachment of cells per se. Preferred materials that prevent such cell attachment include, but are not limited to, agarose, glass, untreated cell culture plastic and polytetrafluoroethylene, i.e., TEFLON. Untreated cell culture plastics, i.e., plastics that have not been treated with or made from materials that have an electrostatic charge are commercially available, and may be purchased, for example, from Falcon Labware, Becton-Dickinson, Lincoln Park, N.J. The aforementioned materials, however, are not meant to be limiting. It is appreciated that any other pliable or moldable biocompatible material that inherently discourages the attachment of PPDCs may be useful in the practice of the instant invention.

The size and shape of the well may be determined by the size and shape of the tissue defect to be repaired. The well should be deep enough to contain culture medium overlaying the tissue patch.

It is contemplated that a tissue patch prepared in accordance with the invention may be "trimmed" or configured to a pre-selected size and/or shape by a surgeon performing surgical repair of the damaged tissue. Trimming may be performed with the use of a sharp cutting implement, i.e., a scalpel, a pair of scissors or an arthroscopic device fitted with a cutting edge, using procedures well known in the art.

The pre-shaped well may be cast in a block of agarose gel under aseptic conditions. Agarose is an economical, biocompatible, pliable and moldable material that can be used to cast pre-shaped wells, quickly and easily. As mentioned above, the dimensions of the well may dependent upon the size of the resulting tissue plug that is desired.

A pre-shaped well may be prepared by pouring a hot solution of molten LT agarose (BioRad, Richmond, Calif.) into a tissue culture dish containing a cylinder, the cylinder having dimensions that mirror the shape of the well to be formed. The size and shape of the well may be chosen by the artisan and may be dependent upon the shape of the tissue defect to be repaired. Once the agarose has cooled and solidified around the cylinder, the cylinder is carefully removed with forceps. The surface of the tissue culture dish that is exposed by the removal of the cylinder is covered with molten agarose. This seals the bottom of the well. When the newly added molten LT agarose cools and solidifies, the resulting pre-shaped well is suitable for culturing and/or inducing the differentiation of PPDCs. It is appreciated, however, that alternative methods may be used to prepare a pre-shaped well useful in the practice of the invention.

PPDCs in suspension may be seeded into and cultured in the pre-shaped well. The PPDCs may be induced to differentiate to a soft tissue phenotype in culture in the well or may have been induced to differentiate prior to seeding in the well. The cells may be diluted by the addition of culture medium to a cell density of about $1\times10^5$ to $1\times10^9$ PPDCs per milliliter.

Once the cells form a cohesive patch, the cohesive plug of cells may be removed from the well and surgically implanted into the tissue defect. It is anticipated that undifferentiated PPDCs may differentiate in situ thereby to form tissue in vivo.

In some embodiments, PPDCs are used to generate cell sheets. The sheets may be multilayered, as described in Shimizu, et al., *Biomaterials*, 24(13):2309-2316 (2003).

Soft tissue defects may be identified by any means known in the art, for example, but not limited to computer aided tomography (CAT scanning); X-ray examination; or magnetic resonance imaging (MRI). Defects in soft tissue also are readily identifiable visually during arthroscopic examination or during open surgery. Treatment of the defects can be effected during an orthoscopic or open surgical procedure using the methods and compositions disclosed herein.

Accordingly, once the defect has been identified, the defect may be treated by (1) surgically implanting at the pre-determined site a tissue patch prepared by the methodologies described herein, and (2) permitting the tissue patch to integrate into pre-determined site.

The tissue patch optimally has a size and shape such that when the patch is implanted into the defect, the edges of the implanted tissue contact directly the edges of the defect. In addition, the tissue patch may be fixed in place during the surgical procedure. This can be effected by surgically fixing the patch into the defect with biodegradable sutures and/or by applying a bioadhesive to the region interfacing the patch and the defect.

In some instances, diseased, damaged, or underdeveloped tissue may be surgically excised prior to implantation of the patch of synthetic tissue. A synthetic tissue patch is implanted subsequently into the defect by the methods described above.

Transplantation of PPDCs Using Scaffolds

The cells of the invention or co-cultures thereof may be seeded onto a scaffold, such as a three-dimensional scaffold, and implanted in vivo, where the seeded cells will proliferate on or in the framework and form a replacement tissue in vivo in cooperation with the cells of the patient.

Growth of PPDCs or co-cultures thereof on the framework results in the formation of a tissue which can be utilized in vivo as a corrective or supplemental structure. For example, and not by way of limitation, the scaffolds of the invention can be used to form tubular structures, like those of the gastrointestinal and genitourinary tracts, as well as blood vessels; tissues for hernia repair; tendons and ligaments.

In accordance with some embodiments of the invention, PPDCs or co-cultures thereof are inoculated and grown on a three-dimensional framework. The framework may be configured into the shape of the corrective structure desired. When grown in this three-dimensional system, the proliferating cells mature and segregate properly to form components of adult tissues analogous to counterparts found naturally in vivo.

Some embodiments of the invention provide a matrix for implantation into a patient. In some embodiments, the matrix is seeded with a population of postpartum-derived cells of the invention. The PPDCs may be differentiation-induced or undifferentiated. The PPDC population may be homogeneous or heterogeneous. The matrix may also be inoculated with cells of another desired cell type, for example but not by way of limitation, epithelial cells (e.g., cells of oral mucosa, gastrointestinal tract, nasal epithelium, respiratory tract epithelium, vaginal epithelium, corneal epithelium), bone marrow cells, adipocytes, stem cells, keratinocytes, melanocytes, dermal fibroblasts, vascular endothelial cells (e.g., aortic endothelial cells, coronary artery endothelial cells, pulmonary artery endothelial cells, iliac artery endothelial cells, microvascular endothelial cells, umbilical artery endothelial cells, umbilical vein endothelial cells, and endothelial progenitors (e.g., CD34+, CD34+/CD117+ cells)), myoblasts, myocytes, stromal cells, and other soft tissue cells or progenitor cells. The matrix may contain or be pre-treated with one or more bioactive factors including, for example, drugs, anti-inflammatory agents, antiapoptotic agents, and growth factors. In some aspects of the invention, the matrix is inoculated with PPDC products of the invention, including for example, extracellular matrix, secreted factors, or cell fractions of the PPDCs. In some embodiments, the matrix is biodegradable. In some embodiments, the matrix comprises extracellular membrane proteins, for example, MATRIGEL. In some aspects of the invention, the matrix comprises natural or synthetic polymers. Matrices of the invention include biocompatible scaffolds, lattices, self-assembling structures and the like, whether biodegradable or not, liquid or solid. Such matrices are known in the arts of cell-based therapy, surgical repair, tissue engineering, and wound healing. Preferably the matrices are pretreated (e.g., seeded, inoculated, contacted with) with PPDCs or PPDC products (e.g., extracellular matrix, conditioned medium, secreted factors, cell fraction, or combination thereof) of the invention. More preferably, PPDCs or PPDC products are in close association to the matrix or its spaces. In some aspects of the invention, the cells or PPDC products adhere to the matrix. In some embodiments, the cells or cell products are contained within or bridge interstitial spaces of the matrix. Most preferred are those seeded matrices wherein PPDCs or PPDC products are in close association with the matrix and which, when used therapeutically, induce or support ingrowth of the patient's cells and/or proper angiogenesis. The seeded or pre-treated matrices can be introduced into a patient's body in any way known in the art, including but not limited to implantation, injection, surgical attachment, transplantation with other tissue, and the like. The matrices of the invention may be configured for use in vivo, for example, to the shape and/or size of a tissue or organ in vivo. The scaffolds of the invention may be flat or tubular or may comprise sections thereof, as described herein. The scaffolds of the invention may be multilayered.

For example, but not by way of limitation, the scaffold may be designed such that the scaffold structure: (1) supports the PPDCs or PPDC products without subsequent degradation; (2) supports the PPDCs or PPDC products from the time of seeding until the scaffold is remodeled by the host tissue; or (3) allows the seeded cells to attach, proliferate, and develop into a tissue structure having sufficient mechanical integrity to support itself in vitro, at which point, the scaffold is degraded. A review of scaffold design is provided by Hutmacher, *J. Biomat. Sci. Polymer Edn.*, 12(1):107-124 (2001).

Scaffolds of the invention can be administered in combination with any one or more growth factors, cells, drugs, or other components described above that stimulate soft tissue formation or stimulate vascularization or innervation thereof or otherwise enhance or improve the practice of the invention.

The cells of the invention can be grown freely in a culture vessel to sub-confluency or confluency, lifted from the culture and inoculated onto a three-dimensional framework. Inoculation of the three-dimensional framework with a high concentration of cells, e.g., approximately $10^6$ to $5\times10^7$ cells per milliliter, will result in the establishment of the three-dimensional support in relatively shorter periods of time.

In some embodiments, it is important to re-create in culture the cellular microenvironment found in vivo, such that the extent to which the cells of the invention are grown prior to in vivo administration or use in vitro may vary. PPDCs, co-cultures thereof, or PPDC products may be inoculated onto the framework before or after forming the desired shape, e.g., ropes, tubes, filaments. Following inoculation of cells onto the framework, the framework is preferably incubated in an appropriate growth medium. During the incubation period, the inoculated cells will grow and envelop the framework and will bridge any interstitial spaces therein. It is preferable but not required to grow the cells to an appropriate degree which reflects the in vivo cell density of the tissue being repaired or regenerated.

Examples of scaffolds which may be used in the present invention include nonwoven mats, porous foams, sutures, beads, microparticles, or hydrogels. Nonwoven mats may, for example, be formed using fibers comprised of poly(lactic acid-co-glycolic acid) polymer (10/90 PLGA), referred to herein as VNW, available for purchase through Biomedical Structures (Slatersville, R.I.). Foams, composed of, for example, poly(epsilon-caprolactone)/poly(glycolic acid) (PCL/PGA) copolymer, formed by processes such as freeze-drying, or lyophilization, as discussed in U.S. Pat. No. 6,355,699, are also possible scaffolds. Hydrogels such as self-assembling peptides (e.g., RAD16) may also be used. Another embodiment of a scaffold or matrix of the invention comprises collagen/ORC, CMC, or ORC. These materials are frequently used as supports for growth of tissue. In some embodiments, the scaffold is lyophilized prior to use. In some embodiments, lyophilized scaffolds are rehydrated, with saline for example, prior to use. According to a preferred embodiment, the framework is a felt, which can be composed of a multifilament yarn made from a bioabsorbable material, e.g., PGA, PLA, PCL copolymers or blends, or hyaluronic acid. The yarn is made into a felt using standard textile processing techniques consisting of crimping, cutting, carding and needling.

In another preferred embodiment PPDCs and PPDC products of the invention are seeded onto foam scaffolds that may be composite structures. In addition, the three-dimensional framework may be molded into a useful shape, such as a specific structure in the body to be repaired, replaced, or augmented.

The framework may be treated prior to inoculation to enhance attachment of the PPDCs or PPDC products. For example, prior to inoculation, nylon matrices could be treated with 0.1 molar acetic acid and incubated in polylysine, PBS, and/or collagen to coat the nylon. Polystyrene could be similarly treated using sulfuric acid.

In addition, the external surfaces of the three-dimensional framework may be modified to improve the attachment or growth of cells and differentiation of tissue, such as by plasma coating the framework or addition of one or more proteins (e.g., collagens, elastic fibers, reticular fibers), glycoproteins, glycosaminoglycans (e.g., heparin sulfate, chondroitin-4-sulfate, chondroitin-6-sulfate, dermatan sulfate, keratin sulfate), a cellular matrix, and/or other materials such as, but not limited to, gelatin, alginates, agar, agarose, and plant gums, among others.

In some embodiments, the scaffold is comprised of or is treated with materials that render it non-thrombogenic. These treatments and materials may also promote and sustain endothelial growth, migration, and extracellular matrix deposition. Examples of these materials and treatments include but are not limited to natural materials such as basement membrane proteins such as laminin and Type IV collagen, synthetic materials such as ePTFE, and segmented polyurethaneurea silicones, such as PURSPAN (The Polymer Technology Group, Inc., Berkeley, Calif.). These materials can be further treated to render the scaffold non-thrombogenic. Such treatments include anti-thrombotic agents such as heparin, and treatments which alter the surface charge of the material such as plasma coating.

Different proportions of the various types of collagen, for example, deposited on the framework can affect the growth of tissue-specific or other cells which may be later inoculated onto the framework or which may grow onto the structure in vivo. For example, for three-dimensional skin culture systems, collagen types I and III are preferably deposited in the initial matrix. Alternatively, the framework can be inoculated with a mixture of cells which synthesize the appropriate collagen types desired. Thus, depending upon the tissue to be cultured, the appropriate collagen type to be inoculated on the framework or produced by the cells seeded thereon may be selected. For example, the relative amounts of collagenic and elastic fibers present in the framework can be modulated by controlling the ratio of collagen-producing cells to elastin-producing cells in the initial inoculum. For example, since the inner walls of arteries are rich in elastin, an arterial scaffold should contain a co-culture of smooth muscle cells which secrete elastin.

The seeded or inoculated three-dimensional framework of the invention can be used in a variety of applications. These include but are not limited to transplantation or implantation of either the cultured cells obtained from the matrix or the cultured matrix itself in vivo. The three-dimensional scaffolds may, according to the invention, be used to replace or augment existing tissue, to introduce new or altered tissue, to modify artificial prostheses, or to join together biological tissues or structures. For example, and not by way of limitation, specific embodiments of the invention include but are not limited to, flat structures and tubular three-dimensional tissue implants for repair or regeneration, for example, of the gastrointestinal tract, genitourinary tract, blood vessels, muscles, ligaments, tendons, skin, pelvic floor, fascia, and hernias.

PPDCs and PPDC products can be inoculated onto a flat scaffold. The scaffold is preferably incubated in culture medium prior to implantation. Two or more flat frameworks can be laid atop another and sutured together to generate a multilayer framework.

For example and not by way of limitation, the three-dimensional framework can be used to construct single and multi-layer tubular tissues in vitro that can serve as a replacement for damaged or diseased tubular tissue in vivo.

The following subsections describe the use of a seeded framework to prepare tubes comprising PPDCs and/or PPDC products that can be implanted into the body.

A scaffold can be cut into a strip (e.g., rectangular in shape) of which the width is approximately equal to the inner circumference of the tubular organ into which it will ultimately be inserted. The cells can be inoculated onto the scaffold and incubated by floating or suspending in liquid media. At the appropriate stage of confluence, the scaffold can be rolled up into a tube by joining the long edges together. The seam can be closed by suturing the two edges together using fibers of a suitable material of an appropriate diameter.

According to the invention, a scaffold can be formed as a tube, inoculated with PPDCs or PPDC products, and suspended in media in an incubation chamber. In order to prevent occlusion of the lumen, one of the open ends of the tubular framework can be affixed to a nozzle. Liquid media can be forced through this nozzle from a source chamber connected to the incubation chamber to create a current through the interior of the tubular framework. The other open end can be affixed to an outflow aperture which leads into a collection chamber from which the media can be recirculated through the source chamber. The tube can be detached from the nozzle and outflow aperture when incubation is complete. This method is described by Ballermann, B. J., et al., Int. Application No. WO 94/25584 and in U.S. application Ser. No. 08/430,768, both of which are incorporated herein by reference in its entirety.

In general, two three-dimensional frameworks can be combined into a tube in accordance with the invention using any of the following methods.

Two or more flat frameworks can be laid atop another and sutured together. This two-layer sheet can then be rolled up, and, as described above, joined together and secured.

One tubular scaffold that is to serve as the inner layer can be inoculated with PPDCs or PPDC products and incubated. A second scaffold can be grown as a flat strip with width slightly larger than the outer circumference of the tubular framework. After appropriate growth is attained, the flat framework can be wrapped around the outside of the tubular scaffold followed by closure of the seam of the two edges of the flat framework and, preferably, securing the flat framework to the inner tube.

Two or more tubular meshes of slightly differing diameters can be grown separately. The framework with the smaller diameter can be inserted inside the larger one and secured.

For each of these methods, more layers can be added by reapplying the method to the double-layered tube. The scaffolds can be combined at any stage of growth of the PPDCs, and incubation of the combined scaffolds can be continued when desirable. Scaffolds comprising PPDC products may be layered with scaffolds comprising PPDCs.

The lumenal aspect of the tubular construct can be comprised of or treated with materials that render the lumenal surface of the tubular scaffold non-thrombogenic. These treatments and materials may also promote and sustain endothelial growth, migration, and extracellular matrix deposition. Examples of these materials and treatments include but are not limited to natural materials such as basement membrane proteins such as laminin and Type IV collagen, synthetic materials such as ePTFE, and segmented polyurethaneurea silicones, such as PURSPAN (The Polymer Technology Group, Inc., Berkeley, Calif.). These materials can be further treated to render the lumenal surface of the tubular scaffold non-thrombogenic. Such treatments include anti-thrombotic agents such as heparin, and treatments which alter the surface charge of the material such as plasma coating.

Advanced bioreactors may be necessary to meet the complex requirements of in vitro engineering of functional skeletal tissues. Bioreactor systems with the ability to apply complex concurrent mechanical strains to three-dimensional matrices, for example, in conjunction with enhanced environmental and fluidic control are provided by Altman et al., J. Biomech. Eng., 124(6):742-749 (2002); U.S. Patent Application Publication No. 2002/0062151. For example but not by way of limitation, such a bioreactor system may be used in the development of a tissue-engineered tendon or ligament, e.g., anterior cruciate ligament.

According to the present invention, any suitable method can be employed to shape the three-dimensional culture to assume the conformation of the natural organ or tissue to be simulated. For example, a framework prepared in accordance with the invention may be "trimmed" to a pre-selected size for surgical repair of the damaged tissue. Trimming may be performed with the use of a sharp cutting implement, i.e., a scalpel, a pair of scissors or an arthroscopic device fitted with a cutting edge, using procedures well known in the art.

The three-dimensional frameworks can be shaped to assume a conformation which simulates the shape of a natural organ or tissue, such as soft tissue including but not limited to pelvic floor, bladder, fascia, skin, muscle, tendon, ligament, or vasculature (e.g., arteries, veins). These constructions simulate biological structures in vivo and may be readily implanted to repair hernias or to replace damaged or diseased tissues, including hernias, tendons, ligaments, skin, muscle, blood vessels, and components of the gastrointestinal tract, genitourinary tract (e.g., urethra, ureter).

In some embodiments, PPDCs or PPDC products are seeded on the scaffold in combination (e.g., as a co-culture or as separate layers of cells) with stem cells and/or cells of a soft tissue phenotype. The cells to be co-inoculated with the PPDCs will depend upon the tissue to be simulated. For example, PPDCs may be inoculated onto the scaffold with epithelial cells (e.g., cells of oral mucosa, gastrointestinal tract, nasal epithelium, respiratory tract epithelium, vaginal epithelium, corneal epithelium), bone marrow cells, adipocytes, stem cells, keratinocytes, vascular endothelial cells (e.g., aortic endothelial cells, coronary artery endothelial cells, pulmonary artery endothelial cells, iliac artery endothelial cells, microvascular endothelial cells, umbilical artery endothelial cells, umbilical vein endothelial cells, and endothelial progenitors (e.g., CD34+, CD34+/CD117+ cells)), bladder urothelial cells, smooth muscle cells, gastrointestinal cells, esophageal cells, larynx cells, mucosal cells, myoblasts, myocytes, stromal cells, and other soft tissue cells or progenitor cells.

The three-dimensional scaffold of the invention may be used in skin grafting. Preferably, the scaffold is about 0.5 to 3 millimeter thick and is in the form of a flat sheet. The scaffold is preferably seeded with PPDCs or PPDC products. The scaffolds may be co-inoculated with at least one of stem cells, epithelial cells, dermal fibroblasts, melanocytes, and keratinocytes. In some embodiments, keratinocytes form a layer over the PPDC-seeded framework. The scaffolds of the invention preferably comprise at least one of collagen, elastin, intercellular adhesion molecules, neural cell adhesion molecules, laminin, heparin binding growth factor, fibronectin, proteoglycan, tenascin, E-cahedrin, and fibrillin.

As another example, the three-dimensional scaffold may be used to generate muscle tissue. The scaffold is preferably seeded with PPDCs or PPDC products. The scaffolds may be co-inoculated with at least one of stem cells, myocytes, and myoblasts.

The three-dimensional framework may be modified so that the growth of cells and the production of tissue thereon or therein is enhanced, or so that the risk of rejection of the implant is reduced. Thus, one or more biologically active compounds, including, but not limited to, antiapoptotic agents, anti-inflammatories, angiogenic factors, immunosuppressants or growth factors, may be added to the framework.

Therapeutic Uses for Extracellular Matrix or Cell Fractions Derived from PPDCs

As an alternative to implanting the cells of the invention, or tissue produced therefrom, a subject in need of tissue repair, replacement, or augmentation may benefit from the administration of a PPDC product, such as extracellular matrix (ECM), conditioned medium, or a cell fraction of PPDCs.

In some embodiments, coculture of PPDCs with a scaffold deposits ECM onto the framework. Once ECM is secreted onto the framework, the cells may be removed. The ECM may be processed for further use, for example, as an injectable preparation. Scaffolds comprising the ECM may be used therapeutically. Alternatively, ECM may be collected from the scaffold. The collection of the ECM can be accomplished in a variety of ways, depending, for example, on whether the scaffold is biodegradable or non-biodegradable. For example, if the framework is non-biodegradable, the ECM can be removed by subjecting the framework to sonication, high pressure water jets, mechanical scraping, or mild treatment with detergents or enzymes, or any combination of the above.

If the framework is biodegradable, the ECM can be collected, for example, by allowing the framework to degrade or dissolve in solution. Alternatively, if the biodegradable framework is composed of a material that can itself be injected along with the ECM, the framework and the ECM product can be processed in toto for subsequent injection. Alternatively, the ECM can be removed from the biodegradable framework by any of the methods described above for collection of ECM from a non-biodegradable framework. All collection processes are preferably designed so as not to denature the ECM produced by the cells of the invention.

Once the ECM has been collected, it may be processed further. The ECM can be homogenized to fine particles using techniques well known in the art such as, for example, by sonication, so that they can pass through a surgical needle. ECM components can be crosslinked, if desired, by gamma irradiation. Preferably, the ECM can be irradiated between 0.25 to 2 mega rads to sterilize and crosslink the ECM. Chemical crosslinking using agents that are toxic, such as glutaraldehyde, is possible but not generally preferred.

Cell fractions prepared from the populations of the postpartum-derived cells also have many utilities. In one embodiment, whole cell lysates are prepared, e.g., by disrupting cells without subsequent separation of cell fractions. In another embodiment, a cell membrane fraction is separated from a soluble fraction of the cells by routine methods known in the art, e.g., centrifugation, filtration, or similar methods. Use of soluble cell fractions or supernatants in vivo allows the beneficial intracellular milieu to be used in a patient without triggering rejection or an adverse response. Methods of lysing cells are well-known in the art and include various means of freeze-thaw disruption, osmotic disruption, mechanical disruption, ultrasonic disruption, enzymatic disruption (e.g., hyaluronidase, dispase, proteases, and nucleases (for example, deoxyribonuclease and ribonuclease)), or chemical disruption (non-ionic detergents such as, for example, alkylaryl polyether alcohol (TRITON® X-100), octylphenoxy polyethoxyethanol (Rohm and Haas Philadelphia, Pa.), BRIJ-35, a polyethoxyethanol lauryl ether (Atlas Chemical Co., San Diego, Calif.), polysorbate 20 (TWEEN 20®), a polyethoxyethanol sorbitan monolaureate (Rohm and Haas), polyethylene lauryl ether (Rohm and Haas); and ionic detergents such as, for example, sodium dodecyl sulphate, sulfated higher aliphatic alcohols, sulfonated alkanes and sulfonated alkylarenes containing 7 to 22 carbon atoms in a branched or unbranched chain), or combinations thereof. Such cell lysates may be prepared from cells directly in their growth medium and thus containing secreted growth factors and the like, or may be prepared from cells washed free of medium in, for example, PBS or other solution. Cells may also be lysed on their growth substrate. Washed cells may be resuspended at concentrations greater than the original population density if preferred. Cell lysates prepared from populations of postpartum-derived cells may be used as is, further concentrated, by for example, ultrafiltration or lyophilization, or even dried, partially purified, combined with pharmaceutically acceptable carriers or diluents as are known in the art, or combined with other compounds such as biologicals, for example pharmaceutically useful protein compositions. In some embodiments, cellular membranes are removed from the lysate, for example by centrifugation, or ultracentrifugation, filtration, chromatograph, or sedimentation, to yield a membrane fraction and supernate fraction. The membrane fraction or the supernate may be used according to the methods of the invention. In some embodiments, cellular debris is removed by treatment with a mild detergent rinse, such as EDTA, CHAPS or a zwitterionic detergent. Cell lysates may be used in vitro or in vivo, alone or, for example, with cells or on a substrate. The cell lysates, if introduced in vivo, may be introduced locally at a site of treatment, or remotely to provide, for example needed cellular growth factors to a patient.

The amounts and/or ratios of proteins may be adjusted by mixing the PPDC product of the invention with cells or with ECM or cell fraction of one or more other cell types. In addition, biologically active substances such as proteins, growth factors and/or drugs, can be incorporated into the PPDC product formulation. Exemplary biologically active substances include anti-inflammatory agents and growth factors which promote healing and tissue repair. Cells may be co-administered with the PPDC products of the invention.

The above described process for preparing PPDC products is preferably carried out under sterile conditions using sterile materials. The processed PPDC product in a pharmaceutically acceptable carrier can be injected intradermally, intraarticularly, or subcutaneously to augment tissue or to repair or correct congenital anomalies, acquired defects or cosmetic defects.

Examples of such conditions are congenital anomalies such as hemifacial microsomia, malar and zygomatic hypoplasia, unilateral mammary hypoplasia, pectus excavatum, pectoralis agenesis (Poland's anomaly) and velopharyngeal incompetence secondary to cleft palate repair or submucous cleft palate (as a retropharyngeal implant); acquired defects (post-traumatic, post-surgical, post-infectious) such as scars, subcutaneous atrophy (e.g., secondary to discoid lupus erythematosus), keratotic lesions, acne pitting of the face, linear scleroderma with subcutaneous atrophy, saddle-nose deformity, Romberg's disease, and unilateral vocal cord paralysis; cosmetic defects such as glabellar frown lines, deep nasolabial creases, circum-oral geographical wrinkles, sunken cheeks and mammary hypoplasia; hernias; tears or ruptures of a tendon or ligament; severe burns, skin ulcers (e.g., decubitus (pressure) ulcers, venous ulcers, and diabetic ulcers), and surgical wounds such as those associated with the excision of skin cancers; vascular diseases such as peripheral arterial disease, abdominal aortic aneurysm, carotid disease, and venous disease; muscle diseases (e.g., congenital myopathies; myasthenia gravis; inflammatory, neurogenic, and myogenic muscle diseases; and muscular dystrophies such as Duchenne muscular dystrophy, Becker muscular dystrophy, myotonic dystrophy, limb-girdle-muscular dystrophy, facioscapulohumeral muscular dystrophy, congenital muscular dystrophies, oculopharyngeal muscular dystrophy, distal muscular dystrophy, and Emery-Dreifuss muscular dystrophy); and replacement and repair of connective tissues such as tendons and ligaments.

Use of PPDCs for In Vitro Screening of Drug Efficacy or Toxicity

The cells and tissues of the invention may be used in vitro to screen for effectiveness as a trophic support or for cytotoxicity of compounds including pharmaceutical agents, growth/regulatory factors, and anti-inflammatory agents. To this end, the cells of the invention, are maintained in vitro and exposed to the compound to be tested. The activity of a cytotoxic compound can be measured by its ability to damage or kill cells in culture. This may readily be assessed by vital staining techniques. The effect of trophic factors may be assessed by analyzing the number of living cells in vitro, e.g., by total cell counts, and differential cell counts or by detecting a marker of differentiation. This may be accomplished using standard cytological and/or histological techniques, including the use of immunocytochemical techniques employing antibodies that define type-specific cellular antigens. The effect of various drugs on the cells of the invention either in suspension culture or in the three-dimensional system described above may be assessed.

The cells and tissues of the invention may be used as model systems for the study of soft tissue conditions.

The cells and tissues of the invention may also be used to study the mechanism of action of cytokines, growth factors and inflammatory mediators, e.g., IL-1, TNF and prostaglandins. In addition, cytotoxic and/or pharmaceutical agents can be screened for those that are most efficacious for a particular patient. Agents that prove to be efficacious in vitro could then be used to treat the patient therapeutically.

Use of PPDCs to Produce Biological Molecules

In a further embodiment, the cells of the invention can be cultured in vitro to produce biological products in high yield. For example, such cells, which either naturally produce a particular biological product of interest (e.g., a growth factor, regulatory factor, or peptide hormone), or have been genetically engineered to produce a biological product, could be clonally expanded using, for example, the three-dimensional culture system described above. If the cells excrete the biological product into the nutrient medium, the product can be readily isolated from the spent or conditioned medium using standard separation techniques, e.g., such as differential protein precipitation, ion-exchange chromatography, gel filtration chromatography, electrophoresis, and high performance liquid chromatography. A "bioreactor" may be used to take advantage of the flow method for feeding, for example, a three-dimensional culture in vitro.

Essentially, as fresh media is passed through the three-dimensional culture, the biological product is washed out of the culture and may then be isolated from the outflow, as above.

Alternatively, a biological product of interest may remain within the cell and, thus, its collection may require that the cells are lysed. The biological product may then be purified using any one or more of the above-listed techniques.

Kits

The PPDCs and PPDC products can conveniently be employed as part of a kit, for example, for culture or in vivo administration. Accordingly, the invention provides a kit including the PPDCs and/or PPDC products and additional components, such as a matrix (e.g., a scaffold), hydrating agents (e.g., physiologically-compatible saline solutions, prepared cell culture media), cell culture substrates (e.g., culture dishes, plates, vials, etc.), cell culture media (whether in liquid or powdered form), antibiotic compounds, hormones, a bioactive factor, a second cell type, a differentiation-inducing agent, cell culture media, and the like. While the kit can include any such components, preferably it includes all ingredients necessary for its intended use. If desired, the kit also can include cells (typically cryopreserved), which can be seeded into the lattice as described herein.

In another aspect, the invention provides kits that utilize the PPDCs, PPDC populations, products of PPDCs in various methods for augmentation, regeneration, and repair as described above. In some embodiments, the kits may include one or more cell populations, including at least PPDCs and a pharmaceutically acceptable carrier (liquid, semi-solid or solid). The kits also optionally may include a means of administering the cells, for example by injection. The kits further may include instructions for use of the cells. Kits prepared for field hospital use, such as for military use, may include full-procedure supplies including tissue scaffolds, surgical sutures, and the like, where the cells are to be used in conjunction with repair of acute injuries. Kits for assays and in vitro methods as described herein may contain one or more of (1) PPDCs or products of PPDCs, (2) reagents for practicing the in vitro method, (3) other cells or cell populations, as appropriate, and (4) instructions for conducting the in vitro method.

Cryopreservation and Banking PPDCs

PPDCs of the invention can be cryopreserved and maintained or stored in a "cell bank". Cryopreservation of cells of the invention may be carried out according to known methods. For example, but not by way of limitation, cells may be suspended in a "freeze medium" such as, for example, culture medium further comprising 0 to 95 percent FBS and 0 to 10 percent dimethylsulfoxide (DMSO), with or without 5 to 10 percent glycerol, at a density, for example, of about 0.5 to $10 \times 10^6$ cells per milliliter. The cryopreservation medium may comprise cryopreservation agents including but not limited to methylcellulose. The cells are dispensed into glass or plastic ampoules that are then sealed and transferred to the freezing chamber of a controlled rate freezer. The optimal rate of freezing may be determined empirically. A programmable rate freezer for example, can give a change in temperature of −1 to −10° C. per minute. The preferred cryopreservation temperature is about −80° C. to about −180° C., more preferably is about −90° C. to about −160° C., and most preferably is about −125 to about −140° C. Cryopreserved cells preferably are transferred to liquid nitrogen prior to thawing for use. In some embodiments, for example, once the ampoules have reached about −90° C., they are transferred to a liquid nitrogen storage area. Cryopreserved cells can be stored for a period of years. Alternatively, cells could be freeze-dried using agents such as but not limited to trehalose, sucrose, maltose, and sorbitol.

The cryopreserved cells of the invention constitute a bank of cells, portions of which can be "withdrawn" by thawing and then used as needed. Thawing should generally be carried out rapidly, for example, by transferring an ampoule from liquid nitrogen to a 37° C. water bath. The thawed contents of the ampoule should be immediately transferred under sterile conditions to a culture vessel containing an appropriate medium such as DMEM conditioned with 10 percent FBS.

In another aspect, the invention provides for banking of tissues, cells, PPDC derivatives, and cell populations in freeze-dried form. A trehalose pre-incubation step is necessary to achieve this. In addition to trehalose, sucrose or other additives might be used. This will allow the generation of room temperature stable products with long shelf lives.

The following examples describe several aspects of embodiments of the invention in greater detail. These examples are provided to further illustrate, not to limit, aspects of the invention described herein.

EXAMPLES

Example 1

Derivation of Cells from Postpartum Tissues

The objective of this study was to derive populations of cells from placental and umbilicus tissues. Postpartum umbilicus and placenta were obtained upon birth of either a full term or pre-term pregnancy. Cells were harvested from 5 separate donors of umbilicus and placental tissue. Different methods of cell isolation were tested for their ability to yield cells with: 1) the potential to differentiate into cells with different phenotypes, or 2) the potential to provide critical trophic factors useful for other cells and tissues.

Methods & Materials

Umbilicus Cell Derivation.

Umbilical cords were obtained from National Disease Research Interchange (NDRI, Philadelphia, Pa.). The tissues were obtained following normal deliveries. The cell isolation protocol was performed aseptically in a laminar flow hood. To remove blood and debris, the umbilicus was washed in phosphate buffered saline (PBS; Invitrogen, Carlsbad, Calif.) in the presence of antimycotic and antibiotic (100 Units/milliliter penicillin, 100 micrograms/milliliter streptomycin, 0.25 micrograms/milliliter amphotericin B) (Invitrogen Carlsbad, Calif.)). The tissues were then mechanically dissociated in 150 cm$^2$ tissue culture plates in the presence of 50 milliliters of medium (DMEM-Low glucose or DMEM-High glucose; Invitrogen) until the tissue was minced into a fine pulp. The chopped tissues were transferred to 50 milliliter conical tubes (approximately 5 grams of tissue per tube). The tissue was then digested in either DMEM-Low glucose medium or DMEM-High glucose medium, each containing antimycotic and antibiotic (100 Units/milliliter penicillin, 100 micrograms/milliliter streptomycin, 0.25 micrograms/milliliter amphotericin B (Invitrogen)) and digestion enzymes. In some experiments, an enzyme mixture of collagenase and dispase was used ("C:D;" collagenase (Sigma, St Louis, Mo.), 500 Units/milliliter; and dispase (Invitrogen), 50 Units/milliliter in DMEM-Low glucose medium). In other experiments a mixture of collagenase, dispase and hyaluronidase ("C:D:H") was used (collagenase, 500 Units/milliliter; dispase, 50 Units/milliliter; and hyaluronidase (Sigma), 5 Units/milliliter, in DMEM-Low glucose). The conical tubes containing the tissue, medium and digestion enzymes were incubated at 37° C. in an orbital shaker (Environ, Brooklyn, N.Y.) at 225 rpm for 2 hrs.

After digestion, the tissues were centrifuged at 150×g for 5 minutes, and the supernatant was aspirated. The pellet was resuspended in 20 milliliters of Growth medium (DMEM-Low glucose (Invitrogen), 15 percent (v/v) fetal bovine serum (FBS; defined bovine serum; Lot#AND18475; Hyclone, Logan, Utah), 0.001% (v/v) 2-mercaptoethanol (Sigma), 100 Units/milliliter of penicillin, 100 microgram/milliliter streptomycin, 0.25 microgram/milliliter amphotericin B (Invitrogen, Carlsbad, Calif.). The cell suspension was filtered through a 70-micrometer nylon cell strainer (BD Biosciences). An additional 5 milliliter rinse comprising Growth medium was passed through the strainer. The cell suspension was then passed through a 40-micrometer nylon cell strainer (BD Biosciences) and chased with a rinse of an additional 5 milliliters of Growth medium.

The filtrate was resuspended in Growth medium (total volume 50 milliliters) and centrifuged at 150×g for 5 minutes. The supernatant was aspirated, and the cells were resuspended in 50 milliliters of fresh Growth medium. This process was repeated twice more.

Upon the final centrifugation supernatant was aspirated and the cell pellet was resuspended in 5 milliliters of fresh Growth medium. The number of viable cells was determined using Trypan Blue staining. Cells were then cultured under standard conditions.

The cells isolated from umbilicus were seeded at 5,000 cells/cm$^2$ onto gelatin-coated T-75 cm$^2$ flasks (Corning Inc., Corning, N.Y.) in Growth medium (DMEM-Low glucose (Invitrogen), 15 percent (v/v) defined bovine serum (Hyclone, Logan, Utah; Lot#AND18475), 0.001 percent (v/v) 2-mercaptoethanol (Sigma), 100 Units/milliliter penicillin, 100 micrograms/milliliter streptomycin, 0.25 micrograms/milliliter amphotericin B (Invitrogen)). After about 2-4 days, spent medium was aspirated from the flasks. Cells were washed with PBS three times to remove debris and blood-derived cells. Cells were then replenished with Growth medium and allowed to grow to confluence (about 10 days from passage 0 to passage 1). On subsequent passages (from passage 1 to 2, etc.), cells reached sub-confluence (75-85 percent confluence) in 4-5 days. For these subsequent passages, cells were seeded at 5000 cells/cm$^2$. Cells were grown in a humidified incubator with 5 percent carbon dioxide and 20 percent oxygen at 37° C.

Placental Cell Isolation.

Placental tissue was obtained from NDRI (Philadelphia, Pa.). The tissues were from a pregnancy and were obtained at the time of a normal surgical delivery. Placental cells were isolated as described for umbilicus cell isolation.

The following example applies to the isolation of separate populations of maternal-derived and neonatal-derived cells from placental tissue.

The cell isolation protocol was performed aseptically in a laminar flow hood. The placental tissue was washed in phosphate buffered saline (PBS; Invitrogen, Carlsbad, Calif.) in the presence of antimycotic and antibiotic (100 Units/milliliter penicillin, 100 microgram/milliliter streptomycin, 0.25 microgram/milliliter amphotericin B; Invitrogen) to remove blood and debris. The placental tissue was then dissected into three sections: top-line (neonatal side or aspect), mid-line (mixed cell isolation neonatal and maternal or villous region), and bottom line (maternal side or aspect).

The separated sections were individually washed several times in PBS with antibiotic/antimycotic to further remove blood and debris. Each section was then mechanically dissociated in 150 cm$^2$ tissue culture plates in the presence of 50 milliliters of DMEM-Low glucose (Invitrogen) to a fine pulp. The pulp was transferred to 50 milliliter conical tubes. Each tube contained approximately 5 grams of tissue. The tissue was digested in either DMEM-Low glucose or DMEM-High glucose medium containing antimycotic and antibiotic (100 Units/milliliter penicillin, 100 micrograms/milliliter streptomycin, 0.25 micrograms/milliliter amphotericin B (Invitrogen)) of PBS and digestion enzymes. In some experiments an enzyme mixture of collagenase and dispase ("C:D") was used containing collagenase (Sigma, St Louis, Mo.) at 500 Units/milliliter and dispase (Invitrogen) at 50 Units/milliliter in DMEM-Low glucose medium. In other experiments a mixture of collagenase, dispase, and hyaluronidase (C:D:H) was used (collagenase, 500 Units/milliliter; dispase, 50 Units/milliliter; and hyaluronidase (Sigma), 5 Units/milliliter in DMEM-Low glucose). The conical tubes containing the tissue, medium, and digestion enzymes were incubated for 2 h at 37° C. in an orbital shaker (Environ, Brooklyn, N.Y.) at 225 rpm.

After digestion, the tissues were centrifuged at 150×g for 5 minutes, the resultant supernatant was aspirated off. The pellet was resuspended in 20 milliliter of Growth medium (DMEM-Low glucose (Invitrogen), 15% (v/v) fetal bovine serum (FBS; defined bovine serum; Lot#AND18475; Hyclone, Logan, Utah), 0.001% (v/v) 2-mercaptoethanol (Sigma, St. Louis, Mo.), antibiotic/antimycotic (100 Units/milliliter penicillin, 100 microgram/milliliter streptomycin, 0.25 microgram/milliliter amphotericin B; Invitrogen)). The cell suspension was filtered through a 70 micrometer nylon cell strainer (BD Biosciences), chased by a rinse with an additional 5 milliliters of Growth medium. The total cell suspension was passed through a 40 micrometer nylon cell strainer (BD Biosciences) followed with an additional 5 milliliters of Growth medium as a rinse.

The filtrate was resuspended in Growth medium (total volume 50 milliliters) and centrifuged at 150×g for 5 minutes. The supernatant was aspirated and the cell pellet was resuspended in 50 milliliters of fresh Growth medium. This process was repeated twice more. After the final centrifugation, supernatant was aspirated and the cell pellet was resuspended in 5 milliliters of fresh Growth medium. A cell count was determined using the Trypan Blue Exclusion test. Cells were then cultured at standard conditions.

LIBERASE (Boehringer Mannheim Corp., Indianapolis, Ind.) Cell Isolation.

Cells were isolated from umbilicus in DMEM-Low glucose medium with LIBERASE (Boehringer Mannheim Corp., Indianapolis, Ind.) (2.5 milligrams per milliliter, Blendzyme 3; Roche Applied Sciences, Indianapolis, Ind.) and hyaluronidase (5 Units/milliliter, Sigma). Digestion of the tissue and isolation of the cells was as described for other protease digestions above using a LIBERASE (Boehringer Mannheim Corp., Indianapolis, Ind.)/hyaluronidase mixture in place of the C:D or C:D:H enzyme mixture. Tissue digestion with LIBERASE (Boehringer Mannheim Corp., Indianapolis, Ind.) resulted in the isolation of cell populations from postpartum tissues that expanded readily.

Cell Isolation Using Other Enzyme Combinations.

Procedures were compared for isolating cells from the umbilicus using differing enzyme combinations. Enzymes compared for digestion included: i) collagenase; ii) dispase; iii) hyaluronidase; iv) collagenase:dispase mixture (C;D); v) collagenase:hyaluronidase mixture (C:H); vi) dispase:hyaluronidase mixture (D:H); and vii) collagenase:dispase:hyaluronidase mixture (C:D:H). Differences in cell isolation utilizing these different enzyme digestion conditions were observed (Table 1-1).

Isolation of Cells from Residual Blood in the Cords.

Attempts were made to isolate pools of cells from umbilicus by different approaches. In one instance umbilical cord was sliced and washed with Growth medium to dislodge the blood clots and gelatinous material. The mixture of blood, gelatinous material, and Growth medium was collected and centrifuged at 150×g. The pellet was resuspended and seeded onto gelatin-coated flasks in Growth medium. From these experiments a cell population was isolated that readily expanded.

Isolation of Cells from Cord Blood.

Cells have also been isolated from cord blood samples attained from NDRI. The isolation protocol used here was that of International Patent Application PCT/US2002/029971 by Ho et al. Samples (50 milliliters and 10.5 milliliters, respectively) of umbilical cord blood (NDRI, Philadelphia Pa.) were mixed with lysis buffer (filter-sterilized 155 millimolar ammonium chloride, 10 millimolar potassium bicarbonate, 0.1 millimolar EDTA buffered to pH 7.2 (all components from Sigma, St. Louis, Mo.)). Cells were lysed at a ratio of 1:20 cord blood to lysis buffer. The resulting cell suspension was vortexed for 5 seconds, and incubated for 2 minutes at ambient temperature. The lysate was centrifuged (10 minutes at 200×g). The cell pellet was resuspended in complete minimal essential medium (Gibco, Carlsbad Calif.) containing 10 percent fetal bovine serum (Hyclone, Logan Utah), 4 millimolar glutamine (Mediatech Herndon, Va.), 100 Units penicillin per 100 milliliters and 100 micrograms streptomycin per 100 milliliters (Gibco, Carlsbad, Calif.). The resuspended cells were centrifuged (10 minutes at 200×g), the supernatant was aspirated, and the cell pellet was washed in complete medium. Cells were seeded directly into either T75 flasks (Corning, N.Y.), T75 laminin-coated flasks, or T175 fibronectin-coated flasks (both Becton Dickinson, Bedford, Mass.).

Isolation of Postpartum-Derived Cells using Different Enzyme Combinations and Growth Conditions.

To determine whether cell populations can be isolated under different conditions and expanded under a variety of conditions immediately after isolation, cells were digested in Growth medium with or without 0.001 percent (v/v) 2-mercaptoethanol (Sigma, St. Louis, Mo.), using the enzyme combination of C:D:H, according to the procedures provided above. Placenta-derived cells so isolated were seeded under a variety of conditions. All cells were grown in the presence of penicillin/streptomycin. (Table 1-2).

In all conditions, cells attached and expanded well between passage 0 and 1 (Table 1-2). Cells in conditions 5 to 8 and 13 to 16 were demonstrated to proliferate well up to 4 passages after seeding at which point they were cryopreserved. All cells were banked.

Results

Cell Isolation Using Different Enzyme Combinations.

The combination of C:D:H provided the best cell yield following isolation and generated cells which expanded for many more generations in culture than the other conditions (Table 1-1). An expandable cell population was not attained using collagenase or hyaluronidase alone. No attempt was made to determine if this result is specific to the collagen that was tested.

Isolation of Postpartum-Derived Cells using Different Enzyme Combinations and Growth Conditions.

Cells attached and expanded well between passage 0 and 1 under all conditions tested for enzyme digestion and growth (Table 1-2). Cells in experimental conditions 5-8 and 13-16 proliferated well up to 4 passages after seeding, at which point they were cryopreserved. All cells were banked.

Isolation of Cells from Residual Blood in the Cords.

Nucleated cells attached and grew rapidly. These cells were analyzed by flow cytometry and were similar to cells obtained by enzyme digestion.

Isolation of Cells from Cord Blood.

The preparations contained red blood cells and platelets. No nucleated cells attached and divided during the first 3 weeks. The medium was changed 3 weeks after seeding and no cells were observed to attach and grow.

Summary.

Populations of cells can be isolated from umbilical cord and placental tissue most efficiently using the enzyme combination collagenase (a matrix metalloprotease), dispase (neutral protease), and hyaluronidase (a mucolytic enzyme which breaks down hyaluronic acid). LIBERASE (Boehringer Mannheim Corp., Indianapolis, Ind.), which is a Blendzyme, may also be used. In the present study Blendzyme 3 which is collagenase (4 Wunsch units/g) and thermolysin (1714 casein Units/g) was also used together with hyaluronidase to isolate cells. These cells expand readily over many passages when cultured in Growth medium on gelatin-coated plastic.

Postpartum-derived cells were isolated from residual blood in the cords but not from cord blood. The presence of cells in blood clots washed from the tissue that adhere and grow under the conditions used may be due to cells being released during the dissection process.

TABLE 1-1

Isolation of cells from umbilical cord tissue using varying enzyme combinations

| Enzyme Digest | Cells Isolated | Cell Expansion |
|---|---|---|
| Collagenase | X | X |
| Dispase | + (>10 h) | + |
| Hyaluronidase | X | X |
| Collagenase:Dispase | ++ (<3 h) | ++ |
| Collagenase:Hyaluronidase | ++ (<3 h) | + |
| Dispase:Hyaluronidase | + (>10 h) | + |
| Collagenase:Dispase:Hyaluronidase | +++ (<3 h) | +++ |

Key:
+ = good,
++ = very good,
+++ = excellent,
X = no success

REFERENCE

1. Ho et al., WO2003/025149 A2, CELL POPULATIONS WHICH CO-EXPRESS CD49C AND CD90, NEURONYX, INC., Application No. PCT/US02/29971, Filed 2002 Sep. 20, A2 Published 2003 Mar. 27, A3 Published 2003 Dec. 18.

Example 2

Evaluation of Growth Media for Postpartum-Derived Cells

Several cell culture media were evaluated for their ability to support the growth of placenta-derived cells. The growth of placenta-derived cells in normal (20%) and low (5%) oxygen was assessed after 3 days using the MTS calorimetric assay.

Methods & Materials

Placenta-derived cells at passage 8 (P8) were seeded at $1 \times 10^3$ cells/well in 96 well plates in Growth medium (DMEM-low glucose (Gibco, Carlsbad Calif.), 15% (v/v) fetal bovine serum (Cat. #SH30070.03; Hyclone, Logan, Utah), 0.001% (v/v) betamercaptoethanol (Sigma, St. Louis, Mo.), 50 Units/milliliter penicillin, 50 micrograms/milliliter streptomycin (Gibco)). After 8 hours, the medium was changed as described in Table 2-1, and cells were incubated in normal (20%, v/v) or low (5%, v/v) oxygen at 37° C., 5% $CO_2$ for 48 hours. MTS was added to the culture medium (CELLTITER 96 AQueous One Solution Cell Proliferation Assay, Promega, Madison, Wis.) for 3 hours and the absorbance measured at 490 nanometers (Molecular Devices, Sunnyvale Calif.).

TABLE 1-2

Isolation and culture expansion of postpartum-derived cells under varying conditions:

| Condition | Medium | 15% FBS | BME | Gelatin | 20% O2 | Growth Factors |
|---|---|---|---|---|---|---|
| 1 | DMEM-Lg | Y | Y | Y | Y | N |
| 2 | DMEM-Lg | Y | Y | Y | N (5%) | N |
| 3 | DMEM-Lg | Y | Y | N | Y | N |
| 4 | DMEM-Lg | Y | Y | N | N (5%) | N |
| 5 | DMEM-Lg | N (2%) | Y | N (Laminin) | Y | EGF/FGF (20 ng/mL) |
| 6 | DMEM-Lg | N (2%) | Y | N (Laminin) | N (5%) | EGF/FGF (20 ng/mL) |
| 7 | DMEM-Lg | N (2%) | Y | N (Fibronectin) | Y | PDGF/VEGF |
| 8 | DMEM-Lg | N (2%) | Y | N (Fibronectin) | N (5%) | PDGF/VEGF |
| 9 | DMEM-Lg | Y | N | Y | Y | N |
| 10 | DMEM-Lg | Y | N | Y | N (5%) | N |
| 11 | DMEM-Lg | Y | N | N | Y | N |
| 12 | DMEM-Lg | Y | N | N | N (5%) | N |
| 13 | DMEM-Lg | N (2%) | N | N (Laminin) | Y | EGF/FGF (20 ng/mL) |
| 14 | DMEM-Lg | N (2%) | N | N (Laminin) | N (5%) | EGF/FGF (20 ng/mL) |
| 15 | DMEM-Lg | N (2%) | N | N (Fibronectin) | Y | PDGF/VEGF |
| 16 | DMEM-Lg | N (2%) | N | N (Fibronectin) | N (5%) | PDGF/VEGF |

TABLE 2-1

Culture medium

| Culture Medium | Supplier | Added fetal bovine serum % (v/v) |
| --- | --- | --- |
| DMEM-low glucose | Gibco Carlsbad CA | 0, 2, 10 |
| DMEM-high glucose | Gibco | 0, 2, 10 |
| RPMI 1640 | Mediatech, Inc. Herndon, VA | 0, 2, 10 |
| Cell gro-free (Serum-free, Protein-free) | Mediatech, Inc. | — |
| Ham's F10 | Mediatech, Inc. | 0, 2, 10 |
| MSCGM (complete with serum) | Cambrex, Walkersville, MD | 0, 2, 10 |
| Complete-serum free w/albumin | Mediatech, Inc. | — |
| Growth medium | NA | — |
| Ham's F12 | Mediatech, Inc. | 0, 2, 10 |
| Iscove's | Mediatech, Inc. | 0, 2, 10 |
| Basal Medium Eagle's | Mediatech, Inc. | 0, 2, 10 |
| DMEM/F12 (1:1) | Mediatech, Inc. | 0, 2, 10 |

Results

Standard curves for the MTS assay established a linear correlation between an increase in absorbance and an increase in cell number. The absorbance values obtained were converted into estimated cell numbers and the change (%) relative to the initial seeding was calculated.

The Effect of Serum.

The addition of serum to media at normal oxygen conditions resulted in a reproducible dose-dependent increase in absorbance and thus the viable cell number. The addition of serum to complete MSCGM resulted in a dose-dependent decrease in absorbance. In the media without added serum, cells grew in Cellgro, Ham's F10, and DMEM.

The Effect of Oxygen.

Reduced oxygen appeared to increase the growth rate of cells in Growth Medium, Ham's F10, and MSCGM.

In decreasing order of growth, the media resulting in the best growth of the cells were Growth medium>MSCGM>Iscove's+10% FBS=DMEM-HG+10% FBS=Ham's F12+10% FBS=RPMI 1640+10% FBS.

Summary.

Postpartum-derived cells may be grown in a variety of culture media in normal or low oxygen. Short-term growth of placenta-derived cells was determined in 12 basal media with 0, 2, and 10% (v/v) serum in 5% or 20% $O_2$. In general placenta-derived cells did not grow in serum-free conditions with the exceptions of Ham's F10 and Cellgro-free, which are also protein-free. Growth in these serum-free media was approximately 25-33% of the maximal growth observed with Growth medium containing 15% serum. This study demonstrates that placenta-derived cells may be grown in serum-free conditions and that Growth medium is one of several media (10% serum in Iscove's, RPMI or Ham's F12 media) that can be used to grow placenta-derived cells.

The most promising serum-free media was CELLGRO-FREE, a serum and protein-free medium without hormones or growth factors, which is designed for the growth of mammalian cells in vitro (Mediatech product information).

Complete-serum free medium also developed for serum-free culture was not as effective in supporting growth of the placenta-derived cells. Complete-serum free was developed by Mediatech, based on a 50/50 mix of DMEM/F12 with smaller percentages of RPMI 1640 and McCoy's 5A. This medium also contains selected trace elements and high molecular weight carbohydrates, extra vitamins, a non-animal protein source, and a small amount of BSA (1 gram/liter). It does not contain any insulin, transferrin, cholesterol, or growth or attachment factors. It is bicarbonate buffered for use with 5% $CO_2$. Originally designed for hybridomas and suspension cell lines, it may be suitable for some anchorage dependent cell lines.

Example 3

Growth of Postpartum-Derived Cells in Medium Containing D-Valine

It has been reported that medium containing D-valine instead of the normal L-valine isoform can be used to selectively inhibit the growth of fibroblast-like cells in culture (Hongpaisan, 2000; Sordillo et al., 1988). The growth of postpartum-derived cells in medium containing D-valine in the absence of L-valine was evaluated.

Methods & Materials

Placenta-derived cells (P3), fibroblasts (P9), and umbilicus-derived cells (P5) were seeded at $5 \times 10^3$ cells/cm$^2$ in gelatin-coated T75 flasks (Corning, Corning, N.Y.). After 24 hours the medium was removed and the cells were washed with phosphate buffered saline (PBS) (Gibco, Carlsbad, Calif.) to remove residual medium. The medium was replaced with a Modified Growth medium (DMEM with D-valine (special order Gibco), 15% (v/v) dialyzed fetal bovine serum (Hyclone, Logan, Utah), 0.001% (v/v) beta-mercaptoethanol (Sigma), 50 Units/milliliter penicillin, 50 micrograms/milliliter streptomycin (Gibco)).

Results

Placenta-derived, umbilicus-derived, and fibroblast cells seeded in the D-valine-containing medium did not proliferate, unlike cells seeded in Growth medium containing dialyzed serum. Fibroblasts changed morphologically, increasing in size and changing shape. All of the cells died and eventually detached from the flask surface after 4 weeks.

Summary.

Postpartum-derived cells require L-valine for cell growth and for long-term viability. L-valine is preferably not removed from the growth medium for postpartum-derived cells.

REFERENCES

Hongpaisan J. (2000) Inhibition of proliferation of contaminating fibroblasts by D-valine in cultures of smooth muscle cells from human myometrium. Cell Bio. Int. 24:1-7.

Sordillo L M, Oliver S P, Akers R M. (1988) Culture of bovine mammary epithelial cells in D-valine modified medium: selective removal of contaminating fibroblasts. Cell Biol. Int. Rep. 12:355-64.

Example 4

Cryopreservation Media for Postpartum-Derived Cells

The objective of this study was to determine a suitable cryopreservation medium for the cryopreservation of postpartum-derived cells.

Methods & Materials

Placenta-derived cells grown in Growth medium (DMEM-low glucose (Gibco, Carlsbad Calif.), 15% (v/v) fetal bovine serum (Cat. #SH30070.03, Hyclone, Logan, Utah), 0.001% (v/v) betamercaptoethanol (Sigma, St. Louis, Mo.), 50 Units/milliliter penicillin, 50 microgram/milliliter streptomycin (Gibco)), in a gelatin-coated T75 flask were washed with phosphate buffered saline (PBS; Gibco) and trypsinized using 1 milliliter Trypsin/EDTA (Gibco). The trypsinization was stopped by adding 10 milliliters Growth medium. The cells were centrifuged at 150×g, supernatant removed, and the cell pellet was resuspended in 1 milliliter Growth medium. An aliquot of cell suspension, 60 microliter, was removed and added to 60 microliter trypan blue (Sigma). The viable cell number was estimated using a hemocytometer. The cell suspension was divided into four equal aliquots each containing $88 \times 10^4$ cells each. The cell suspension was centrifuged and resuspended in 1 milliliter of each media below and transferred into Cryovials (Nalgene).

1.) Growth medium+10% (v/v) DMSO (Hybrimax, Sigma, St. Louis, Mo.)
2.) Cell Freezing medium w/DMSO, w/methylcellulose, serum-free (C6295, Sigma, St. Louis, Mo.)
3.) Cell Freezing medium serum-free (C2639, Sigma, St. Louis, Mo.)
4.) Cell Freezing Medium w/glycerol (C6039, Sigma, St. Louis, Mo.)

The cells were cooled at approximately 1° C./min overnight in a −80° C. freezer using a "Mr Frosty" freezing container according to the manufacturer's instructions (Nalgene, Rochester, N.Y.). Vials of cells were transferred into liquid nitrogen for 2 days before thawing rapidly in a 37° C. water bath. The cells were added to 10 milliliters Growth medium and centrifuged before the cell number and viability was estimated as before. Cells were seeded onto gelatin-coated flasks at 5,000 cells/cm$^2$ to determine whether the cells would attach and proliferate.

Results

The initial viability of the cells to be cryopreserved was assessed by trypan blue staining to be 100%.

There was a commensurate reduction in cell number with viability for C6295 due to cells lysis. The viable cells cryopreserved in all four solutions attached, divided, and produced a confluent monolayer within 3 days. There was no discernable difference in estimated growth rate.

Summary.

The cryopreservation of cells is one procedure available for preparation of a cell bank or a cell product. Four cryopreservation mixtures were compared for their ability to protect human placenta-derived cells from freezing damage. Dulbecco's modified Eagle's medium (DMEM) and 10% (v/v) dimethylsulfoxide (DMSO) is the preferred medium of those compared for cryopreservation of placenta-derived cells.

Example 5

Growth Characteristics of Postpartum-Derived Cells

The cell expansion potential of postpartum-derived cells was compared to other populations of isolated stem cells. The art of cell expansion to senescence is referred to as Hayflick's limit (Hayflick L. The longevity of cultured human cells. *J. Am. Geriatr. Soc.* 22(1):1-12, 1974; Hayflick L. The strategy of senescence. *Gerontologist* 14(1):37-45), 1974). Postpartum-derived cells are highly suited for therapeutic use because they can be readily expanded to sufficient cell numbers.

Methods & Materials
Gelatin-Coating Flasks.

Tissue culture plastic flasks were coated by adding 20 milliliters 2% (w/v) porcine gelatin (Type B: 225 Bloom; Sigma, St Louis, Mo.) to a T75 flask (Corning, Corning, N.Y.) for 20 minutes at room temperature. After removing the gelatin solution, 10 milliliters phosphate-buffered saline (PBS) (Invitrogen, Carlsbad, Calif.) were added and then aspirated.

Comparison of Expansion Potential of Postpartum-Derived Cells to Other Cell Populations.

For comparison of growth expansion potential, the following cell populations were utilized: i) Mesenchymal stem cells (MSC; Cambrex, Walkersville, Md.); ii) Adipose-derived cells (U.S. Pat. No. 6,555,374 B1; U.S. Patent Application Publication No. US2004/0058412); iii) Normal dermal skin fibroblasts (cc-2509 lot # 9F0844; Cambrex, Walkersville, Md.); iv) Umbilicus-derived cells; and v) Placenta-derived cells. Cells were initially seeded at 5,000 cells/cm$^2$ on gelatin-coated T75 flasks in DMEM-Low glucose growth medium ((Invitrogen, Carlsbad, Calif.), with 15% (v/v) defined bovine serum (Hyclone, Logan, Utah; Lot#AND18475), 0.001% (v/v) 2-mercaptoethanol (Sigma, St. Louis, Mo.), 100 Units/milliliter penicillin, 100 micrograms/milliliter streptomycin, 0.25 micrograms/milliliter amphotericin B; Invitrogen, Carlsbad, Calif.). For subsequent passages, cell cultures were treated as follows. After trypsinization, viable cells were counted after Trypan Blue staining. Cell suspension (50 microliters) was combined with Trypan Blue (50 microliters, Sigma, St. Louis Mo.). Viable cell numbers were estimated using a hemocytometer.

Following counting, cells were seeded at 5,000 cells/cm$^2$ onto gelatin-coated T 75 flasks in 25 milliliters of fresh Growth medium. Cells were grown under standard atmosphere with 5% carbon dioxide at 37° C. The growth medium was changed twice per week. When cells reached about 85 percent confluence, they were passaged; this process was repeated until the cells reached senescence.

At each passage, cells were trypsinized and counted. The viable cell yield, population doubling [ln (cell final/cell initial)/ln 2] and doubling time (time in culture (h)/population doubling) were calculated. For the purposes of determining optimal cell expansion, the total cell yield per passage was determined by multiplying the total yield for the previous passage by the expansion factor for each passage (i.e., expansion factor=cell final/cell initial).

Expansion Potential of Cell Banks at Low Density.

The expansion potential of cells banked at passage 10 was also tested. A different set of conditions was used. Normal dermal skin fibroblasts (cc-2509 lot # 9F0844; Cambrex, Walkersville, Md.), umbilicus-derived cells, and placenta-derived cells were tested. These cell populations had been banked at passage 10 previously, having been seeded at 5,000 cells/cm$^2$ and grown to confluence at each passage to that point. The effect of cell density on the cell populations following cell thaw at passage 10 was determined. Cells were thawed under standard conditions, counted using Trypan Blue staining. Thawed cells were then seeded at 1,000 cells/cm$^2$ in Growth medium (DMEM-Low glucose (Invitrogen, Carlsbad, Calif.) with 15 percent (v/v) defined bovine serum (Hyclone, Logan, Utah; Lot#AND18475), 0.001 percent 2-mercaptoethanol (Sigma, St. Louis, Mo.), 100 Units/milliliter penicillin, 100 micrograms/milliliter streptomycin, 0.25 micrograms/milliliter amphotericin B (Invitrogen, Carlsbad, Calif.)). Cells were grown under standard atmospheric conditions at 37° C. Growth medium was changed twice a week and cells were passaged as they reached about 85% confluence. Cells were subsequently passaged until senescence, i.e., until they could not be expanded any further. Cells were trypsinized and counted at each passage. The cell yield, population doubling (ln (cell final/cell initial)/ln 2) and doubling time (time in culture (h)/population doubling) were calculated. The total cell yield per passage was determined by multiplying total yield for the previous passage by the expansion factor for each passage (i.e., expansion factor=cell final/cell initial).

Expansion of Postpartum-Derived Cells at Low Density from Initial Cell Seeding.

The expansion potential of freshly isolated postpartum-derived cell cultures under low cell seeding conditions was tested in another experiment. Umbilicus- and placenta-derived cells were isolated as described herein. Cells were seeded at 1000 cells/cm$^2$ and passaged as described above until senescence. Cells were grown under standard atmospheric conditions at 37° C. Growth medium was changed twice per week. Cells were passaged as they reached about 85% confluence. At each passage, cells were trypsinized and counted by Trypan Blue staining. The cell yield, population doubling (ln (cell final/cell initial)/ln 2), and doubling time (time in culture (h)/population doubling) were calculated for each passage. The total cell yield per passage was determined by multiplying the total yield for the previous passage by the expansion factor for each passage (i.e., expansion factor=cell final/cell initial). Cells were grown on gelatin- and non-gelatin-coated flasks.

Expansion of Clonal Neonatal or Maternal Placenta-Derived Cells.

Cloning may be used in order to expand a population of neonatal or maternal cells successfully from placental tissue. Following isolation of three different cell populations from the placenta (neonatal aspect, maternal aspect, and villous region), these cell populations are expanded under standard growth conditions and then karyotyped to reveal the identity of the isolated cell populations. By isolating the cells from a mother who delivers a boy, it is possible to distinguish between the male and female chromosomes by performing metaphase spreads. These experiments can be used to demonstrate that top-line cells are karyotype positive for neonatal phenotype, mid-line cells are karyotype positive for both neonatal and maternal phenotypes, and bottom-line cells are karyotype positive for maternal cells.

Expansion of Cells in Low Oxygen Culture Conditions.

It has been demonstrated that low $O_2$ cell culture conditions can improve cell expansion in certain circumstances (Csete et al. Low oxygen culturing of central nervous system progenitor cells. US2004/0005704). In order to determine if cell expansion of postpartum-derived cells could be improved by altering cell culture conditions, cultures of umbilicus-derived cells were grown in low oxygen conditions. Cells were seeded at 5,000 cells/cm$^2$ in Growth medium on gelatin-coated flasks. Cells were initially cultured under standard atmospheric conditions through passage 5, at which point they were transferred to low oxygen (5% $O_2$) culture conditions.

Evaluation of Other Growth Conditions.

In other experiments, postpartum-derived cells were expanded on non-coated, collagen-coated, fibronectin-coated, laminin-coated, and extracellular membrane protein (e.g., MATRIGEL (BD Discovery Labware, Bedford, Mass.))-coated plates. Cultures have been demonstrated to expand well on each.

Results

Comparison of Expansion Potential of Postpartum-Derived Cells vs. Other Stem Cell and Non-Stem Cell Populations.

Both umbilicus-derived and placenta-derived cells expanded for greater than 40 passages generating cell yields of >1E17 cells in 60 days. In contrast, MSCs and fibroblasts senesced after <25 days and <60 days, respectively. Although both adipose-derived and omental cells expanded for almost 60 days, they generated total cell yields of 4.5E12 and 4.24E13 respectively. Thus, when seeded at 5,000 cells/cm$^2$ under the experimental conditions utilized, postpartum-derived cells expanded much better than the other cell types grown under the same conditions (Table 5-1).

Expansion of Potential of Cell Banks at Low Density.

Umbilicus-derived, placenta-derived, and fibroblast cells expanded for greater than 10 passages generating cell yields of >1E11 cells in 60 days (Table 5-2). After 60 days under these conditions, the fibroblasts became senescent, whereas the umbilicus-derived and placenta-derived cell populations senesced after 80 days, completing >50 and >40 population doublings, respectively.

Expansion of Postpartum-Derived Cells at Low Density from Initial Cell Seeding.

Postpartum-derived cells were seeded at low density (1,000 cells/cm$^2$) on gelatin-coated and uncoated plates or flasks. Growth potential of these cells under these conditions was good. The cells expanded readily in a log phase growth. The rate of cell expansion was similar to that observed when postpartum-derived cells were seeded at 5,000 cells/cm$^2$ on gelatin-coated flasks in Growth medium. No differences were observed in cell expansion potential between culturing on either uncoated flasks or gelatin-coated flasks. However, cells appeared phenotypically much smaller on gelatin-coated flasks, and more, larger cell phenotypes were observed on uncoated flasks.

Expansion of Clonal Neonatal or Maternal Placenta-Derived Cells.

A clonal neonatal or maternal cell population can be expanded from placenta-derived cells isolated from the neonatal aspect or the maternal aspect, respectively, of the placenta. Cells are serially diluted and then seeded onto gelatin-coated plates in Growth medium for expansion at 1 cell/well in 96-well gelatin-coated plates. From this initial cloning, expansive clones are identified, trypsinized, and reseeded in 12-well gelatin-coated plates in Growth medium and then subsequently passaged into T25 gelatin-coated flasks at 5,000 cells/cm$^2$ in Growth medium. Subcloning is performed to ensure that a clonal population of cells has been identified. For subcloning experiments, cells are trypsinized and reseeded at 0.5 cells/well. The subclones that grow well are expanded in gelatin-coated T25 flasks at 5,000 cells cm$^2$/flask. Cells are passaged at 5,000 cells cm$^2$/T75 flask. The growth characteristics of a clone may be plotted to demonstrate cell expansion. Karyotyping analysis can confirm that the clone is either neonatal or maternal.

Expansion of Cells in Low Oxygen Culture Conditions.

Postpartum-derived cells expanded well under the reduced oxygen conditions. Culturing under low oxygen conditions does not appear to have a significant effect on cell expansion for postpartum-derived cells. Standard atmospheric conditions have already proven successful for growing sufficient numbers of cells, and low oxygen culture is not required for the growth of postpartum-derived cells.

Summary.

Commercially viable cell products must be able to be produced in sufficient quantities to provide therapeutic treatment to patients in need of the treatment. Postpartum-derived cells can be expanded in culture for such purposes. Comparisons were made of the growth of postpartum-derived cells in culture to that of other cell populations including mesenchymal stem cells. The data demonstrated that postpartum-derived cell lines as developed herein can expand for greater than 40 doublings to provide sufficient cell numbers, for example, for pre-clinical banks. Furthermore, these postpartum-derived cell populations can be expanded well at low or high density. This study has demonstrated that mesenchymal stem cells, in contrast, cannot be expanded to obtain large quantities of cells.

The current cell expansion conditions of growing isolated postpartum-derived cells at densities of about 5,000 cells/$cm^2$ in Growth medium on gelatin-coated or uncoated flasks, under standard atmospheric oxygen, are sufficient to generate large numbers of cells at passage 11. Furthermore, the data suggests that the cells can be readily expanded using lower density culture conditions (e.g. 1,000 cells/$cm^2$). Postpartum-derived cell expansion in low oxygen conditions also facilitates cell expansion, although no incremental improvement in cell expansion potential has yet been observed when utilizing these conditions for growth. Presently, culturing postpartum-derived cells under standard atmospheric conditions is preferred for generating large pools of cells. However, when the culture conditions are altered, postpartum-derived cell expansion can likewise be altered. This strategy may be used to enhance the proliferative and differentiative capacity of these cell populations.

Under the conditions utilized, while the expansion potential of MSC and adipose-derived cells is limited, postpartum-derived cells expand readily to large numbers.

REFERENCES

1) Hayflick L. The longevity of cultured human cells. *J Am Geriatr Soc.* 1974 Jan. 22(1):1-12.
2) Hayflick L. The strategy of senescence. *Gerontologist.* 1974 Feb. 14(1):37-45.
3) US2004/0058412
4) US2004/0048372
6) Csete et al. Low oxygen culturing of central nervous system progenitor cells. US2004/0005704.

TABLE 5-1

Growth characteristics for different cell populations grown to senescence

| Cell Type | Senescence | Total Population Doublings | Total Cell Yield |
| --- | --- | --- | --- |
| MSC | 24 days | 8 | 4.72 E7 |
| Adipose-derived cells (Artecel, U.S. Pat. No. 6,555,374) | 57 days | 24 | 4.5 E12 |
| Fibroblasts | 53 days | 26 | 2.82 E13 |
| Umbilicus-derived cells | 65 days | 42 | 6.15 E17 |
| Placenta-derived cells | 80 days | 46 | 2.49 E19 |

TABLE 5-2

Growth characteristics for different cell populations using low density growth expansion from passage 10 to senescence

| Cell Type | Senescence | Total Population Doublings | Total Cell Yield |
| --- | --- | --- | --- |
| Fibroblast (P10) | 80 days | 43.68 | 2.59 E11 |
| Umbilicus-derived cells (P10) | 80 days | 53.6 | 1.25 E14 |
| Placenta-derived cells (P10) | 60 days | 32.96 | 6.09 E12 |

Example 6

Karyotype Analysis of PPDCs

Cell lines used in cell therapy are preferably homogeneous and free from any contaminating cell type. Human cells used in cell therapy should have a normal chromosome number (46) and structure. To identify postpartum-derived placental and umbilicus cell lines that are homogeneous and free from cells of non-postpartum tissue origin, karyotypes of cell samples were analyzed.

Methods & Materials

PPDCs from postpartum tissue of a male neonate were cultured in Growth medium (DMEM-low glucose (Gibco Carlsbad, Calif.), 15% (v/v) fetal bovine serum (FBS) (Hyclone, Logan, Utah), 0.001% (v/v) betamercaptoethanol (Sigma, St. Louis, Mo.), and 50 Units/milliliter penicillin, 50 micrograms/milliliter streptomycin (Gibco, Carlsbad, Calif.)). Postpartum tissue from a male neonate (X,Y) was selected to allow distinction between neonatal-derived cells and maternal-derived cells (X,X). Cells were seeded at 5,000 cells per square centimeter in Growth medium in a T25 flask (Corning, Corning, N.Y.) and expanded to about 80% confluence. A T25 flask containing cells was filled to the neck with Growth medium. Samples were delivered to a clinical cytogenetics lab by courier (estimated lab to lab transport time is one hour). Chromosome analysis was performed by the Center for Human & Molecular Genetics at the New Jersey Medical School, Newark, N.J. Cells were analyzed during metaphase when the chromosomes are best visualized. Of twenty cells in metaphase counted, five were analyzed for normal homogeneous karyotype number (two). A cell sample was characterized as homogeneous if two karyotypes were observed. A cell sample was characterized as heterogeneous if more than two karyotypes were observed. Additional metaphase cells were counted and analyzed when a heterogeneous karyotype number (four) was identified.

Results

All cell samples sent for chromosome analysis were interpreted by the cytogenetics laboratory staff as exhibiting a normal appearance. Three of the sixteen cell lines analyzed exhibited a heterogeneous phenotype (XX and XY) indicating the presence of cells derived from both neonatal and maternal origins (Table 6-1). Cells derived from tissue Placenta-N were isolated from the neonatal aspect of placenta. At passage zero, this cell line appeared homogeneous XY. However, at passage nine, the cell line was heterogeneous (XX/XY), indicating a previously undetected presence of cells of maternal origin.

TABLE 6-1

Karyotype results of PPDCs

| Tissue | passage | Metaphase cells counted | Metaphase cells analyzed | Number of ISCN karyotypes | Karyotype |
|---|---|---|---|---|---|
| Placenta | 22 | 20 | 5 | 2 | 46, XX |
| Umbilical | 23 | 20 | 5 | 2 | 46, XX |
| Umbilical | 6 | 20 | 5 | 2 | 46, XY |
| Placenta | 2 | 20 | 5 | 2 | 46, XX |
| Umbilical | 3 | 20 | 5 | 2 | 46, XX |
| Placenta-N | 0 | 20 | 5 | 2 | 46, XY |
| Placenta-V | 0 | 20 | 5 | 2 | 46, XY |
| Placenta-M | 0 | 21 | 5 | 4 | 46, XY[18]/46, XX[3] |
| Placenta-M | 4 | 20 | 5 | 2 | 46, XX |
| Placenta-N | 9 | 25 | 5 | 4 | 46, XY[5]/46, XX[20] |
| Placenta-N C1 | 1 | 20 | 5 | 2 | 46, XY |
| Placenta-N C3 | 1 | 20 | 6 | 4 | 46, XY[2]/46, XX[18] |
| Placenta-N C4 | 1 | 20 | 5 | 2 | 46, XY |
| Placenta-N C15 | 1 | 20 | 5 | 2 | 46, XY |
| Placenta-N C20 | 1 | 20 | 5 | 2 | 46, XY |
| Placenta-N C22 | 1 | 20 | 5 | 2 | 46, XY |

Key:
N—Neonatal side;
V—villous region;
M—maternal side;
C—clone

Summary.

Chromosome analysis identified placenta- and umbilicus-derived PPDCs whose karyotypes appear normal as interpreted by a clinical cytogenetic laboratory. Karyotype analysis also identified cell lines free from maternal cells, as determined by homogeneous karyotype.

Example 7

Evaluation of Human Postpartum-Derived Cell Surface Markers by Flow Cytometry

Characterization of cell surface proteins or "markers" by flow cytometry can be used to determine a cell line's identity. The consistency of expression can be determined from multiple donors and in cells exposed to different processing and culturing conditions. Postpartum-derived cell lines isolated from the placenta and umbilicus were characterized by flow cytometry, thereby providing a profile for the identification of the cells of the invention.

Methods & Materials

Media.

Cells were cultured in DMEM-low glucose Growth medium (Gibco Carlsbad, Calif.), with 15% (v/v) fetal bovine serum (FBS); (Hyclone, Logan, Utah), 0.001% (v/v) betamercaptoethanol (Sigma, St. Louis, Mo.), and 50 Units/milliliter penicillin, 50 micrograms/milliliter streptomycin (Gibco, Carlsbad, Calif.).

Culture Vessels.

Cells were cultured in plasma-treated T75, T150, and T225 tissue culture flasks (Corning, Corning, N.Y.) until confluent. The growth surfaces of the flasks were coated with gelatin by incubating 2% (w/v) gelatin (Sigma, St. Louis, Mo.) for 20 minutes at room temperature.

Antibody Staining.

Adherent cells in flasks were washed in phosphate buffered saline (PBS) (Gibco, Carlsbad, Calif.) and detached with Trypsin/EDTA (Gibco, Carlsbad, Calif.). Cells were harvested, centrifuged, and resuspended in 3% (v/v) FBS in PBS at a cell concentration of $1 \times 10^7$ per milliliter. In accordance with the manufacturer's specifications, antibody to the cell surface marker of interest (Table 7-1) was added to one hundred microliters of cell suspension and the mixture was incubated in the dark for 30 minutes at 4° C. After incubation, cells were washed with PBS and centrifuged to remove unbound antibody. Cells were resuspended in 500 microliters PBS and analyzed by flow cytometry.

Flow Cytometry Analysis.

Flow cytometry analysis was performed with a FACScalibur instrument (Becton Dickinson, San Jose, Calif.).

Antibodies to Cell Surface Markers.

The following antibodies to cell surface markers were used.

TABLE 7-1

Antibodies to Cell Surface markers

| Antibody | Manufacture | Catalog Number |
|---|---|---|
| CD10 | BD Pharmingen (San Diego, CA) | 555375 |
| CD13 | BD Pharmingen (San Diego, CA) | 555394 |
| CD31 | BD Pharmingen (San Diego, CA) | 555446 |
| CD34 | BD Pharmingen (San Diego, CA) | 555821 |
| CD44 | BD Pharmingen (San Diego, CA) | 555478 |
| CD45RA | BD Pharmingen (San Diego, CA) | 555489 |
| CD73 | BD Pharmingen (San Diego, CA) | 550257 |
| CD90 | BD Pharmingen (San Diego, CA) | 555596 |
| CD117 | BD Biosciences (San Jose, CA) | 340529 |
| CD141 | BD Pharmingen (San Diego, CA) | 559781 |
| PDGFr-alpha | BD Pharmingen (San Diego, CA) | 556002 |
| HLA-A, B, C | BD Pharmingen (San Diego, CA) | 555553 |
| HLA-DR, DP, DQ | BD Pharmingen (San Diego, CA) | 555558 |
| IgG-FITC | Sigma (St. Louis, MO) | F-6522 |
| IgG-PE | Sigma (St. Louis, MO) | P-4685 |

Placenta- and Umbilicus-Derived Cell Comparison.

Placenta-derived cells were compared to umbilicus-derived cells at passage 8.

Passage to Passage Comparison.

Placenta- and umbilicus-derived cells were analyzed at passages 8, 15, and 20.

Donor to Donor Comparison.

To compare differences among donors, placenta-derived cells from different donors were compared to each other, and umbilicus-derived cells from different donors were compared to each other.

Surface Coating Comparison.

Placenta-derived cells cultured on gelatin-coated flasks were compared to placenta-derived cells cultured on uncoated flasks. Umbilicus-derived cells cultured on gelatin-coated flasks were compared to umbilicus-derived cells cultured on uncoated flasks.

Digestion Enzyme Comparison.

Four treatments used for isolation and preparation of cells were compared. Cells derived from postpartum tissue by treatment with 1) collagenase; 2) collagenase/dispase; 3) collagenase/hyaluronidase; and 4) collagenase/hyaluronidase/dispase were compared.

Placental Layer Comparison.

Cells isolated from the maternal aspect of placental tissue were compared to cells isolated from the villous region of placental tissue and cells isolated from the neonatal fetal aspect of placenta.

Results

Placenta-Derived Cells were Compared to Umbilicus-Derived Cells.

Placenta- and umbilicus-derived cells analyzed by flow cytometry showed positive for production of CD10, CD13, CD44, CD73, CD90, PDGFr-alpha and HLA-A, B, C, indicated by the increased values of fluorescence relative to the IgG control. These cells were negative for detectable production of CD31, CD34, CD45, CD117, CD141, and HLA-DR, DP, DQ, indicated by fluorescence values comparable to the IgG control. Variations in fluorescence values of positive curves was accounted. The mean (i.e., CD13) and range (i.e., CD90) of the positive curves showed some variation, but the curves appeared normal, confirming a homogeneous population. Both curves individually exhibited values greater than the IgG control.

Passage to Passage Comparison of Placenta-Derived Cells.

Placenta-derived cells at passages 8, 15, and 20 analyzed by flow cytometry all were positive for production of CD10, CD13, CD44, CD73, CD90, PDGFr-alpha and HLA-A, B, C, as reflected in the increased value of fluorescence relative to the IgG control. The cells were negative for production of CD31, CD34, CD45, CD117, CD141, and HLA-DR, DP, DQ having fluorescence values consistent with the IgG control.

Passage to Passage Comparison of Umbilicus-Derived Cells.

Umbilicus-derived cells at passage 8, 15, and 20 analyzed by flow cytometry all expressed CD10, CD13, CD44, CD73, CD90, PDGFr-alpha and HLA-A, B, C, indicated by increased fluorescence relative to the IgG control. These cells were negative for CD31, CD34, CD45, CD117, CD141, and HLA-DR, DP, DQ, indicated by fluorescence values consistent with the IgG control.

Donor to Donor Comparison of Placenta-Derived Cells.

Placenta-derived cells isolated from separate donors analyzed by flow cytometry each expressed CD10, CD13, CD44, CD73, CD90, PDGFr-alpha and HLA-A, B, C, with increased values of fluorescence relative to the IgG control. The cells were negative for production of CD31, CD34, CD45, CD117, CD141, and HLA-DR, DP, DQ as indicated by fluorescence value consistent with the IgG control.

Donor to Donor Comparison of Umbilicus-Derived Cells.

Umbilicus-derived cells isolated from separate donors analyzed by flow cytometry each showed positive for production of CD10, CD13, CD44, CD73, CD90, PDGFr-alpha and HLA-A, B, C, reflected in the increased values of fluorescence relative to the IgG control. These cells were negative for production of CD31, CD34, CD45, CD117, CD141, and HLA-DR, DP, DQ with fluorescence values consistent with the IgG control.

The Effect of Surface Coating with Gelatin on Placenta-Derived Cells.

Placenta-derived cells expanded on either gelatin-coated or uncoated flasks analyzed by flow cytometry all expressed CD10, CD13, CD44, CD73, CD90, PDGFr-alpha and HLA-A, B, C, reflected in the increased values of fluorescence relative to the IgG control. These cells were negative for production of CD31, CD34, CD45, CD117, CD141, and HLA-DR, DP, DQ indicated by fluorescence values consistent with the IgG control.

The Effect of Surface Coating with Gelatin on Umbilicus-Derived Cells.

Umbilicus-derived cells expanded on gelatin and uncoated flasks analyzed by flow cytometry all were positive for production of CD10, CD13, CD44, CD73, CD 90, PDGFr-alpha and HLA-A, B, C, with increased values of fluorescence relative to the IgG control. These cells were negative for production of CD31, CD34, CD45, CD117, CD141, and HLA-DR, DP, DQ, with fluorescence values consistent with the IgG control.

Evaluation of Effect of Enzyme Digestion Procedure Used for Preparation and Isolation of the Cells on the Cell Surface Marker Profile.

Placenta-derived cells isolated using various digestion enzymes analyzed by flow cytometry all expressed CD10, CD13, CD44, CD73, CD90, PDGFr-alpha and HLA-A, B, C, as indicated by the increased values of fluorescence relative to the IgG control. These cells were negative for production of CD31, CD34, CD45, CD117, CD141, and HLA-DR, DP, DQ as indicated by fluorescence values consistent with the IgG control.

Placental Layer Comparison.

Cells derived from the maternal, villous, and neonatal layers of the placenta, respectively, analyzed by flow cytometry showed positive for production of CD10, CD13, CD44, CD73, CD90, PDGFr-alpha and HLA-A, B, C, as indicated by the increased value of fluorescence relative to the IgG control. These cells were negative for production of CD31, CD34, CD45, CD117, CD141, and HLA-DR, DP, DQ as indicated by fluorescence values consistent with the IgG control.

Summary.

Analysis of placenta- and umbilicus-derived postpartum cells by flow cytometry has established of an identity of these cell lines. Placenta- and umbilicus-derived postpartum cells are positive for CD10, CD13, CD44, CD73, CD90, PDGFr-alpha, HLA-A, B, C and negative for CD31, CD34, CD45, CD117, CD141 and HLA-DR, DP, DQ. This identity was consistent between variations in variables including the donor, passage, culture vessel surface coating, digestion enzymes, and placental layer. Some variation in individual fluorescence value histogram curve means and ranges were observed, but all positive curves under all conditions tested were normal and expressed fluorescence values greater than the IgG control, thus confirming that the cells comprise a homogeneous population which has positive expression of the markers.

Example 8

Analysis of Postpartum Tissue-Derived Cells by Affymetrix GeneChip® Arrays

Affymetrix GeneChip® arrays were used to compare gene expression profiles of umbilicus- and placenta-derived cells with fibroblasts, human mesenchymal stem cells, and another cell line derived from human bone marrow. This analysis provided a characterization of the postpartum-derived cells and identified unique molecular markers for these cells.

Methods & Materials

Isolation and Culture of Cells

Postpartum Tissue-Derived Cells.

Human umbilical cords and placenta were obtained from National Disease Research Interchange (NDRI, Philadelphia, Pa.) from normal full term deliveries with patient consent. The tissues were received and cells were isolated as described in Example 1. Cells were cultured in Growth medium (Dulbecco's Modified Essential Media (DMEM-low glucose; Invitrogen, Carlsbad, Calif.) with 15% (v/v) fetal bovine serum (Hyclone, Logan Utah), 100 Units/milliliter penicillin, 100 micrograms/milliliter streptomycin (Invitrogen, Carlsbad, Calif.), and 0.001% (v/v) 2-mercaptoethanol (Sigma, St. Louis Mo.)) on gelatin-coated tissue culture plastic flasks. The cultures were incubated at 37° C. in standard atmosphere.

Fibroblasts.

Human dermal fibroblasts were purchased from Cambrex Incorporated (Walkersville, Md.; Lot number 9F0844) and were obtained from ATCC CRL-1501 (CCD39SK). Both lines were cultured in DMEM/F12 medium (Invitrogen, Carlsbad, Calif.) with 10% (v/v) fetal bovine serum (Hyclone) and 100 Units/milliliter penicillin, 100 micrograms/milliliter streptomycin (Invitrogen). The cells were grown on standard tissue-treated plastic.

Human Mesenchymal Stem Cells (hMSC).

hMSCs were purchased from Cambrex Incorporated (Walkersville, Md.; Lot numbers 2F1655, 2F1656 and 2F1657) and cultured according to the manufacturer's specifications in MSCGM Media (Cambrex). The cells were grown on standard tissue cultured plastic at 37° C. with 5% $CO_2$.

Human Iliac Crest Bone Marrow Cells (ICBM).

Human iliac crest bone marrow was received from NDRI with patient consent. The marrow was processed according to the method outlined by Ho et al. (WO03/025149). The marrow was mixed with lysis buffer (155 micromolar $NH_4Cl$, 10 micromolar $KHCO_3$, and 0.1 micromolar EDTA, pH 7.2) at a ratio of 1 part bone marrow to 20 parts lysis buffer. The cell suspension was vortexed, incubated for 2 minutes at ambient temperature, and centrifuged for 10 minutes at 500×g. The supernatant was discarded and the cell pellet was resuspended in Minimal Essential Medium-alpha (Invitrogen) supplemented with 10% (v/v) fetal bovine serum and 4 micromolar glutamine. The cells were centrifuged again and the cell pellet was resuspended in fresh medium. The viable mononuclear cells were counted using trypan-blue exclusion (Sigma, St. Louis, Mo.). The mononuclear cells were seeded in tissue-cultured plastic flasks at $5 \times 10^4$ cells/cm$^2$. The cells were incubated at 37° C. with 5% $CO_2$ at either standard atmospheric $O_2$ or at 5% $O_2$. Cells were cultured for 5 days without a media change. Media and non-adherent cells were removed after 5 days of culture. The adherent cells were maintained in culture.

Isolation of mRNA and Gene Chip Analysis.

Actively growing cultures of cells were removed from the flasks with a cell scraper in cold phosphate buffered saline (PBS). The cells were centrifuged for 5 minutes at 300×g. The supernatant was removed and the cells were resuspended in fresh PBS and centrifuged again. The supernatant was removed and the cell pellet was immediately frozen and stored at −80° C. Cellular mRNA was extracted and transcribed into cDNA. cDNA was then transcribed into cRNA and biotin-labeled. The biotin-labeled cRNA was hybridized with HG-U133A (August 2003) Affymetrix oligonucleotide arrays (Affymetrix, Santa Clara Calif.). The hybridization and data collection was performed according to the manufacturer's specifications.

Results

Fourteen different populations of cells were analyzed in this study. The cells along with passage information, culture substrate, and culture media are listed in Table 8-1.

TABLE 8-1

Cells analyzed by the microarray study. The cell lines are listed by their identification code along with passage at the time of analysis, cell growth substrate, and Growth medium.

| Cell Population | Passage | Substrate | Media |
|---|---|---|---|
| Umbilical (022803) | 2 | Gelatin | DMEM, 15% FBS, BME |
| Umbilical (042103) | 3 | Gelatin | DMEM, 15% FBS, BME |
| Umbilical (071003) | 4 | Gelatin | DMEM, 15% FBS, BME |
| Placenta (042203) | 12 | Gelatin | DMEM, 15% FBS, BME |
| Placenta (042903) | 4 | Gelatin | DMEM, 15% FBS, BME |
| Placenta (071003) | 3 | Gelatin | DMEM, 15% FBS, BME |
| ICBM (070203) (5% $O_2$) | 3 | Plastic | MEM 10% FBS |
| ICBM (062703) (std $O_2$) | 5 | Plastic | MEM 10% FBS |
| ICBM (062703)(5% $O_2$) | 5 | Plastic | MEM 10% FBS |
| hMSC (Lot 2F1655) | 3 | Plastic | MSCGM |
| hMSC (Lot 2F1656) | 3 | Plastic | MSCGM |
| hMSC (Lot 2F1657) | 3 | Plastic | MSCGM |
| hFibroblast (9F0844) | 9 | Plastic | DMEM-F12, 10% FBS |
| hFibroblast (ATCC CRL-1501) | 4 | Plastic | DMEM-F12, 10% FBS |

The data were evaluated by a Principle Component Analysis, analyzing the 290 genes that were differentially expressed in the cells. This analysis allows for a relative comparison for the similarities between the populations. Table 8-2 shows the Euclidean distances that were calculated for the comparison of the cell pairs. The Euclidean distances were based on the comparison of the cells based on the 290 genes that were differentially expressed among the cell types. The Euclidean distance is inversely proportional to similarity between the expression of the 290 genes.

TABLE 8-2

The Euclidean Distances for the Cell Pairs. The Euclidean distance was calculated for the cell types using the 290 genes that were differentially expressed between the cell types. Similarity between the cells is inversely proportional to the Euclidean distance.

| Cell Pair | Euclidean Distance |
|---|---|
| ICBM-hMSC | 24.71 |
| Placenta-umbilical | 25.52 |
| ICBM-Fibroblast | 36.44 |
| Fibroblast-placenta | 37.09 |
| Fibroblast-MSC | 39.63 |
| ICBM-Umbilical | 40.15 |
| Fibroblast-Umbilical | 41.59 |
| MSC-Placenta | 42.84 |
| MSC-Umbilical | 46.86 |
| ICBM-placenta | 48.41 |

Tables 8-3, 8-4, and 8-5 show the expression of genes increased in placenta-derived cells (Table 8-3), increased in umbilicus-derived cells (Table 8-4), and reduced in umbilicus- and placenta-derived cells (Table 8-5). The column entitled "Probe Set ID" refers to the manufacturer's identification code for the sets of several oligonucleotide probes located on a particular site on the chip, which hybridize to the named gene (column "Gene Name"), comprising a sequence that can be found within the NCBI (GenBank) database at the specified accession number (column "NCBI Accession Number").

TABLE 8-3

Genes shown to have specifically increased expression in the placenta-derived cells as compared to the other cell lines assayed.
Genes Increased in Placenta-Derived Cells

| Probe Set ID | Gene Name | NCBI Accession Number |
| --- | --- | --- |
| 209732_at | C-type (calcium dependent, carbohydrate-recognition domain) lectin, superfamily member 2 (activation-induced) | AF070642 |
| 206067_s_at | Wilms tumor 1 | NM_024426 |
| 207016_s_at | aldehyde dehydrogenase 1 family, member A2 | AB015228 |
| 206367_at | renin | NM_000537 |
| 210004_at | oxidised low density lipoprotein (lectin-like) receptor 1 | AF035776 |
| 214993_at | *Homo sapiens*, clone IMAGE: 4179671, mRNA, partial cds | AF070642 |
| 202178_at | protein kinase C, zeta | NM_002744 |
| 209780_at | hypothetical protein DKFZp564F013 | AL136883 |
| 204135_at | downregulated in ovarian cancer 1 | NM_014890 |
| 213542_at | *Homo sapiens* mRNA; cDNA DKFZp547K1113 (from clone DKFZp547K1113) | AI246730 |

TABLE 8-4

Genes shown to have specifically increased expression in umbilicus-derived cells as compared to the other cell lines assayed.
Genes Increased in Umbilicus-Derived Cells

| Probe Set ID | Gene Name | NCBI Accession Number |
| --- | --- | --- |
| 202859_x_at | interleukin 8 | NM_000584 |
| 211506_s_at | interleukin 8 | AF043337 |
| 210222_s_at | reticulon 1 | BC000314 |
| 204470_at | chemokine (C—X—C motif) ligand 1 (melanoma growth stimulating activity | NM_001511 |
| 206336_at | chemokine (C—X—C motif) ligand 6 (granulocyte chemotactic protein 2) | NM_002993 |
| 207850_at | chemokine (C—X—C motif) ligand 3 | NM_002090 |
| 203485_at | reticulon 1 | NM_021136 |
| 202644_s_at | tumor necrosis factor, alpha-induced protein 3 | NM_006290 |

TABLE 8-5

Genes that were shown to have decreased expression in the umbilicus- and placenta-derived cells as compared to the other cell lines assayed.
Genes Decreased in Umbilicus- and Placenta-Derived Cells

| Probe Set ID | Gene name | NCBI Accession Number |
| --- | --- | --- |
| 210135_s_at | short stature homeobox 2 | AF022654.1 |
| 205824_at | heat shock 27 kDa protein 2 | NM_001541.1 |
| 209687_at | chemokine (C—X—C motif) ligand 12 (stromal cell-derived factor 1) | U19495.1 |
| 203666_at | chemokine (C—X—C motif) ligand 12 (stromal cell-derived factor 1) | NM_000609.1 |
| 212670_at | elastin (supravalvular aortic stenosis, Williams-Beuren syndrome) | AA479278 |
| 213381_at | *Homo sapiens* mRNA; cDNA DKFZp586M2022 (from clone DKFZp586M2022) | N91149 |
| 206201_s_at | mesenchyme homeobox 2 (growth arrest-specific homeobox) | NM_005924.1 |
| 205817_at | sine oculis homeobox homolog 1 (*Drosophila*) | NM_005982.1 |
| 209283_at | crystallin, alpha B | AF007162.1 |
| 212793_at | dishevelled associated activator of morphogenesis 2 | BF513244 |
| 213488_at | DKFZP586B2420 protein | AL050143.1 |
| 209763_at | similar to neuralin 1 | AL049176 |

TABLE 8-5-continued

Genes that were shown to have decreased expression in the
umbilicus- and placenta-derived cells as compared to the other cell lines
assayed.
Genes Decreased in Umbilicus- and Placenta-Derived Cells

| Probe Set ID | Gene name | NCBI Accession Number |
|---|---|---|
| 205200_at | tetranectin (plasminogen binding protein) | NM_003278.1 |
| 205743_at | src homology three (SH3) and cysteine rich domain | NM_003149.1 |
| 200921_s_at | B-cell translocation gene 1, anti-proliferative | NM_001731.1 |
| 206932_at | cholesterol 25-hydroxylase | NM_003956.1 |
| 204198_s_at | runt-related transcription factor 3 | AA541630 |
| 219747_at | hypothetical protein FLJ23191 | NM_024574.1 |
| 204773_at | interleukin 11 receptor, alpha | NM_004512.1 |
| 202465_at | procollagen C-endopeptidase enhancer | NM_002593.2 |
| 203706_s_at | frizzled homolog 7 (*Drosophila*) | NM_003507.1 |
| 212736_at | hypothetical gene BC008967 | BE299456 |
| 214587_at | collagen, type VIII, alpha 1 | BE877796 |
| 201645_at | tenascin C (hexabrachion) | NM_002160.1 |
| 210239_at | iroquois homeobox protein 5 | U90304.1 |
| 203903_s_at | hephaestin | NM_014799.1 |
| 205816_at | integrin, beta 8 | NM_002214.1 |
| 203069_at | synaptic vesicle glycoprotein 2 | NM_014849.1 |
| 213909_at | *Homo sapiens* cDNA FLJ12280 fis, clone MAMMA1001744 | AU147799 |
| 206315_at | cytokine receptor-like factor 1 | NM_004750.1 |
| 204401_at | potassium intermediate/small conductance calcium-activated channel, subfamily N, member 4 | NM_002250.1 |
| 216331_at | integrin, alpha 7 | AK022548.1 |
| 209663_s_at | integrin, alpha 7 | AF072132.1 |
| 213125_at | DKFZP586L151 protein | AW007573 |
| 202133_at | transcriptional co-activator with PDZ-binding motif (TAZ) | AA081084 |
| 206511_s_at | sine oculis homeobox homolog 2 (*Drosophila*) | NM_016932.1 |
| 213435_at | KIAA1034 protein | AB028957.1 |
| 206115_at | early growth response 3 | NM_004430.1 |
| 213707_s_at | distal-less homeobox 5 | NM_005221.3 |
| 218181_s_at | hypothetical protein FLJ20373 | NM_017792.1 |
| 209160_at | aldo-keto reductase family 1, member C3 (3-alpha hydroxysteroid dehydrogenase, type II) | AB018580.1 |
| 213905_x_at | biglycan | AA845258 |
| 201261_x_at | biglycan | BC002416.1 |
| 202132_at | transcriptional co-activator with PDZ-binding motif (TAZ) | AA081084 |
| 214701_s_at | fibronectin 1 | AJ276395.1 |
| 213791_at | proenkephalin | NM_006211.1 |
| 205422_s_at | integrin, beta-like 1 (with EGF-like repeat domains) | NM_004791.1 |
| 214927_at | *Homo sapiens* mRNA full length insert cDNA clone EUROIMAGE 1968422 | AL359052.1 |
| 206070_s_at | EphA3 | AF213459.1 |
| 212805_at | KIAA0367 protein | AB002365.1 |
| 219789_at | natriuretic peptide receptor C/guanylate cyclase C (atrionatriuretic peptide receptor C) | AI628360 |
| 219054_at | hypothetical protein FLJ14054 | NM_024563.1 |
| 213429_at | *Homo sapiens* mRNA; cDNA DKFZp564B222 (from clone DKFZp564B222) | AW025579 |
| 204929_s_at | vesicle-associated membrane protein 5 (myobrevin) | NM_006634.1 |
| 201843_s_at | EGF-containing fibulin-like extracellular matrix protein 1 | NM_004105.2 |
| 221478_at | BCL2/adenovirus E1B 19 kDa interacting protein 3-like | AL132665.1 |
| 201792_at | AE binding protein 1 | NM_001129.2 |
| 204570_at | cytochrome c oxidase subunit VIIa polypeptide 1 (muscle) | NM_001864.1 |
| 201621_at | neuroblastoma, suppression of tumorigenicity 1 | NM_005380.1 |
| 202718_at | insulin-like growth factor binding protein 2, 36 kDa | NM_000597.1 |

Tables 8-6, 8-7, and 8-8 show the expression of genes increased in human fibroblasts (Table 8-6), ICBM cells (Table 8-7), and MSCs (Table 8-8).

TABLE 8-6

Genes that were shown to have increased expression in fibroblasts as compared to the other cell lines assayed.
Genes increased in fibroblasts dual specificity phosphatase 2
KIAA0527 protein
*Homo sapiens* cDNA: FLJ23224 fis, clone ADSU02206
dynein, cytoplasmic, intermediate polypeptide 1
ankyrin 3, node of Ranvier (ankyrin G)
inhibin, beta A (activin A, activin AB alpha polypeptide)
ectonucleotide pyrophosphatase/phosphodiesterase 4 (putative function)
KIAA1053 protein
microtubule-associated protein 1A
zinc finger protein 41
HSPC019 protein
*Homo sapiens* cDNA: FLJ23564 fis, clone LNG10773
*Homo sapiens* mRNA; cDNA DKFZp564A072 (from clone DKFZp564A072)
LIM protein (similar to rat protein kinase C-binding enigma)
inhibitor of kappa light polypeptide gene enhancer in B-cells, kinase complex-associated protein
hypothetical protein FLJ22004
Human (clone CTG-A4) mRNA sequence
ESTs, Moderately similar to cytokine receptor-like factor 2; cytokine receptor CRL2 precursor [Homo sapiens]
transforming growth factor, beta 2
hypothetical protein MGC29643
antigen identified by monoclonal antibody MRC OX-2

TABLE 8-7

Genes that were shown to have increased expression in the ICBM-derived cells as compared to the other cell lines assayed.
Genes Increased In ICBM Cells cardiac ankyrin repeat protein
MHC class I region ORF
integrin, alpha 10
hypothetical protein FLJ22362
UDP-N-acetyl-alpha-D-galactosamine:polypeptide N-acetylgalactosaminyltransferase 3 (GalNAc-T3)
interferon-induced protein 44
SRY (sex determining region Y)-box 9 (campomelic dysplasia, autosomal sex-reversal)
Keratin associated protein 1-1
hippocalcin-like 1
Jagged 1 (Alagille syndrome)
proteoglycan 1, secretory granule

TABLE 8-8

Genes that were shown to have increased expression in the MSC cells as compared to the other cell lines assayed.
Genes Increased In MSC Cells interleukin 26
maltase-glucoamylase (alpha-glucosidase)
nuclear receptor subfamily 4, group A, member 2
v-fos FBJ murine osteosarcoma viral oncogene homolog
hypothetical protein DC42
nuclear receptor subfamily 4, group A, member 2
FBJ murine osteosarcoma viral oncogene homolog B
WNT1 inducible signaling pathway protein 1
MCF.2 cell line derived transforming sequence
potassium channel, subfamily K, member 15
cartilage paired-class homeoprotein 1

TABLE 8-8-continued

Genes that were shown to have increased expression in the MSC cells as compared to the other cell lines assayed.
Genes Increased In MSC Cells

*Homo sapiens* cDNA FLJ12232 fis, clone MAMMA1001206
*Homo sapiens* cDNA FLJ34668 fis, clone LIVER2000775
jun B proto-oncogene
B-cell CLL/lymphoma 6 (zinc finger protein 51)
zinc finger protein 36, C3H type, homolog (mouse)

Summary.

The GENECHIP analysis was performed to provide a molecular characterization of the postpartum cells derived from umbilicus and placenta. This analysis included cells derived from three different umbilical cords and three different placentas. The study also included two different lines of dermal fibroblasts, three lines of mesenchymal stem cells, and three lines of iliac crest bone marrow cells. The mRNA that was expressed by these cells was analyzed by AffyMetrix GENECHIP that contained oligonucleotide probes for 22,000 genes.

Results showed that 290 genes are differentially expressed in these five different cell types. These genes include ten genes that are specifically increased in the placenta-derived cells and seven genes specifically increased in the umbilicus-derived cells. Fifty-four genes were found to have specifically lower expression levels in placenta and umbilical cord.

The expression of selected genes has been confirmed by PCR in Example 9. These results demonstrate that the postpartum-derived cells have a distinct gene expression profile, for example, as compared to bone marrow-derived cells and fibroblasts.

REFERENCE

Lockhart et al., Expression monitoring by hybridization to high-density oligonucleotide arrays. *Nat. Biotechnol.* 1996, 14(13): 1675-1680.

Example 9

Cell Markers in Postpartum-Derived Cells

Similarities and differences in cells derived from the human placenta and the human umbilical cord were assessed by comparing their gene expression profiles with those of cells derived from other sources (using an Affymetrix GENECHIP array). Six "signature" genes were identified: oxidized LDL receptor 1, interleukin-8, renin, reticulon, chemokine receptor ligand 3 (CXC ligand 3), and granulocyte chemotactic protein 2 (GCP-2). These "signature" genes were expressed at relatively high levels in postpartum-derived cells.

The present studies were conducted to verify the microarray data and to identify accordance/discordance between gene and protein expression, as well as to establish a series of reliable assays for detection of unique identifiers for placenta- and umbilicus-derived cells.

Methods & Materials

Cells.

Placenta-derived cells (three isolates, including one isolate predominately neonatal as identified by karyotyping analysis), umbilicus-derived cells (four isolates), and Normal Human Dermal Fibroblasts (NHDF; neonatal and adult) were grown in Growth medium (DMEM-low glucose (Gibco, Carlsbad, Calif.), 15% (v/v) fetal bovine serum (Cat. #SH30070.03; Hyclone, Logan, Utah), 0.001% (v/v) beta-mercaptoethanol (Sigma, St. Louis, Mo.), 50 Units/milliliter penicillin, 50 micrograms/milliliter streptomycin (Gibco, Carlsbad, Calif.) in a gelatin-coated T75 flask. Mesenchymal Stem Cells (MSCs) were grown in Mesenchymal Stem Cell Growth Medium Bullet kit (MSCGM; Cambrex, Walkerville, Md.).

For the IL-8 secretion experiment, cells were thawed from liquid nitrogen and plated in gelatin-coated flasks at 5,000 cells/cm$^2$, grown for 48 hours in Growth medium, and then grown for an additional 8 hours in 10 milliliters of serum starvation medium (DMEM-low glucose (Gibco, Carlsbad, Calif.), 50 Units/milliliter penicillin, 50 micrograms/milliliter streptomycin (Gibco, Carlsbad, Calif.), and 0.1% (w/v) Bovine Serum Albumin (BSA; Sigma, St. Louis, Mo.)). After this treatment, RNA was extracted and the supernatants were centrifuged at 150×g for 5 minutes to remove cellular debris. Supernatants were then frozen at −80° C. for ELISA analysis.

Cell Culture for ELISA Assay.

Postpartum cells derived from placenta and umbilical cord, as well as human fibroblasts derived from human neonatal foreskin, were cultured in Growth medium in gelatin-coated T75 flasks. Cells were frozen at passage 11 in liquid nitrogen. Cells were thawed and transferred to 15 milliliter centrifuge tubes. After centrifugation at 150×g for 5 minutes, the supernatant was discarded. Cells were resuspended in 4 milliliters culture medium and counted. Cells were grown in a 75 cm$^2$ flask containing 15 milliliters of Growth medium at 375,000 cells/flask for 24 hours. The medium was changed to a serum starvation medium for 8 hours. Serum starvation medium was collected at the end of incubation, centrifuged at 14,000×g for 5 minutes, and stored at −20° C.

To estimate the number of cells in each flask, 2 milliliters of trypsin/EDTA (Gibco, Carlsbad, Calif.) was added to each flask. After cells detached from the flask, trypsin activity was neutralized with 8 milliliters of Growth medium. Cells were transferred to a 15 milliliter centrifuge tube and centrifuged at 150×g for 5 minutes. Supernatant was removed, and 1 milliliter Growth medium was added to each tube to resuspend the cells. Cell number was estimated using a hemocytometer.

ELISA Assay.

The amount of IL-8 secreted by the cells into serum starvation medium was analyzed using ELISA assays (R&D Systems, Minneapolis, Minn.). All assays were tested according to the instructions provided by the manufacturer.

Total RNA Isolation.

RNA was extracted from confluent postpartum-derived cells and fibroblasts. RNA was extracted from cells treated as described above for IL-8 expression analysis. Cells were lysed with 350 microliters buffer RLT containing beta-mercaptoethanol (Sigma, St. Louis, Mo.) according to the manufacturer's instructions (RNeasy Mini Kit; Qiagen, Valencia, Calif.). RNA was extracted according to the manufacturer's instructions (RNeasy Mini Kit; Qiagen, Valencia, Calif.) and subjected to DNase treatment (2.7 U/sample) (Sigma St. Louis, Mo.). RNA was eluted with 50 microliters DEPC-treated water and stored at −80° C. RNA was also extracted from human placenta and umbilical cord. Tissue (30 milligram) was suspended in 700 microliters of buffer RLT containing beta-mercaptoethanol. Samples were mechanically homogenized, and the RNA extraction proceeded according to manufacturer's specification. RNA was extracted with 50 microliters of DEPC-treated water and stored at −80° C.

Reverse Transcription.

RNA was reverse-transcribed using random hexamers with the TaqMan® reverse transcription reagents (Applied Biosystems, Foster City, Calif.) at 25° C. for 10 minutes, 37° C. for 60 minutes, and 95° C. for 10 minutes. Samples were stored at −20° C.

Genes identified by cDNA microarray as uniquely regulated in postpartum-derived cells (signature genes—including oxidized LDL receptor, interleukin-8, renin, and reticulon) were further investigated using real-time and conventional PCR.

Real-Time PCR.

PCR was performed on cDNA samples using ASSAYS-ON-DEMAND gene expression products: oxidized LDL receptor (Hs00234028); renin (Hs00166915); reticulon (Hs00382515); CXC ligand 3 (Hs00171061); GCP-2 (Hs00605742); IL-8 (Hs00174103); and GAPDH were mixed with cDNA and TaqMan Universal PCR master mix according to the manufacturer's instructions (Applied Biosystems, Foster City, Calif.) using a 7000 sequence detection system with ABI Prism 7000 SDS software (Applied Biosystems, Foster City, Calif.). Thermal cycle conditions were initially 50° C. for 2 minutes and 95° C. for 10 min, followed by 40 cycles of 95° C. for 15 seconds and 60° C. for 1 minute. PCR data was analyzed according to manufacturer's specifications (User Bulletin #2 from Applied Biosystems for ABI Prism 7700 Sequence Detection System).

Conventional PCR.

Conventional PCR was performed using an ABI PRISM 7700 (Perkin Elmer Applied Biosystems, Boston, Mass.) to confirm the results from real-time PCR. PCR was performed using 2 microliters of cDNA solution, 1×TAQ polymerase (tradename AMPLITAQ GOLD) universal mix PCR reaction buffer (Applied Biosystems, Foster City, Calif.), and initial denaturation at 94° C. for 5 minutes. Amplification was optimized for each primer set: for IL-8, CXC ligand 3, and reticulon (94° C. for 15 seconds, 55° C. for 15 seconds and 72° C. for 30 seconds for 30 cycles); for renin (94° C. for 15 seconds, 53° C. for 15 seconds and 72° C. for 30 seconds for 38 cycles); for oxidized LDL receptor and GAPDH (94° C. for 15 seconds, 55° C. for 15 seconds and 72° C. for 30 seconds for 33 cycles). Primers used for amplification are listed in Table 1. Primer concentration in the final PCR reaction was 1 micromolar except for GAPDH which was 0.5 micromolar. GAPDH primers were the same as real-time PCR, except that the manufacturer's TaqMan probe was not added to the final PCR reaction. Samples were run on 2% (w/v) agarose gel and stained with ethidium bromide (Sigma, St. Louis, Mo.). Images were captured using a 667 Universal Twinpack film (VWR International, South Plainfield, N.J.) using a focal-length POLAROID camera (VWR International, South Plainfield, N.J.).

TABLE 9-1

Primers used

| Primer name | Primers | | |
|---|---|---|---|
| Oxidized LDL receptor | S: 5'-GAGAAATCCAAAGAGCAAATGG-3'<br>A: 5'-AGAATGGAAAACTGGAATAGG-3' | (SEQ ID NO:1)<br>(SEQ ID NO:2) | |
| Renin | S: 5'-TCTTCGATCCTTCCGATTCC-3'<br>A: 5'-GAATTCTCGGAATCTCTGTTG-3' | (SEQ ID NO:3)<br>(SEQ ID NO:4) | |
| Reticulon | S: 5'- TTACAAGCAGTGCAGAAAACC-3'<br>A: 5'- AGTAAACATTGAAACCACAGCC-3' | (SEQ ID NO:5)<br>(SEQ ID NO:6) | |
| Interleukin-8 | S: 5'- TCTGCAGCTCTGTGTGAAGG-3'<br>A: 5'-CTTCAAAAACTTCTCCACAACC- 3' | (SEQ ID NO:7)<br>(SEQ ID NO:8) | |
| Chemokine (CXC) ligand 3 | S: 5'- CCCACGCCACGCTCTCC-3'<br>A: 5'-TCCTGTCAGTTGGTGCTCC -3' | (SEQ ID NO:9)<br>(SEQ ID NO:10) | |

Immunofluorescence.

Postpartum-derived cells were fixed with cold 4% (w/v) paraformaldehyde (Sigma-Aldrich, St. Louis, Mo.) for 10 minutes at room temperature. One isolate each of umbilicus- and placenta-derived cells at passage 0 (P0) (directly after isolation) and passage 11 (P11) (two isolates of Placenta-derived, two isolates of Umbilicus-derived cells) and fibroblasts (P11) were used. Immunocytochemistry was performed using antibodies directed against the following epitopes: vimentin (1:500, Sigma, St. Louis, Mo.), desmin (1:150; Sigma—raised against rabbit; or 1:300; Chemicon, Temecula, Calif.—raised against mouse), alpha-smooth muscle actin (SMA; 1:400; Sigma), cytokeratin 18 (CK18; 1:400; Sigma), von Willebrand Factor (vWF; 1:200; Sigma), and CD34 (human CD34 Class III; 1:100; DAKOCytomation, Carpinteria, Calif.). In addition, the following markers were tested on passage 11 postpartum-derived cells: anti-human GROalpha—PE (1:100; Becton Dickinson, Franklin Lakes, N.J.), anti-human GCP-2 (1:100; Santa Cruz Biotech, Santa Cruz, Calif.), anti-human oxidized LDL receptor 1 (ox-LDL R1; 1:100; Santa Cruz Biotech), and anti-human NOGA-A (1:100; Santa Cruz, Biotech).

Cultures were washed with phosphate-buffered saline (PBS) and exposed to a protein blocking solution containing PBS, 4% (v/v) goat serum (Chemicon, Temecula, Calif.), and 0.3% (v/v) Triton (Triton X-100; Sigma, St. Louis, Mo.) for 30 minutes to access intracellular antigens. Where the epitope of interest was located on the cell surface (CD34, ox-LDL R1), Triton X-100 was omitted in all steps of the procedure in order to prevent epitope loss. Furthermore, in instances where the primary antibody was raised against goat (GCP-2, ox-IDL R1, NOGO-A), 3% (v/v) donkey serum was used in place of goat serum throughout the process. Primary antibodies, diluted in blocking solution, were then applied to the cultures for a period of 1 hour at room temperature. The primary antibody solutions were removed and the cultures were washed with PBS prior to application of secondary antibody solutions (1 hour at room temperature) containing block along with goat anti-mouse IgG—Texas Red (1:250; Molecular Probes, Eugene, Oreg.) and/or goat anti-rabbit IgG—Alexa 488 (1:250; Molecular Probes) or donkey anti-goat IgG—FITC (1:150, Santa Cruz Biotech). Cultures were then washed and 10 micromolar DAPI (Molecular Probes) applied for 10 minutes to visualize cell nuclei.

Following immunostaining, fluorescence was visualized using an appropriate fluorescence filter on an Olympus inverted epi-fluorescent microscope (Olympus, Melville, N.Y.). In all cases, positive staining represented fluorescence signal above control staining where the entire procedure outlined above was followed with the exception of application of a primary antibody solution (no 1° control). Representative images were captured using a digital color videocamera and ImagePro software (Media Cybernetics, Carlsbad, Calif.). For triple-stained samples, each image was taken using only one emission filter at a time. Layered montages were then prepared using Adobe Photoshop software (Adobe, San Jose, Calif.).

Preparation of Cells for FACS Analysis.

Adherent cells in flasks were washed in phosphate buffered saline (PBS) (Gibco, Carlsbad, Calif.) and detached with Trypsin/EDTA (Gibco, Carlsbad, Calif.). Cells were harvested, centrifuged, and re-suspended in 3% (v/v) FBS in PBS at a cell concentration of $1 \times 10^7$/milliliter. One hundred microliter aliquots were delivered to conical tubes. Cells stained for intracellular antigens were permeabilized with Perm/Wash buffer (BD Pharmingen, San Diego, Calif.). Antibody was added to aliquots as per manufacturer's specifications, and the cells were incubated in the dark for 30 minutes at 4° C. After incubation, cells were washed with PBS and centrifuged to remove excess antibody. Cells requiring a secondary antibody were resuspended in 100 microliters of 3% FBS. Secondary antibody was added as per manufacturer's specification, and the cells were incubated in the dark for 30 minutes at 4° C. After incubation, cells were washed with PBS and centrifuged to remove excess secondary antibody. Washed cells were resuspended in 0.5 milliliter PBS and analyzed by flow cytometry. The following antibodies were used: oxidized LDL receptor 1 (sc-5813; Santa Cruz, Biotech), GROa (555042; BD Pharmingen, Bedford, Mass.), Mouse IgG1 kappa, (P-4685 and M-5284; Sigma), and Donkey against Goat IgG (sc-3743; Santa Cruz, Biotech.).

FACS Analysis.

Flow cytometry analysis was performed with FACScalibur (Becton Dickinson San Jose, Calif.).

Results

Results of real-time PCR for selected "signature" genes performed on cDNA from cells derived from human placentas, adult and neonatal fibroblasts, and Mesenchymal Stem Cells (MSCs) indicate that both oxidized LDL receptor and renin were expressed at higher level in the placenta-derived cells as compared to other cells. The data obtained from real-time PCR were analyzed by the ΔΔCT method and expressed on a logarithmic scale. Levels of reticulon and oxidized LDL receptor expression were higher in umbilicus-derived cells as compared to other cells. No significant difference in the expression levels of CXC ligand 3 and GCP-2 were found between postpartum-derived cells and controls (data not shown). CXC-ligand 3 was expressed at very low levels. GCP-2 was expressed at levels comparable to human adult and neonatal fibroblasts. The results of real-time PCR were confirmed by conventional PCR. Sequencing of PCR products further validated these observations. No significant difference in the expression level of CXC ligand 3 was found between postpartum-derived cells and controls using conventional PCR CXC ligand 3 primers listed in Table 9-1.

The expression of the cytokine IL-8 in postpartum-derived cells is elevated in both Growth medium-cultured and serum-starved postpartum-derived cells. All real-time PCR data was validated with conventional PCR and by sequencing PCR products.

When supernatants of cells grown in serum-free medium were examined for the presence of IL-8, the highest amounts were detected in media derived from umbilicus-derived cells and some isolates of placenta-derived cells (Table 9-2). No IL-8 was detected in medium derived from human dermal fibroblasts.

TABLE 9-2

IL-8 protein expression measured by ELISA

| Cell type | IL-8 |
| --- | --- |
| Human fibroblasts | ND |
| Placenta Isolate 1 | ND |
| UMBC Isolate 1 | 2058.42 ± 144.67 |
| Placenta Isolate 2 | ND |
| UMBC Isolate 2 | 2368.86 ± 22.73 |
| Placenta Isolate3 (normal $O_2$) | 17.27 ± 8.63 |
| Placenta Isolate 3 (low$O_2$, W/O BME) | 264.92 ± 9.88 |

Results of the ELISA assay for interleukin-8 (IL-8) performed on placenta-and umbilicus-derived cells as well as human skin fibroblasts. Values are presented here are picogram/million cells, n = 2, sem.
ND: Not Detected Placenta-derived cells were also examined for the expression of oxidized LDL receptor, GCP-2, and GROalpha by FACS analysis. Cells tested positive for GCP-2. Oxidized LDL receptor and GRO were not detected by this method.

Placenta-derived cells were also tested for the expression of selected proteins by immunocytochemical analysis. Immediately after isolation (passage 0), cells derived from the human placenta were fixed with 4% paraformaldehyde and exposed to antibodies for six proteins: von Willebrand Factor, CD34, cytokeratin 18, desmin, alpha-smooth muscle actin, and vimentin. Cells stained positive for both alpha-smooth muscle actin and vimentin. This pattern was preserved through passage 11. Only a few cells (<5%) at passage 0 stained positive for cytokeratin 18.

Cells derived from the human umbilical cord at passage 0 were probed for the expression of selected proteins by immunocytochemical analysis. Immediately after isolation (passage 0), cells were fixed with 4% paraformaldehyde and exposed to antibodies for six proteins: von Willebrand Factor, CD34, cytokeratin 18, desmin, alpha-smooth muscle actin, and vimentin. Umbilicus-derived cells were positive for alpha-smooth muscle actin and vimentin, with the staining pattern consistent through passage 11.

Placenta-derived cells at passage 11 were also investigated by immunocytochemistry for the expression of GROalpha and GCP-2. Placenta-derived cells were GCP-2 positive, but GROalpha expression was not detected by this method.

The expression of GROalpha, GCP-2, oxidized LDL receptor 1 and reticulon (NOGO-A) in umbilicus-derived cells at passage 11 was investigated by immunocytochemistry. Umbilicus-derived cells were GCP-2 positive, but GRO alpha expression was not detected by this method. Furthermore, cells were NOGO-A positive.

Summary.

Accordance between gene expression levels measured by microarray and PCR (both real-time and conventional) has been established for four genes: oxidized LDL receptor 1, renin, reticulon, and IL-8. The expression of these genes was differentially regulated at the mRNA level in postpartum-derived cells, with IL-8 also differentially regulated at the protein level. The presence of oxidized LDL receptor was not detected at the protein level by FACS analysis in cells derived from the placenta. Differential expression of GCP-2 and CXC ligand 3 was not confirmed at the mRNA level; however, GCP-2 was detected at the protein level by FACS analysis in the placenta-derived cells. Although this result does not support data originally obtained from the microarray experiment, this may be due to a difference in the sensitivity of the methodologies.

Immediately after isolation (passage 0), cells derived from the human placenta stained positive for both alpha-smooth muscle actin and vimentin. This pattern was also observed in cells at passage 11. These results suggest that vimentin and alpha-smooth muscle actin expression may be preserved in cells with passaging, at least in the Growth medium used here.

Cells derived from the human umbilicus at passage 0 were probed for the expression of alpha-smooth muscle actin and vimentin and were positive for both. The staining pattern was preserved through passage 11.

In conclusion, the complete mRNA data at least partially verifies the data obtained from the microarray experiments.

Example 10

Immunohistochemical Characterization of PPDC Phenotype

The phenotypes of cells found within human postpartum tissues, namely umbilical cord and placenta, were analyzed by immunohistochemistry.

Methods & Materials

Tissue Preparation.

Human umbilical cord and placental tissue were harvested and immersion-fixed in 4% (w/v) paraformaldehyde overnight at 4° C. Immunohistochemistry was performed using antibodies directed against the following epitopes (see Table 10-1): vimentin (1:500; Sigma, St. Louis, Mo.), desmin (1:150, raised against rabbit; Sigma; or 1:300, raised against mouse; Chemicon, Temecula, Calif.), alpha-smooth muscle actin (SMA; 1:400; Sigma), cytokeratin 18 (CK18; 1:400; Sigma), von Willebrand Factor (vWF; 1:200; Sigma), and CD34 (human CD34 Class III; 1:100; DAKOCytomation, Carpinteria, Calif.). In addition, the following markers were tested: anti-human GROalpha—PE (1:100; Becton Dickinson, Franklin Lakes, N.J.), anti-human GCP-2 (1:100; Santa Cruz Biotech, Santa Cruz, Calif.), anti-human oxidized LDL receptor 1 (ox-LDL R1; 1:100; Santa Cruz Biotech), and anti-human NOGO-A (1:100; Santa Cruz Biotech). Fixed specimens were trimmed with a scalpel and placed within OCT embedding compound (Tissue-Tek OCT; Sakura, Torrance, Calif.) on a dry ice bath containing ethanol. Frozen blocks were then sectioned (10 micron thick) using a standard cryostat (Leica Microsystems) and mounted onto glass slides for staining.

TABLE 10-1

Summary of Primary Antibodies Used

| Antibody | Concentration | Vendor |
|---|---|---|
| Vimentin | 1:500 | Sigma, St. Louis, MO |
| Desmin (rb) | 1:150 | Sigma |
| Desmin (m) | 1:300 | Chemicon, Temecula, CA |
| alpha-smooth muscle actin (SMA) | 1:400 | Sigma |
| Cytokeratin 18 (CK18) | 1:400 | Sigma |
| von Willebrand factor (vWF) | 1:200 | Sigma |
| CD34 III | 1:100 | DakoCytomation, Carpinteria, CA |
| GROalpha-PE | 1:100 | BD, Franklin Lakes, NJ |
| GCP-2 | 1:100 | Santa Cruz Biotech |
| Ox-LDL R1 | 1:100 | Santa Cruz Biotech |
| NOGO-A | 1:100 | Santa Cruz Biotech |

Immunohistochemistry.

Immunohistochemistry was performed similar to previous studies (e.g., Messina, et al. (2003) *Exper. Neurol.* 184: 816-829). Tissue sections were washed with phosphate-buffered saline (PBS) and exposed to a protein blocking solution containing PBS, 4% (v/v) goat serum (Chemicon, Temecula, Calif.), and 0.3% (v/v) Triton (Triton X-100; Sigma) for 1 hour to access intracellular antigens. In instances where the epitope of interest would be located on the cell surface (CD34, ox-LDL R1), triton was omitted in all steps of the procedure in order to prevent epitope loss. Furthermore, in instances where the primary antibody was raised against goat (GCP-2, ox-LDL R1, NOGO-A), 3% (v/v) donkey serum was used in place of goat serum throughout the procedure. Primary antibodies, diluted in blocking solution, were then applied to the sections for a period of 4 hours at room temperature. Primary antibody solutions were removed, and cultures washed with PBS prior to application of secondary antibody solutions (1 hour at room temperature) containing block along with goat anti-mouse IgG—Texas Red (1:250; Molecular Probes, Eugene, Oreg.) and/or goat anti-rabbit IgG—Alexa 488 (1:250; Molecular Probes) or donkey anti-goat IgG—FITC (1:150; Santa Cruz Biotech). Cultures were washed, and 10 micromolar DAPI (Molecular Probes) was applied for 10 minutes to visualize cell nuclei.

Following immunostaining, fluorescence was visualized using the appropriate fluorescence filter on an Olympus inverted epi-fluorescent microscope (Olympus, Melville, N.Y.). Positive staining was represented by fluorescence signal above control staining. Representative images were captured using a digital color videocamera and ImagePro software (Media Cybernetics, Carlsbad, Calif.). For triple-stained samples, each image was taken using only one emission filter at a time. Layered montages were then prepared using Adobe Photoshop software (Adobe, San Jose, Calif.).

Results

Umbilical Cord Characterization.

Vimentin, desmin, SMA, CK18, vWF, and CD34 markers were expressed in a subset of the cells found within umbilical cord (data not shown). In particular, vWF and CD34 expression were restricted to blood vessels contained within the cord. CD34+ cells were on the innermost layer (lumen side). Vimentin expression was found throughout the matrix and blood vessels of the cord. SMA was limited to the matrix and outer walls of the artery and vein but was not contained within the vessels themselves. CK18 and desmin were observed within the vessels only, desmin being restricted to the middle and outer layers.

Placenta Characterization.

Vimentin, desmin, SMA, CK18, vWF, and CD34 were all observed within the placenta and regionally specific.

GROalpha, GCP-2, ox-LDL R1, and NOGO-A Tissue Expression.

None of these markers were observed within umbilical cord or placental tissue (data not shown).

Summary.

Vimentin, desmin, alpha-smooth muscle actin, cytokeratin 18, von Willebrand Factor, and CD 34 are expressed in cells within human umbilical cord and placenta. Based on in vitro characterization studies showing that only vimentin and alpha-smooth muscle actin are expressed, the data suggests that the current process of postpartum cell isolation harvests a subpopulation of cells or that the cells isolated change expression of markers to express vimentin and alpha-smooth muscle actin.

Example 11

In Vitro Immunology of Postpartum-Derived Cells

Postpartum-derived cell lines were evaluated in vitro for their immunological characteristics in an effort to predict the immunological response, if any, these cells would elicit upon in vivo transplantation. Postpartum-derived cell lines were assayed by flow cytometry for the expression of HLA-DR, HLA-DP, HLA-DQ, CD80, CD86, and B7-H2. These proteins are expressed by antigen-presenting cells (APC) and are required for the direct stimulation of naïve CD4$^+$ T cells (Abbas & Lichtman, CELLULAR AND MOLECULAR IMMUNOLOGY, 5th Ed. (2003) Saunders, Philadelphia, p. 171). The cell lines were also analyzed by flow cytometry for the expression of HLA-G (Abbas & Lichtman, CELLULAR AND MOLECULAR IMMUNOLOGY, 5th Ed. (2003) Saunders, Philadelphia, p. 171), CD 178 (Coumans, et. al., (1999) *Journal of Immunological Methods* 224, 185-196), and PD-L2 (Abbas & Lichtman, CELLULAR AND MOLECULAR IMMUNOLOGY, 5th Ed. (2003) Saunders, Philadelphia, p. 171; Brown, et. al. (2003) *The Journal of Immunology* 170, 1257-1266). The expression of these proteins by cells residing in placental tissues is thought to mediate the immuno-privileged status of placental tissues in utero. To predict the extent to which postpartum placenta- and umbilicus-derived cell lines elicit an immune response in vivo, the cell lines were tested in a one-way mixed lymphocyte reaction (MLR).

Materials and Methods

Cell Culture.

Cells were cultured in Growth medium (DMEM-low glucose (Gibco, Carlsbad, Calif.), 15% (v/v) fetal bovine serum (FBS); (Hyclone, Logan, Utah), 0.001% (v/v) beta-mercaptoethanol (Sigma, St. Louis, Mo.), 50 Units/milliliter penicillin, 50 micrograms/milliliter streptomycin (Gibco, Carlsbad, Calif.)) until confluent in T75 flasks (Corning, Corning, N.Y.) coated with 2% gelatin (Sigma, St. Louis, Mo.).

Antibody Staining.

Cells were washed in phosphate buffered saline (PBS) (Gibco, Carlsbad, Calif.) and detached with Trypsin/EDTA (Gibco, Carlsbad, Calif.). Cells were harvested, centrifuged, and re-suspended in 3% (v/v) FBS in PBS at a cell concentration of $1 \times 10^7$ per milliliter. Antibody (Table 11-1) was added to one hundred microliters of cell suspension as per manufacturer's specifications and incubated in the dark for 30 minutes at 4° C. After incubation, cells were washed with PBS and centrifuged to remove unbound antibody. Cells were re-suspended in five hundred microliters of PBS and analyzed by flow cytometry using a FACSCalibur instrument (Becton Dickinson, San Jose, Calif.).

TABLE 11-1

Antibodies

| Antibody | Manufacturer | Catalog Number |
|---|---|---|
| HLA-DRDPDQ | BD Pharmingen (San Diego, CA) | 555558 |
| CD80 | BD Pharmingen (San Diego, CA) | 557227 |
| CD86 | BD Pharmingen (San Diego, CA) | 555665 |
| B7-H2 | BD Pharmingen (San Diego, CA) | 552502 |
| HLA-G | Abcam (Cambridgeshire, UK) | ab 7904-100 |
| CD 178 | Santa Cruz (San Cruz, CA) | sc-19681 |
| PD-L2 | BD Pharmingen (San Diego, CA) | 557846 |
| Mouse IgG2a | Sigma (St. Louis, MO) | F-6522 |
| Mouse IgG1kappa | Sigma (St. Louis, MO) | P-4685 |

Mixed Lymphocyte Reaction.

Cryopreserved vials of passage 10 umbilicus-derived PPDCs labeled as cell line A and passage 11 placenta-derived PPDCs labeled as cell line B were sent on dry ice to CTBR (Senneville, Quebec) to conduct a mixed lymphocyte reaction using CTBR SOP no. CAC-031. Peripheral blood mononuclear cells (PBMCs) were collected from multiple male and female volunteer donors. Stimulator (donor) allogeneic PBMC, autologous PBMC, and postpartum-derived cell lines were treated with mitomycin C. Autologous and mitomycin C-treated stimulator cells were added to responder (recipient) PBMCs and cultured for 4 days. After incubation, [$^3$H]thymidine was added to each sample and cultured for 18 hours. Following harvest of the cells, radiolabeled DNA was extracted, and [$^3$H]-thymidine incorporation was measured using a scintillation counter.

The stimulation index for the allogeneic donor (SIAD) was calculated as the mean proliferation of the receiver plus mitomycin C-treated allogeneic donor divided by the baseline proliferation of the receiver. The stimulation index of the postpartum-derived cells was calculated as the mean proliferation of the receiver plus mitomycin C-treated postpartum-derived cell line divided by the baseline proliferation of the receiver.

Results

Mixed Lymphocyte Reaction-Placenta.

Seven human volunteer blood donors were screened to identify a single allogeneic donor that would exhibit a robust proliferation response in a mixed lymphocyte reaction with the other six blood donors. This donor was selected as the allogeneic positive control donor. The remaining six blood donors were selected as recipients. The allogeneic positive control donor and placenta-derived cell lines were treated with mitomycin C and cultured in a mixed lymphocyte reaction with the six individual allogeneic receivers. Reactions were performed in triplicate using two cell culture plates with three receivers per plate (Table 11-2). The average stimulation index ranged from 1.3 (plate 2) to 3 (plate 1) and the allogeneic donor positive controls ranged from 46.25 (plate 2) to 279 (plate 1) (Table 11-3).

TABLE 11-2

Mixed Lymphocyte Reaction Data - Cell Line B (Placenta)
DPM for Proliferation Assay

| Analytical number | Culture System | Replicates | | | Mean | SD | CV |
|---|---|---|---|---|---|---|---|
| | | 1 | 2 | 3 | | | |
| Plate ID: Plate1 | | | | | | | |
| IM03-7769 | Proliferation baseline of receiver | 79 | 119 | 138 | 112.0 | 30.12 | 26.9 |
| | Control of autostimulation(Mitomycin C treated autologous cells) | 241 | 272 | 175 | 229.3 | 49.54 | 21.6 |
| | MLR allogenic donor IM03-7768 (Mitomycin C treated) | 23971 | 22352 | 20921 | 22414.7 | 1525.97 | 6.8 |
| | MLR with cell line (Mitomycin C treated cell type B) | 664 | 559 | 1090 | 771.0 | 281.21 | 36.5 |
| SI (donor) | | | | | 200 | | |
| SI (cell line) | | | | | 7 | | |
| IM03-7770 | Proliferation baseline of receiver | 206 | 134 | 262 | 200.7 | 64.17 | 32.0 |
| | Control of autostimulation(Mitomycin C treated autologous cells) | 1091 | 602 | 524 | 739.0 | 307.33 | 41.6 |
| | MLR allogenic donor IM03-7768 (Mitomycin C treated) | 45005 | 43729 | 44071 | 44268.3 | 660.49 | 1.5 |
| | MLR with cell line (Mitomycin C treated cell type B) | 533 | 2582 | 2376 | 1830.3 | 1128.24 | 61.6 |
| SI (donor) | | | | | 221 | | |
| SI (cell line) | | | | | 9 | | |
| IM03-7771 | Proliferation baseline of receiver | 157 | 87 | 128 | 124.0 | 35.17 | 28.4 |
| | Control of autostimulation(Mitomycin C treated autologous cells) | 293 | 138 | 508 | 313.0 | 185.81 | 59.4 |
| | MLR allogenic donor IM03-7768 (Mitomycin C treated) | 24497 | 34348 | 31388 | 30077.7 | 5054.53 | 16.8 |
| | MLR with cell line (Mitomycin C treated cell type B) | 601 | 643 | a | 622.0 | 29.70 | 4.8 |
| SI (donor) | | | | | 243 | | |
| SI (cell line) | | | | | 5 | | |
| IM03-7772 | Proliferation baseline of receiver | 56 | 98 | 51 | 68.3 | 25.81 | 37.8 |
| | Control of autostimulation(Mitomycin C treated autologous cells) | 133 | 120 | 213 | 155.3 | 50.36 | 32.4 |
| | MLR allogenic donor IM03-7768 (Mitomycin C treated) | 14222 | 20076 | 22168 | 18822.0 | 4118.75 | 21.9 |
| | MLR with cell line (Mitomycin C treated cell type B) | a | a | a | a | a | a |
| SI (donor) | | | | | 275 | | |
| SI (cell line) | | | | | a | | |
| IM03-7768 (allogenic donor) | Proliferation baseline of receiver | 84 | 242 | 208 | 178.0 | 83.16 | 46.7 |
| | Control of autostimulation(Mitomycin treated autologous cells) | 361 | 617 | 304 | 427.3 | 166.71 | 39.0 |
| Cell line type B | Proliferation baseline of receiver | 126 | 124 | 143 | 131.0 | 10.44 | 8.0 |
| | Control of autostimulation (Mitomycin treated autologous cells) | 822 | 1075 | 487 | 794.7 | 294.95 | 37.1 |

TABLE 11-2-continued

Mixed Lymphocyte Reaction Data - Cell Line B (Placenta)
DPM for Proliferation Assay

| Analytical number | Culture System | Replicates 1 | 2 | 3 | Mean | SD | CV |
|---|---|---|---|---|---|---|---|
| | Plate ID: Plate 2 | | | | | | |
| IM03-7773 | Proliferation baseline of receiver | 908 | 181 | 330 | 473.0 | 384.02 | 81.2 |
| | Control of autostimulation(Mitomycin C treated autologous cells) | 269 | 405 | 572 | 415.3 | 151.76 | 36.5 |
| | MLR allogenic donor IM03-7768 (Mitomycin C treated) | 29151 | 28691 | 28315 | 28719.0 | 418.70 | 1.5 |
| | MLR with cell line (Mitomycin C treated cell type B) | 567 | 732 | 905 | 734.7 | 169.02 | 23.0 |
| SI (donor) | | | | | 61 | | |
| SI (cell line) | | | | | 2 | | |
| IM03-7774 | Proliferation baseline of receiver | 893 | 1376 | 185 | 818.0 | 599.03 | 73.2 |
| | Control of autostimulation (Mitomycin C treated autologous cells) | 261 | 381 | 568 | 403.3 | 154.71 | 38.4 |
| | MLR allogenic donor IM03-7768 (Mitomycin C treated) | 53101 | 42839 | 48283 | 48074.3 | 5134.18 | 10.7 |
| | MLR with cell line (Mitomycin C treated cell type B) | 515 | 789 | 294 | 532.7 | 247.97 | 46.6 |
| SI (donor) | | | | | 59 | | |
| SI (cell line) | | | | | 1 | | |
| IM03-7775 | Proliferation baseline of receiver | 1272 | 300 | 544 | 705.3 | 505.69 | 71.7 |
| | Control of autostimulation (Mitomycin C treated autologous cells) | 232 | 199 | 484 | 305.0 | 155.89 | 51.1 |
| | MLR allogenic donor IM03-7768 (Mitomycin C treated) | 23554 | 10523 | 28985 | 21014.0 | 9479.74 | 45.1 |
| | MLR with cell line (Mitomycin C treated cell type B) | 768 | 924 | 563 | 751.7 | 181.05 | 24.1 |
| SI (donor) | | | | | 30 | | |
| SI (cell line) | | | | | 1 | | |
| IM03-7776 | Proliferation baseline of receiver | 1530 | 137 | 1046 | 904.3 | 707.22 | 78.2 |
| | Control of autostimulation (Mitomycin C treated autologous cells) | 420 | 218 | 394 | 344.0 | 109.89 | 31.9 |
| | MLR allogenic donor IM03-7768 (Mitomycin C treated) | 28893 | 32493 | 34746 | 32044.0 | 2952.22 | 9.2 |
| | MLR with cell line (Mitomycin C treated cell type B) | a | a | a | a | a | a |
| SI (donor) | | | | | 35 | | |
| SI (cell line) | | | | | a | | |

TABLE 11-3

Average stimulation index of placenta cells and an allogeneic donor in a mixed lymphocyte reaction with six individual allogeneic receivers.
Average Stimulation Index

| | Recipient | Placenta |
|---|---|---|
| Plate 1 (receivers 1- 3) | 279 | 3 |
| Plate 2 (receivers 4- 6) | 46.25 | 1.3 |

Mixed Lymphocyte Reaction—Umbilicus.

Six human volunteer blood donors were screened to identify a single allogeneic donor that will exhibit a robust proliferation response in a mixed lymphocyte reaction with the other five blood donors. This donor was selected as the allogeneic positive control donor. The remaining five blood donors were selected as recipients. The allogeneic positive control donor and umbilicus-derived cell lines were mitomycin C-treated and cultured in a mixed lymphocyte reaction with the five individual allogeneic receivers. Reactions were performed in triplicate using two cell culture plates with three receivers per plate (Table 11-4). The average stimulation index ranged from 6.5 (plate 1) to 9 (plate 2) and the allogeneic donor positive controls ranged from 42.75 (plate 1) to 70 (plate 2) (Table 11-5).

TABLE 11-4

Mixed Lymphocyte Reaction Data-Cell Line A (Umbilicus)
DPM for Proliferation Assay

| Analytical number | Culture System | Replicates 1 | 2 | 3 | Mean | SD | CV |
|---|---|---|---|---|---|---|---|
| | Plate ID: Plate1 | | | | | | |
| IM04-2478 | Proliferation baseline of receiver | 1074 | 406 | 391 | 623.7 | 390.07 | 62.5 |
| | Control of autostimulation (Mitomycin C treated autologous cells) | 672 | 510 | 1402 | 861.3 | 475.19 | 55.2 |
| | MLR allogenic donor IM04-2477 (Mitomycin C treated) | 43777 | 48391 | 38231 | 43466.3 | 5087.12 | 11.7 |
| | MLR with cell line (Mitomycin C treated cell type A) | 2914 | 5622 | 6109 | 4881.7 | 1721.36 | 35.3 |
| SI (donor) | | | | | 70 | | |
| SI (cell line) | | | | | 8 | | |
| IM04-2479 | Proliferation baseline of receiver | 530 | 508 | 527 | 521.7 | 11.93 | 2.3 |
| | Control of autostimulation (Mitomycin C treated autologous cells) | 701 | 567 | 1111 | 793.0 | 283.43 | 35.7 |
| | MLR allogenic donor IM04-2477 (Mitomycin C treated) | 25593 | 24732 | 22707 | 24344.0 | 1481.61 | 6.1 |
| | MLR with cell line (Mitomycin C treated cell type A) | 5086 | 3932 | 1497 | 3505.0 | 1832.21 | 52.3 |
| SI (donor) | | | | | 47 | | |
| SI (cell line) | | | | | 7 | | |

TABLE 11-4-continued

Mixed Lymphocyte Reaction Data-Cell Line A (Umbilicus)
DPM for Proliferation Assay

| Analytical number | Culture System | Replicates | | | Mean | SD | CV |
|---|---|---|---|---|---|---|---|
| | | 1 | 2 | 3 | | | |
| IM04-2480 | Proliferation baseline of receiver | 1192 | 854 | 1330 | 1125.3 | 244.90 | 21.8 |
| | Control of autostimulation (Mitomycin C treated autologous cells) | 2963 | 993 | 2197 | 2051.0 | 993.08 | 48.4 |
| | MLR allogenic donor IM04-2477 (Mitomycin C treated) | 25416 | 29721 | 23757 | 26298.0 | 3078.27 | 11.7 |
| | MLR with cell line (Mitomycin C treated cell type A) | 2596 | 5076 | 3426 | 3699.3 | 1262.39 | 34.1 |
| SI (donor) | | | | | 23 | | |
| SI (cell line) | | | | | 3 | | |
| IM04-2481 | Proliferation baseline of receiver | 695 | 451 | 555 | 567.0 | 122.44 | 21.6 |
| | Control of autostimulation (Mitomycin C treated autologous cells) | 738 | 1252 | 464 | 818.0 | 400.04 | 48.9 |
| | MLR allogenic donor IM04-2477 (Mitomycin C treated) | 13177 | 24885 | 15444 | 17835.3 | 6209.52 | 34.8 |
| | MLR with cell line (Mitomycin C treated cell type A) | 4495 | 3671 | 4674 | 4280.0 | 534.95 | 12.5 |
| SI (donor) | | | | | 31 | | |
| SI (cell line) | | | | | 8 | | |
| | Plate ID: Plate 2 | | | | | | |
| IM04-2482 | Proliferation baseline of receiver | 432 | 533 | 274 | 413.0 | 130.54 | 31.6 |
| | Control of autostimulation (Mitomycin C treated autologous cells) | 1459 | 633 | 598 | 896.7 | 487.31 | 54.3 |
| | MLR allogenic donor IM04-2477 (Mitomycin C treated) | 24286 | 30823 | 31346 | 28818.3 | 3933.82 | 13.7 |
| | MLR with cell line (Mitomycin C treated cell type A) | 2762 | 1502 | 6723 | 3662.3 | 2724.46 | 74.4 |
| SI (donor) | | | | | 70 | | |
| SI (cell line) | | | | | 9 | | |
| IM04-2477 (allogenic donor) | Proliferation baseline of receiver | 312 | 419 | 349 | 360.0 | 54.34 | 15.1 |
| | Control of autostimulation (Mitomycin treated autologous cells) | 567 | 604 | 374 | 515.0 | 123.50 | 24.0 |
| Cell line type A | Proliferation baseline of receiver | 5101 | 3735 | 2973 | 3936.3 | 1078.19 | 27.4 |
| | Control of autostimulation (Mitomycin treated autologous cells) | 1924 | 4570 | 2153 | 2882.3 | 1466.04 | 50.9 |

TABLE 11-5

Average stimulation index of umbilicus-derived cells and an allogeneic donor in a mixed lymphocyte reaction with five individual allogeneic receivers.

| Average Stimulation Index | | |
|---|---|---|
| | Recipient | Umbilical Cord |
| Plate 1 (receivers 1- 4) | 42.75 | 6.5 |
| Plate 2 (receiver 5) | 70 | 9 |

Antigen Presenting Cell Markers—Placenta.

Histograms of placenta-derived cells analyzed by flow cytometry show negative expression of HLA-DR, DP, DQ, CD80, CD86, and B7-H2, as noted by fluorescence value consistent with the IgG control, indicating that placenta-derived cell lines lack the cell surface molecules required to directly stimulate allogeneic PBMCs (e.g., CD4+ T cells).

Immuno-Modulating Markers—Placenta-Derived Cells.

Histograms of placenta-derived cells analyzed by flow cytometry show positive expression of PD-L2, as noted by the increased value of fluorescence relative to the IgG control, and negative expression of CD178 and HLA-G, as noted by fluorescence value consistent with the IgG control (data not shown).

Antigen Presenting Cell Markers—Umbilicus-Derived Cells.

Histograms of umbilicus-derived cells analyzed by flow cytometry show negative expression of HLA-DR, DP, DQ, CD80, CD86, and B7-H2, as noted by fluorescence value consistent with the IgG control, indicating that umbilicus-derived cell lines lack the cell surface molecules required to directly stimulate allogeneic PBMCs (e.g., CD4+ T cells).

Immuno-Modulating Markers—Umbilicus-Derived Cells.

Histograms of umbilicus-derived cells analyzed by flow cytometry show positive expression of PD-L2, as noted by the increased value of fluorescence relative to the IgG control, and negative expression of CD178 and HLA-G, as noted by fluorescence value consistent with the IgG control.

Summary.

In the mixed lymphocyte reactions conducted with placenta-derived cell lines, the average stimulation index ranged from 1.3 to 3, and that of the allogeneic positive controls ranged from 46.25 to 279. In the mixed lymphocyte reactions conducted with umbilicus-derived cell lines, the average stimulation index ranged from 6.5 to 9, and that of the allogeneic positive controls ranged from 42.75 to 70. Placenta- and umbilicus-derived cell lines were negative for the expression of the stimulating proteins HLA-DR, HLA-DP, HLA-DQ, CD80, CD86, and B7-H2, as measured by flow cytometry. Placenta- and umbilicus-derived cell lines were negative for the expression of immuno-modulating proteins HLA-G and CD178 and positive for the expression of PD-L2, as measured by flow cytometry. Allogeneic donor PBMCs contain antigen-presenting cells expressing HLA-DP, DR, DQ, CD80, CD86, and B7-H2, thereby allowing for the stimulation of allogeneic PBMCs (e.g., naïve CD4+ T cells). The absence of antigen-presenting cell surface molecules on placenta- and umbilicus-derived cells required for the direct stimulation of allogeneic PBMCs (e.g., naïve CD4+ T cells) and the presence of PD-L2, an immuno-modulating protein, may account for the low stimulation index exhibited by these cells in a MLR as compared to allogeneic controls.

REFERENCES

Bruder S P et. al. U.S. Pat. No. 6,355,239 B1 (2002)
Abbas, A K, Lichtman, A H Cellular and Molecular Immunology 5th Ed. (2003) Saunders, Philadelphia, p. 171
Bouteiller P. Le et. al., (2003) Placenta 24; S10-S15
Coumans B et. al., (1999) Journal of Immunological Methods 224, 185-196]
Brown, Julia et. al. (2003) The Journal of Immunology 170, 1257-1266

Example 12

Secretion of Trophic Factors by Postpartum-Derived Cells

The secretion of selected trophic factors from placenta- and umbilicus-derived PPDCs was measured. Factors were selected that have angiogenic activity (i.e., hepatocyte growth factor (HGF) (Rosen et al. (1997) Ciba Found. Symp. 212:215-26), monocyte chemotactic protein 1 (MCP-1) (Salcedo et al. (2000) Blood 96; 34-40), interleukin-8 (IL-8) (Li et al. (2003) J. Immunol. 170:3369-76), keratinocyte growth factor (KGF), basic fibroblast growth factor (bFGF), vascular endothelial growth factor (VEGF) (Hughes et al. (2004) Ann. Thorac. Surg. 77:812-8), tissue inhibitor of matrix metalloproteinase 1 (TIMP1), angiopoietin 2 (ANG2), platelet derived growth factor (PDGF-bb), thrombopoietin (TPO), heparin-binding epidermal growth factor (HB-EGF), stromal-derived factor 1a (SDF-1a)), neurotrophic/neuroprotective activity (brain-derived neurotrophic factor (BDNF) (Cheng et al. (2003) Dev. Biol. 258; 319-33), interleukin-6 (IL-6), granulocyte chemotactic protein-2 (GCP-2), transforming growth factor beta2 (TGF-beta2)), or chemokine activity (macrophage inflammatory protein 1a (MIP1a), macrophage inflammatory protein 1beta (MIP1b), monocyte chemoattractant-1 (MCP-1), Rantes (regulated on activation, normal T cell expressed and secreted), I309, thymus and activation-regulated chemokine (TARC), Eotaxin, macrophage-derived chemokine (MDC), IL-8).

Methods & Materials

Cell Culture.

PPDCs derived from placenta and umbilicus as well as human fibroblasts derived from human neonatal foreskin were cultured in Growth medium (DMEM-low glucose (Gibco, Carlsbad, Calif.), 15% (v/v) fetal bovine serum (SH30070.03; Hyclone, Logan, Utah), 50 Units/milliliter penicillin, 50 micrograms/milliliter streptomycin (Gibco)) on gelatin-coated T75 flasks. Cells were cryopreserved at passage 11 and stored in liquid nitrogen. After thawing of the cells, Growth medium was added to the cells followed by transfer to a 15 milliliter centrifuge tube and centrifugation of the cells at 150×g for 5 minutes. The supernatant was discarded. The cell pellet was resuspended in 4 milliliters Growth medium, and cells were counted. Cells were seeded at 5,000 cells/cm$^2$ on a T75 flask containing 15 milliliters of Growth medium and cultured for 24 hours. The medium was changed to a serum-free medium (DMEM-low glucose (Gibco), 0.1% (w/v) bovine serum albumin (Sigma), 50 Units/milliliter penicillin, 50 micrograms/milliliter streptomycin (Gibco)) for 8 hours. Conditioned serum-free media was collected at the end of incubation by centrifugation at 14,000×g for 5 minutes and stored at −80° C. To estimate the number of cells in each flask, cells were washed with phosphate-buffered saline (PBS) and detached using 2 milliliters trypsin/EDTA (Gibco). Trypsin activity was inhibited by addition of 8 milliliters Growth medium. Cells were centrifuged at 150×g for 5 minutes. Supernatant was removed, and cells were resuspended in 1 milliliter Growth Medium. Cell number was estimated using a hemocytometer.

ELISA Assay.

Cells were grown at 37° C. in 5% carbon dioxide and atmospheric oxygen. Placenta-derived PPDCs (101503) also were grown in 5% oxygen or beta-mercaptoethanol (BME). The amount of MCP-1, IL-6, VEGF, SDF-1a, GCP-2, IL-8, and TGF-beta2 produced by each cell sample was measured by an ELISA assay (R&D Systems, Minneapolis, Minn.). All assays were performed according to the manufacturer's instructions. Values presented are picogram/milliliter/million cells (n=2, sem).

SearchLight Multiplexed ELISA Assay.

Chemokines (MIP1a, MIP1b, MCP-1, Rantes, I309, TARC, Eotaxin, MDC, IL8), BDNF, and angiogenic factors (HGF, KGF, bFGF, VEGF, TIMP1, ANG2, PDGF-bb, TPO, HB-EGF) were measured using SearchLight Proteome Arrays (Pierce Biotechnology Inc.). The Proteome Arrays are multiplexed sandwich ELISAs for the quantitative measurement of two to 16 proteins per well. The arrays are produced by spotting a 2×2, 3×3, or 4×4 pattern of four to 16 different capture antibodies into each well of a 96-well plate. Following a sandwich ELISA procedure, the entire plate is imaged to capture chemiluminescent signal generated at each spot within each well of the plate. The amount of signal generated in each spot is proportional to the amount of target protein in the original standard or sample.

Results

ELISA Assay.

MCP-1 and IL-6 were secreted by placenta- and umbilicus-derived PPDCs and dermal fibroblasts (Table 12-1). Umbilicus-derived cells secreted at least 10-fold higher amounts of MCP-1 and IL6 than other cell populations. GCP-2 and IL-8 were highly expressed by umbilicus-derived PPDCs. TGF-beta2 was not detectable. VEGF was detected in fibroblast medium.

The amount of HGF, FGF, and BDNF secreted from umbilicus-derived cells were noticeably higher than fibroblasts and placenta-derived cells (Tables 12-2 and 12-3). Similarly, TIMP1, TPO, HBEGF, MCP-1, TARC, and IL-8 were higher in umbilicus-derived cells than other cell populations (Table 12-3). No ANG2 or PDGF-bb were detected.

TABLE 12-1

ELISA assay results

| | MCP-1 | IL-6 | VEGF | SDF-1a | GCP-2 | IL-8 | TGF-beta2 |
|---|---|---|---|---|---|---|---|
| Fibroblast | 17 ± 1 | 61 ± 3 | 29 ± 2 | 19 ± 1 | 21 ± 1 | ND | ND |
| Placenta (042303) | 60 ± 3 | 41 ± 2 | ND | ND | ND | ND | ND |
| Umbilical (022803) | 1150 ± 74 | 4234 ± 289 | ND | ND | 160 ± 11 | 2058 ± 145 | ND |
| Placenta (071003) | 125 ± 16 | 10 ± 1 | ND | ND | ND | ND | ND |
| Umbilical (071003) | 2794 ± 84 | 1356 ± 43 | ND | ND | 2184 ± 98 | 2369 ± 23 | ND |

TABLE 12-1-continued

ELISA assay results

| | MCP-1 | IL-6 | VEGF | SDF-1a | GCP-2 | IL-8 | TGF-beta2 |
|---|---|---|---|---|---|---|---|
| Placenta (101503) BME | 21 ± 10 | 67 ± 3 | ND | ND | 44 ± 9 | 17 ± 9 | ND |
| Placenta (101503) 5% $O_2$, W/O BME | 77 ± 16 | 339 ± 21 | ND | 1149 ± 137 | 54 ± 2 | 265 ± 10 | ND |

Key:
ND: Not Detected.

TABLE 12-2

SearchLight Multiplexed ELISA assay results

| | TIMP1 | ANG2 | PDGFbb | TPO | KGF | HGF | FGF | VEGF | HBEGF | BDNF |
|---|---|---|---|---|---|---|---|---|---|---|
| hFB | 19306.3 | ND | ND | 230.5 | 5.0 | ND | ND | 27.9 | 1.3 | ND |
| P1 | 24299.5 | ND | ND | 546.6 | 8.8 | 16.4 | ND | ND | 3.81.3 | ND |
| U1 | 57718.4 | ND | ND | 1240.0 | 5.8 | 559.3 | 148.7 | ND | 9.3 | 165.7 |
| P3 | 14176.8 | ND | ND | 568.7 | 5.2 | 10.2 | ND | ND | 1.9 | 33.6 |
| U3 | 21850.0 | ND | ND | 1134.5 | 9.0 | 195.6 | 30.8 | ND | 5.4 | 388.6 |

Key:
hFB (human fibroblasts),
P1 (placenta-derived PPDC (042303)),
U1 (umbilicus-derived PPDC (022803)),
P3 (placenta-derived PPDC (071003)),
U3 (umbilicus-derived PPDC (071003)).
ND: Not Detected.

TABLE 12-3

SearchLight Multiplexed ELISA assay results

| | MIP1a | MIP1b | MCP1 | RANTES | I309 | TARC | Eotaxin | MDC | IL8 |
|---|---|---|---|---|---|---|---|---|---|
| hFB | ND | ND | 39.6 | ND | ND | 0.1 | ND | ND | 204.9 |
| P1 | 79.5 | ND | 228.4 | 4.1 | ND | 3.8 | 12.2 | ND | 413.5 |
| U1 | ND | 8.0 | 1694.2 | ND | 22.4 | 37.6 | ND | 18.9 | 51930.1 |
| P3 | ND | ND | 102.7 | ND | ND | 0.4 | ND | ND | 63.8 |
| U3 | ND | 5.2 | 2018.7 | 41.5 | 11.6 | 21.4 | ND | 4.8 | 10515.9 |

Key:
hFB (human fibroblasts),
P1 (placenta-derived PPDC (042303)),
U1 (umbilicus-derived PPDC (022803)),
P3 (placenta-derived PPDC (071003)),
U3 (umbilicus-derived PPDC (071003)).
ND: Not Detected.

Summary.

Umbilicus derived-cells secreted significantly higher amount of trophic factors than placenta-derived cells and fibroblasts. Some of these trophic factors, such as HGF, bFGF, MCP-1 and IL-8, play important roles in angiogenesis. Other trophic factors, such as BDNF and IL-6, have important roles in neural regeneration. Under these conditions, the expression of some factors was confined to umbilicus-derived cells, such as MIP1b, Rantes, I309, and FGF.

REFERENCES

Le Belle J E, Svendsen C N. (2002) Stem cells for neurodegenerative disorders: where can we go from here? *BioDrugs.* 16; 389-401

Rosen E M, Lamszus K, Laterra J, Polverini P J, Rubin J S, Goldberg I D. (1997) HGF/SF in angiogenesis. *Ciba Found Symp.* 212; 215-26.

Salcedo R, Ponce M L, Young H A, Wasserman K, Ward J M, Kleinman H K, Oppenheim J J, Murphy W J. (2000) Human endothelial cells express CCR2 and respond to MCP-1: direct role of MCP-1 in angiogenesis and tumor progression. *Blood.* 96; 34-40.

Li A, Dubey S, Varney M L, Dave B J, Singh R K (2003) IL-8 directly enhanced endothelial cell survival, proliferation, and matrix metalloproteinases production and regulated angiogenesis. *J. Immunol.* 170; 3369-76

Hughes G C, Biswas S S, Yin B, Coleman R E, DeGrado T R, Landolfo C K, Lowe J E, Annex B H, Landolfo K P. (2004) Therapeutic angiogenesis in chronically ischemic porcine myocardium: comparative effects of bFGF and VEGF. *Ann. Thorac. Surg.* 77; 812-8.

Cheng A, Wang S, Cai J, Rao M S, Mattson M P (2003) Nitric oxide acts in a positive feedback loop with BDNF to regulate neural progenitor cell proliferation and differentiation in the mammalian brain. *Dev. Biol.* 258; 319-33.

Sebire G, Emilie D, Wallon C, Hery C, Devergne O, Delfraissy J F, Galanaud P, Tardieu M. (1993) In vitro production of IL-6, IL-1 beta, and tumor necrosis factor-alpha by human embryonic microglial and neural cells. *J. Immunol.* 150; 1517-23.

Example 13

Plasma Clotting Assay

Cell therapy may be injected systemically for certain applications where cells are able to target the site of action. It is important that injected cells not cause thrombosis, which may be fatal. Tissue factor, a membrane-bound procoagulant glycoprotein, is the initiator of the extrinsic clotting cascade, which is the predominant coagulation pathway in vivo. Tissue factor also plays an important role in embryonic vessel formation, for example, in the formation of the primitive vascular wall (Brodsky et al. (2002) *Exp. Nephrol.* 10:299-306). To determine the potential for PPDCs to initiate clotting, umbilicus- and placenta-derived PPDCs were evaluated for tissue factor expression and their ability to initiate plasma clotting.

Methods & Materials

Human Tissue Factor.

Human tissue factor SIMPLASTIN (Organon Tekailca Corporation, Durham, N.C.) was reconstituted with 20 milliliters distilled water. The stock solution was serially diluted (1:2) in eight tubes. Normal human plasma (George King BioMedical, Overland Park, Kans.) was thawed at 37° C. in a water bath and then stored in ice before use. To each well of a 96-well plate was added 100 microliters phosphate buffered saline (PBS), 10 microliters diluted Simplastin® (except a blank well), 30 microliters 0.1 molar calcium chloride, and 100 microliters of normal human plasma. The plate was immediately placed in a temperature-controlled microplate reader and absorbance measured at 405 nanometers at 40 second intervals for 30 minutes.

J-82 and Postpartum-Derived Cells.

J-82 cells (ATCC, MD) were grown in Iscove's modified Dulbecco's medium (IMDM; Gibco, Carlsbad, Calif.) containing 10% (v/v) fetal bovine serum (FBS; Hyclone, Logan Utah), 1 millimolar sodium pyruvate (Sigma Chemical, St. Louis, Mo.), 2 millimolar L-Glutamin (Mediatech Herndon, Va.), 1× non-essential amino acids (Mediatech Herndon, Va.). At 70% confluence, cells were transferred to wells of a 96-well plate at 100,000, 50,000, and 25,000 cells/well. Postpartum-derived cells derived from placenta and umbilicus were cultured in Growth Medium (DMEM-low glucose (Gibco), 15% (v/v) FBS, 50 Units/milliliter penicillin, 50 micrograms/milliliter streptomycin (Gibco), and 0.001% betamercaptoethanol (Sigma)) in gelatin-coated T75 flasks (Corning, Corning, N.Y.). Placenta-derived cells at passage 5 and umbilicus-derived cells at passages 5 and 11 were transferred to wells at 50,000 cells/well. Culture medium was removed from each well after centrifugation at 150×g for 5 minutes. Cells were suspended in PBS without calcium and magnesium. Cells incubated with anti-tissue factor antibody cells were incubated with 20 microgram/milliliter CNTO 859 (Centocor, Malvern, Pa.) for 30 minutes. Calcium chloride (30 microliter) was added to each well. The plate was immediately placed in a temperature-controlled microplate reader and absorbance measured at 405 nanometers at 40 second intervals for 30 minutes.

Antibody Staining.

Cells were washed in PBS and detached from the flask with Trypsin/EDTA (Gibco Carlsbad, Calif.). Cells were harvested, centrifuged, and re-suspended 3% (v/v) FBS in PBS at a cell concentration of $1 \times 10^7$ per milliliter. Antibody was added to 100 microliter cell suspension as per the manufacturer's specifications, and the cells were incubated in the dark for 30 minutes at 4° C. After incubation, cells were washed with PBS and centrifuged at 150×g for 5 minutes to remove unbound antibody. Cells were re-suspended in 100 microliter of 3% FBS and secondary antibody added as per the manufacturer's instructions. Cells were incubated in the dark for 30 minutes at 4° C. After incubation, cells were washed with PBS and centrifuged to remove unbound secondary antibody. Washed cells were re-suspended in 500 microliters of PBS and analyzed by flow cytometry.

Flow Cytometry Analysis.

Flow cytometry analysis was performed with a FACSCalibur instrument (Becton Dickinson, San Jose, Calif.).

Results

Flow cytometry analysis revealed that both placenta- and umbilicus-derived postpartum-derived cells express tissue factor. A plasma clotting assay demonstrated that tissue factor was active. Both placenta- and umbilicus-derived cells increased the clotting rate as indicated by the time to half maximal absorbance (T ½ to max; Table 13-1). Clotting was observed with both early (P5) and late (P18) cells. The T ½ to max is inversely proportional to the number of J82 cells. Preincubation of umbilical cells with CNTO 859, an antibody to tissue factor, inhibited the clotting reaction, thereby showing that tissue factor was responsible for the clotting.

TABLE 13-1

The effect of human tissue factor (SIMPLASTIN), placenta-derived cells (Pla), and umbilicus-derived cells (Umb) on plasma clotting was evaluated. The time to half maximal absorbance (T ½ to max) at the plateau in seconds was used as a measurement unit.

|  | T ½ to max (seconds) |
|---|---|
| Simplastin ® Dilution |  |
| 1:2 | 61 |
| 1:4 | 107 |
| 1:8 | 147 |
| 1:16 | 174 |
| 1:32 | 266 |
| 1:64 | 317 |
| 1:128 | 378 |
| 0 (negative control) | 1188 |
| J-82 cells |  |
| 100,000 | 122 |
| 50,000 | 172 |
| 25,000 | 275 |
| Pla P5 |  |
| 50,000 | 757 |
| Umb P5 |  |
| 50,000 | 833 |
| Umb P18 |  |
| 50,000 | 443 |

Summary.

Placenta- and umbilicus-derived PPDCs express tissue factor, which can induce clotting. The addition of an antibody to tissue factor can inhibit tissue factor. Tissue factor is normally found on cells in a conformation that is inactive but is activated by mechanical or chemical (e.g., LPS) stress (Sakariassen et al. (2001) *Thromb. Res.* 104:149-74; Engstad et al. (2002) *Int. Immunopharmacol.* 2:1585-97). Thus, minimization of stress during the preparation process of PPDCs may prevent activation of tissue factor. In addition to the thrombogenic activity, tissue factor has been associated with angiogenic activity. Thus, tissue factor activity may be beneficial when umbilicus- or placenta-derived PPDCs are transplanted in tissue but should be inhibited when PPDCs are injected intravenously.

REFERENCES

Doshi and Marmur, *Critical Care Med.*, 30:S241-S250 (2002).
Moll and Ortel, *Ann. Intern. Med.*, 127:177-185 (1997).

Example 14

Endothelial Network Formation Assay

Angiogenesis, or the formation of new vasculature, is necessary for the growth of new tissue. Induction of angiogenesis is an important therapeutic goal in many pathological conditions. The present study was aimed at identifying potential angiogenic activity of the postpartum-derived cells in in vitro assays. The study followed a well-established method of seeding endothelial cells onto a culture plate coated with MATRIGEL (BD Discovery Labware, Bedford, Mass.), a basement membrane extract (Nicosia and Ottinetti (1990) *In Vitro Cell Dev. Biol.* 26(2): 119-28). Treating endothelial cells on MATRIGEL (BD Discovery Labware, Bedford, Mass.) with angiogenic factors will stimulate the cells to form a network that is similar to capillaries. This is a common in vitro assay for testing stimulators and inhibitors of blood vessel formation (Ito et al. (1996) *Int. J. Cancer* 67(1):148-52). The present studies made use of a co-culture system with the postpartum-derived cells seeded onto culture well inserts. These permeable inserts allow for the passive exchange of media components between the endothelial and the postpartum-derived cell culture media.

Material & Methods
Cell Culture
Postpartum Tissue-Derived Cells.

Human umbilical cords and placenta were received and cells were isolated as previously described (Example 1). Cells were cultured in Growth medium (Dulbecco's Modified Essential Media (DMEM; Invitrogen, Carlsbad, Calif.), 15% (v/v) fetal bovine serum (Hyclone, Logan Utah), 100 Units/milliliter penicillin, 100 microgram/milliliter streptomycin (Invitrogen), 0.001% (v/v) 2-mercaptoethanol (Sigma, St. Louis, Mo.)) on gelatin-coated tissue culture plastic flasks. The cultures were incubated at 37° C. with 5% $CO_2$. Cells used for experiments were between passages 4 and 12.

Actively growing postpartum-derived cells were trypsinized, counted, and seeded onto COSTAR TRANSWELL 6.5 millimeter diameter tissue culture inserts (Corning, Corning, N.Y.) at 15,000 cells per insert. Cells were cultured on the inserts for 48-72 hours in Growth medium at 37° C. under standard growth conditions.

Human Mesenchymal Stem Cells (hMSC).

hMSCs were purchased from Cambrex (Walkersville, Md.) and cultured in MSCGM (Cambrex). The cultures were incubated under standard growth conditions.

Actively growing MSCs were trypsinized and counted and seeded onto COSTAR TRANSWELL 6.5 millimeter diameter tissue culture inserts (Corning, Corning, N.Y.) at 15,000 cells per insert. Cells were cultured on the inserts for 48-72 hours in Growth medium under standard growth conditions.

Human Umbilical Vein Endothelial Cells (HUVEC).

HUVEC were obtained from Cambrex (Walkersville, Md.). Cells were grown in separate cultures in either EBM or EGM endothelial cell media (Cambrex). Cells were grown on standard tissue cultured plastic under standard growth conditions. Cells used in the assay were between passages 4 and 10.

Human Coronary Artery Endothelial Cells (HCAEC).

HCAEC were purchased from Cambrex Incorporated (Walkersville, Md.). These cells were also maintained in separate cultures in either the EBM or EGM media formulations. Cells were grown on standard tissue cultured plastic under standard growth conditions. Cells used for experiments were between passages 4 and 8.

Endothelial Network Formation (MATRIGEL) Assays.

Culture plates were coated with MATRIGEL (BD Discovery Labware, Bedford, Mass.) according to manufacturer's specifications. Briefly, MATRIGEL™ (BD Discovery Labware, Bedford, Mass.) was thawed at 4° C. and approximately 250 microliters were aliquoted and distributed evenly onto each well of a chilled 24-well culture plate (Corning). The plate was then incubated at 37° C. for 30 minutes to allow the material to solidify. Actively growing endothelial cell cultures were trypsinized and counted. Cells were washed twice in Growth medium with 2% FBS by centrifugation, resuspension, and aspiration of the supernatant. Cells were seeded onto the coated wells 20,000 cells per well in approximately 0.5 milliliter Growth medium with 2% (v/v) FBS. Cells were then incubated for approximately 30 minutes to allow cells to settle.

Endothelial cell cultures were then treated with either 10 nanomolar human bFGF (Peprotech, Rocky Hill, N.J.) or 10 nanomolar human VEGF (Peprotech, Rocky Hill, N.J.) to serve as a positive control for endothelial cell response. Transwell inserts seeded with postpartum-derived cells were added to appropriate wells with Growth medium with 2% FBS in the insert chamber. Cultures were incubated at 37° C. with 5% $CO_2$ for approximately 24 hours. The well plate was removed from the incubator, and images of the endothelial cell cultures were collected with an Olympus inverted microscope (Olympus, Melville, N.Y.).

Results

In a co-culture system with placenta-derived cells or with umbilicus-derived cells, HUVEC form cell networks (data not shown). HUVEC cells form limited cell networks in co-culture experiments with hMSC and with 10 nanomolar bFGF (data not shown). HUVEC cells without any treatment showed very little or no network formation (data not shown). These results suggest that the postpartum-derived cells release angiogenic factors that stimulate the HUVEC.

In a co-culture system with placenta-derived cells or with umbilicus-derived cells, CAECs form cell networks (data not shown).

Table 14-1 shows levels of known angiogenic factors released by the postpartum-derived cells in Growth medium. Postpartum-derived cells were seeded onto inserts as described above. The cells were cultured at 37° C. in atmospheric oxygen for 48 hours on the inserts and then switched to a 2% FBS media and returned at 37° C. for 24 hours. Media was removed, immediately frozen and stored at −80° C., and analyzed by the SearchLight Multiplex ELISA assay (Pierce Chemical Company, Rockford, Ill.). Results shown are the averages of duplicate measurements. The results show that the postpartum-derived cells do not release detectable levels of platelet-derived growth factor-bb (PDGF-bb) or heparin-binding epidermal growth factor (HBEGF). The cells do release measurable quantities of tissue inhibitor of metallinoprotease-1 (TIMP-1), angiopoietin 2 (ANG2), thrombopoietin (TPO), keratinocyte growth factor (KGF), hepatocyte growth factor (HGF), fibroblast growth factor (FGF), and vascular endothelial growth factor (VEGF).

Summary.

The results of the present study show that postpartum-derived cells can stimulate both human umbilical vein and coronary artery endothelial cells to form networks in an in vitro MATRIGEL™ (BD Discovery Labware, Bedford, Mass.) assay. This effect is similar to that seen with known angiogenic factors in this assay system. These results suggest that the postpartum-derived cells are useful for stimulating angiogenesis in vivo.

TABLE 14-1

Potential angiogenic factors released from postpartum-derived cells. Postpartum-derived cells were cultured in 24 hours in media with 2% FBS in atmospheric oxygen. Media was removed and assayed by the SearchLight multiplex ELISA assay (Pierce). Results are the means of a duplicate analysis. Values are concentrations in the media reported in picograms per milliliter of culture media.

| | TIMP1 (pg/ml) | ANG2 (pg/ml) | PDGFBB (pg/ml) | TPO (pg/ml) | KGF (pg/ml) | HGF (pg/ml) | FGF (pg/ml) | VEGF (pg/ml) | HBEGF (pg/ml) |
|---|---|---|---|---|---|---|---|---|---|
| Plac (P4) | 91655.3 | 175.5 | <2.0 | 275.5 | 3.0 | 58.3 | 7.5 | 644.6 | <1.2 |
| Plac (P11) | 1592832.4 | 28.1 | <2.0 | 1273.1 | 193.3 | 5960.3 | 34.8 | 12361.1 | 1.7 |
| Umb cord (P4) | 81831.7 | <9.8 | <2.0 | 365.9 | 14.1 | 200.2 | 5.8 | <4.0 | <1.2 |
| Media alone | <9.8 | 25.1 | <2.0 | <6.4 | <2.0 | <3.2 | <5.4 | <4.0 | <1.2 |

Plac: placenta derived cells;
Umb cord: Umbilicus derived cells

Table 14-2 shows levels of known angiogenic factors released by the postpartum-derived cells. Postpartum-derived cells were seeded onto inserts as described above. The cells were cultured in Growth medium at 5% oxygen for 48 hours on the inserts and then switched to a 2% FBS medium and returned to 5% $O_2$ incubation for 24 hours. Media was removed, immediately frozen, and stored at −80° C., and analyzed by the SearchLight Multiplex ELISA assay (Pierce Chemical Company, Rockford, Ill.). Results shown are the averages of duplicate measurements. The results show that the postpartum-derived cells do not release detectable levels of platelet-derived growth factor-bb (PDGF-BB) or heparin-binding epidermal growth factor (HBEGF). The cells do release measurable quantities of tissue inhibitor of metallinoprotease-1 (TIMP-1), angiopoietin 2 (ANG2), thrombopoietin (TPO), keratinocyte growth factor (KGF), hepatocyte growth factor (HGF), fibroblast growth factor (FGF), and vascular endothelial growth factor (VEGF).

Example 15

Transplantation of PPDCs

Cells derived from the postpartum umbilical cord and placenta are useful for regenerative therapies. The tissue produced by postpartum-derived cells transplanted into SCID mice with a biodegradable material was evaluated. The materials evaluated were non-woven comprised of poly(lactic acid-co-glycolic acid) polymer (10/90 PLGA), 35/65 PCL/PGA foam, and RAD16 self-assembling peptide hydrogel.

TABLE 14-2

Potential angiogenic factors released from postpartum-derived cells. Postpartum-derived cells were cultured in 24 hours in media with 2% FBS in 5% oxygen. Media was removed and assayed by the SearchLight multiplex ELISA assay (Pierce). Results are the means of a duplicate analysis. Values are concentrations in the media reported in picograms per milliter of culture media.

| | TIMP1 (pg/ml) | ANG2 (pg/ml) | PDGFBB (pg/ml) | TPO (pg/ml) | KGF (pg/ml) | HGF (pg/ml) | FGF (pg/ml) | VEGF (pg/ml) | HBEGF (pg/ml) |
|---|---|---|---|---|---|---|---|---|---|
| Plac (P4) | 72972.5 | 253.6 | <2.0 | 743.1 | 2.5 | 30.2 | 15.1 | 1495.1 | <1.2 |
| Plac (P11) | 458023.1 | 55.1 | <2.0 | 2562.2 | 114.2 | 2138.0 | 295.1 | 7521.3 | 1.8 |
| Umb cord (P4) | 50244.7 | <9.8 | <2.0 | 403.3 | 10.7 | 156.8 | 5.7 | <4.0 | <1.2 |
| Media alone | <9.8 | 25.1 | <2.0 | <6.4 | <2.0 | <3.2 | <5.4 | <4.0 | <1.2 |

Plac: placenta derived cells;
Umb cord: Umbilicus derived cells

Methods & Materials

Cell Culture.

Placenta-derived cells and umbilicus derived cells were grown in Growth medium (DMEM-low glucose (Gibco, Carlsbad Calif.), 15% (v/v) fetal bovine serum (Cat. #SH30070.03; Hyclone, Logan, Utah), 0.001% (v/v) beta-mercaptoethanol (Sigma, St. Louis, Mo.), 50 Units/milliliter penicillin, 50 microgram/milliliter streptomycin (Gibco)) in a gelatin-coated flasks.

Matrix Preparation.

A nonwoven scaffold was prepared using a traditional needle punching technique as described below. Fibers, comprised of a synthetic absorbable copolymer of glycolic and lactic acids (10/90 PLGA), were obtained from Ethicon, Inc. (Somerville, N.J.). The fibers were filaments of approximately 20 microns in diameter. The fibers were then cut and crimped into uniform 2-inch lengths to form 2-inch staple fiber. A dry lay needle-punched nonwoven matrix (VNW) was then prepared utilizing the 10/90 PLGA staple fibers. The staple fibers were opened and carded on standard nonwoven machinery. The resulting mat was in the form of webbed staple fibers. The webbed staple fibers were needle-punched to form the dry lay needle-punched nonwoven scaffold. The nonwoven scaffold was rinsed in water followed by another incubation in ethanol to remove any residual chemicals or processing aids used during the manufacturing process.

Foams, composed of 35/65 poly(epsilon-caprolactone)/poly(glycolic acid) (35/65 PCL/PGA) copolymer, were formed by the process of lyophilization, as discussed in U.S. Pat. No. 6,355,699.

Sample Preparation.

One million viable cells were seeded in 15 microliter Growth medium onto 5 millimeter diameter, 2.25 millimeter thick VNW scaffolds (64.33 milligram/cubic centimeters; Lot#3547-47-1) or 5 millimeter diameter 35/65 PCL/PGA foam (Lot# 3415-53). Cells were allowed to attach for two hours before adding more Growth medium to cover the scaffolds. Cells were grown on scaffolds overnight. Scaffolds without cells were also incubated in medium.

Test Material (N=4/Rx)
1. VNW+1×$10^6$ umbilicus-derived cells
2. 35/65 PCL/PGA foam+1×$10^6$ umbilicus-derived cells
3. RAD 16 self-assembling peptide+1×$10^6$ umbilicus-derived cells
4. VNW+1×$10^6$ placenta-derived cells
5. 35/65 PCL/PGA foam+1×$10^6$ placenta-derived cells
6. RAD 16 self-assembling peptide+1×$10^6$ placenta-derived cells
7. 35/65 PCL/PGA foam
8. VNW Animal Preparation.

The animals utilized in this study were handled and maintained in accordance with the current requirements of the Animal Welfare Act. Compliance with the above Public Laws were accomplished by adhering to the Animal Welfare regulations (9 CFR) and conforming to the current standards promulgated in the Guide for the Care and Use of Laboratory Animals, 7th edition.

Mice (*Mus Musculus*)/Fox Chase SCID/Male (Harlan Sprague Dawley, Inc., Indianapolis, Ind.), 5 Weeks of Age.

All handling of the SCID mice took place under a hood. The mice were individually weighed and anesthetized with an intraperitoneal injection of a mixture of 60 milligram/kilogram KETASET (ketamine hydrochloride, Aveco Co., Inc., Fort Dodge, Iowa) and 10 milligram/kilogram ROMPUN (xylazine, Mobay Corp., Shawnee, Kans.) and saline. After induction of anesthesia, the entire back of the animal from the dorsal cervical area to the dorsal lumbosacral area was clipped free of hair using electric animal clippers. The area was then scrubbed with chlorhexidine diacetate, rinsed with alcohol, dried, and painted with an aqueous iodophor solution of 1% available iodine. Ophthalmic ointment was applied to the eyes to prevent drying of the tissue during the anesthetic period.

Subcutaneous Implantation Technique.

Four skin incisions, each approximately 1.0 cm in length, were made on the dorsum of the mice. Two cranial sites were located transversely over the dorsal lateral thoracic region, about 5-mm caudal to the palpated inferior edge of the scapula, with one to the left and one to the right of the vertebral column. Another two were placed transversely over the gluteal muscle area at the caudal sacro-lumbar level, about 5-mm caudal to the palpated iliac crest, with one on either side of the midline. Implants were randomly placed in these sites. The skin was separated from the underlying connective tissue to make a small pocket and the implant placed (or injected for RAD16) about 1-cm caudal to the incision. The appropriate test material was implanted into the subcutaneous space. The skin incision was closed with metal clips.

Animal Housing.

Mice were individually housed in microisolator cages throughout the course of the study within a temperature range of 64° F.-79° F. and relative humidity of 30% to 70% and maintained on an approximate 12 hour light/12 hour dark cycle. The temperature and relative humidity were maintained within the stated ranges to the greatest extent possible. Diet consisted of Irradiated Pico Mouse Chow 5058 (Purina Co.) and water fed ad libitum.

Mice were euthanized at their designated intervals by carbon dioxide inhalation. The subcutaneous implantation sites with their overlying skin were excised and frozen for histology.

Histology.

Excised skin with implant was fixed with 10% neutral buffered formalin (Richard-Allan Kalamazoo, Mich.). Samples with overlying and adjacent tissue were centrally bisected, paraffin-processed, and embedded on cut surface using routine methods. Five-micron tissue sections were obtained by microtome and stained with hematoxylin and eosin (Poly Scientific Bay Shore, N.Y.) using routine methods.

Results

There was minimal ingrowth of tissue into foams implanted subcutaneously in SCID mice after 30 days (data not shown). In contrast there was extensive tissue fill in foams implanted with umbilicus-derived cells or placenta-derived cells (data not shown).

There was some tissue in growth in VNW scaffolds. Non-woven scaffolds seeded with umbilicus- or placenta-derived cells showed increased matrix deposition and mature blood vessels (data not shown).

Summary.

The purpose of this study was to determine the type of tissue formed by cells derived from human umbilicus or placenta in scaffolds in immune deficient mice. Synthetic absorbable non-woven/foam discs (5.0 millimeter diameter× 1.0 millimeter thick) or self-assembling peptide hydrogel were seeded with either cells derived from human umbilical cord or placenta and implanted subcutaneously bilaterally in the dorsal spine region of SCID mice. The present study demonstrates that postpartum-derived cells can dramatically increase good quality tissue formation in biodegradable scaffolds.

Example 16

Analyses of Factors Present in the Cell Lysate as Determined by Multiplex ELISA Methods & Materials
Preparation of Cell Lysate.

Approximately 25 million human umbilicus-derived cells (UDCs) at passage 11 were seeded into gelatin-coated T225 flasks. Because of the number of cells that were necessary to complete the study, the flasks were split, for trypsinization, into two sets which were combined to prepare the cell lysate. The cells ranged from approximately 70-95% confluent. Flasks were trypsinized with 0.05% trypsin/EDTA for 5 minutes until the cells began lifting from the dish. The trypsinization process was inactivated using 15% serum containing Dulbecco's Modified Eagle's growth media. Cells were pelleted in growth media and then resuspended in a total volume of 40 milliliters of PBS. The cells were washed three times in PBS to remove residual FBS from the growth media. This was done by centrifuging the cells for 5 minutes at 1.5 RPM and then resuspending the cells in 40 milliliters of PBS until the three washes were complete.

In order to facilitate the freeze-thaw procedure, the cells were equally divided into two tubes with PBS for the freeze/thaw procedure. The lysates were prepared by repeated freeze/thaw cycles. To freeze the cells, the tubes were placed in a slurry of dry ice and isopropanol for 10 minutes. After 10 minutes, the tubes were placed in a 37° C. water bath for 10 minutes.

The cell suspensions were transferred to ten sterile siliconized microcentrifuge tubes, to prevent protein adsorption, and centrifuged at 13,000×g for 10 minutes at 4° C. to separate the cell membranes from the cytosolic components. The tubes (cell pellet) were then placed on ice and the supernatant was very gently mixed by tapping the centrifuge tube to ensure uniformity. The supernatant was transferred to new siliconized tubes and placed on ice.

SEARCHLIGHT Multiplexed ELISA Assay.

Chemokines, BDNF and angiogenic factors were measured using SEARCHLIGHT Proteome Arrays (Pierce Biotechnology Inc.). The proteome arrays are multiplexed sandwich ELISAs for the quantitative measurement of two to 16 proteins per well. The arrays are produced by spotting a 2×2, 3×3, or 4×4 pattern of four to 16 different capture antibodies into each well of a 96-well plate. Following a typical sandwich ELISA procedure, the entire plate is imaged to capture chemiluminescent signal generated at each spot within each well of the plate. The amount of signal generated in each spot is proportional to the amount of target protein in the original standard or sample.

Results

Summary.

UDC lysate contains significant levels of beneficial factors including pro-angiogenic as well as factors that can stimulate cell proliferation and extracellular matrix production (KGF, PDGF-BB, HGF, TGFa) and neurotrophic factors (BDNF, IL-6). These factors might have beneficial effects on local environment by inducing cell proliferation, differentiation and survival. In addition, pro-angiogenic factors might induce new blood vessel formation in the wound environment and stimulate extracellular matrix formation. Furthermore, the high level of TIMPs might be extremely beneficial in the chronic wound environment, since chronic wounds are known to be associated with high levels of MMPs, known to mediate extracellular matrix degradation.

Example 17

Production of Lyophilized Umbilicus Derived Cell Lysate

Umbilicus-derived cells produce and secrete various growth factors involved in tissue regeneration, including basic Fibroblast Growth Factor (bFGF), hepatocyte growth factor (HGF), brain-derived neurotrophic factor (BDNF), and keratinocyte growth factor (KGF). The supernatant of lysed umbilicus-derived cells also contains these growth factors. The application of the lysate to biomaterials followed by lyophilization produces a device that, upon clinical application, will release the growth factors and enhance tissue regeneration.

The purpose of the present study was to provide methods for the production of lyophilized UDC lysate. The method consistently allowed the harvest of proteins from lysed UDCs. The amount of total protein (57.53+/−38.69 picograms per cell) correlates to the harvest density of the cells (R—Sq (adj)=71.5%). The growth factor bFGF was present in six separate production lots of lyophilized UDC lysate averaging 3.09+/−1.06 picograms per microgram of total protein. SDS-PAGE analysis of UDC lysate showed the banding pattern of protein was consistent between separate production lots, pre- and post-lyophilization, and lyophilization into a synthetic biomaterial. The current method allowed reproducible production of lyophilized material containing growth factors for application in tissue regeneration.

Methods & Materials
Cell Growth and Harvest.

UDCs were seeded at 5,000 cells per $cm^2$ in gelatin-coated flasks with growth media (Dulbecco's Modified Eagles Media (DMEM)-low glucose, 15% fetal bovine serum (FBS), penicillin/streptomycin (P/S), Betamercaptoethanol (BME) and expanded for 3 to 4 days (25,000 cells per $cm^2$ target harvest density). Cells were harvested with trypsin, collected, and centrifuged at 300 rcf for 5 minutes. The trypsin/media was removed by aspiration and cells were washed three times with phosphate buffered saline (PBS).

TABLE 16-1

SEARCHLIGHT Multiplexed ELISA results. Average for duplicate adjusted for dilution.

| ANG2 (pg/ml) | HGF (pg/ml) | HBEGF (pg/ml) | KGF (pg/ml) | FGF (pg/ml) | PDGFbb (pg/ml) | VEGF (pg/ml) | IL6 (pg/ml) | IL8 (pg/ml) | MCP1 (pg/ml) | TGFa (pg/ml) | TIMP1 (pg/ml) | TIMP2 (pg/ml) | HGH (pg/ml) | BDNF (pg/ml) |
|---|---|---|---|---|---|---|---|---|---|---|---|---|---|---|
| <41.2 | 64500.0 | 68.0 | 260.8 | 167500.0 | 4.8 | 76.6 | 258.8 | 14700.0 | 197.4 | 208.0 | 6865.0 | 25460.0 | 236.0 | 1115.2 |

Cell Wash and Aliquoting.

After washing, the cells were re-suspended at 1.0E+07 cell/ml in PBS and delivered as 1 ml aliquots into 1.5 ml sterile siliconized micro-centrifuge tubes. The cells were centrifuged at 300 rcf for 5 minutes and the PBS was removed by aspiration. Tubes containing cell pellets were optionally stored at −80° C.

Cell Lysis.

Tubes containing cell pellets were immersed in liquid nitrogen (LN2) for 60 seconds. The tubes were then removed from LN2 and immediately immersed in a 37° C. water bath for 60 seconds or until thawed (3 minute maximum incubation time). This process was repeated two additional times.

Centrifugation and Lysate Harvest.

The freeze-thawed samples were centrifuged for 10 minutes at 13,000 rcf at 4° C. and placed on ice. The supernatant fluid from each tube was removed by pipette and transferred to a single sterile siliconized 1.5 ml tube. This process was repeated until no additional supernatant fluid could be recovered.

Fluid Volume Measurement.

To approximate supernatant fluid volume, the 1.5 ml tube containing recovered supernatant fluid was weighed on a balance previously tared with an empty 1.5 ml micro-centrifuge tube (1 milligram=~1 microliter).

Protein Assay.

To determine total protein content, 10 microliters of lysate supernatant fluid was diluted into 990 microliters PBS, and the dilution was analyzed by Bradford assay (standard range 1.25-25 micrograms). This value was used to calculate the total protein per cell, the main metric used to ensure the consistency of the process.

Lysate Lyophilization.

Multiple 1.5 milliliter sterile labeled cryovials were loaded into a sterile heat transfer block. Aliquots of lysate supernatant fluid at defined total protein concentration were loaded into the cryovials. The heat block containing uncapped cryovials was aseptically loaded into an autoclaved pouch with tube openings facing the paper side of the pouch. The pouch was sealed before removal from the laminar flow hood. The pouch was loaded into the lyophilizer.

Pre-cut materials (i.e., 90/10 PGA/PLA non-woven) were aseptically placed into the wells of 24- or 48-well sterile, ultra low cluster cell culture dishes (Corning Inc., Corning N.Y.). Lysate supernatant fluid was delivered at a defined total protein concentration onto the material. For example, a material measuring 6 mm in diameter and 0.5 mm in thickness received 2 microliters of a 15 microgram/microliter total protein solution to create a 30 microgram lysate protein material. The lid of the dish was replaced and secured with tape. The dish with materials was loaded into the lyophilizer Test materials with applied lysate were loaded into a FTS Systems Dura-Stop MP Stoppering Tray Dryer and lyophilized using the following ramping program. All steps had a ramping rate of 2.5° C./minute and a 100-mT vacuum.

TABLE 17-1

Ramping program utilized for the lyophilization of UDC lysate

| Step | Shelf Temp (° C.) | Hold Time (minutes) |
|---|---|---|
| a | −40 | 180 |
| b | −25 | 2160 |
| c | −15 | 180 |
| d | −5 | 180 |
| e | 5 | 120 |
| f | 20 | 120 |
| g | −20 | 60 | bFGF Enzyme Linked Immunosorbent Assay (ELISA) Analysis.

Vials from six separate production lots of lyophilized lysate powder were reconstituted in PBS and analyzed for total protein content by Bradford assay. The samples were then further diluted to achieve a 20 microgram/milliliter solution. Solutions further serially diluted in PBS and analyzed by ELISA using a Quantikine human bFGF kit (R&D Systems cat. no. DFB50).

SDS-PAGE.

Polyacrylamide Gel Electrophoresis (PAGE) was conducted under denaturing conditions using sodium dodecyl-sulfate (SDS) using the NOVEX mini gel system (Invitrogen, Carlsbad, Calif.). Samples were prepared with the NOVEX Tris-Glycine SDS Sample Buffer (Invitrogen, Carlsbad, Calif.) using the manufacturer's suggested protocol. Samples for analysis included: a) UDC lysate prior to lyophilization, b) UDC lysate lyophilized in vials, and c) UDC lysate lyophilized onto 90/10 PGA/PLA non-woven materials. The samples were loaded onto a NOVEX Pre-Cast Tris-Glycine 4-20% Stacking Mini Gel and run in the XCell Sure Lock Mini-Cell with NOVEX Tris-Glycine Running Buffer for the manufacturer suggested time and voltage (Invitrogen, Carlsbad, Calif.). Gels were stained with SIMPLYBLUE Safe Stain and dried using the DRYEASE Mini-Gel Drying System (Invitrogen, Carlsbad, Calif.) according to the manufacturer's instructions.

Results

Lyophilized Lysate Production Summary

TABLE 17-2

Metrics summary from multiple production lots of UDC lysate

| Lot | Total cells harvested | Total T225 culture flasks used | Harvest density (cells/cm$^2$) | Total ul lysate fluid | Total Protein (ug) | Total protein (ug)/total lysate fluid (ul) |
|---|---|---|---|---|---|---|
| L011905A | 2.55E+08 | 30 | 38000 | 875 | 27063.8 | 30.93 |
| L011905B | 5.42E+07 | 8 | 31000 | 117 | 3068.9 | 26.23 |
| L011905C | 1.84E+08 | 26 | 32000 | 597 | 18614.5 | 31.18 |
| L030705 | 1.05E+08 | 20 | 23000 | 389 | 7869.5 | 20.23 |
| L033105 | 1.05E+08 | 25 | 18700 | 257 | 6296.5 | 24.5 |

TABLE 17-2-continued

Metrics summary from multiple production lots of UDC lysate

| Lot | Total cells harvested | Total T225 culture flasks used | Harvest density (cells/cm$^2$) | Total ul lysate fluid | Total Protein (ug) | Total protein (ug)/total lysate fluid (ul) |
|---|---|---|---|---|---|---|
| L040405 | 5.95E+08 | 165 | 16000 | 1394 | 16072.8 | 11.53 |
| L042205 | 2.64E+08 | 100 | 11700 | 528 | 7920 | 15 |
| L051305 | 1.70E+08 | 101 | 7500 | 609 | 2192.4 | 3.6 |
| L052505 | 4.00E+07 | 8 | 22222 | 147 | 529 | 3.6 |
| L061305 | 3.60E+08 | 39 | 40600 | 934 | 46700 | 50 |
| L062405 | 3.20E+08 | 60 | 23800 | 424 | 17000 | 40 |
| L071305 | 4.60E+08 | 100 | 20400 | 922 | 10879 | 11.8 |
| Totals | 2.91E+09 | — | — | 7.19E+03 | 1.64E+05 | — |

Total Protein Per Cell/Harvest Density Correlation.

The total protein content of recovered lysate supernatant fluid prior to lyophilization is a function of the cell density at time of harvest (R–Sq (adj)=71.5%).

TABLE 17-3

Correlation between total protein per cell and cell density at time of harvest

| Lot | Total Cells | Harvest density (cells/cm$^2$) | Total protein (picograms) | Protein per cell (picograms) |
|---|---|---|---|---|
| L011905A | 2.55E+08 | 38000 | 2.71E+10 | 106.13 |
| L011905B | 5.42E+07 | 31000 | 3.07E+09 | 56.62 |
| L011905C | 1.84E+08 | 32000 | 1.86E+10 | 101.17 |
| L030705 | 1.05E+08 | 23000 | 7.87E+09 | 74.95 |
| L033105 | 1.05E+08 | 18700 | 6.30E+09 | 59.97 |
| L040405 | 5.95E+08 | 16000 | 1.61E+10 | 27.01 |
| L042205 | 2.64E+08 | 11700 | 7.92E+09 | 30.00 |
| L051305 | 1.70E+08 | 7500 | 2.19E+09 | 12.90 |
| L052505 | 4.00E+07 | 22222 | 5.29E+08 | 13.23 |
| L061305 | 3.60E+08 | 40600 | 4.67E+10 | 129.72 |
| L062405 | 3.20E+08 | 23800 | 1.70E+10 | 53.00 |
| L071305 | 4.60E+08 | 21000 | 1.18E+10 | 25.65 |
| Avg. | — | — | — | 57.53 |
| Std. Dev. | — | — | — | 38.69 | bFGF ELISA Analysis of Umbilicus Derived Cell Lysate

TABLE 17-4

Summary of bFGF (picograms) per given quantity of total lysate protein as measured by ELISA assay

| | 2.5 micrograms total protein | 5 micrograms total protein | 10 micrograms total protein | 20 micrograms total protein |
|---|---|---|---|---|
| L040405 | 16.3 | 29.48 | 64.07 | 129.14 |
| L042205 | 16.61 | 26.399 | 54.944 | 116.521 |
| L051305 | 11.08 | 17.01 | 34.6 | 79.02 |
| L052505 | 14.277 | 22.105 | 47.28 | 110.39 |
| L061305 | 10.26 | 15.13 | 28.92 | 61.936 |
| L062405 | 15.5 | 24.5 | 51.89 | 112.951 |

TABLE 17-5

Regression analysis of bFGF content of PBS reconstituted and serially diluted lyophilized UDC lysate from six separate production lots

| Lot | Slope | y-intercept | R squared | Picograms bFGF per microgram total protein |
|---|---|---|---|---|
| L040405 | 37.31 | −33.53 | 0.91 | 3.78 |
| L042205 | 32.82 | −28.45 | 0.89 | 4.37 |
| L051305 | 22.14 | −19.95 | 0.87 | 2.19 |
| L052505 | 31.35 | −29.86 | 0.86 | 1.49 |
| L061305 | 16.88 | −13.43 | 0.88 | 3.45 |
| L062405 | 31.97 | −28.72 | 0.88 | 3.25 |
| Average | 28.75 | −25.66 | — | 3.09 |
| Std. Dev. | 7.64 | 7.47 | — | 1.06 |

Calculated concentration of bFGF per lyophilized UDC lysate total protein yielded the following equation:

bFGF (picograms/milliliter)=(28.745) total protein (micrograms/milliliter)−25.656.

Equation slope and Y-intercept are derived from the average slope and Y-intercept values obtained from regression analysis of six production lots.

SDS-PAGE Analysis of UDC Lysate.

Banding pattern of protein is consistent between separate production lots, pre- and post-lyophilization, and lyophilization onto a synthetic biomaterial.

Summary.

The method presented here consistently allowed for the harvest of protein from lysed, centrifuged UDCs. The amount of total protein—57.53+/−38.69 picograms per cell—correlates to the harvest density of the cells (R—Sq (adj)=71.5%). The growth factor bFGF was present in six separate production lots of lyophilized UDC lysate averaging 3.09±1.06 picograms per micrograms of total protein. SDS-PAGE analysis of umbilicus derived cell lysate showed that the banding pattern of protein was consistent between separate production lots, pre- and post-lyophilization, and following lyophilization onto a synthetic biomaterial. This method allows reproducible production of lyophilized material containing growth factors for application in tissue regeneration.

Example 18

Evaluation of the Potential of Cell Lysate-Coated Scaffolds to Induce Cell Infiltration in a Rodent Subcutaneous Implantation Model The purpose of this study was to evaluate the ability of human umbilicus cell-derived cell lysate when delivered in a scaffold to induce cellular infiltration and tissue formation. Since this is a xenogeneic source of cells, an early time-point was chosen to evaluate the inflammatory response the cell lysate might exhibit. Two types of scaffolds (VNW and 35/65 PCL/PGA foam) were tested to determine their potential to act as carriers for lysate delivery. As a nonlimiting example of the invention, the cellular components of human umbilicus-derived cells (UDCs), loaded on two different scaffold types, were tested to evaluate the cell infiltration and inflammatory response elicited in a subcutaneous rat implantation study. UDC cellular lysate and cellular supernatant were prepared by different methods. In two of the methods the cell membranes remained in the preparation. In one method, the cell membranes were removed. All treatments were lyophilized prior to implantation. This study included an n of 4 per treatment, except controls, which were matched on every animal (n=28).

Several trends surfaced upon analysis of the data. The amount of ingrowth into the foams was increased in the UDC supernatant and HF cell groups. The amount of ingrowth into the VNW differed the greatest in the UDC cells (caudal) as opposed to the VNW scaffold (caudal). The cranial sites demonstrated near 100% ingrowth for all VNW treatment groups. In the cranial sites of the UDC supernatant, there was increased cellularity of ingrowth (fibroblasts and capillaries within the VNW scaffold) as compared to the VNW alone. There appears to be an increase in the amount of collagen deposition within the VNW scaffold for the UDC lysate group (caudal sites), the UDC supernatant, and HF groups (cranial sites).

As expected, the Growth medium control group did not increase cell ingrowth. The amount of ingrowth into the foam and VNW (caudal sites) was diminished.

Even though no statistical conclusions can be made from this study, the data obtained suggest that the UDC supernatant preparation has a positive impact on cellular infiltration. The UDC supernatant group demonstrated increases in cellularity of ingrowth and collagen deposition in the VNW scaffold.

Methods & Materials

General Methods.

Four (4) sub-cutaneous pockets (2 cranial; 2 caudal) were created on the dorsal region of 32 rats. The treatment groups were assigned to the sites and left in place throughout the study period. The treatments (6 mm punches) were placed flat into the subcutaneous pocket. The implants were placed approximately 1 cm caudal to the incision. Metal wound clips were used to close the incision. Four animals were included in the study for only 3 days. These animals, implanted with VNW scaffolds only, were used to determine if there was an immediate immune reaction to the human cells in the rats. Tissues were harvested from the animals on days 3 and 14. The entire scaffold and surrounding skin was excised. The excised tissue was placed in 10% neutral buffered formalin for histological processing (paraffin sections) and stained with hematoxylin and eosin and trichrome. Tissue sections were histologically analyzed for the percentage of ingrowth into the scaffold, the quality of ingrowth into the scaffold, the encapsulation of the scaffold, and the inflammatory response within the scaffold.

Treatment Groups.

The VNW was purchased from Biomedical Structures (Slatersville, R.I.). The scaffolds were placed in desiccant paper pillows that were then packaged in T-vent aluminum pouches and sterilized via ethylene oxide sterilization (nominal B cycle). The scaffolds were stored at room temperature prior to use. The following treatment groups were included in the study:
1. VNW and human umbilicus-derived cells (UDC)
2. 3% 35/65 PCL/PGA foam (Foam) and UDC
3. VNW and human fibroblasts (HF)
4. Foam and HF
5. VNW and UDC cell lysate
6. Foam and UDC cell lysate
7. VNW and HF cell lysate
8. Foam and HF cell lysate
9. VNW and UDC cell supernatant
10. Foam and UDC cell supernatant
11. VNW and HF cell supernatant
12. Foam and HF cell supernatant
13. VNW control
14. Foam control
15. VNW Growth medium control
16. Foam Growth medium control Lot Numbers:
Foam: 3551-14-6
VNW: 3551-14-HD
Fibroblasts (human adult; passage 10): 1F1853
UDCs (passage 10): Lot 1; Day of isolation 022803
Growth medium (DMEM): 1192731

Test Article Preparation

Foam Preparation.

A 5% w/w solution of 35/65 epsilon-Caprolactone/Glycolide molar composition of high purity grade (99+%) 1,4-Dioxane (Fisher Scientific, Pittsburgh, Pa.) was prepared by dissolving five parts polymer to ninety-five parts of solvent at 60° C. for 4 hours. The polymer solution was filtered through an extra coarse thimble prior to making the foam scaffolds. This polymer solution was diluted with dioxane to make a 3% w/w solution. A pre-determined amount of polymer solution was poured into a pre-cooled aluminum mold and lyophilized to remove the solvent from the frozen structure by phase separation resulting in the interconnecting pore structure.

Scouring of VNW.

VNWs were scoured to remove residual processing oils. The material was scoured twice. The VNW was agitated in isopropanol (IPA) in the BRANSONIC Ultrasonic Cleaner (BUC) for at least 30 minutes. The IPA was drained, and the VNW was washed with deionized water three times. The VNW was then agitated in deionized water in the BUC for an additional 30 minutes. The VNW was dried under vacuum overnight or until dry to the touch.

Sample Preparation (Scaffold+Cellular Components).

Approximately 30 million cells from each cell type (UDC and HF) were trypsinized and washed with PBS three times. Conceptually, there are multiple ways in which a cell lysate could be prepared. Cells can be lysed by sonication, freeze thaw, or any number of other methods available to those skilled in the art. In this study, three different methods of preparing a cell lysate fraction were examined. For this example, the three preps will be referred to as "cell," "lysate," and "supernatant". A cell suspension of $1 \times 10^7$/ml was prepared and divided into three groups. The cell groups (UDC and HF) were created from the original suspension. 100 microliters was added to each scaffold. The cell-loaded scaffolds were placed in a shaker for 20 minutes to encourage incorporation of the cells into the scaffolds. The cell-loaded scaffolds were then lyophilized, in tissue culture plates, prior to implantation in the rat.

The lysate groups were prepared by freezing and thawing cells for three cycles (−80° C. for 10 min/37° C.) and then 100 microliters was added to each scaffold. The lysate-loaded scaffolds were placed in a shaker for 20 minutes to encourage incorporation of the lysate into the scaffolds. The lysate loaded scaffolds were then lyophilized, in tissue culture plates, prior to implantation in the rat.

The supernatant groups were prepared by freezing and thawing cells for three cycles (−80° C. for 10 min/37° C.) and then centrifuged at 13,000×g for 10 minutes at 4° C. The supernatant was collected and 100 microliters was added to each scaffold. The supernatant-loaded scaffolds were placed in a shaker for 20 minutes to encourage incorporation of supernatant into the scaffolds. The supernatant-loaded scaffolds were then lyophilized, in tissue culture plates, prior to implantation in the rat.

The Growth medium control group was prepared by adding 100 microliters of Growth medium (containing 10% fetal bovine serum) to each scaffold; these scaffolds were washed with PBS three times after the addition of growth medium. These scaffolds were then lyophilized, in tissue culture plates, prior to implantation in the rat.

The scaffold alone groups were prepared by adding 100 microliters of PBS to each scaffold. The scaffolds were then lyophilized, in tissue culture plates, prior to implantation in the rat.

Scaffold Characterization.

The 3% w/w 35/65 PCL/PGA sample was analyzed for percent porosity and pore size distribution analysis using helium picnometry and mercury porosimetry, respectively (Quantochrome Instruments (Boynton Beach, Fla.)). The percent porosity was in the range of about 97 to 98 and the mean of bimodal pore size distribution was 55.5. This scaffold batch was made from a copolymer epsilon-caprolactone/glycolide, which was analyzed for molar composition of epsilon-caprolactone and glycolide and residual monomers. 35 mole % and 63.3 mole % were determined for epsilon-caprolactone and glycolide, respectively, and 0.11 mole % of CAP and 0.58 mole % of GLY. The morphology of pores was analyzed by SEM method.

The VNW scaffold used in this study was 2.06 mm thick. The density, as determined by Biomechanical Structures, was 108.49 mg/cc. The percent porosity was calculated to be 92.8%. The VNW was tested in triplicate for residual IPA and residual ethylene oxide (EtO). The samples all demonstrated less than 1 ppm residual IPA. The residual EtO levels in the VNW were 8, 9, and 10 ppm. The residual EtO in each sample was much less than the 250 ppm limit.

Surgical Preparation.

Each rat was anesthetized via Isoflurane inhalant anesthesia. After induction of anesthesia, the entire back of the animal from the dorsal cervical area to the dorsal lumbrosacral area was clipped free of hair using electric animal clippers. The area was then scrubbed with Chlorhexidine diacetate, rinsed with alcohol, dried and painted with an aqueous iodophor solution of 1% available iodine. The anesthetized and surgically prepared animal was placed in the desired recumbent position.

Surgical Approach.

Four skin incisions, each approximately 1.0 cm in length, were made on the dorsum of the rat. Two cranial sites were located transversely over the dorsal lateral thoracic region, about 2 cm caudal to the palpated inferior edge of the scapula, with one to the left and one to the right of the vertebral column. Another two were placed transversely over the gluteal muscle area at the caudal sacrolumbar level, about 1 cm caudal to the palpated iliac crest, with one on either side of the midline. The skin was separated from the underlying connective tissue to make a small pocket and the implant placed about 1 cm caudal to the incision. Six mm implants were placed in these sites according to the predetermined randomized implantation scheme. The skin incisions were closed with metal wound clips.

At the predetermined time points (3 and 14 days post-implant), the animals were euthanized via carbon dioxide inhalation. The animals were observed to ensure that respiratory function had ceased and there was no palpable cardiac function.

Tissue Processing.

Immediately following euthanasia, each subcutaneous implantation site with the overlying skin was excised. The wound was fixed in 10% neutral buffered formalin, processed and embedded in paraffin. Samples were sectioned at 5 microns and stained for hematoxylin and eosin by PAI Associates (Charles River Laboratories, West Chester, Ohio).

Histological Assessments.

Tissue sections were histologically analyzed for the percentage of ingrowth into the scaffold, the quality of ingrowth into the scaffold, the encapsulation of the scaffold, and inflammatory response within the scaffold.

Results

Day 3

Samples tested at day 3 included UDC lysate, UDC supernatant, HF, and VNW scaffold. All treatments were incorporated into the VNW scaffold. The purpose of a three day time-point was to determine if there was an immediate immune response to the implanted cellular components.

Observations at Necropsy

Vascularization.

At the time of necropsy, the ventral surface of each implant was evaluated for the amount of vascularization. A difference was observed at day 3 in the degree of vascularization and position of the wound. The cranial sites were more vascularized. No clinical evidence of immune response was noted at this timepoint.

Histological Assessments

Percent Ingrowth into the Scaffold:

As expected, at day 3, all treatment groups demonstrated very limited ingrowth with some presence of inflammatory cells. Three sites (1 UDC supernatant and 2 HF) demonstrated some fibrovascular ingrowth. Two sites (1 UDC lysate and 1 VNW) demonstrated relatively acellular implants at day 3 post-implantation.

Type of Infiltrate Noted in Scaffold:

The majority (3 of 4) sites of the UDC lysate, UDC supernatant and VNW scaffold demonstrated typical ingrowth (macrophages, neutrophils, and lymphocytes) as expected on day 3 post-implantation. One site each of UDC lysate and VNW scaffold had less than the normal amount of ingrowth at day 3. One UDC supernatant site demonstrated more fibrovascular ingrowth as compared to other sites. All of the four HF sites had several clumps of large irregular cells (dark granular eosinophilic cytoplasm; nuclei were quite variable in color). Two of the four HF sites also demonstrated more fibrovascular ingrowth.

Collagen Deposition:

As expected, there was no evidence of collagen deposition at any site at day 3 post-implantation.

Inflammatory Response within the Scaffold:

All day 3 sites demonstrated an inflammatory response of 'minimal.'

Day 14

Histological Assessments

Percent Ingrowth into the Scaffold:

The treatments incorporated into the foam scaffold demonstrated a wide range of ingrowth. The average amount of ingrowth ranged from about 31% to 90%. In general, there was more ingrowth seen in the cranial sites.

The treatments incorporated into the VNW demonstrated a narrower range of ingrowth into the scaffold. The average amount of ingrowth ranged from about 69% to 100%. All cranial sites with VNW demonstrated the same or more ingrowth than the caudal sites.

Cellularity of Ingrowth (VNW Scaffolds Only):

This measurement examined the ingrowth of fibroblasts and capillaries in between the foreign body reaction zones, more specifically around the fibrils of the VNW scaffold. This parameter was scored as 0=below notable level (the elements were present, but there was nothing notable about the amount), 0.5=trace (notable), 1=minimal (small increase in the elements), 2=slight (greater increase in the elements), 3=moderate (greatest increase on this comparative scale). All sites averaged between minimal and slight. Table 18-1.

TABLE 18-1

Mean and SEM of the score of cellularity of ingrowth of the VNW scaffold

| | | VNW | | |
|---|---|---|---|---|
| | | Average (all sites) | Cranial sites | Caudal Sites |
| UDC | Cells | 2 (0) | 2 (0) | 2 (0) |
| | Lysate | 1.8 (0.5) | 1.5 (0.5) | 2 (1) |
| | Supernatant | 2 (0.4) | 2.5 (0.5) | 1.5 (0.5) |
| HF | Cells | 1.5 (0.3) | 2 (0) | 1 (0) |
| | Lysate | 1 (0) | 1 (0) | 1 (0) |
| | Supernatant | 1.3 (0.3) | 1.5 (0.5) | 1 (0) |
| Controls | Growth medium | 1 (0) | 1 (0) | 0 (0) |
| | Empty Scaffold | 1.2 (1) | 1.2 (0.2) | 1.3 (0.2) |

Collagen Deposition (VNW Scaffolds Only):

This measurement evaluated the collagen deposition in the spaces between fibrils of the VNW. This parameter was scored as 0=below notable level (the elements were present, but there was nothing notable about the amount), 0.5=trace (notable), 1=minimal (small increase in the elements), 2=slight (greater increase in the elements), 3=moderate (greatest increase on this comparative scale). All sites averaged between minimal and slight. Table 18-2.

TABLE 18-2

Mean and (SEM) of the score of collagen deposition for the VNW scaffold

| | | VNW | | |
|---|---|---|---|---|
| | | Average (all sites) | Cranial sites | Caudal Sites |
| UDC | Cells | 1.8 (0.3) | 2 (0) | 1.5 (0.5) |
| | Lysate | 2 (0.4) | 1.5 (0.5) | 2.5 (0.5) |
| | Supernatant | 2.1 (0.6) | 2.5 (0.5) | 1.8 (1.3) |
| HF | Cells | 2.3 (0.5) | 3 (0) | 1.5 (0.5) |
| | Lysate | 1.3 (0.3) | 1 (0) | 1.5 (0.5) |
| | Supernatant | 1.3 (0.6) | 2 (1) | 0.5 (0) |
| Controls | Growth medium | 1 (0) | 1 (0) | 0 (0) |
| | Empty Scaffold | 1.2 (0.1) | 1.2 (0.2) | 1.2 (0.2) |

Inflammatory Response within the Scaffold:

The inflammatory response was graded at each site. The grades were: 1=minimal; 2=slight; 3=moderate; 4=pronounced.

For the foams, the grade 'minimal' was given for reactions mainly concentrated at the surface of the material with no significant extension into the scaffold or outwards from the surface. 'Slight' indicated partial cellular infiltration of the scaffold as noted above, but with no significant cellular response outwards from the surface. Foams were given a 'moderate' score when there was total or almost total infiltration of the cell types noted above, but there was no significant extension of the reaction beyond the surface of the scaffold. A 'pronounced' score indicated that, in addition to the 'moderate' score, there was a pronounced degree of inflammatory cell infiltration surrounding the scaffold or the primary response to the material was neutrophilic.

For the VNW, the grade 'minimal' indicated only small collections of cells around individual fibers or fiber bundles and these infiltrates did not tend to coalesce. 'Slight' reactions for VNWs were given when there were greater concentrations of the cell types noted above (plus possibly other mononuclear cells). VNWs were given a 'moderate' score when there was total or almost total infiltration of the cell types noted above, but there was no significant extension of the reaction beyond the surface of the scaffold. A 'pronounced' score indicated that, in addition to the 'moderate' score, there was a pronounced degree of inflammatory cell infiltration surrounding the scaffold or the primary response to the material was neutrophilic. Table 18-3.

TABLE 18-3

Mean and (SEM) of the grade of inflammatory response within the scaffold

| | | Foam | | | VNW | | |
|---|---|---|---|---|---|---|---|
| | | Average (all sites) | Cranial Sites | Caudal Sites | Average (All sites) | Cranial Sites | Caudal Sites |
| UDC | Cells | 1.5 (0.5) | 2 (1) | 1 (0) | 2 (0.4) | 2.3 (0.3) | 1.8 (0.8) |
| | Lysate | 1.5 (0.3) | 1.5 (0.5) | 1.5 (0.5) | 1.9 (0.2) | 1.8 (0.3) | 2 (0.5) |
| | Supernatant | 2.5 (0.3) | 3 (0) | 2 (0) | 1.6 (0.2) | 1.8 (0.3) | 1.5 (0.5) |
| HF | Cells | 2.3 (0.3) | 2.5 (0.5) | 2 (0) | 1.5 (0) | 1.5 (0) | 1.5 (0) |
| | Lysate | 1.8 (0.3) | 1.5 (0.5) | 2 (0) | 1.5 (0) | 1.5 (0) | 1.5 (0) |
| | Supernatant | 2 (0.4) | 2.5 (0.5) | 1.5 (0.5) | 1.3 (0.1) | 1.3 (0.3) | 1.3 (0.3) |
| Controls | Growth medium | 1.4 (0.2) | 1.5 (0.5) | 1.3 (0.3) | 1.1 (0.1) | 1.3 (0.3) | 1 (0) |
| | Empty scaffold | 2 (0.2) | 2.4 (0.2) | 1.6 (0.2) | 1.3 (0.1) | 1.2 (0.1) | 1.3 (0.1) |

Summary.

The purpose of this study was to evaluate the ability of human umbilicus cell-derived lysate when delivered in a scaffold to induce cellular infiltration and tissue formation upon in vivo administration, for example, when implanted subcutaneously in a rat. Two types of scaffolds (VNW and 35/65 PCL/PGA foam) were tested to determine their potential to act as carriers for lysate delivery. Both scaffolds elicited a minimal to slight inflammatory reaction.

A limited number of samples were tested at day 3 (UDC lysate, UDC supernatant, HF and scaffold alone) for potential immune/inflammatory response. This was done because of the xenogeneic nature of the cell source. All treatments evaluated at three days were incorporated into the VNW scaffold. It had been proposed that the UDC cells are immunoprivileged but to this point they had never been implanted into a non-immunocompromised animal. No immunological responses were noted; very limited inflammatory cellular infiltrates (mainly macrophages, some residual neutrophils and rare lymphocytes) were seen at this time-point. These observations are typical after a three-day implantation period. Any inflammatory response that was seen was scored as 'minimal' at day three.

This study was designed so that each animal had a control of each scaffold type and one treatment group of each scaffold type. This was done because in a previous experiment, a difference was seen between the cranial and caudal implantation sites. Differences were also seen in this study at the cranial versus caudal sites. Although this study cannot be analyzed statistically due to the low n number, there were several positive findings of interest. The amount of ingrowth into the foams was increased in the UDC supernatant and HF cell groups. Additionally, the amount of ingrowth into the VNW differed the greatest in the UDC cells (caudal) as opposed to the VNW scaffold (caudal). The cranial sites demonstrated near 100% ingrowth for all VNW treatment groups. In the cranial sites of the UDC supernatant, there was increased cellularity of ingrowth (fibroblasts and capillaries within the VNW scaffold) as compared to the VNW alone. There appeared to be an increase in the amount of collagen deposition within the VNW scaffold for the UDC lysate group (caudal sites), the UDC supernatant and HF groups (cranial sites).

As expected, the Growth medium control group (negative control) appeared to impact the scaffolds in a negative way. The amount of ingrowth into the foam and VNW (caudal sites) was diminished. The caudal VNW sites demonstrated no collagen deposition for the Growth medium controls.

Of particular note in this study was the effect of position on tissue ingrowth in this model. Scaffolds which were located in the cranial position, in general, had significantly more tissue ingrowth than those scaffolds located in the caudal position. The sites which were located in the caudal position could be thought of as a "delayed tissue ingrowth" model since at 14 days post-implantation there was a subjective grade of 1 on a scale of 1-3 with the cranial sites equal to 2 or greater. When testing multiple methods of preparing the lysate, all caudal sites treated with three different UDC lysates showed more tissue ingrowth and collagen deposition when compared to three identical methods used to prepare lysate from Human Fibroblasts.

Even though no statistical conclusions can be made from this study, the data obtained suggest that the UDC supernatant preparation has a positive impact on cellular infiltration. The UDC supernatant group demonstrated increases in cellularity of ingrowth and collagen deposition in the VNW scaffold.

Example 19

Evaluation of the Tissue Response of Cell Lysate in a Rodent Subcutaneous Model

The purpose of this study was to determine whether increased cell infiltration and extracellular matrix deposition in response to scaffolds treated with cell lysate would provide statistical significance when repeated with a larger number of animals per treatment group.

The cellular components of human umbilicus-derived cells (UDC), human dermal fibroblasts, and Growth medium were loaded on scaffold and were tested to evaluate the cell infiltration and inflammatory response elicited in a subcutaneous rat implantation study. These were compared to the scaffold alone. All treatments were lyophilized prior to implantation.

No immunological responses were noted in this study. The amount of inflammatory response for all groups ranged from minimal to slight.

The amount of ingrowth into the VNW was very similar across the treatment groups, both in the cranial and caudal positions. The UDC Supernatant demonstrated significantly increased cellularity of ingrowth (fibroblasts and capillaries within the VNW scaffold) as compared to the GM Control and the VNW alone. The UDC Supernatant demonstrated greater cellularity of ingrowth at both the cranial and caudal sites compared to all other treatments. Collagen deposition was statistically greater for the cranial sites compared to GM Control and Scaffold Control. Additionally, the caudal sites demonstrated statistically greater collagen deposition than the Scaffold Control.

In conclusion, two subcutaneous rat studies have been completed to assess tissue ingrowth and inflammatory reaction to scaffolds treated with cell lysates from UDC or HF. In both studies, there was increased tissue ingrowth and extracellular matrix deposition in scaffolds treated with lysate according to qualitative histopathology assessment. In addition, this positive tissue response may be considered to be of "greater quality" (based generally on both cellular infiltration and inflammatory response) due to the decreased inflammatory response to UDC as compared to HF.

Methods & Materials

Experimental Design.

Four (4) subcutaneous pockets (2 cranial; 2 caudal) were created on the dorsal region of 32 rats. The treatment groups were assigned to the sites and left in place throughout the study period. The treatments (6 mm punches) were placed flat into the subcutaneous pocket. The implants were placed approximately 1 cm caudal to the incision. Metal wound clips were used to close the incision. Tissues were harvested from the animals on day 14. The entire scaffold and surrounding skin was excised. The excised tissue was placed in 10% neutral buffered formalin for histological processing (paraffin sections) and stained with hematoxylin and eosin and trichrome. Tissue sections were histologically analyzed for the percentage of ingrowth into the scaffold, the quality of ingrowth into the scaffold, the encapsulation of the scaffold, and inflammatory response within the scaffold.

Treatment Groups.

The VNW was purchased from Biomedical Structures (Slatersville, R.I.). The scaffolds were placed in desiccant paper pillows that were then packaged in T-vent aluminum pouches and sterilized via EtO sterilization (nominal B cycle). The scaffolds were stored at room temperature prior to use. The following treatment groups were included in the study:

1. Human Umbilicus-derived Cell Lysate (UDC Supernatant)
2. Human Skin Fibroblast Cell Lysate (HF Supernatant)
3. Growth medium Control (GM Control)
4. VNW Scaffold Control All treatments were lyophilized onto VNW scaffolds.

Lot Numbers:
VNW: 3551-73-1
Fibroblasts (human adult; passage 10): 1F1853
UDC (passage 11): 040604B
Growth medium (Hayflick media): 1192731

Test Article Preparation

Scouring of VNW.

VNWs were scoured to remove residual processing oils. The material was scoured twice. The VNW was agitated in isopropanol (IPA) in the BRANSON ULTRASONIC CLEANER (BUC) for at least 30 minutes. The IPA was drained, and the VNW was washed with deionized water three times. The VNW was then agitated in deionized water in the BUC for an additional 30 minutes. The VNW was dried under vacuum overnight or until dry to the touch.

Preparation of Cell Lysate.

Human umbilicus-derived cells (UDCs) and human skin fibroblasts (HF) at passage 11 were seeded into gelatin-coated T225 flasks. Flasks were trypsinized with 0.05% trypsin/EDTA for 5 minutes until the cells began lifting from the dish. The trypsinization process was inactivated using 15% serum containing Dulbecco's Modified Eagle's growth media at a ratio of 4 milliliters trypsin to 4 milliliters Growth media. Twelve million cells were obtained for both UDCs and HFs. Cells were pelleted in Growth media, combined into one pellet and then resuspended in a total volume of 20 milliliters of PBS. The cells were washed three times in PBS to remove residual FBS from the Growth media. This was done by centrifuging the cells for 5 minutes at 1.5 RPM and then resuspending the cells in 20 ml of PBS until the three washes were complete.

The lysates were prepared by repeated freeze/thaw cycles. The cell pellets (UDC and HF) were resuspended in 425 microliters of PBS. To freeze the cells, the tubes were placed in a slurry of dry ice and isopropanol for 10 minutes. After 10 minutes, the tubes were placed in a 37° C. water bath for 10 minutes. This procedure was repeated for a total of three cycles of freezing and thawing.

The cell suspensions were transferred to sterile siliconized microcentrifuge tubes, to prevent protein adsorption, and centrifuged at 13,000×g for 10 minutes at 4° C. to separate the cell membranes from the cytosolic components. After removal of the cell membranes, the supernatant was gently mixed by tapping the centrifuge tube to ensure uniformity. The supernatant was transferred to new siliconized tubes and placed on ice. Approximately 425 microliters of UDC supernatant was collected. To ensure that there was enough UDC supernatant to be loaded onto the scaffolds 50 microliters of PBS was added to make a final volume of 475 microliters.

Preparation of the Treatment Groups

UDC Supernatant and HF Supernatant.

Sterile VNW scaffolds (6 mm punches) were aseptically transferred to sterile multi-well plates. 25 microliters of cell lysate supernatant (UDC or HF) were placed on the VNW; the drop of cell lysate sank into the scaffold. The dish was covered with a sterile lid and taped to ensure the lid would stay in place during the lyophilization process. The dishes were then immediately placed on dry ice until lyophilization.

GM Control.

Sterile VNW scaffolds (6 mm punches) were aseptically transferred to sterile multi-well plates. 30 microliters of Hayflick media was placed in the same manner onto each of the scaffolds as described above. The scaffolds were washed three times in PBS to remove residual media. The dish was covered with a sterile lid and taped to ensure the lid would stay in place during the lyophilization process. The dishes were then immediately placed on dry ice until lyophilization.

VNW Control.

Sterile VNW scaffolds (6 mm punches) were aseptically transferred to sterile multi-well plates. The dish was covered with a sterile lid and taped to ensure the lid would stay in place during the lyophilization process. The dishes were then immediately placed on dry ice until lyophilization.

The treatments were lyophilized using a 48-hour lyophilization cycle. After the lyophilization was complete, the dishes were wrapped in parafilm and stored at −80° C. until the day of surgery. On the day of surgery, the treatments were removed from the freezer and placed into a foil-covered ice bucket to prevent proteolytic activity.

Treatment Characterization

VNW Scaffold.

VNW scaffold (Lot 355-73-1) was purchased from Biomedical Structures (Slatersville, R.I.). The VNW scaffold used in this study was 2.06 mm thick. The density, as determined by Biomedical Structures, was 108.49 mg/cc. The percent porosity was calculated to be 92.8%. The sample demonstrated less than 1 ppm residual IPA. Residual ethylene oxide (EtO) levels were tested four times. The residual EtO levels in the VNW were 130, 132, 133 and 137 ppm. The residual EtO in the sample was much less than the 250 ppm limit.

Cell Lysate (UDC and HF).

Prior to use of the cells, preliminary pathogen testing was conducted. The cells were tested for HIV1, HIV2, HCV, HTLV, HBV and EBV. Detection of virus DNA and RNA was done via PCR. The cells tested negative for all viruses.

Implantation Scheme

This study was conducted in accordance with the rules and regulations of the Institutional Animal Care and Use Committee of Ethicon Research & Development, Somerville, N.J.

The scaffolds were placed in desiccant paper pillows that were then packaged in T-vent aluminum pouches and sterilized via EtO sterilization (nominal B cycle). The scaffolds were stored at room temperature prior to use. The cell isolates were co-lyophilized with the scaffolds in an aseptic manner.

Each rat was anesthetized via Isoflurane inhalant anesthesia. After induction of anesthesia, the entire back of the animal from the dorsal cervical area to the dorsal lumbrosacral area was clipped free of hair using electric animal clippers. The area was then scrubbed with Chlorhexidine diacetate, rinsed with alcohol, dried and painted with an aqueous iodophor solution of 1% available iodine. The anesthetized and surgically prepared animal was placed in the desired recumbent position.

Four skin incisions, each approximately 1.0 cm in length, were made on the dorsum of the rat. Two cranial sites were located transversely over the dorsal lateral thoracic region, about 2 cm caudal to the palpated inferior edge of the scapula, with one to the left and one to the right of the vertebral column. Another two were placed transversely over the gluteal muscle area at the caudal sacrolumbar level, about 1 cm caudal to the palpated iliac crest, with one on either side of the midline. The skin was separated from the underlying connective tissue to make a small pocket and the implant placed about 1 cm caudal to the incision. Six mm implants were placed in these sites according to the predetermined randomized implantation scheme. The skin incisions were closed with metal wound clips.

Analysis

At the predetermined time point (14 days post-implant), the animals were euthanized via carbon dioxide inhalation. Immediately following euthanasia, each subcutaneous implantation site with its overlying skin was excised. The wound was fixed in 10% neutral buffered formalin, processed and embedded in paraffin. Samples were sectioned at 5 microns and stained for hematoxylin and eosin.

Histological Assessment.

Tissue sections were histologically analyzed for the percentage of ingrowth into the scaffold, the quality of ingrowth into the scaffold, the encapsulation of the scaffold, and inflammatory response within the scaffold.

Statistical Analysis.

Treatments were assigned so that the UDC Supernatant, HF Supernatant and GM Control were equally distributed over the cranial and caudal wounds. The Scaffold Control was paired to each cranial or caudal wound. Shapiro-Wilk-W Test was performed prior to data analysis to determine normality. Nominal and Ordinal data was analyzed using Chi-Square. Continuous data was analyzed using One-way ANOVA. The Tukey-Kramer test for multiple comparisons was performed to determine differences between groups following One-way ANOVA. A value of $p<0.05$ was used as the level of significance.

Results

Histological Assessments

Percent Ingrowth into the Scaffold.

There was no statistical difference between the treatments for the amount of in-growth into the scaffold. All treatments ranged from 92.64 to 97.94% ingrowth. The cranial sites demonstrated numerically superior amount of ingrowth than the caudal sites although the difference is not significant. See Table 19-1.

TABLE 19-1

Mean and (SEM) of the percent ingrowth into the VNW scaffold

| Treatment | Average (All sites) | Cranial Sites | Caudal Sites |
|---|---|---|---|
| UDC Supernatant | 96.38 (2.39) | 100 (0) | 93.29 (4.21) |
| HF Supernatant | 92.64 (3.57) | 99.86 (1.04) | 85.46 (6.15) |
| GM Control | 97.94 (0.98) | 98.13 (1.49) | 97.75 (1.37) |
| Scaffold Control | 93.08 (1.72) | 98.50 (0.87) | 87.67 (2.96) |

Cellularity of Ingrowth.

This measurement examined the ingrowth of fibroblasts and capillaries in between the foreign body reaction zones, more specifically around the fibrils of the VNW scaffold. This parameter was scored as follows: 0=below notable level (the elements—e.g., capillaries and fibroblasts—were present, but there was nothing notable about the amount), 0.5=trace (notable), 1=minimal (small increase in the elements), 2=slight (greater increase in the elements), 3=moderate (greatest increase on this comparative scale).

UDC Supernatant demonstrated statistically significant more cellularity than either the GM Control or Scaffold Control groups ($p<0.05$, Tukey-Kramer). When the data was separated into cranial and caudal sites, there were no statistical differences demonstrated. See Table 19-2.

TABLE 19-2

Mean and (SEM) of the score for cellularity of ingrowth

| Treatment | Average (All sites) | Cranial Sites | Caudal Sites |
|---|---|---|---|
| UDC Supernatant | 1.19 (0.23) | 1.25 (0.44) | 1.14 (0.24) |
| HF Supernatant | 0.89 (0.19) | 0.93 (0.32) | 0.86 (0.24) |
| GM Control | 0.50 (0.11) | 0.50 (0.16) | 0.50 (0.16) |
| Scaffold Control | 0.53 (0.06) | 0.44 (0.08) | 0.63 (0.09) |

Collagen Deposition.

This measurement evaluated the collagen deposition in the spaces between fibrils of the VNW. This parameter was scored as follows: 0=below notable level (the elements were present, but there was nothing notable about the amount), 0.5=trace (notable), 1=minimal (small increase in the elements), 2=slight (greater increase in the elements), 3=moderate (greatest increase on this comparative scale).

UDC Supernatant and HF Supernatant demonstrated statistically significant greater amounts of collagen deposition than either GM Control or Scaffold Control. Additionally, GM Control demonstrated statistically significant greater amounts of collagen deposition than Scaffold Control ($p<0.05$, Tukey-Kramer).

When the data was split into cranial and caudal sites, similar differences were determined. The cranial sites of UDC Supernatant and HF Supernatant demonstrated statistically significant greater amounts of collagen deposition than either GM Control or Scaffold Control. For the caudal sites, all treatment groups demonstrated statistically significant greater amounts of collagen deposition than Scaffold Control ($p<0.05$, Tukey-Kramer). Table 19-3.

TABLE 19-3

Mean and (SEM) of the score for collagen deposition

| Treatment | Average (All sites) | Cranial Sites | Caudal Sites |
|---|---|---|---|
| UDC Supernatant | 1.85 (0.19) | 2.17 (0.31) | 1.57 (0.20) |
| HF Supernatant | 1.68 (0.21) | 2.00 (0.22) | 1.36 (0.32) |
| GM Control | 1.09 (0.15) | 1.00 (0.25) | 1.19 (0.19) |
| Scaffold Control | 0.63 (0.07) | 0.67 (0.12) | 0.58 (0.07) |

Inflammatory Response within the Scaffold.

The inflammatory response was graded at each site. The responses were graded as follows: 1=minimal; 2=slight; 3=moderate; 4=pronounced.

For VNWs, the grade 'minimal' indicated only small collections of cells (macrophages and macrophage giant cells) around individual fibers or fiber bundles and these infiltrates did not tend to coalesce. 'Slight' reactions for VNWs were given when there were greater concentrations of the cell types (macrophages and macrophage giant cells plus possibly other mononuclear cells). VNWs were given a 'moderate' score when there was total or almost total infiltration of the cell types noted above, but there was no significant extension of the reaction beyond the surface of the scaffold. A 'pronounced' score indicated that, in addition to the 'moderate' score, there was a pronounced degree of inflammatory cell infiltration surrounding the scaffold, or if the primary response to the material was neutrophilic.

There were no statistical differences demonstrated among the groups for inflammatory response. All treatment groups performed very similarly. The average scores for the groups ranged from 1.18 to 1.58. No differences were determined when the data was split into cranial and caudal sites. See Table 19-4.

TABLE 19-4

Mean and (SEM) of the score for inflammatory response within the VNW

| Treatment | Average (All sites) | Cranial Sites | Caudal Sites |
|---|---|---|---|
| UDC Supernatant | 1.58 (0.11) | 1.58 (0.15) | 1.57 (0.45) |
| HF Supernatant | 1.50 (0.12) | 1.50 (0.19) | 1.50 (0.41) |
| GM Control | 1.34 (0.09) | 1.25 (0.13) | 1.44 (0.32) |
| Scaffold Control | 1.18 (0.03) | 1.15 (0.05) | 1.21 (0.25) |

Summary.

Two well-documented models of wound healing are the swine full thickness excisional wound model and the rat subcutaneous implant model. The swine model has utility because of similarity of the cutaneous architecture to that of human skin. The rat model is most often used to assess biocompatibility and tissue ingrowth. Therefore these models are the preferred models used to screen prototype devices. Based on the tissue reaction, tissue infiltration, extracellular matrix deposition, and the inflammatory response in these acute models, the efficacy of a device for chronic wound healing is inferred.

This was a randomized study to evaluate the ability of human umbilicus-derived cell lysate to stimulate cell invasion in a rat subcutaneous implantation model. Comparators in this study were human skin fibroblast-derived cell lysate, growth medium control, and scaffold control. We chose to only evaluate the VNW scaffold in this study because this scaffold is more readily infiltrated in the rat subcutaneous model than the foam. This study was designed so that each animal had a VNW control both cranially and caudally; in addition it was ensured that the other treatments were randomized equally across the cranial and caudal positions to minimize a potential difference in tissue response due to the anatomical position. This was done because in a previous experiment, a difference was seen between the cranial and caudal implantation sites. Differences were observed in this study at the cranial versus caudal sites. One possible explanation for the differences between the implantation sites is that the cranial sites are more vascularized due to the anatomical position than the caudal sites.

No immunological responses were noted in this study. The amount of inflammatory response for all groups ranged from minimal to slight. The types of cells seen were predominantly PMNs (polymorphonuclear neutrophils) and mononuclear cells. The HF Supernatant group had the most notations of inflammatory cells in association with the scaffold. Six of 14 sites had notations of PMNs and mononuclear cells within the scaffold; three additional sites had notations of PMNs alone within the scaffold. Of these nine sites, four were cranial and five were caudal sites. The GM Control group and the UDC Supernatant group had notations of inflammatory cells in 5 and 4 sites, respectively.

When comparing the overall quality of tissue which has grown into the scaffolds, several conclusions could be drawn. In 10/14 UDC-treated sites there were significantly more "higher quality" tissue (e.g., having extracellular matrix and cellular components including fibroblasts and endothelial cells) when compared to the untreated scaffold within the same animal. In 9/14 HF-treated sites there were significantly more "higher quality" tissue when compared to the untreated scaffold within the same animal. Importantly, when comparing the amount of inflammatory cell infiltration between the groups, it was noted that UDC-treated scaffolds exhibited only a slightly increased inflammatory response in 6/14 sites compared to 5/14 growth media controls. When comparing this result to the HF-treated scaffold, 9/14 sites exhibited an increased inflammatory response. This demonstrates that inflammatory response of UDC-treated scaffold was similar to GM control scaffold, while the HF-treated groups exhibited increased inflammation.

An important consideration when examining the inflammatory response to these lysates is that this study is an example of xenogeneic transplantation with human cells being transplanted into a rodent model. It is expected that a degree of inflammation would be present as the host animal "reacts" to the introduction of human cells. Interestingly, the UDC lysate groups performed similar to that of the control scaffolds with regard to inflammatory response.

The amount of ingrowth into the VNW was very similar across the treatment groups, both in the cranial and caudal positions. The UDC Supernatant demonstrated significantly increased cellularity of ingrowth (fibroblasts and capillaries within the VNW scaffold) as compared to the GM Control and the VNW alone. Collagen deposition was statistically greater for the cranial sites compared to GM Control and Scaffold Control. Additionally, the caudal sites demonstrated statistically greater collagen deposition than the Scaffold Control.

The GM Control demonstrated reduced amounts of cellularity of ingrowth and greater collagen deposition than the Scaffold Control.

In conclusion, two subcutaneous rat studies have been completed to assess tissue ingrowth and inflammatory reaction to scaffolds treated with cell lysates from UDC or HF. In both studies there was increased tissue ingrowth and extracellular matrix deposition in scaffolds treated with lysate. In addition, this positive tissue response may be considered to be of "greater quality" due to the decreased inflammatory response to UDCs compared to HFs.

Example 20

Increased Mouse NIH/3T3 Fibroblast Proliferation when Co-Cultured in Transwells with Collagen/ORC Material Containing UDC Lysate UDCs produce various growth factors involved in tissue regeneration, including basic Fibroblast Growth Factor (bFGF), hepatocyte growth factor (HGF), brain derived neurotrophic factor (BDNF), and keratinocyte growth factor (KGF). The supernatant of lysed UDCs also has been demonstrated to contain these growth factors. The application of the lysate to biomaterials followed by lyophilization produces a device that, upon clinical application, will deliver the growth factors to the defect site and enhance tissue regeneration.

The present study evaluated the ability of UDC lysate, lyophilized onto a material, to increase mouse NIH/3T3 fibroblast proliferation when co-cultured in a transwell system. Collagen/oxidized regenerated cellulose (ORC) containing lyophilized UDC lysate was placed in the upper portion of a transwell system and co-cultured with mouse NIH/3T3 fibroblasts plated at low density in the lower portion of the system. After three days the cells were harvested and counted. The transwells containing materials were transferred to new transwell systems and again co-cultured with mouse NIH/3T3 fibroblasts plated at low density in the lower portion of the system. After an additional three days (six days total material time in culture), the cells were harvested and counted. This second culture timepoint was performed to assess the release kinetics of the UDC lysate from the biomaterial.

After three days, a near significant (t-test, p=0.06) increase in proliferation was noted in mouse NIH/3T3 fibroblasts co-cultured with collagen/ORC containing UDC lysate versus collagen/ORC alone. After the transwells containing materials were transferred to new systems and co-cultured for an additional three days (six days total material time in culture), a near significant (t-test, p=0.09) increase in proliferation was again noted in mouse NIH/3T3 fibroblasts co-cultured with collagen/ORC containing UDC lysate versus collagen/ORC alone.

These results demonstrate the ability of growth factors from lyophilized UDC lysate to be released from a material and exhibit biological efficacy. The ability of the materials to exhibit biological efficacy after transfer to new transwell systems demonstrated that growth factors of lyophilized UDC lysate were released over time.

Methods & Materials

Cell Lysate Preparation.

UDC lysate supernatant was prepared as set forth in Example 17.

Lysate Application and Lyophilization.

Collagen/ORC pre-cut to 1.5×1.5 $cm^2$ in size were aseptically placed into the wells of 12 well sterile, ultra low cluster cell culture dishes (Corning Inc., Corning N.Y.). The supernatant fluid was applied to the material as five 30 microgram aliquots. An aliquot was placed at each corner of the 1.5×1.5 $cm^2$ material approximately 1 mm from the material edge and one aliquot was placed in the center of the material. The dish with materials was loaded into the lyophilizer.

Test materials with applied lysate were loaded into a FTS Systems Dura-Stop MP Stoppering Tray Dryer and lyophilized using the ramping program set forth in Example 17. All steps had a ramping rate of 2.5° C./minute and a 100-mT vacuum.

Mouse Fibroblasts.

Mouse NIH/3T3 fibroblasts (ATCC CRL-1658) were expanded in growth media (DMEM high glucose with 10% fetal calf serum and penicillin/streptomycin). All treatments were in triplicate.

10% FCS (empty transwell)

1% FCS (empty transwell)

Collagen/ORC (two 1.5×1.5 cm materials per transwell) in 1% FCS

Lysate+Collagen/ORC (two 1.5×1.5 cm materials each with 150 micrograms lysate per transwell) in 1% FCS Transwell Assay.

The mouse NIH/3T3 fibroblasts were plated into the lower portion of a 6-well transwell plate (Corning cat. no. 3412) at 5,000 cells per $cm^2$ and cultured overnight. The media was removed by aspiration and the appropriate media (2.5 ml per well, 1.5 ml per transwell), transwells, and treatments were added. On day 3, transwell containing materials were removed and transferred to new 6 well plates that were seeded with NIH/3T3 at 5,000 cells per $cm^2$ and the prior day. Cells in transwells were harvested by trypsinization and counted using a Guava PCA instrument (Guava Technologies, Hayward Calif.)

Results

Table 20-1 shows the number of cells per well (6-well plate) after 3 days transwell co-culture with treatment as calculated by Guava PCA Instrument.

TABLE 20-1

Day 3 Materials in Study

| | 1% FCS | Collagen/ORC | Collagen/ORC + 300 ug UDC Lysate | 10% FCS |
|---|---|---|---|---|
| −1 | 3.07E+05 | 1.63E+05 | 3.31E+05 | 2.23E+06 |
| −2 | 2.33E+05 | 1.37E+05 | 5.75E+05 | 2.69E+06 |
| −3 | 1.16E+05 | 1.25E+05 | 3.89E+05 | 2.86E+06 |
| Avg. | 2.19E+05 | 1.42E+05 | 4.32E+05 | 2.59E+06 |
| Std. | 78631.348 | 15860.503 | 104081.1649 | 266124.4487 |

Table 20-2 shows the number of cells per well (6-well plate) after 3 days transwell co-culture with transferred treatment (total six days in study) as calculated by Guava PCA Instrument.

TABLE 20-2

Day 6 Materials in Study

| | 1% FCS | Collagen/ORC | Collagen/ORC + 300 ug UDC Lysate | 10% FCS |
|---|---|---|---|---|
| −1 | 2.53E+05 | 7.60E+04 | 1.11E+05 | 3.51E+06 |
| −2 | 1.54E+05 | 7.93E+04 | 1.75E+05 | 2.51E+06 |
| −3 | 1.94E+05 | 7.12E+04 | 1.23E+05 | 2.11E+06 |
| Avg. | 2.00E+05 | 7.55E+04 | 1.36E+05 | 2.71E+06 |
| Std. | 40663.93433 | 3325.65783 | 27776.88887 | 588784.0578 |

A near significant increase in proliferation (t-test, p=0.06) was noted in mouse NIH/3T3 fibroblasts co-cultured with collagen/ORC treated with 300 micrograms UDC lysate in transwell versus collagen/ORC in transwell for three days.

A near significant increase in proliferation (t-test, p=0.09) was noted in mouse NIH/3T3 fibroblasts co-cultured with collagen/ORC treated with 300 micrograms UDC lysate in transwells transferred from the first three days of the study versus collagen/ORC in transwells transferred from the first three days of the study for three days (total 6 days material in study).

Summary.

After three days a near significant (t-test, p=0.06) increase in proliferation was note in mouse NIH/3T3 fibroblasts co-cultured with collagen/ORC containing UDC lysate versus collagen/ORC alone. After the transwells containing materials were transferred to new systems and co-cultured for an additional three days, a near significant (t-test, p=0.09) increase in proliferation was again noted in mouse NIH/3T3 fibroblasts co-cultured with collagen/ORC containing UDC lysate versus collagen/ORC alone.

These results demonstrated the ability of lyophilized UDC lysate to be released from a material and to exhibit biological efficacy. The ability of the materials to exhibit biological efficacy after transfer to new transwell systems demonstrated the proliferative factors of lyophilized UDC lysate were released over time.

Example 21

Implantation of VNW Scaffolds Loaded with Cell Lysate or Self Assembling Peptide in Swine The purpose of this study was to determine the cellular infiltration and inflammatory response of human umbilicus cell-derived (UDC) cell lysate when delivered in a scaffold of a swine full-thickness excisional defect. This study was designed to determine the cellular infiltration of full-thickness excisional defects in the presence of scaffolds that have been lyophilized with an active agent.

As demonstrated in the data obtained from quantitative histomorphometry, a statistically significant increase in granulation tissue area, average granulation tissue height, and greatest granulation tissue height when compared to all other treatment groups. However, the overall grade of the quality of the granulation tissue was poor. This assessment was based on the increased inflammatory cell presence in the large volume of tissue which had filled the scaffolds. This increased inflammatory cell presence may be attributed to the timepoint for analysis (7 day study) or the cell concentration in this model. When the groups were ranked to exclude one pig because of cell concentration differences, the cell lysate alone group showed an inflammatory cell presence similar to that of untreated controls with positive effects seen for epithelial tongue length, cell infiltration, greatest granulation tissue height, and average granulation tissue height.

The data generated from the two subcutaneous rat studies and this swine full thickness excisional wound model indicate that treatment of wounds/scaffolds with cell lysate has a stimulatory effect on tissue ingrowth.

Methods & Materials

Experimental Design.

Twelve (12) full-thickness excisions (1.5×1.5 cm) were created on the dorsal region of four swine. The treatment groups were assigned to the sites and left in place throughout the study period. Each animal had an equal distribution of the treatment groups. The treatment squares (1.5×1.5 cm) were trimmed to fit the wound, if needed, and covered with 2×2 cm NU-GEL (Johnson & Johnson Medical, Arlington, Tex.). All wounds were then covered with BIOCLUSIVE (Id.). Strips of self-adhering foam (RESTON, 3M Medical-Surgical Division, St. Paul, Minn.) were placed between sites to prevent cross-contamination due to wound fluid leakage. Sterile gauze (RAY-TEK, Johnson & Johnson Medical, Arlington, Tex.) was secured over the dorsum of the back with ZONAS (Id.) porous tape. A body stockinette (SPANDAGE, Medi-tech International Corporation, Brooklyn, N.Y.) was used to hold the dressings in place. Digital images of each wound were taken at days 0, 4 and 7 post-wounding. A bandage change was done on day 4 of the study. Tissues were harvested from the animals on day 7. The entire wound and surrounding normal skin was excised. The cranial half of the excised tissue was placed in 10% neutral buffered formalin for histological processing (paraffin sections) and stained with hematoxylin and eosin and trichrome. The caudal portion of each sample was retained for possible future analysis. Tissue sections were histologically analyzed for the presence of the scaffold, overgrowth of scaffold by granulation tissue, quality of ingrowth, and inflammatory response. Measurements of granulation tissue area and epithelial tongue length were also made.

Treatment Groups.

The VNW scaffold was purchased from Biomedical Structures (Slatersville, R.I.). The samples were foil-wrapped and sterilized via EtO sterilization and stored at room temperature prior to use.
  A. Cell Lysate applied directly to wound bed (Cell Lysate)
  B. Cell Lysate lyophilized in VNW (Cell Lysate/VNW)
  C. VNW scaffold (VNW)
  D. Untreated Control (Untreated)
  N=8 per treatment VNW was obtained from lot 3551-73-2. The cell lysate was obtained from cell lot 050604B.

Scouring of VNW.

Scouring occurred after the VNW was obtained from the supplier. The VNW was agitated in IPA in the BRANSONIC ULTRASONIC CLEANER (BUC) for at least 30 minutes. The IPA was drained and the VNW was washed with deionized water three times. The VNW was then agitated in deionized water in the BUC for an additional 30 minutes. The VNW was dried under vacuum overnight or until dry to the touch.

Preparation of Cell Lysate.

Approximately 25 million human umbilicus-derived cells (UDCs) at passage 11 were seeded into gelatin-coated T225 flasks. Because of the number of cells that were necessary to complete the study, the flasks were split, for trypsinization, into two sets which were combined to prepare the cell lysate. The cells ranged from approximately 70-95% confluent. Flasks were trypsinized with 0.05% trypsin/EDTA for 5 minutes until the cells began lifting from the dish. The trypsinization process was inactivated using Dulbecco's Modified Eagle's Growth media containing 15% serum. A total of 34 million cells were obtained from the first batch and approximately 58 million cells were obtained from the second batch; the total yield was approximately 92 million cells. Cells were pelleted in Growth media, combined into one pellet, and then resuspended in a total volume of 40 milliliters of PBS. The cells were washed three times in PBS to remove residual FBS from the growth media. This was done by centrifuging the cells for 5 minutes at 1.5 RPM and then resuspending the cells in 40 milliliters of PBS until the three washes were complete.

In order to facilitate the freeze-thaw procedure, the cells were equally divided into two tubes with 9.2 ml of PBS for the freeze/thaw procedure. The lysates were prepared by repeated freeze/thaw cycles. To freeze the cells, the tubes were placed in a slurry of dry ice and isopropanol for 10 minutes. After 10 minutes, the tubes were placed in a 37° C. water bath for 10 minutes. After two cycles, the cycle time was lengthened to 20 minutes to ensure that complete thawing/freezing of the samples had occurred.

The cell suspensions were transferred to ten sterile siliconized microcentrifuge tubes, to prevent protein adsorption, and centrifuged at 13,000×g for 10 minutes at 4° C. to separate the cell membranes from the cytosolic components. The tubes (cell pellet) were then placed on ice and the supernatant was very gently mixed by tapping the centrifuge tube to ensure uniformity. The supernatant was transferred to new siliconized tubes and placed on ice.

Preparation of the Treatment Groups.

Cell Lysate:

Cell lysate supernatant was pipetted into a sterile 96-well deep well dish (conical bottom). Wells were marked to indicate presence of lysate. The dish was covered with a sterile lid and taped to ensure the lid would stay in place during the lyophilization process. At the time of surgery, the lysate from 5 million cells was reconstituted with 550 microliters of PBS. Approximately 250 microliters was applied to each of the wounds on pig one. The approximate cell lysate concentration added to the wounds on pig 1 was 2.5 million cells/wound. Upon treatment of pig 1, it was apparent that much of the volume of the reconstituted cell lysate did not remain in the wound bed. Therefore, less volume of cell lysate was used to treat pigs 2-4. The approximate cell concentration applied to wounds on pigs 2-4 was 0.5-1 million cells/wound.

Cell Lysate/VNW: Sterile VNW scaffolds (1.5×1.5 cm) were aseptically transferred to sterile multi-well plates. 400 microliters of cell lysate supernatant were placed next to the VNW; the dish was tilted to wick in the suspension since it appeared that the VNW would wick better from the sides than the top of the VNW. After approximately 10 minutes, VNW had absorbed the drop contents. The dish was covered with a sterile lid and taped to ensure the lid would stay in place during the lyophilization process. The dishes were then immediately placed on dry ice until lyophilization.

VNW: Sterile VNW scaffolds (1.5×1.5 cm) were aseptically transferred to sterile multi-well plates. The dish was covered with a sterile lid and taped to ensure the lid would stay in place during the lyophilization process. The dishes were then immediately placed on dry ice until lyophilization.

The treatments were lyophilized using a 48 hour lyophilization cycle. After the lyophilization was complete, the dishes were wrapped in parafilm and stored at −80° C. until the day of surgery. On the day of surgery, the treatments were removed from the freezer and placed into a foil covered ice bucket to prevent proteolytic activity.

Treatment Characterization

VNW.

VNW scaffold used in this study was 1.14 mm thick and had a density of 92.85 mg/cc. These values were obtained by the supplier. The calculated percent porosity was 93.8% for this sample. The residual EtO was run four times and averaged 142 ppm. The residual IPA was less than 1 ppm.

Cell Lysate.

Cells were subjected to preliminary pathogen testing prior to use. The pathogens tested for were HIV1, HIV2, HCV, HTLV, HBV and EBV. Detection of virus DNA and RNA was done via PCR. The cells tested negative for all viruses.

Surgical Approach

This study was conducted in accordance with the rules and regulations of the Institutional Animal Care and Use Committee of Ethicon R&D, Somerville, N.J.

Twelve (12) full-thickness excisions (1.5×1.5 cm) were created on the dorsal region of four female domestic swine (Animal Biotech Industries, Inc., Danboro, Pa.). The treatment groups were assigned to the sites and left in place throughout the study period. Each animal had an equal distribution of the treatment groups. The treatment squares (1.5×1.5 cm) were trimmed to fit the wound, if needed, and covered with 2×2 cm NU-GEL (Johnson & Johnson Medical, Arlington, Tex.). All wounds were then covered with BIOCLUSIVE (Johnson & Johnson Medical, Arlington, Tex.). Strips of self-adhering foam (RESTON; 3M Medical-Surgical Division, St. Paul, Minn.) were placed between sites to prevent cross-contamination due to wound fluid leakage. Sterile gauze (RAY-TEK; Johnson & Johnson Medical, Arlington, Tex.) was secured over the dorsum of the back with ZONAS (Johnson & Johnson Medical, Arlington, Tex.) porous tape. A body stockinette (SPANDAGE; Medi-Tech International Corporation, Brooklyn, N.Y.) was used to hold the dressings in place. Digital images of each wound were taken at days 0, 4 and 7 post-wounding. A bandage change was done on day 4 of the study. Tissues were harvested from the animals on day 7. The entire wound and surrounding normal skin was excised. The cranial half of the excised tissue was placed in 10% neutral buffered formalin for histological processing (paraffin sections) and stained with hematoxylin and eosin and trichrome (MPI Research, Mattawan, Mich.). The caudal portion of each sample was retained for possible future analysis. Tissue sections were histologically analyzed for the presence of the scaffold, overgrowth of scaffold by granulation tissue, quality of ingrowth, and inflammatory response. Measurements of granulation tissue area and epithelial tongue length were also made.

VNW scaffold was purchased from Biomedical Structures (Slaterville, R.I.). All VNW was obtained from lot 3551-73-2. The samples were foil-wrapped and sterilized via ethylene oxide sterilization and stored at room temperature prior to use. The cell lysate was obtained from cell lot CBAT 050604B.

Each pig was anesthetized with an intramuscular injection of Telazol (4 mg/kg), Xylazine (4 mg/kg), and Glycopyrrolate (0.011 mg/kg). The animal was maintained on Isoflurane via nosecone. Each pig was given a pre-operation dose of Buprenorphine (0.02 mg/kg, IM) at the time of surgical preparation.

The animals were prepared for surgery under general anesthesia. Hair was removed from the back, shoulder, side, and flank regions. An antiseptic skin cleanser was applied.

Full-thickness excisional wounds (1.5×1.5 cm) were created along the dorsal paravertebral and flank areas with a scalpel. Twelve wounds were made on each animal; six per side. Each wound was submitted to a treatment regime. The scaffolds were placed into the wound bed 'dry' and then a few drops of sterile saline were added to the scaffold. Excised tissue measurements were recorded.

The test materials were undisturbed for the length of the study. The wounds were covered with a 2×2 cm square of NU-GEL. The wounds were dressed with BIOCLUSIVE to keep the wounds moist and to keep the test articles and NU-GEL in place. Strips of polyurethane foam (RESTON) were placed between the wounds to avoid cross-contamination due to wound fluid leakage. The animals were dressed with 4×4 inch squares of RAY-TEK and SPANDAGE to help keep dressings in place and the animal's back clean.

The secondary and tertiary bandages were changed on day 4 of the study. Dressing condition was evaluated daily to determine if additional bandage changes were necessary due to strikethrough, displacement, etc.

Clinical observations were performed at the end of the study under anesthesia, just prior to euthanasia. Assessments included dressing conditions (air exposure, displacement) and wound bed conditions (inflammation, re-injury, infection and wound level). At the predetermined time point (7 days post-wounding), the animals were euthanized under anesthesia with an intravenous injection of pentobarbital sodium and phenytoin sodium euthanasia solution (Euthasol®, Diamond Animal Health, Inc. Des Moines, Iowa, at 1 ml/10 lbs body weight) via the marginal ear vein. Following administration of the drug, the animals were observed to ensure that respiratory function had ceased and there was no palpable cardiac function. A stethoscope facilitated this process. The femoral artery was severed to insure euthanasia.

Tissue Processing

Immediately following euthanasia, each wound along with the underlying fat and margin of surrounding skin was excised. The wound was bisected into cranial and caudal halves. The cranial half of the wound was fixed in 10% neutral buffered formalin, processed and embedded in paraffin. Samples were sectioned at 5 microns and stained for hematoxylin and eosin and Masson's trichrome.

Histological Assessments:

A computer-controlled motorized programmable slide scanning system was used in the process of image acquisition. Separate images of high magnification fields were acquired from a microscope. The images were tiled to preserve the integrity of the entire histological specimen. This allows accurate measurement of the entire tissue sample.

Images from the light microscope were captured into the computer memory via CCD camera and frame grabber board and subsequently analyzed using Image Pro 4.0 Image Analysis software. Capturing the image of the slide and applying the calibration feature of the imaging software at 2× magnification performed spatial calibration.

Histological evaluations for granulation tissue (area and length) and epithelialization were assessed using trichrome stained specimens using a magnification of 20-40×. Average granulation tissue height was determined by dividing the area by the length.

Tissue sections were histologically analyzed for the presence of the scaffold, overgrowth of scaffold by granulation tissue, quality of in-growth, and inflammatory response.

Statistical Analysis:

Treatments were assigned using a Latin Square design. This was to ensure that each treatment would be assigned equally at each wound site and avoid any bias to wound position on the animal. Visual assessments were analyzed using JMP 4.0.4 software (SAS Institute Incorporated, Cary, N.C.). Shapiro-Wilk-W Test was performed prior to data analysis to determine normality. Nominal and Ordinal data was analyzed using Chi-Square. Continuous data was analyzed using One-way ANOVA. Tukey-Kramer or Student-Newman-Keuls (SNK) test for multiple comparisons was performed to determine differences between groups following One-way ANOVA. A value of $p<0.05$ was used as the level of significance. Two-way ANOVA was used to determine if there were differences due to animal effects. Contrast tests with Bonferroni adjustment was used when determining significance with a two-way ANOVA.

Results

Surgery and anesthetic recovery were uneventful. All animals tolerated bandaging well. None of the surgically created wounds were healed by the day 7.

At the time of surgery, each wound was measured with a caliper to determine thickness. There were no differences between the groups for excised tissue thickness. The average excised tissue thickness ranged from 1.84 mm to 1.97 mm.

Histological Assessments

Granulation Tissue Area.

Cell Lysate/VNW demonstrated a statistically significant greater amount of granulation tissue area than all other treatments ($p<0.05$, ANOVA followed by Tukey-Kramer). Two-way ANOVA determined that animal 1 was statistically different than animals 2 and 3 ($p<0.008$, Two-way ANOVA with Bonferroni Adjustment). There were no animal/treatment interactions determined among the groups with the Two-way ANOVA. The Cell Lysate/VNW group averaged 36.72 mm² of granulation tissue area. The other groups averaged from 15.27 mm² to 22.56 mm² of granulation tissue area.

Granulation Tissue Length.

Cell Lysate/VNW and VNW demonstrated statistically significant longer granulation tissue length than Cell Lysate and Untreated ($p<0.05$, ANOVA followed with Tukey-Kramer). Two-way ANOVA did not determine any differences between the animals.

Granulation Tissue Height.

Two measurements of granulation tissue height were obtained, average height and greatest height. Average height is calculated by dividing the granulation tissue area by the granulation tissue length. These parameters consider the entire depth of the wound, not just what is visible above the native epidermis. Cell Lysate/VNW demonstrated statistically significant greater average granulation tissue height than VNW and Untreated ($p<0.05$, ANOVA followed by Tukey-Kramer). Two-way ANOVA determined that animal 2 was statistically different than animals 1 and 4 ($p<0.008$, Two-way ANOVA with Bonferroni Adjustment). Taking into account the animal difference, Cell Lysate/VNW demonstrated statistically significant greater average granulation tissue height than all other treatments ($p<0.003$, Two-way ANOVA with Bonferroni Adjustment). The Cell Lysate/VNW group averaged 2.45 mm for average granulation tissue height; all other treatments averaged 1.28 mm to 1.69 mm.

Cell Lysate/VNW demonstrated statistically significant greater granulation tissue height than Untreated ($p<0.05$, ANOVA followed by Tukey-Kramer). Two-way ANOVA determined that animal 1 was statistically different than animal 3 and animal 2 was statistically different than animals 1 and 4 ($p<0.008$, Two-way ANOVA with Bonferroni Adjustment). With the animal differences, Cell Lysate/VNW demonstrated statistically significant greater granulation tissue height than VNW and Untreated ($p<0.003$, Two-way ANOVA with Bonferroni Adjustment). The Cell Lysate/VNW group averaged 2.76 mm for greatest granulation tissue height; all other treatments averaged 1.65 mm to 2.10 mm.

Epithelial Tongue Length.

Untreated demonstrated statistically significant longer epithelial tongue length than Cell Lysate/VNW ($p<0.05$, ANOVA followed by Tukey-Kramer). Two-way ANOVA determined that animal 1 was statistically different than animals 3 and 4 and that animal 2 was statistically different than animal 3 ($p<0.008$, Two-way ANOVA with Bonferroni Adjustment). Taking into account the animal differences, Untreated demonstrated statistically significant longer epithelial tongue length than Cell Lysate/VNW ($p<0.003$, Two-way ANOVA with Bonferroni Adjustment). Additionally, Cell Lysate demonstrated statically significant longer epithelial tongue length than Cell Lysate/VNW ($p<0.003$, Two-way ANOVA with Bonferroni Adjustment).

Area of Implant.

Cell Lysate and Untreated wounds were not evaluated in this parameter. Cell Lysate/VNW demonstrated statistically significant greater implant area than VNW ($p<0.05$, ANOVA followed by Tukey-Kramer). Two-way ANOVA did not determine any differences between the animals. Cell Lysate/VNW averaged 23.0 mm² for area of implant; the other treatments averaged 15.96 mm² to 17.25 mm².

Percent Length of Wound with Exposed Scaffold.

This parameter takes into account the length of scaffold that was above the granulation tissue and epithelial tongues. This scaffold is considered exposed and will most likely be extruded from the wound. Cell Lysate/VNW demonstrated statistically significant greater amount of exposed scaffold at the surface of the wound bed than VNW ($p<0.05$, ANOVA followed by Tukey-Kramer). Two-way ANOVA did not determine any differences between the animals. Cell Lysate and Untreated wounds were not evaluated for this parameter.

Histopathological Assessments

Scaffold/Tissue Interaction at the End of the Scaffold.

At each end of the scaffold, the interaction between the scaffold and the tissue was graded as follows: 1: VNW fibers were totally embedded with neo-dermis with sufficient re-epithelialization to cover the end of the scaffold; 2: Re-epithelialization had occurred over the surface of the tissue at the wound edge, but VNW fibers were embedded into the epithelial tongue; 3: Re-epithelialization was not occurring in an orderly manner at the wound edge because the epidermal cells were either within the VNW fibers or were undermining the scaffold's edge. Cell Lysate and Untreated wounds were not evaluated for this parameter. Due to the compact scale of this parameter, the data cannot be analyzed as continuous data and therefore Two-way ANOVA cannot be performed. The average scores for this parameter ranged from 1.56 to 2.50.

Conformation of Granulation Overgrowth of the Main Portion of Scaffold.

This parameter was scored as follows: 1: The overgrowth was approximately 0.5 to 1 mm thick with relative uniformity and complete coverage; 2: Either there was variable depth of the overgrowth or relatively uniform depth of less than 0.5 mm, but complete coverage nonetheless; 3: Any conformation of the overgrowth, but with one or more areas of lack of overgrowth totaling less than 10% of the surface area; 4: As grade 3 but with lack of overgrowth totaling approximately 10-50% of surface area; 5: As grade 4 but with lack of overgrowth totaling approximately 50-100% of the surface area; 6: There was complete lack of overgrowth of the scaffold by granulation tissue and there was exudate within the outer portion of the scaffold.

Cell Lysate and Untreated wounds were not evaluated for this parameter. VNW demonstrated statistically significant better grades than Cell Lysate/VNW for conformation of granulation over-growth ($p<0.05$, ANOVA followed by Tukey-Kramer). Two-way ANOVA demonstrated that animal 1 was statistically different from all other animals ($p<0.008$, Two-way ANOVA with Bonferroni Adjustment). Although there were differences in the animal response no additional animal/treatment interactions were determined.

Inflammation within Overgrowth Tissue (or in Granulation Tissue Bed for Sites without Scaffolds).

This parameter was a subjective ranking of slides. The scores are: 1: The least amount in this group of slides; 2: In the mid-range for this group of slides; 3: The highest amount for this group of slides. Half grades were assigned to sites that fell in between two grades. Untreated demonstrated statistically significant less inflammation within the granulation tissue than Cell Lysate/VNW ($p<0.05$, ANOVA followed by Tukey-Kramer). Two-way ANOVA did not determine any differences between the animals.

Overall Inflammation Associated with the Scaffold Fibers.

This parameter was a subjective ranking of slides. The scores are: 1: The least amount in this group of slides; 2: In the mid-range for this group of slides; 3: The highest amount for this group of slides. Half grades were assigned to sites that fell in between two grades. Cell Lysate and Untreated wounds were not evaluated for this parameter. VNW demonstrated statistically significant lower ranks for inflammation associated with scaffold fibers than Cell Lysate/VNW ($p<0.05$, ANOVA followed by Tukey-Kramer). Two-way ANOVA demonstrated that animal 1 was statistically different from all other animals and animal 3 differed from animals 2 and 4 ($p<0.008$, Two-way ANOVA with Bonferroni Adjustment). Considering the difference in animal response, VNW demonstrated statistically significant lower mounts of inflammation associated with the scaffold fibers than Cell Lysate/VNW ($p<0.003$, Two-way ANOVA with Bonferroni Adjustment).

Qualitative Histologic Assessments (Overall Assessment).

Histopathological evaluation was determined by evaluating the following parameters: sloughing of the scaffold, overgrowth of scaffold by granulation tissue, inflammation within the overgrowth tissue, presence of exudate and inflammation within the scaffold. An overall result/grade was then given to each site based on the parameters listed above.

There were eight grades used in this evaluation:

Excellent (significant re-epithelialization; significant and complete granulation tissue overgrowth of the scaffold; low level of inflammation within the over-growth; an expected amount of inflammation within the scaffold (for the scaffold type); no scaffold sloughing);

Very Good (as for 'excellent' but with less re-epithelialization);

Good (re-epithelialization has started at ends of wound bed but may not be very good coverage; significant granulation overgrowth of scaffold but the thickness and quality are less than in higher grades; very slightly greater inflammation within the overgrowth than of higher grades; an expected amount of inflammation within the scaffold; very little (if any) sloughing);

Relatively Good (similar to the features noted for 'good' but with a flaw such as a minor zone of complete overgrowth/minor surface contact of the scaffold, minor increase of inflammation and slightly more sloughing than 'good');

Average (no significant re-epithelialization; irregular amounts or depth of overgrowth or relative lack of overgrowth; very slightly greater inflammation within the overgrowth than of higher grades; minor increase in the amount of inflammation within the scaffold; ends of scaffold my be exposed);

Relatively Poor (as for 'average' but with general lack of any good quality overgrowth);

Poor (no significant re-epithelialization; no significant overgrowth; slight to moderate inflammation due to surface exposure of scaffold; greater than expected inflammation and significant slough, although some scaffold remains); and Very Poor (possibly some to good re-epithelialization due to slough of scaffold early on; total slough of scaffold).

Table 21-1 lists the summary of the overall histologic quality scores.

TABLE 21-1

Numbers indicate the number of wounds fitting that criterion

| Test Material | Excellent | Very Good | Good | Relatively Good | Average | Relatively Poor | Poor | Very Poor |
|---|---|---|---|---|---|---|---|---|
| Cell Lysate | 0 | 0 | 0 | 5 | 3 | 0 | 0 | 0 |
| Cell Lysate/VNW | 0 | 0 | 0 | 0 | 0 | 2 | 6 | 0 |
| VNW | 0 | 1 | 1 | 0 | 3 | 3 | 0 | 0 |
| Untreated | 0 | 0 | 5 | 0 | 2 | 1 | 0 | 0 |

Summary.

Two well-documented models for wound healing are the swine full thickness excisional wound model and the rat subcutaneous implant model. The swine model has utility because of similarity of the cutaneous architecture to that of human skin. The rat model is most often used to assess biocompatibility and tissue ingrowth. Therefore, these models are the preferred method used to screen prototype devices for the skin tissue engineering program. Based on the tissue reaction, tissue infiltration, extracellular matrix deposition, and inflammatory response in these models, the efficacy of a device for wound healing is inferred.

The purpose of this study was to determine the cellular infiltration and inflammatory response of VNW scaffolds lyophilized with active agents. Human umbilicus cell-derived (UDC) cell lysate was the active agents tested in the porcine full-thickness excisional model.

An important consideration when examining the inflammatory response to these lysates is that this study is an example of xenogeneic transplantation with human cells being transplanted into a swine model. It is expected that a degree of inflammation would be present as the host animal "reacts" to the introduction of human cells. Interestingly, the UDC lysate groups performed similar to that of the control scaffolds with regard to inflammatory response in previous studies in rodent models (Examples 18 and 19). In both of the rodent studies, no increase in inflammatory response was noted.

As demonstrated in the data obtained from quantitative histomorphometry, there was a statistically significant increase in granulation tissue area, average granulation tissue height and greatest granulation tissue height when compared to all other treatment groups. However, the overall grade of the quality of the granulation tissue was poor. This assessment was based on the increased inflammatory cell presence in the large volume of tissue which had filled the scaffolds. Several important factors need to be considered when interpreting this data. It has been demonstrated in previous rat sub-cutaneous implant studies (Example 18 and 19) that cell lysate showed increased cell infiltration and greater extracellular matrix deposition at 14 days post-implantation. The swine model was evaluated at 7 days post wounding. It is postulated that in the swine model, by 14 days, the observed increase in inflammatory cell presence may resolve. This may be reasonable to infer since it is known that in acute wound healing, the normal inflammatory process usually resolves within 10 days post wounding. In fact, the presence of inflammatory cells at day 7 may provide enhanced healing response in a chronic wound based on its ability to provide an acute inflammatory stimulus in addition to the added benefit of the growth factors and MMP inhibitors present in the lysate mixture. This strategy of adding an acute inflammatory stimulus has been used with success in recent years, in several clinical studies (Zuloff-Shani et al., *Transfus Apheresis Sci.* 2004; 30(2): 163-7; Danon et al., *Exp. Gerontol.* 1997; 32(6):633-41; Danon et al., *J Wound Care* 1998; 7(6):281-3; Frenkel et al., *Clin Exp Immunol.* 2002; 128(1):59-66) which have demonstrated the utility of adding exogenous macrophage suspensions to help stimulate nonhealing wounds.

The cell concentration used in the cell lysate/VNW treatment group was equal to 4 million cells per scaffold. This concentration was equal to the dose/area[3] that was seen have to beneficial effects in the rat subcutaneous model. A cell lysate alone group was included in this study to determine the interaction of the scaffold with the "active agents." At the time of surgery, the cell lysates were reconstituted for application to the wound bed. The intent of this study was to examine the same concentration of cell lysate which was incorporated into the lysate/VNW group to the cell lysate alone group. At the time of surgery, however, it was determined that the volume of cell lysate to be administered to the wound bed was too great to maintain the treatment in place (the volume of a 1.5×1.5 cm full thickness excisional wound was determined to be approximately 100 microliters due to the depth of the wound and the contour of the pig). Therefore, the first pig was treated with approximately 2.5 million cells in 250 microliters. This was reduced further for pigs 2-4 when it was determined that this volume was also in excess of what was thought to reproducibly remain in the wound bed. The number of cells used in pigs 2-4 was approximately 0.5-1 million cells. When pig number 1 (cell concentration of 2.5 million cells) is excluded from the data, the ranking for scaffold performance demonstrates that the cell lysate alone group performed the best out of all groups (5 rel good, 1 ave) followed closely by untreated control wounds (3 good, 2 ave, 1 rel poor compared to VNW scaffold alone pigs 2-4 (3 rel poor, 3 ave). This data would seem to indicate that, in the swine full thickness wound model, a lower cell lysate concentration may have a beneficial effect if the dose was optimized for the pigs. Another important aspect to consider with regard to the cell lysate alone group is the positive effect that was noted for epithelial tongue length. In addition, the cell lysate group was also similar to untreated controls with regard to inflammation, apoptosis, and overall grade. This group demonstrated numerically superior epithelial outgrowth and showed similar tongue length to the untreated control. It may be assumed that the increased cell infiltration seen in this group, coupled with the positive epithelial tongue data, may have utility in chronic wound healing.

The data generated from the two subcutaneous rat studies and this swine full thickness excisional wound model indicate that treatment of wounds/scaffolds with cell lysate has a stimulatory effect on tissue ingrowth.

Example 22

Evaluation Human UDC Lysate (CL) Loaded onto Collagen/ORC Scaffolds in a Swine Full-Thickness Excisional Skin Model Previous data generated in a swine model testing UDC lysate at day 7 post wounding (Example 21) demonstrated a significant increase in granulation tissue formation with a slight increase in inflammatory response. It is believed that this phenomenon was due to the time point for evaluation (7 days post wounding); it is believed that by 14 days, the observed increase in inflammatory cell presence would resolve. This is reasonable to infer since it is known that in acute wound healing, the normal inflammatory process usually resolves within 10 days post wounding.

The purpose of this study was to determine the cellular infiltration and inflammatory response of human UDC lysate lyophilized onto and released from a collagen/ORC scaffold in a swine full-thickness excisional wound defect. The addition of a scaffold or the scaffold with CL was not statistically more inflammatory than an untreated wound at 14 days. As expected, there was a small mononuclear inflammatory cell response to any foreign body (scaffold) that is implanted into the body. However, the addition of CL to the scaffold did not statistically increase this response.

Interestingly, the UDC lysate groups performed similar to that of the control scaffolds with regard to inflammatory response in two rat subcutaneous wound studies (Examples 18 and 19) and in this swine full thickness excision model.

This study suggests that the addition of UDC lysate to a scaffold does not increase the inflammatory response in an acute wound model.

Methods & Materials

Twelve (12) full-thickness excisions (1.5×1.5 cm) were created on the dorsal region of eight swine. The treatment groups were assigned to the sites and left in place throughout the study period. Each animal had an equal distribution of the treatment groups. The treatment squares (1.5×1.5 cm) were covered with approximately 2×2 cm NU-GEL Wound Dressing (Johnson & Johnson MEDICAL Limited, Gargrave, United Kingdom). All wounds were then covered with BIOCLUSIVE* Transparent Dressing (Johnson & Johnson MEDICAL Limited, Gargrave, United Kingdom). Strips of self-adhering foam (RESTON; 3M Medical-Surgical Division, St. Paul, Minn.) were placed between sites to prevent cross-contamination due to wound fluid leakage. Lap sponges (Hermitage Hospital Products, Inc., Niantic, Conn.) were secured over the dorsum of the back with WATERPROOF* (Johnson & Johnson MEDICAL, Arlington, Tex.) tape. A body stockinette (SPANDAGE; Medi-Tech International Corporation, Brooklyn, N.Y.) was used to hold the dressings in place.

Animals were bandage changed on days 2, 5, 7, 9, and 14. Digital images of each wound were taken during the bandage change.

Tissues were harvested from the animals on day 14. The entire wound and surrounding normal skin was excised. The cranial half of the excised tissue was placed in 10% neutral buffered formalin for histological processing (paraffin sections) and stained with hematoxylin and eosin and trichrome. The caudal portion of each sample was retained for future analysis.

Tissue sections were histologically analyzed for the presence of the scaffold, overgrowth of scaffold by granulation tissue, quality of ingrowth, and inflammatory response. Measurements of granulation tissue area and epithelial tongue length were also made.

| Treatment Groups | | |
|---|---|---|
| | Complete Description | As Referred to in Report |
| A. | Untreated | Untreated |
| B. | Collagen/ORC | Collagen/ORC |
| C. | Collagen/ORC + 35 ug CL Protein | Collagen/ORC + Low CL |
| D. | Collagen/ORC + 70 ug CL Protein | Collagen/ORC + Mid CL |
| E. | Collagen/ORC + 140 ug CL Protein | Collagen/ORC + High CL |

N = 8 per treatment/time point

All Collagen/ORC was obtained from lot 1271278; Expiration Date: February 2007. The cell lysate was obtained from cell lot 050604B.

UDC Isolation and Culture

Tissue Procurement.

Umbilical cords were obtained for research purposes with patient consent. Cell isolation and culture were performed as per patent application # WO2005/003334 A2.

Lysate Production and Scaffold Preparation.

Human UDCs were thawed from cryopreserved stocks and seeded into gelatin-coated flasks at 5,000 cell/cm$^2$. Expanded cells, at 25,000 cell/cm$^2$ (passage 10), were harvested with trypsin and counted. Cells were distributed into siliconized micro-centrifuge tubes at 1.0E+07, pelleted by centrifugation and frozen at −80° C. Tubes containing the frozen cell pellets were placed in a 37° C. water bath, thawed and then promptly placed in a liquid nitrogen bath. This procedure was repeated twice. Upon the last thaw, the cell pellets were centrifuged at 13,000 g, 4° C. for 10 minutes. The total protein content of the collected supernatant fluid was assessed by Bradford assay and the dose volume of supernatant fluid (30 micrograms total protein per material or 150 micrograms total protein per material) was calculated. The dose volume of supernatant fluid was applied to the material as five one-fifth total dose volume aliquots. An aliquot was placed at each corner of the 1.5×1.5 cm material approximately 1 mm from the material edge and one aliquot was placed in the center of the material. This ensured even distribution of lysate within the wound bed.

Lyophilization.

Test materials with applied lysate were loaded into a FTS Systems Dura-Stop MP Stoppering Tray Dryer and lyophilized using the ramping program of Example 17. All steps had a ramping rate of 2.5° C./minute and a 100-mT vacuum.

Animal Study

Anesthesia, Analgesia and Surgical Preparation.

Analgesia was achieved using a Fentanyl patch (25 micrograms/hour). The day before surgery, a small area was shaved at the base of the neck and the patch was applied. On the day of surgery, each pig was anesthetized with an intramuscular injection of Telazol (4 mg/kg), Xylazine (4 mg/kg) and Glycopyrrolate (0.011 mg/kg). The animal was maintained on Isoflurane via endotracheal tube.

The animals were prepared for surgery under general anesthesia. Skin depilation from the back, shoulder, side and flank regions was accomplished with an electric animal clipper equipped with a surgical shaving blade (#40). The area was vacuumed to remove hair clippings and stratum corneum debris, shaved with a razor and shaving cream and rinsed with tap water, finally the animal was prepared for surgery with an application of an antiseptic skin cleanser.

Surgical Approach

Full-thickness excisional wounds (1.5×1.5 cm) were created along the dorsal paravertebral and flank areas with a scalpel. Twelve wounds were made on each animal; six per side. Each wound was submitted to a treatment regimen. The scaffolds were placed into the wound bed 'dry' and then a few drops of sterile saline were added to the scaffold. Excised tissue measurements were recorded.

Bandaging Technique.

The test materials were undisturbed for the length of the study. The wounds were covered with a 2×2 cm$^2$ of NU-GEL. The wounds were dressed with BIOCLUSIVE to keep the wounds moist and to keep the test articles and NU-GEL in place. Strips of polyurethane foam (Reston™) were placed between the wounds to avoid cross-contamination due to wound fluid leakage. The animals were dressed with lap sponges and Spandage™ to help keep dressings in place and the animal's back clean.

The secondary and tertiary bandages were changed on days 2 or 3, 5, 7, and 9 of the study. Dressing condition was evaluated daily to determine if additional bandage changes were necessary due to strikethrough, displacement, etc.

Post-Operative Care and Clinical Observations.

After recovering from surgery and general anesthesia, each pig was observed for behavioral signs of discomfort or pain. No signs of discomfort or pain were observed. Animals were returned to their cage when fully conscious and ambulatory.

The health status of each pig was determined by general appearance and attitude, food consumption, fecal and urinary excretion and the presence of abnormal discharges. Each pig was observed twice daily during the first 36 hours following surgery. Following recovery from surgery, the observations were reduced to once daily until the end of the study.

Evaluations.

Clinical observations were performed at the end of the study under anesthesia, just prior to euthanasia. Assessments included dressing conditions (air exposure, displacement) and wound bed conditions (inflammation, re-injury, infection and wound level).

Euthanasia.

At the predetermined time point (14 days post-wounding), the animals were euthanized under anesthesia with an intravenous injection of pentobarbital sodium and phenytoin sodium euthanasia solution (EUTHASOL at 1 ml/10 lbs body weight) via the marginal ear vein. Following administration of the drug, the animals were observed to ensure that respiratory function had ceased and there was no palpable cardiac function. A stethoscope facilitated this process. The femoral artery was severed to assure euthanasia.

Tissue Processing.

Immediately following euthanasia, each wound along with the underlying fat and margin of surrounding skin was excised. The wound was bisected into cranial and caudal halves. The cranial half of the wound was fixed in 10% neutral buffered formalin, processed and embedded in paraffin. Samples were sectioned at 5 microns and stained for hematoxylin and eosin and Masson's trichrome by MPI Research.

Histological Assessments.

A computer-controlled motorized programmable slide scanning system was used in the process of image acquisition. Separate images of high magnification fields were acquired from a microscope. The images were tiled to preserve the integrity of the entire histological specimen. This allows accurate measurement of the entire tissue sample.

Images from the light microscope were captured into the computer memory via CCD camera and frame grabber board and subsequently analyzed using Image Pro 4.0 Image Analysis software. The captured image of the slide was calibrated and measurements were recorded.

Quantitative histological measurements for granulation tissue (area and length) and epithelialization were assessed using trichrome stained specimens using a magnification of 20-40×. Average granulation tissue height was determined by dividing the area by the length.

Qualitative histopathology assessments were performed. Tissue sections were analyzed for the presence of the scaffold quality of in-growth and inflammatory response.

Photographic Documentation.

Digital images were taken of individual wounds on days 2, 5, 7, 9 and 14.

Statistical Analysis.

Treatments were assigned using a Latin Square design. This was to ensure that each treatment would be assigned equally at each wound site and avoid any bias to wound position on the animal. Visual assessments were analyzed using JMP 4.0.4 software. Shapiro-Wilk-W Test was performed prior to data analysis to determine normality. Nominal and Ordinal data was analyzed using Chi-Square. Continuous data was analyzed using One-way ANOVA. Tukey-Kramer or Student-Newman-Keuls (SNK) test for multiple comparisons was performed to determine differences between groups following One-way ANOVA. A value of $p<0.05$ was used as the level of significance.

Results

Surgery and anesthetic recovery were uneventful. All animals tolerated bandaging well.

Excised Tissue Thickness.

At the time of surgery, each wound is measured with a caliper to determine thickness. There were no differences between the groups for excised tissue thickness. The average excised tissue thickness ranged from 1.94 mm to 2.05 mm.

Clinical Observations.

Each animal was assessed for air exposure to the wound, displacement of the secondary dressings, channeling of wound fluid, communication of wound fluid between wounds, the amount of exudate present, inflammation associated with the wound, re-injury, the presence of clots or folliculitis, infection, erythema, wound bed color and wound bed level on the days of bandage change and necropsy. The animals were assessed on days 2, 5, 7, 9, and 14. Tables 22-2 and 22-3 summarize the findings.

Histological Assessments.

There were no statistically significant differences among the treatment groups for granulation tissue area, granulation tissue length, average granulation tissue height, amount of re-epithelialization or percent re-epithelialization. Table 22-1 summarizes the averages for each parameter.

Average granulation tissue height was calculated by dividing the area by the length. The percent re-epithelialization was calculated based on the surface of the wound that was and was not covered by the epithelial tongues.

TABLE 22-1

Average (and SEM) for each histological assessment - Day 14

| | Untreated | Collagen/ORC | Collagen/ORC + Low CL | Collagen/ORC + Mid CL | Collagen/ORC + High CL |
|---|---|---|---|---|---|
| Granulation Tissue Area ($mm^2$) | 26.12 (1.16) | 28.52 (2.37) | 26.81 (2.71) | 30.15 (3.51) | 29.24 (3.13) |
| Granulation Tissue Length (mm) | 9.86 (0.45) | 10.23 (0.46) | 10.71 (0.45) | 10.36 (0.68) | 9.67 (0.41) |
| Average Granulation Tissue Height (mm) | 2.68 (0.14) | 2.79 (0.18) | 2.52 (0.24) | 2.86 (0.19) | 3.02 (0.27) |

TABLE 22-1-continued

Average (and SEM) for each histological assessment - Day 14

|  | Untreated | Collagen/ORC | Collagen/ORC + Low CL | Collagen/ORC + Mid CL | Collagen/ORC + High CL |
|---|---|---|---|---|---|
| Length of re-epithelialization (mm) | 11.27 (0.70) | 11.81 (0.59) | 11.60 (0.69) | 12.25 (0.81) | 11.67 (0.57) |
| Percent re-epithelialization | 98.79 (1.21) | 97.63 (2.37) | 89.62 (5.26) | 100 (0) | 99.14 (0.86) |

Wound Closure.

There were no statistical differences demonstrated between the treatment groups for rate of wound closure. Day 9 measurements were not included because the majority of wounds were not measurable due to a film of secondary dressing that covered the wound. The secondary dressing was not removed for fear of disturbing the wound bed.

Qualitative Histopathology Assessments

Rank Scoring for Inflammation in the Wound.

There were no statistical differences the amount of inflammation that was present in the wound at day 14.

Rank Scoring for Extracellular Matrix (ECM) in the Wound.

There were no statistical differences the amount of ECM that was present in the wound at day 14.

Rank Scoring for Mononuclear Inflammatory Cell Foci in the Wound.

The Untreated group demonstrated statistically significant less mononuclear inflammatory cell foci than the Collagen/ORC+Low CL and Collagen/ORC+Mid CL the Collagen/ORC ($p<0.05$, Tukey-Kramer).

TABLE 22-2

Clinical Observations by Treatment

| Treatment | Sites with Air Exposure | | | | | Wound Bed Moisture (M = moist; D = Dry) | | | | |
|---|---|---|---|---|---|---|---|---|---|---|
|  | Day 2 | Day 5 | Day 7 | Day 9 | Day 14 | Day 2 | Day 5 | Day 7 | Day 9* | Day 14 |
| Untreated | 1/8 | 1/8 | 0 | 0 | 0 | 5/8 M; 3/8 M/D | 5/8 M/D; 3/8 D/M | 1/8 M/D; 7/8 D/M | 1/6 M/D; 5/6 D/M | 8/8 D/M |
| Collagen/ORC | 1/8 | 2/8 | 0 | 0 | 0 | 3/8 M; 5/8 M/D | 2/8 M; 5/8 M/D; 1/8 D/M | 5/8 M/D; 3/8 D/M | 6/6 D/M | 8/8 D/M |
| Collagen/ORC + Low CL | 0 | 2/8 | 0 | 0 | 0 | 6/8 M; 2/8 M/D | 2/8 M; 5/8 M/D; 1/8 D/M | 3/8 M/D; 5/8 D/M | 2/6 M/D; 4/6 D/M | 8/8 D/M |
| Collagen/ORC + Mid CL | 0 | 1/8 | 0 | 0 | 0 | 6/8 M; 2/8 M/D | 1/8 M; 6/8 M/D; 1/8 D/M | 3/8 M/D; 5/8 D/M | 3/6 M/D; 3/6 D/M | 8/8 D/M |
| Collagen/ORC + High CL | 0 | 2/8 | 0 | 0 | 1/8 | 6/8 M; 2/8 M/D | 7/8 M/D; 1/8 D/M | 4/8 M/D; 4/8 D/M | 2/6 M/D; 4/6 D/M | 8/8 D/M |

TABLE 22-3

Clinical Observations by Treatment

| Treatment | Sites Demonstrating Inflammation (grade) | | | | | Sites where Clots Visible (CD = can't determine) | | | | |
|---|---|---|---|---|---|---|---|---|---|---|
|  | Day 2 | Day 5 | Day 7 | Day 9 | Day 14 | Day 2 | Day 5 | Day 7 | Day 9* | Day 14 |
| Untreated | 0 | 1/8 | 2/8 | 0 | 0 | 8/8 | 8/8 | 5/8 | 2/8 (1/8 CD) | 1/8 |
| Collagen/ORC | 0 | 0 | 1/8 | 0 | 0 | 7/8 | 5/8 (2/8 CD) | 7/8 | 3/8 (2/8 CD) | 1/8 |
| Collagen/ORC + Low CL | 0 | 0 | 0 | 0 | 0 | 8/8 | 7/8 (1/8 CD) | 6/8 | 4/8 | 2/8 |

TABLE 22-3-continued

Clinical Observations by Treatment

| Treatment | Sites Demonstrating Inflammation (grade) | | | | | Sites where Clots Visible (CD = can't determine) | | | | |
|---|---|---|---|---|---|---|---|---|---|---|
| | Day 2 | Day 5 | Day 7 | Day 9 | Day 14 | Day 2 | Day 5 | Day 7 | Day 9* | Day 14 |
| Collagen/ORC + Mid CL | 0 | 0 | 0 | 0 | 0 | 6/8 | 5/8 | 6/8 | 3/8 | 5/8 (1/8 CD) |
| Collagen/ORC + High CL | 0 | 0 | 0 | 0 | 1/8 | 7/8 | 5/8 | 6/8 | 3/8 (1/8 CD) | 2/8 |

TABLE 22-4

Clinical Observations by Treatment

| Treatment | Wound Bed Level (grade) | | | | | Sites Demonstrating Erythema | | | | |
|---|---|---|---|---|---|---|---|---|---|---|
| | Day 2 | Day 5 | Day 7 | Day 9 | Day 14 | Day 2 | Day 5 | Day 7 | Day 9* | Day 14 |
| Untreated | 8/8 depressed | 8/8 even | 5/8 even; 3/8 depressed and even | 8/8 even | 8/8 even | 0 | 0 | 0 | 0 | 0 |
| Collagen/ORC | 2/8 depressed and even; 6/8 depressed | 1/8 even and raised; 7/8 even | 6/8 even; 1/8 depressed and even; 1/8 depressed | 1/8 even and raised; 6/8 even; 1/8 depressed and even | 8/8 even | 0 | 1/8 | 0 | 0 | 0 |
| Collagen/ORC + Low CL | 1/8 even; 2/8 depressed and even; 5/8 depressed | 1/8 even and raised; 5/8 even; 2/8 depressed and even | 3/8 even; 2/8 depressed and even; 3/8 depressed | 8/8 even | 1/8 even and raised; 7/8 even | 0 | 0 | 0 | 0 | 0 |
| Collagen/ORC + Mid CL | 1/8 depressed and even; 7/8 depressed | 7/8 even; 1/8 depressed and even | 3/8 even; 3/8 depressed and even; 2/8 depressed | 1/8 even and raised; 5/8 even; 2/8 depressed and even | 8/8 even | 0 | 0 | 0 | 0 | 0 |
| Collagen/ORC + High CL | 1/8 even; 1/8 depressed and even; 6/8 depressed | 7/8 even; 1/8 depressed and even | 2/8 even; 3/8 depressed and even; 3/8 depressed | 6/8 even; 2/8 depressed and even | 2/8 even and raised; 5/8 even; 1/8 depressed and even | 0 | 0 | 0 | 0 | 0 |

Summary.

The swine full thickness excisional wound model has utility for wound healing because of the similarity of the cutaneous architecture to that of human skin. This model is the preferred method used to screen prototype devices to determine whether there are effects on inflammatory cell infiltration in this acute wound healing model. However, this type study does not assess efficacy on wound closure. To determine efficacy, an impaired or delayed healing model will be used.

The purpose of this study was to determine the inflammatory response to UDC lysate lyophilized on a collagen/ORC scaffold in the porcine full-thickness excisional model. This study demonstrates that the addition of UDC lysate to scaffolds does not increase the inflammatory response.

An important consideration when examining the inflammatory response to these lysates is that this study is an example of xenogeneic transplantation with human cells being transplanted into a swine model. It is expected that a degree of inflammation would be present as the host animal "reacts" to the introduction of human cells. Interestingly, the UDC lysate groups performed similar to that of the control scaffolds with regard to inflammatory response in two rat subcutaneous wound studies (Examples 18 and 19) and in this swine full thickness excisional model.

In this acute healing model, it was unlikely that an increase in the healing rates with the addition of an active agent would be observed because acute wounds heal rapidly without intervention. As expected, no differences were observed in the rate of wound closure.

The addition of a scaffold or the scaffold with CL was not statistically more inflammatory than an untreated wound. As expected there is a small mononuclear inflammatory cell response to any foreign body (scaffold) that is implanted into the body. However, the addition of CL to the scaffold did not statistically increase this response. In general, the amount of inflammation seen in this study is innocuous and is suggestive of the typical response noted when any foreign material is implanted.

Example 23

The Biological Effect of Umbilicus-Derived Cell (UDC) Lysate Combined with a Synthetic Biomaterial Scaffold on the Healing of Delayed Wounds in a Rat Ischemic Wound Model Ischemia results in impaired cutaneous wound healing by decreasing arterial perfusion at the wound site. The decrease in arterial perfusion deprives the wound site of oxygen and nutrients derived from arterial blood. An ischemic wound healing model has been developed in Sprague-Dawley rats. This model contains non-, mildly-, and highly ischemic regions in which full thickness incisional wounds are created.

The purpose of this study was to evaluate the biological effect of umbilicus-derived cell (UDC) lysate lyophilized onto and released from a synthetic biomaterial in a rat full thickness incisional ischemic wound healing model. In this study, UDCs were expanded in culture, harvested, lysed by repeated freeze-thaw cycles, applied to 90/10 PGA/PLA non-woven scaffolds at two protein concentrations (30 micrograms and 150 micrograms total protein per non-woven scaffold), and lyophilized. The lyophilized scaffolds were applied to rat full thickness excisional ischemic wounds.

Increased angiogenesis was observed in wounds treated with biomaterials containing UDC lysate compared to saline control with a greater than two-fold increase in the angiogenic response in the biomaterials treated with 150 micrograms UDC lysate/scaffold when compared to the saline control. Angiogenesis is the most critical factor to healing of an ischemic wound site and of chronic wounds in general. These results demonstrate the biological effect of UDC lysate lyophilized onto and released from a synthetic biomaterial in a rat full thickness excisional ischemic wound healing model.

Methods & Materials

Test materials used in this study are set forth in Table 23-1.

TABLE 23-1

Test Materials

| Material | Lot Number | Cell Line |
| --- | --- | --- |
| A 90/10 PGA/PLA non-woven, 150 micrograms total lysate protein | 5248-46-1 Albany International 10.50 mm thick, 65.2 mg/cc | CBAT Umb 050604B P10 |
| B 90/10 PGA/PLA non-woven, 30 micrograms total lysate protein | 5248-46-1 Albany International 10.50 mm thick, 65.2 mg/cc | CBAT Umb 050604B P10 |
| C 90/10 PGA/PLA non-woven | 5248-46-1 Albany International 10.50 mm thick, 65.2 mg/cc | — |
| D Saline control | — | — |

All material measures 6 mm in diameter and 0.5 mm in thickness.

UDC Cell Isolation and Culture

Tissue Procurement.

Umbilical cords were obtained from The National Disease Research Interchange (Philadelphia, Pa.) for research purposes with full patient consent. Cell isolation and culture were performed according to the methods of PCT Patent Publication WO2005/003334 A2.

Lysate Production.

Human UDC lysate supernatant was prepared as in Example 22. The cell lysate supernatant was applied to tested materials at 30 micrograms or 150 micrograms total protein per individual sample.

Lyophilization.

Test materials with applied lysate were loaded into a FTS Systems Dura-Stop MP Stoppering Tray Dryer and lyophilized using the ramping program set forth in Example 17.

Ischemic Rat Model

Animals.

Twenty (n=8/treatment group/location) female Sprague Dawley Rats ranging from 200 to 350 grams in weight were obtained from Harlan Sprague Dawley, Inc., (Indianapolis, Ind.) and Charles River Laboratories (Portage, Mich.). The animals were selected without any apparent systematic bias. The animals were identified by sequential numbering on the base of the tail with an indelible ink marker and/or a subcutaneously implanted identification microchip.

Study Design.

Twenty rats, 6 defects per animal; 5 treatments; n=8/R×/location (cranial and caudal flap). An eccentric H-flap is surgically created on the dorsum of the back. Six full-thickness excisional defects are created with a 6 mm biopsy punch; two defects are placed lateral to the vertical arms of the H-flap (non-ischemic area); two defects are placed at the edge of the cranial flap (severely ischemic area) and two defects are placed at the edge of the caudal flap (mildly ischemic area). The duration of the study was 10 days.

Each animal was weighed prior to being anesthetized and at necropsy. The rats were anesthetized with either isofluorane via face mask or an intraperitoneal injection of a mixture of ketamine hydrochloride [60 mg/kg] and xylazine [10 mg/kg].

After induction of anesthesia, the entire back of the animal from the dorsal cervical area to the dorsal lumbosacral area was clipped free of hair using electric animal clippers. The area was then scrubbed with chlorhexidine diacetate, rinsed with alcohol, dried, and painted with an aqueous iodophor solution of 1% available iodine. Ophthalmic ointment was applied to the eyes to prevent drying of the tissue during the anesthetic period. The anesthetized and surgically prepared animal was placed in the desired recumbent position.

An eccentric H-flap was created by making two skin incisions, parallel to the dorsal midline. The skin was separated from the body and a silicone sheet was place underneath the flap. Four stay-sutures were used to tack the corners of the silicone sheet in place. The skin was repositioned in the anatomical position. The horizontal incision was sutured at several points along that incision line. Skin staples were used to close the longitudinal skin incisions. Four full-thickness excisional wounds were created in two rows parallel to the midline via biopsy punch. Two additional defects were created lateral to the vertical arms of the flap. Four of the wounds were ischemic and two had normal blood flow. Test materials, in the form of 6 mm disks were immediately applied to each wound site, according to the designated treatment scheme. Each wound site was covered with NuGel or another similar dressing. Tincture of benzoin was painted around the periphery of the surgical site to secure the outer covering of Bioclusive.

Clinical Observations.

Each animal was observed daily after surgery as directed by the Study Director or attending veterinarian to determine its health status on the basis of general attitude and appearance, food consumption, fecal and urinary excretion and presence of abnormal discharges. All animals were observed BID (twice daily) for the first three days after surgery for the presence of pain and/or discomfort and given analgesics (as indicated by the study director and/or attending veterinarian) by appropriately trained LAR personnel. Analgesics were given for 3 days, starting prior to creation of the defect. Assessment for pain and distress were based on the following "Evaluation of Pain": attempting to protect, move away, or bite; crying out when palpated or forced to use affected areas; licking, biting, scratching, shaking, or rubbing; pacing, lying down and getting up, or shifting weight; significant decrease in mobility; unusual length of time for recumbency; reluctance to move or difficulty in rising; and head down, tucked abdomen, hunched, facial distortion, or pallor. BID observations and treatments continued until the animals were judged to be pain free. If analgesics were given, subsequent evaluations for pain and the need for re-medication were based on the duration of action of the analgesics used, e.g., animals were evaluated every 10 to 12 hours for drugs requiring twice daily administration. Any animal demonstrating signs of severe pain was euthanized immediately. No animals involved in this study showed signs of pain.

Necropsy and Histological Preparation.

Rats were euthanized at day 10 by $CO_2$ inhalation. Gross observations of the implanted sites were recorded. The subcutaneous implantation sites with their overlying skin were excised and preserved in 10% buffered formalin fixative. Following fixation, each implant was marked and trimmed. These specimens were processed for paraffin embedding, then sectioned and stained with H&E and Masson's Trichrome. Histologic evaluation included assessment of the tissue reaction to the scaffold and bioactive.

Results

Implantation Scheme.

The ischemic rat model implantation scheme included control sites L1 and R2 with normal perfusion, mildly ischemic sites L2 and R1, and highly ischemic sites L3 and R3.

Histology Data.

Angiogenesis, epithelialization, granulation tissue, inflammation, and collagen were scored as follows:

Angiogenesis
1. Little evidence of vascularization
2. Sparse capillary density
3. Considerable vessel density
4. Dense, dilated capillary formation Epithelialization
1. Epidermal ingrowth stalled at wound margin
2. Partial epidermal resurfacing with minimal differentiation, ample hyperplasia
3. Well-advanced wound coverage and differentiation
4. Complete epithelization and diminished hyperplasia Granulation Tissue
1. Poor cellular invasion with predominance of fibrin and inflammatory cells
2. High cellularity and fibroplasia with minimal organization
3. Moderate cellularity, good organization, and matrix accumulation
4. Progression into scar with markedly reduced cellularity Inflammation
1. Modest mononuclear cell infiltrate and little foreign body response
2. Mixed reaction with monocytes and neutrophils
3. Prominent neutrophil reactivity and/or giant cell reaction to implant material
4. Intense inflammation; predominantly neutrophils; abscess Collagen
1. Little or no evidence of connective tissue
2. Modest accumulation of collagen
3. Abundant collagen accumulation with modest organization
4. Collagen density and organization approach that of surrounding Histological Scoring

TABLE 23-2

Histological Scoring of 90/10 PGA non-woven, 150 micrograms total lysate protein treatments

| | Rat Position | Epithelialization | Granulation Tissue | Inflammation | Angiogenesis | Collagen |
|---|---|---|---|---|---|---|
| Wound region | | | | | | |
| Highly Ischemic | 6 sli-a | 4 | 3 | 2 | 2 | 2 |
| | 7 sri-a | 3 | 4 | 2 | 1 | 4 |
| | 11 sli-a | 3 | 2 | 3 | 2 | 2 |
| | 12 sri-a | 2 | 2 | 2 | 3 | 2 |
| | 16 sli-a | 1 | 2 | 3 | 4 | 2 |
| | 17 sli-a | 1 | 3 | 2 | 2 | 2 |
| Mean Treatment | — — | 2.33 | 2.67 | 2.33 | 2.33 | 2.33 |
| Mildly Ischemic | 4 ili-a | 1 | 3 | 2 | 2 | 3 |
| | 9 ili-a | 2 | 2 | 3 | 2 | 2 |
| | 14 ili-a | 4 | 3 | 2 | 3 | 4 |
| | 19 ili-a | 1 | 2 | 2 | 3 | 3 |
| | 18 iri-a | 3 | 3 | 2 | 2 | 3 |

TABLE 23-2-continued

Histological Scoring of 90/10 PGA non-woven,
150 micrograms total lysate protein treatments 90/10 PGA/PLA non-woven 150 micrograms total lysate protein

|  | Rat Position | Epithelialization | Granulation Tissue | Inflammation | Angiogenesis | Collagen |
|---|---|---|---|---|---|---|
| Mean |  — — | 2.20 | 2.60 | 2.20 | 2.40 | 3.00 |
| Non- | 13 rc-a | 2 | 3 | 2 | 4 | 3 |
| ischemic | 3 rc-a | 1 | 3 | 3 | 2 | 4 |
|  | 6 rc-a | 1 | 4 | 2 | 2 | 3 |
|  | 8 rc-a | 1 | 4 | 3 | 2 | 4 |
|  | 18 rc-a | 4 | 3 | 2 | 2 | 3 |
|  | 16 lc-a | 4 | 3 | 2 | 2 | 3 |
| Mean | — — | 2.20 | 3.40 | 2.40 | 2.00 | 3.40 |

Position key-

S = superior,

I (prefix) = inferior,

I (suffix) = ischemic,

C = control,

R = right,

L = left

TABLE 23-3

Histological scoring of 90/10 PGA non-woven,
30 micrograms total lysate protein treatments 90/10 PGA/PLA non-woven, 30 micrograms total lysate protein

|  | Rat Position | Epithelialization | Granulation Tissue | Inflammation | Angiogenesis | Collagen |
|---|---|---|---|---|---|---|
| Wound region |  |  |  |  |  |  |
| Highly | 1 sri-b | 1 | 1 | 4 | 1 | 1 |
| Ischemic | 6 sri-b | 1 | 4 | 2 | 2 | 3 |
|  | 15 sli-b | 3 | 2 | 3 | 3 | 2 |
|  | 20 ski-b | 2 | 3 | 2 | 2 | 3 |
|  | 11 sri-b | 4 | 2 | 3 | 3 | 2 |
|  | 16 sri-b | 2 | 3 | 3 | 2 | 3 |
| Mean Treatment | — — | 2.40 | 2.80 | 2.60 | 2.40 | 2.60 |
| Mildly | 3 ili-b | 1 | 2 | 3 | 1 | 2 |
| Ischemic | 13 ili-b |  |  |  | 1 |  |
|  | 98 ili-b | 1 | 2 | 3 | 2 | 2 |
|  | 18 ili-b | 3 | 3 | 2 | 2 | 2 |
|  | 2 iri-b | 2 | 2 | 2 | 3 | 2 |
|  | 7 iri-b | 3 | 4 | 1 | 2 | 4 |
|  | 12 iri-b | 1 | 3 | 3 | 2 | 3 |
|  | 17 iri-b | 2 | 3 | 2 | 3 | 3 |
| Mean | — — | 2.00 | 2.83 | 2.17 | 2.33 | 2.67 |
| Non- | 2 rc-b | 4 | 4 | 1 | 2 | 3 |
| ischemic | 5 lc-b | 1 | 3 | 1 | 1 | 3 |
|  | 12 rc-b | 1 |  |  |  |  |
|  | 7 rc-b | 1 | 1 | 3 | 2 | 2 |
|  | 17 rc-b | 3 | 3 | 2 | 2 | 3 |
|  | 20 lc-b |  |  |  |  | 4 |
| Mean |  — | 1.50 | 2.33 | 2.00 | 1.67 | 3.00 |

TABLE 23-4

Histological Scoring of 90/10 PGA non-woven

90/10 PGA/PLA non-woven

| | Rat | Position | Epithelialization | Granulation Tissue | Inflammation | Angiogenesis | Collagen |
|---|---|---|---|---|---|---|---|
| Wound region | | | | | | | |
| Highly Ischemic | 19 | sli-c | 1 | 2 | 4 | 2 | 2 |
| | 20 | sri-c | 3 | 2 | 4 | 1 | 1 |
| | 15 | sri-c | | 3 | 1 | 1 | 3 |
| | 14 | sli-c | 3 | 3 | 1 | 1 | 3 |
| | 9 | sli-c | 3 | 4 | 1 | 1 | 3 |
| | 4 | sli-c | 2 | 2 | 2 | 1 | 2 |
| Mean Treatment | — | — | 2.75 | 2.80 | 1.80 | 1.00 | 2.40 |
| Mildly Ischemic | 3 | iri-c | 2 | 3 | 3 | 3 | 3 |
| | 6 | iri-c | 2 | 2 | 2 | 2 | 2 |
| | 11 | iri-c | 1 | 3 | 3 | 3 | 2 |
| | 16 | iri-c | 4 | 3 | 2 | 4 | 2 |
| | 2 | ili-c | 2 | 1 | 2 | 1 | 1 |
| | 7 | ili-c | 1 | 1 | 1 | 1 | 3 |
| | 12 | ili-c | 1 | 3 | 2 | 2 | 3 |
| | 17 | ili-c | 3 | 3 | 2 | 3 | 2 |
| | 1 | iri-c | 3 | 3 | 3 | 1 | 2 |
| Mean | — | — | 2.33 | 2.33 | 2.00 | 2.00 | 2.17 |
| Non-ischemic | 1 | rc-c | 1 | 1 | 1 | 1 | 4 |
| | 6 | rc-c | 1 | 4 | 2 | 2 | 3 |
| | 9 | lc-c | 1 | 2 | 1 | 1 | 4 |
| | 11 | rc-c | 1 | 3 | 2 | 2 | 3 |
| | 14 | lc-c | 2 | 4 | 2 | 2 | 4 |
| | 16 | rc-c | 3 | 3 | 2 | 2 | 2 |
| | 19 | lc-c | 3 | 4 | 2 | 2 | 4 |
| Mean | — | — | 1.83 | 3.33 | 1.83 | 1.83 | 3.33 |

TABLE 23-5

Histological Scoring of Saline Treatment

Saline control

| | Rat | Position | Epithelialization | Granulation Tissue | Inflammation | Angiogenesis | Collagen |
|---|---|---|---|---|---|---|---|
| Wound region | | | | | | | |
| Highly Ischemic | 13 | sri-e | 4 | 3 | 1 | 1 | 3 |
| | 2 | sli-e | 2 | 1 | 4 | 1 | 1 |
| | 3 | sri-e | 1 | 2 | 1 | 1 | 2 |
| | 7 | sli-e | 3 | 2 | 1 | 2 | 2 |
| | 12 | sli-e | 4 | 3 | 2 | 1 | 1 |
| | 8 | sri-e | 4 | 4 | 1 | 1 | 4 |
| | 18 | sri-e | 1 | 4 | 1 | 2 | 3 |
| Mean Treatment | — | — | 2.60 | 3.00 | 1.20 | 1.40 | 2.40 |
| Mildly Ischemic | 9 | iri-e | | 4 | 1 | 1 | 3 |
| | 14 | iri-e | 4 | 3 | 1 | 2 | 2 |
| | 15 | ili-e | 3 | 4 | 2 | 3 | 3 |
| | 20 | ili-e | 2 | 4 | 1 | 1 | 4 |
| | 19 | iri-e | 4 | 4 | 2 | 2 | 2 |
| | 4 | iri-e | 2 | 4 | 1 | 1 | 3 |
| Mean | — | — | 3.00 | 3.80 | 1.40 | 1.80 | 2.80 |
| Non-ischemic | 4 | rc-e | 4 | 3 | 1 | 1 | 3 |
| | 2 | lc-e | 3 | 3 | 3 | 1 | 3 |
| | 9 | rc-e | 4 | 4 | 1 | 1 | 3 |
| | 7 | lc-e | | | | | 4 |
| | 12 | lc-e | 4 | 4 | 1 | 1 | 3 |
| | 14 | rc-e | 3 | 3 | 3 | 1 | 3 |
| | 19 | rc-e | 4 | 4 | 1 | 1 | 3 |
| Mean | — | — | 3.75 | 3.75 | 1.50 | 1.00 | 3.20 |

Increased re-epithelialization rate was not observed in 90/10 PGA/PLA nonwoven/lysate-treated wounds as compared to saline controls. This is expected because the retention time of mesh, selected for this study as a representative synthetic biomaterial delivery device, which is considerably thick compared to rat skin, is greater than 14 days and therefore would slow superficial wound closure and re-epithelialization.

A mild increase in inflammation was observed when compared to the saline-treated control group.

A greater than two-fold increase in the angiogenic response in the biomaterials treated with 150 micrograms UDC lysate/scaffold was seen when compared to the saline control group.

Summary.

Increased angiogenesis was observed in wounds treated with biomaterial scaffolds containing UDC lysate compared to saline control with greater than two-fold increase in the angiogenic response in the biomaterials treated with 150 micrograms UDC lysate/scaffold when compared to the saline control group. This parameter would be of most critical importance in the healing of an ischemic wound site. The granulation tissue of the 90/10 PGA/PLA non-woven scaffold containing UDC lysate ranged form high cellularity and fibroplasia with minimal organization to moderate cellularity, good organization, and matrix accumulation. A mixed reaction with monocytes and neutrophils was also noted with the UDC lysate biomaterials. As expected in this study, increased re-epithelialization rate was not observed in 90/10 PGA/PLA nonwoven/lysate treated wounds as compared to saline controls. This is expected because in rat wound healing re-epithelialization is partially facilitated by cutaneous contraction. The retention time of 90/10-PGA/PLA non-woven scaffold, selected for this study as a representative synthetic biomaterial delivery device, is greater than 10 days and therefore would impede cutaneous contraction. This impedance would be exhibited as slow superficial wound closure and re-epithelialization.

These results demonstrate the biological effect of UDC lysate lyophilized onto and released from a synthetic biomaterial in a rat full thickness excisional ischemic wound healing model.

Example 24

The Biological Effect of Umbilicus Derived Cell (UDC) Lysate Lyophilized onto a Synthetic Biomaterial in a db/db Mouse Full Thickness Excisional Wound Healing Model Diabetic foot ulcers are the most prevalent type of non-healing chronic wounds. The db/db mouse is a strain of diabetic mice recognized for delay in wound healing, making this animal model a valuable tool in which to study chronic wounds.

The present study evaluated the biological effect of UDC lysate lyophilized onto a synthetic biomaterial in a db/db mouse full thickness excisional wound healing model. In this study, UDCs were expanded in culture, harvested, lysed by repeated freeze-thaw cycles, applied to 90/10 PGA/PLA knitted mesh at two protein concentrations (30 micrograms and 150 micrograms total protein per mesh), and lyophilized. A knitted mesh was chosen for use in this study because the thickness (200 microns) is comparable to the thickness of thickness of db/db mouse dermis (~800 microns). The lyophilized meshes were applied to full thickness excisional wounds created in db/db mice. Positive control db/db mice were treated with collagen/ORC and negative control db/db mice were treated with saline. Blood glucose levels were obtained at day zero and day 14 to confirm diabetes. The study was completed on day 14 and the wounds were processed for histology.

Histological evaluation of the wounds treated with meshes containing lysate at both concentrations showed increases in granulation tissue area and granulation tissue depth as compared to saline control. Increased granulation tissue is essential to permanent wound healing without recurrence, since it is presumed that wounds which contain greater amounts of extracellular matrix would have enhanced durability. The results demonstrate the biological effect of UDC lysate, lyophilized onto and released from a synthetic biomaterial, in a db/db mouse full thickness dermal wound healing model.

Methods & Materials

UDC Isolation and Culture

Tissue Procurement.

Umbilical cords were obtained from The National Disease Research Interchange (Philadelphia, Pa.) for research purposes with full patient consent. Cell isolation and culture were performed as described in International Patent Publication WO2005/00331482.

Lysate Production.

Human UDC lysate was produced as set forth in Example 22. The cell lysate was applied to tested materials at 30 micrograms or 150 micrograms total protein per individual sample.

Lyophilization.

Test materials with applied lysate were loaded into a FTS Systems Dura-Stop MP Stoppering Tray Dryer and lyophilized using the ramping program set forth in Example 17. All steps had a ramping rate of 2.5° C./minute and a 100-mT vacuum.

Each of the following materials was applied as a 6 mm disc.

90/10 PGA/PLA Knitted Mesh 30 micrograms total lysate protein;

90/10 PGA/PLA Knitted Mesh 150 micrograms total lysate protein;

90/10 PGA/PLA Knitted Mesh; and

55/45 Oxidized Regenerated Cellulose Collagen (ORC).

C57BLKs/Bom db/db Diabetic Mouse Model

Animal Husbandry.

40 female diabetic mice (C57BLKs/Bom db/db; B&M, Denmark) together with 8 female non-diabetic littermates (C57BLKs/Bom db/+; B&M, Denmark) aged approximately 16 weeks were used in this study. Mice were housed in groups of 5 to 10. On the first day of the study period, animals were housed in individual cages (cage dimensions 35×15×15 cm with sawdust bedding, changed twice weekly) in an environment maintained at an ambient temperature of 23° C. with 12-hour light/dark cycles. They were provided with food and water ad libitum. To acclimate the animals to their surroundings prior to experimentation, they were housed for a minimum of one week without disturbance other than to refresh their bedding and to replenish their food and water provisions. Following wounding, animals were monitored until they recovered from the procedure and then housed in individual cages for the remainder of the study period.

Creation of Full Thickness Wounds and Treatment.

Prior to anesthesia, each animal's glucose level was obtained via tail nick. The blood sample was analyzed with a glucometer. Animals were anesthetized (halothane and air) and shaved. A single standardized full thickness wound (7.5 mm×7.5 mm) was created in the flank skin of each experimental animal. Wounds received one of the treatments described below (Experimental Groups). Treatments were applied directly to the surface of wounds (no pre-wetting required prior to application). All materials were applied as 6.0 mm diameter discs, one disc applied to each wound.

All wounds were secondarily dressed with a 1.5×1.5 cm pad of RELEASE (Johnson & Johnson, UK) moistened with a fixed volume of sterile saline (excess moisture was squeezed out). The RELEASE pad was held in place using a circumferential band of the occlusive film dressing BIO-CLUSIVE (Johnson & Johnson). All animals were re-anesthetized and wounds redressed (standard secondary redressing) on post wounding days 4, 7, and 10. Wounds allocated to Collagen/ORC group had this material reapplied on post wounding days 4, 7 and 10. Immediately after wounding and subsequently on days 4, 7, 10, and 14, all wounds were digitally photographed together with a calibration/identity plate. On day 14 of the study, animals were euthanized. Animals 1, 2, 24, 27, 33, and 40 died during the course of the study.

Experimental Groups

The treatment groups are set forth in Table 24-1.

TABLE 24-1

Treatment Groups

| Treatment Group | Treatment | Animal Code | Number of Animals |
|---|---|---|---|
| 1 | db/db 90/10 PGA/PLA Knitted Mesh 30 micrograms total lysate protein | JJ-11.02–JJ-11.09 | 8 |
| 2 | db/db 90/10 PGA/PLA Knitted Mesh 150 micrograms total lysate protein | JJ-11.010–JJ-11.17 | 8 |
| 3 | db/db 90/10 PGA/PLA Knitted Mesh | JJ-11.18–JJ-11.25 | 8 |
| 4 | db/db 55/45 Collagen/ORC (positive control) | JJ-11.26–JJ-11.32 | 7 |
| 5 | db/db saline control (db/db control) | JJ-11.33–JJ-11.40 | 8 |
| 6 | db/+ saline control (db/+control) | JJ-11.41–JJ-11.48 | 8 |

Euthanasia and Tissue Processing.

Prior to euthanasia, the blood glucose level of each animal was measured from tail nick samples. All animals were painlessly euthanized using $CO_2$ asphyxiation (confirmed by cervical dislocation) on day 14 post-wounding. Wounds with surrounding normal tissue were excised and subsequently fixed in 10% formalin for routine histological assessment. Excised tissue was sandwiched between two pieces of filter paper, prior to being placed in fixative, to reduce the extent of tissue curling. Fixed specimens were trimmed and bisected, generating two half wounds per site. Both halves were processed and embedded in paraffin wax. Specimens too small to bisect were embedded whole. Specimens were oriented in such a fashion as to ensure that appropriate transverse sections of the wound were taken. Wax embedded tissue was sectioned (7 microns) and representative sections stained with Haematoxylin and Eosin (H&E).

Histological Evaluation.

The following evaluations were undertaken on representative H&E sections of each wound: image analysis-based quantitative assessment of wound re-epithelialization and granulation tissue deposition.

Statistical Analysis.

Non-parametric analysis (Kruskal Wallace—Multivariate Analysis followed by ad hoc two sample Mann Whitney U-test analysis) was used to test the significance of any inter-group differences in re-epithelialisation, wound width and granulation tissue deposition.

Results

Quantitative Histology Data

Values for wound width, granulation tissue area, and percent re-epithelialization are means of three measurements taken from three representative sections. Values for granulation tissue depth are means of 15 measurements—5 from each of three representative sections.

TABLE 24-2

Summarized Quantitative Histology Data

| | | Histology Parameters | | | |
|---|---|---|---|---|---|
| Treatment group | Animal | Wound Width Mean (mm) | Granulation Tissue Area Mean (mm²) | Granulation Tissue Depth Mean (mm) | Re-epithelialization Mean (%) |
| db/db 90/10 PGA/PLA Knitted Mesh 30 micrograms total lysate protein | 11.03 | 6.67 | 1.68 | 0.31 | 100.00 |
| | 11.04 | 4.91 | 1.90 | 0.52 | 100.00 |
| | 11.05 | 4.83 | 3.16 | 0.63 | 95.58 |
| | 11.06 | 5.83 | 3.09 | 0.59 | 100.00 |
| | 11.07 | 6.43 | 2.13 | 0.41 | 39.19 |
| | 11.08 | 5.50 | 1.70 | 0.33 | 42.42 |
| | 11.09 | 4.27 | 2.30 | 0.65 | 71.30 |
| Mean area | | 5.30 | 2.28 | 0.49 | 78.35 |
| Std. Dev. | | 0.78 | 0.62 | 0.14 | 27.62 |
| Std. Error | | 0.29 | 0.23 | 0.05 | 10.44 |
| db/db 90/10 PGA/PLA Knitted Mesh 150 micrograms | 11.10 | 6.37 | 2.88 | 0.40 | 30.99 |
| | 11.11 | 4.93 | 2.52 | 0.54 | 61.7 |
| | 11.12 | 3.71 | 1.76 | 0.46 | 100.00 |
| | 11.13 | 6.64 | 3.17 | 0.54 | 96.49 |
| | 11.15 | 6.33 | 3.22 | 0.54 | 40.40 |
| Total Lysate Protein | 11.16 | 3.91 | 3.86 | 0.90 | 52.32 |
| | 11.17 | 6.89 | 3.78 | 0.49 | 65.89 |
| Mean area | | 5.40 | 3.03 | 0.55 | 63.97 |
| Std. Dev. | | 1.41 | 0.80 | 0.16 | 23.98 |
| Std. Error | | 0.53 | 0.30 | 0.06 | 9.06 |
| db/db 90/10 PGA/PLA Knitted Mesh | 11.18 | 4.88 | 3.25 | 0.55 | 52.39 |
| | 11.19 | 6.32 | 3.16 | 0.48 | 42.20 |
| | 11.20 | 6.94 | 1.79 | 0.31 | 66.27 |
| | 11.21 | 6.86 | 2.09 | 0.29 | 64.11 |
| | 11.22 | 5.71 | 2.53 | 0.51 | 100.00 |
| | 11.23 | 5.42 | 2.99 | 0.58 | 56.71 |
| | 11.25 | 4.50 | 1.45 | 0.38 | 100.00 |
| Mean area | | 5.80 | 2.47 | 0.44 | 68.81 |
| Std. Dev. | | 0.95 | 0.71 | 0.12 | 22.73 |
| Std. Error | | 0.36 | 0.27 | 0.04 | 8.59 |
| db/db 55/45 ORC/Collagen | 11.26 | 1.33 | 0.35 | 100.00 | |
| | 11.28 | 3.32 | 0.65 | 100.00 | |
| | 11.29 | 4.25 | 0.31 | 100.00 | |
| | 11.30 | 4.17 | 0.32 | 100.00 | |
| | 11.31 | 2.57 | 0.26 | 100.00 | |
| | 11.32 | 3.22 | 0.41 | 100.00 | |
| Mean area | | | 3.47 | 0.38 | 100.00 |
| Std. Dev. | | | 0.64 | 0.14 | 0.00 |
| Std. error | | | 0.26 | 0.06 | 0.00 |
| db/db Saline | 11.34 | 3.86 | 0.46 | 100.00 | |
| | 11.35 | 5.06 | 0.23 | 67.51 | |
| | 11.36 | 4.30 | 0.45 | 100.00 | |
| | 11.37 | 6.72 | 0.52 | 100.00 | |
| | 11.38 | 5.99 | 0.31 | 69.85 | |
| | 11.39 | 4.61 | 0.40 | 100.00 | |

TABLE 24-2-continued

Summarized Quantitative Histology Data

| Treatment group | Animal | Wound Width Mean (mm) | Granulation Tissue Area Mean (mm²) | Granulation Tissue Depth Mean (mm) | Re-epithelialization Mean (%) |
|---|---|---|---|---|---|
| Mean area | | | 5.09 | 0.39 | 89.56 |
| Std. Dev. | | | 1.08 | 0.11 | 16.19 |
| Std. error | | | 0.44 | 0.04 | 6.61 |
| db/+Saline | 11.42 | 2.44 | 0.51 | 100.00 | |
| | 11.43 | 1.62 | 0.54 | 100.00 | |
| | 11.44 | 4.54 | 0.57 | 100.00 | |
| | 11.45 | 2.90 | 0.93 | 62.16 | |
| | 11.46 | 4.16 | 0.56 | 100.00 | |
| | 11.47 | 1.83 | 0.48 | 100.00 | |
| | 11.48 | 2.37 | 0.85 | 100.00 | |
| Mean area | | | 2.84 | 0.63 | 94.59 |
| Std. Dev. | | | 1.12 | 0.18 | 14.30 |
| Std. error | | | 0.42 | 0.07 | 5.41 |

Significantly more granulation tissue area is noted in the db/db 90/10 PGA/PLA knitted mesh 150 microgram total lysate protein treated samples vs. db/db saline samples ($p<0.006$, t-test).

Qualitative Histology Data

Qualitative histology results are set forth in Table 24-3.

TABLE 24-3

Summary of qualitative histological scoring of wound sites.

| Treatment | Animal No. | Treatment Code | Scaffold Visible? (S = sloughing) | Was adipose tissue near wound surface? | SQ Fat necrosis | Inflammation in Superficial Wound Bed | Inflammation in SQ Fat | Granulation Tissue in Wound Bed |
|---|---|---|---|---|---|---|---|---|
| 90/10 | 3 | 1 | S | N | N | NN | 1 | good |
| PGA/PL | 4 | 1 | N | N | N | 1.5 | NN | good |
| A | 5 | 1 | S | N | N | 1 | NN | good |
| Knitted | 6 | 1 | N | N | N | 1 | NN | good |
| Mesh | 7 | 1 | Yes + S | N | N | 1.5 | NN | good |
| 30 | 8 | 1 | N | N | N | 1 | NN | good |
| micrograms total lysate protein | 9 | 1 | N | N | N | 1 | NN | good |
| 90/10 | 10 | 2 | Yes + S | N | N | 1 | NN | good |
| PGA/PL | 11 | 2 | S | N | N | 1.5 | NN | good |
| A Knitted | 12 | 2 | S | N | N | 1 | NN | good |
| Mesh | 13 | 2 | S | N | N | 1 | NN | good |
| 150 | 14 | 2 | S | N | N | 1 | NN | good |
| micrograms | 15 | 2 | S | N | N | 1 | NN | good |
| total | 16 | 2 | S | N | N | 1 | NN | good |
| lysate protein | 17 | 2 | S | N | N | 1 | NN | good |
| 90/10 | 18 | 3 | S | N | N | 1 | NN | good |
| PGA/PL | 19 | 3 | S | N | N | 1.5 | NN | good |
| A Knitted | 20 | 3 | S | Minor | N | 1 | NN | good |
| Mesh | 21 | 3 | S | N | N | 1 | NN | good |
| | 22 | 3 | S | N | N | NN | NN | good |
| | 23 | 3 | S | N | N | 1 | NN | good |
| | 25 | 3 | N | Minor | N | 1 | 1 | good |
| 55/45 | 26 | 4 | N | N | N | 1 | NN | good |
| ORC | 28 | 4 | N | Minor | N | 2* | NN | good |
| | 29 | 4 | N | N | N | 1 | NN | good |
| | 30 | 4 | N | N | N | 1 | NN | good |
| | 31 | 4 | N | N | N | 1 | NN | good |
| | 32 | 4 | N | N | N | 1 | NN | good |
| Saline | 34 | 5 | N | N | N | 1 | NN | good |
| | 35 | 5 | N | Minor | N | 1 | 1 | good |
| | 36 | 5 | N | Minor | N | 1 | NN | good |
| | 37 | 5 | N | N | N | 1 | NN | good |
| | 38 | 5 | N | N | N | 1 | NN | good |
| | 39 | 5 | N | N | N | 2 | NN | good |

TABLE 24-3-continued

Summary of qualitative histological scoring of wound sites.

| Treatment | Animal No. | Treatment Code | Scaffold Visible? (S = sloughing) | Was adipose tissue near wound surface? | SQ Fat necrosis | Inflammation in Superficial Wound Bed | Inflammation in SQ Fat | Granulation Tissue in Wound Bed |
|---|---|---|---|---|---|---|---|---|
| db/db +/− | 42 | 6 | N | N | N | 1 | NN | good |
| | 43 | 6 | N | N | N | 1 | NN | good |
| | 44 | 6 | N | N | N | 1 | 1 | good |
| | 45 | 6 | N | N | N | 2 | 1 | good |
| | 46 | 6 | N | N | N | 1 | NN | good |
| | 47 | 6 | N | N | N | 1 | NN | good |
| | 48 | 6 | N | N | N | 1 | NN | good |

Table Key:
S = sloughing,
N = no,
NN = not notable (NN = 0 for mean calculations),
SQ = subcutaneous,
*= many hair foreign bodies Blood Glucose Concentration Data Blood glucose readings are set forth in Table 24-4.

TABLE 24-4

Blood Glucose Readings

Blood glucose Concentration (mg/dL)

| | Animal | Start | End | Change | % of start | % change |
|---|---|---|---|---|---|---|
| 90/10 | 11.01 | 470 | Nd | Nd | Nd | Nd |
| PGA/PLA | 11.02 | 492 | Nd | Nd | Nd | Nd |
| Knitted | 11.03 | 420 | 378 | 42 | 90 | −10.00 |
| Mesh | 11.04 | 536 | 347 | 189 | 65 | −35.26 |
| 30 | 11.05 | 600 | 600 | 0 | 100 | 0.00 |
| micrograms | 11.06 | 459 | 600 | −141 | 131 | 30.72 |
| total lysate | 11.07 | 474 | 499 | −25 | 105 | 5.27 |
| protein | 11.08 | 478 | 405 | 73 | 85 | −15.27 |
| | 11.09 | 600 | 600 | 0 | 100 | 0.00 |
| Mean | | 503.22 | 489.86 | | | −3.51 |
| Std. Dev. | | 70.59 | 112.99 | | | 20.26 |
| Std. error | | 23.53 | 42.71 | | | 7.66 |
| 90/10 | 11.10 | 600 | 600 | 0 | 100 | 0.00 |
| PGA/PLA | 11.11 | 504 | 600 | −96 | 119 | 19.05 |
| Knitted | 11.12 | 564 | 565 | −1 | 100 | 0.18 |
| Mesh | 11.13 | 600 | 480 | 120 | 80 | −20.00 |
| 150 | 11.14 | 600 | 587 | 13 | 98 | −2.17 |
| micrograms | 11.15 | 600 | 600 | 0 | 100 | 0.00 |
| total lysate | 11.16 | 600 | 600 | 0 | 100 | 0.00 |
| protein | 11.17 | 459 | 414 | 45 | 90 | −9.80 |
| Mean | | 565.88 | 555.75 | | | −1.59 |
| Std. Dev. | | 54.87 | 70.43 | | | 10.98 |
| Std. error | | 19.40 | 24.90 | | | 3.88 |
| 90/10 | 11.18 | 509 | 600 | −91 | 118 | 17.88 |
| PGA/PLA | 11.19 | 591 | 480 | 111 | 81 | −18.78 |
| Knitted | 11.20 | 302 | 122 | 180 | 40 | −59.60 |
| Mesh | 11.21 | 317 | 211 | 106 | 67 | −33.44 |
| | 11.22 | 600 | 537 | 63 | 90 | −10.50 |
| | 11.23 | 600 | 600 | 0 | 100 | 0.00 |
| | 11.24 | 460 | Nd | Nd | Nd | Nd |
| | 11.25 | 532 | 561 | −29 | 105 | 5.45 |
| Mean | | 488.88 | 444.43 | | | −14.14 |
| Std. Dev. | | 121.12 | 195.91 | | | 26.09 |
| Std. error | | 42.82 | 74.05 | | | 9.86 |
| db/db | 11.26 | 412 | 451 | −39 | 109 | 9.47 |
| 55/45 | 11.27 | 600 | Nd | Nd | Nd | Nd |
| ORC/ | 11.28 | 517 | 504 | 13 | 97 | −2.51 |
| Collagen | 11.29 | 460 | 500 | −40 | 109 | 8.70 |
| | 11.30 | 600 | 486 | 114 | 81 | −19.00 |
| | 11.31 | 474 | 411 | 63 | 87 | −13.29 |
| | 11.32 | 545 | 434 | 111 | 80 | −20.37 |

TABLE 24-4-continued

Blood Glucose Readings

Blood glucose Concentration (mg/dL)

| | Animal | Start | End | Change | % of start | % change |
|---|---|---|---|---|---|---|
| Mean | | 515.43 | 464.33 | | | −6.17 |
| Std. Dev. | | 71.49 | 38.10 | | | 13.38 |
| Std. error | | 29.19 | 15.55 | | | 5.46 |
| db/db | 11.33 | 600 | Nd | Nd | Nd | Nd |
| Saline | 11.34 | 554 | 600 | −46 | 108 | 8.30 |
| | 11.35 | 600 | 470 | 130 | 78 | −21.67 |
| | 11.36 | 197 | 125 | 72 | 63 | −36.55 |
| | 11.37 | 416 | 560 | −144 | 135 | 34.62 |
| | 11.38 | 494 | 453 | 41 | 92 | −8.30 |
| | 11.39 | 292 | 150 | 142 | 51 | −48.63 |
| | 11.40 | 24 | Nd | Nd | Nd | Nd |
| Mean | | 397.13 | 393.00 | | | −12.04 |
| Std. Dev. | | 209.42 | 205.49 | | | 30.45 |
| Std. error | | 85.49 | 83.89 | | | 12.43 |
| db/+Saline | 11.41 | 94 | 108 | −14 | 115 | 14.89 |
| | 11.42 | 107 | 127 | −20 | 119 | 18.69 |
| | 11.43 | 98 | 93 | 5 | 95 | −5.10 |
| | 11.44 | 88 | 87 | 1 | 99 | −1.14 |
| | 11.45 | 128 | 84 | 44 | 66 | −34.38 |
| | 11.46 | 85 | 71 | 14 | 84 | −16.47 |
| | 11.47 | 96 | 77 | 19 | 80 | −19.79 |
| | 11.48 | 116 | 78 | 38 | 67 | −32.76 |
| Mean | | 101.5 | 90.63 | | | −9.51 |
| Std. Dev. | | 14.62 | 18.59 | | | 19.98 |
| Std. error | | 5.17 | 6.57 | | | 7.06 |

Note a significant number of readings were higher than the upper maximum of the glucometer used (i.e., 600 mg/dL). All above-scale readings were thus allocated the value of 600 mg/dL.

Summary.

Histological evaluation of the wounds treated with meshes containing UDC lysate showed increases in granulation tissue area and granulation tissue depth as compared to saline control. The db/db 90/10 PGA/PLA knitted mesh 150 microgram treatment group showed a significant increase in granulation tissue area versus db/db saline and (p>0.006, t test) as well as a near significant increase in granulation tissue depth versus db/db control (p>0.06, t test). Increased granulation tissue is essential to permanent wound healing and reduced incidence of wound recurrence. Decreased wound width and increased re-epithelialization was not observed in lysate-treated wounds as compared to saline controls. This is expected because the retention time of mesh, selected for this study as a representative synthetic biomaterial delivery device with a thickness compatible with db/db mouse skin, is greater than 14 days and therefore would slow superficial wound closure and re-epithelialization. Despite the physical presence of this structure, 75-91% of these wounds closed within the 14-day study. These results demonstrate the biological effect of UDC lysate lyophilized onto a synthetic biomaterial in a db/db mouse full thickness wound healing model.

Example 25

A 14-Day Evaluation of Proprietary Constructs Containing Post-Partum Cell Lysate on Wound Healing in db/db Mice PPDC lysate has been evaluated in several in vivo models previously. Two acute models have been used, a rat subcutaneous implant model and a full-thickness excisional swine model. These studies demonstrated that cell lysate has a good biocompatibility profile, yields increased extracellular matrix formation in the rat subcutaneous implant model (Examples 18 and 19) and results in increased extracellular matrix deposition at early timepoints in the pig with a concomitant increase in inflammation which is not present at day 14 (Examples 21 and 22). Additionally, PPDC lysate has been evaluated in two delayed healing models, an ischemic rat model (Example 23) and in a full-thickness excisional wound model in db/db mice (Example 24). In the ischemic rat model, a greater than two-fold increase in angiogenesis was observed in wounds treated with biomaterials containing PPDC lysate compared to saline control. In the previous db/db model, although wound closure was not achieved due to the nonresorbable scaffold material bridging the wound open, enhanced granulation tissue formation was seen in the cell lysate groups.

The purpose of this study was to evaluate the biological effect of UDC lysate lyophilized onto and released from a natural scaffold consisting of collagen/ORC in a recognized model of delayed healing, the db/db mouse wound healing model. The primary endpoint considered in this evaluation was the effect of this material on the increase in the healing rate (time to complete wound closure) in this impaired model since this is the key requirement set forth from the FDA Guidance for Industry for Development of Products for Treatment of Cutaneous Ulcers. Qualitative and semi-quantitative measurements of granulation tissue and inflammatory response were also assessed.

Quantitative analysis of clinical wound images showed that at days 7, 10, and 14, Collagen/ORC scaffolds containing 90 micrograms PPDC lysate protein demonstrated statistically significant greater wound closure than the Collagen/ORC scaffold alone. In addition, at day 14, Collagen/ORC containing 30 micrograms cell lysate protein demonstrated statistically significant greater wound closure than Collagen/ORC (p<0.05, Tukey-Kramer for all).

Methods & Materials

A single 7.5 mm×7.5 mm full-thickness excisional wound was created on the left side of homozygous db/db mice and on heterozygous control mice. 56 mice were evaluated for 14 days.

The treatments were implanted at the time of surgery and left in place throughout the study period. The treatments (approx. 1×1 cm) were placed in the wound and covered with wound dressing pads sold under the tradename RELEASE (Johnson & Johnson, New Brunswick N.J.). The RELEASE pad was dipped into sterile saline and excess fluid was squeezed out prior to placing it on the animal. All wounds were then covered with transparent wound Dressing sold under the tradename BIOCLUSIVE (Johnson & Johnson, New Brunswick N.J.).

Digital images of each wound were taken at days 0, 4, 7, 10, and 14 post-wounding. These images were used to evaluate wound closure over time.

Bandage changes were done on days 4, 7, and 10 of the study. Additional bandage changes were done if an animal escaped its bandage prior to a scheduled change.

Tissues were harvested from the animals on day 14. The entire wound and surrounding normal skin was excised and placed in 10% neutral buffered formalin. The cranial half of the excised tissue was sent for histological processing (paraffin sections) and stained with H&E and Masson's trichrome. The caudal portion of each sample was retained for possible future analysis.

Tissue sections were histologically analyzed for inflammatory response and quality of repair. Measurements of granulation tissue area and epithelial tongue length were also made.

Treatment Groups

Wound dressings, sold under the tradename PROMOGRAN (Johnson & Johnson, New Brunswick N.J.), (Lot 1305263) was stored at room temperature prior to manipulation for this study. Cell lysate (CL) was aseptically applied to the scaffolds and then lyophilized under aseptic conditions. Scaffolds containing no CL were also lyophilized. The processed PROMOGRAN samples will be referred to as ORC/Collagen.

| Complete Description | As Referred to in Report |
| --- | --- |
| A. Saline treated (heterozygous control animal) | db/db +/− |
| B. Saline | Saline |
| C. Collagen/ORC | Collagen/ORC |
| D. Collagen/ORC + 30 ug cell lysate protein | Collagen/ORC + CL Low |
| E. Collagen/ORC + 90 ug cell lysate protein | Collagen/ORC + CL High |

N = 7 per treatment
The lot of cells used in treatments D & E were CBAT 120304.

Test Article Preparation

Lysate Production and Scaffold Preparation.

Human UDC lysate supernatant was prepared as in Example 22. The total protein content of the collected supernatant fluid was assessed by Bradford assay and the dose volume of supernatant fluid (30 micrograms total protein per material or 90 micrograms total protein per material) was calculated. The dose volume of supernatant fluid was applied to the material as five one-fifth total dose volume aliquots. An aliquot was placed at each corner of the 1.5×1.5 cm material approximately 1 mm from the material edge and one aliquot was placed in the center of the material. This ensured even distribution of lysate within the wound bed.

Lyophilization.

Test materials with applied lysate were loaded into a FTS Systems Dura-Stop MP Stoppering Tray Dryer and lyophilized using the ramping program set forth in Example 17. All steps had a ramping rate of 2.5° C./minute and a 100-mT vacuum.

Anesthesia, Analgesia and Surgical Preparation.

Each animal was weighed and tested for blood glucose level prior to anesthesia. Induction of anesthesia was accomplished by placing each mouse into a pre-charged Isoflurane anesthesia chamber. Once anesthetized, the animal was placed on a nose-cone to maintain the surgical plane of anesthesia. Eye ointment was applied to each animal to prevent corneal ulceration. No analgesics were administered due to the db/db mouse's physiology. Each animal was carefully scrutinized to determine if they were experiencing pain. Analgesics would have been administered if signs had been demonstrated.

Skin depilation from the back, shoulder, side and flank regions was accomplished with an electric animal clipper. The area was vacuumed to remove hair clippings and stratum corneum debris. Each animal was wiped with Betadine and alcohol prior to being placed on the surgical table.

Surgical Approach.

Full-thickness excisional wounds (7.5×7.5 mm) were created on the left side of each animal with a scalpel and scissors. Each wound was submitted to a treatment regimen. The scaffolds were placed into the wound bed. CL treated scaffolds were placed "top-side" down.

Bandaging Technique.

The test materials were undisturbed for the length of the study. The wounds were covered with an approximate 1×1 cm square of RELEASE. The RELEASE was dipped in sterile saline and the excess fluid was squeezed out prior to application. The wounds were further dressed with BIO-CLUSIVE to keep the wounds moist and to keep the test articles and RELEASE in place.

The secondary bandages (RELEASE and BIOCLUSIVE) were changed on days 4, 7, and 10 of the study. Care was taken to ensure that the wound was not disturbed during the dressing changes. Additional bandage changes were performed if an animal escaped it bandages prior to a scheduled change.

Post-Operative Care and Clinical Observations

After recovering from surgery and general anesthesia, each mouse was observed for behavioral signs of discomfort or pain. No signs of discomfort or pain were observed. Animals were returned to their cage when fully conscious and ambulatory.

The health status of each mouse was determined by general appearance and attitude, food consumption, fecal and urinary excretion, the presence of abnormal discharges and bandage integrity. Each mouse was observed twice daily during the first 36 hours following surgery. Following recovery from surgery, the observations were reduced to once daily until the end of the study.

Evaluations.

At each bandage change and at the end of the study, any unique findings were recorded.

Euthanasia.

At the predetermined time point (7 and 14 days post-wounding), the animals were euthanized via carbon dioxide. The animals were observed to ensure that respiratory function had ceased and there was no palpable cardiac function.

Tissue Processing.

Immediately following euthanasia, each wound along with the underlying fat and margin of surrounding skin was excised. The wound was bisected into cranial and caudal halves. The cranial half of the wound was fixed in 10% neutral buffered formalin, processed and embedded in paraffin. Samples were sectioned at 5 microns and stained for H&E and Masson's trichrome by MPI Research. The caudal half of the wound was fixed in 10% neutral buffer formalin and is reserved for any future analysis.

Photographic Documentation.

Digital images were taken of individual wounds on days 0, 4, 7, 10, and 14 post-wounding. These images were used to measure wound closure. Using Image Pro 4.0 Image Analysis software, each image was calibrated using the ruler-label included in the photo. The wound was traced to determine the area that remained open. Day 0 images were used as baseline and the percentage remaining open was calculated based on the day being evaluated versus the area of that wound on day 0.

Histological Assessments.

A computer-controlled motorized programmable slide scanning system was used in the process of image acquisition. Separate images of high magnification fields were acquired from a microscope. The images were tiled to preserve the integrity of the entire histological specimen. This allows accurate measurement of the entire tissue sample.

Images from the light microscope were captured into the computer memory via CCD camera and frame grabber board and subsequently analyzed using Image Pro 4.0 Image Analysis software.

Histological assessments were performed by a consulting pathologist. Tissue sections were histologically analyzed for the presence of the scaffold, granulation tissue quality and inflammatory response.

Statistical Analysis.

Treatments were assigned in a blocked fashion. Visual assessments were analyzed using JMP 4.0.4 software. Shapiro-Wilk-W Test was performed prior to data analysis to determine normality. Nominal and Ordinal data was analyzed using Chi-Square. Continuous data was analyzed using One-way ANOVA. Tukey-Kramer or Student-Newman-Keuls (SNK) test for multiple comparisons was performed to determine differences between groups following One-way ANOVA. A value of $p<0.05$ was used as the level of significance.

Results

Surgery and anesthetic recovery were uneventful. All animals tolerated bandaging well.

Some differences between the diabetic groups were seen in blood glucose level, however all db/db mice were sufficiently diabetic during the course of the study.

Clinical Observations Day 14.

On each day of bandage change and at the time of necropsy, each animal was evaluated. Any unique observations were noted. Table 25-1 summarizes the findings.

TABLE 25-1

| | | | | | ORC/ | ORC/ | | | |
|---|---|---|---|---|---|---|---|---|---|
| Treatment | | | | ORC/ | Collagen + CL | Collagen + CL | | ORC + CL | ORC + CL |
| Obs. | Day | db/db +/− | Saline | Collagen | Low | High | ORC | Low | High |
| Wet | 4 | 2/7 | 7/7 | 4/7 | 0/7 | 0/7 | 0/7 | 1/7 | 0/7 |
| wounds | 7 | 3/7 | 7/7 | 5/7 | 0/7 | 0/7 | 4/7 | 5/7 | 6/7 |
| | 10 | 0/7 | 0/7 | 0/7 | 0/7 | 0/7 | 0/7 | 0/7 | 3/7 |
| | 14 | 0/7 | 0/7 | 0/7 | 0/7 | 0/7 | 0/7 | 1/7 | 3/7 |

Clinical Observation on Day 14

TABLE 25-1-continued

Clinical Observation on Day 14

| Treatment Obs. | Day | db/db +/− | Saline | ORC/ Collagen | ORC/ Collagen + CL Low | ORC/ Collagen + CL High | ORC | ORC + CL Low | ORC + CL High |
|---|---|---|---|---|---|---|---|---|---|
| Treatment visible | 4 | N/A | N/A | 3/7 | 0/7 | 0/7 | 0/7 | 0/7 | 2/7 |
|  | 7 | N/A | N/A | 6/7 | 7/7 | 6/7 | 7/7 | 7/7 | 7/7 |
|  | 10 | N/A | N/A | 4/7 | 5/7 | 2/7 | 0/7 | 6/7 | 4/7 |
|  | 14 | N/A | N/A | 4/7 | 5/7 | 3/7 | 5/7 | 5/7 | 5/7 |
| Escaped Bandage | 4 | 4/7 | 0/7 | 0/7 | 0/7 | 0/7 | 0/7 | 0/7 | 0/7 |
|  | 7 | 2/7 | 0/7 | 0/7 | 0/7 | 0/7 | 0/7 | 0/7 | 0/7 |
|  | 10 | 1/7 | 0/7 | 0/7 | 0/7 | 0/7 | 0/7 | 0/7 | 0/7 |
|  | 14 | 3/7 | 0/7 | 0/7 | 0/7 | 0/7 | 0/7 | 0/7 | 0/7 |

TABLE 25-2

Percentage of Wound Closure

|  | Average | | | | SEM | | | |
|---|---|---|---|---|---|---|---|---|
|  | Day 0 | Day 4 | Day 7 | Day 10 | Day 14 | Day 4 | Day 7 | Day 10 | Day 14 |
| db/db +/− | 100 | 84.2 | 51.94 | 25.61 | 3.65 | 17.17 | 9.18 | 11 | 2.49 |
| ORC/Collagen | 100 | 122.22 | 117.97 | 85.02 | 61.5 | 9.96 | 8.71 | 8.99 | 7.27 |
| ORC/Collagen + CL Low | 100 | 90.58 | 93.47 | 82.63 | 56.1 | 6.53 | 7.59 | 7.74 | 7.2 |
| ORC/Collagen + CL High | 100 | 90.02 | 78.37 | 52.76 | 28.51 | 7.28 | 5.74 | 4.93 | 5.92 |
| Saline | 100 | 99.25 | 101.57 | 77.21 | 51.23 | 7.33 | 10.47 | 3.4 | 6.53 |

Wound Closure (Day 14).

Quantitative analysis of clinical wound images (Table 25-2 shows that at days 7, 10, and 14, Collagen/ORC scaffolds containing 90 micrograms cell lysate protein demonstrated statistically significant greater wound closure than the Collagen/ORC scaffold alone. In addition, at day 14, Collagen/ORC containing 30 micrograms cell lysate protein demonstrated statistically significant greater wound closure than Collagen/ORC (p<0.05, Tukey-Kramer for all).

For the ORC/Collagen treated groups at days 7, 10, and 14, db/db +/− demonstrated statistically significant greater wound closure than ORC/Collagen and ORC/Collagen+CL Low. At days 7, 10 and 14, ORC/Collagen+CL High demonstrated statistically significant greater wound closure than ORC/Collagen. In addition, at day 14, ORC/Collagen+CL Low demonstrated statistically significant greater wound closure than ORC/Collagen (p<0.05, Tukey-Kramer for all).

Qualitative Histopathogical Assessments

Scaffold Visibility.

Most scaffolds were visible in the histological sections.

Presence of Adipose Tissue Near Wound Surface.

Several wounds in the db/db mice had adipose tissue near the wound surface.

Subcutaneous Fat Necrosis.

At day 14, the db/db +/− group demonstrated statistically less subcutaneous fat necrosis than all other groups. (p<0.05, Tukey-Kramer).

Inflammation in Superficial Wound Bed.

At day 14, the Saline treated group demonstrated less inflammation in the superficial wound bed than all Collagen/ORC treated groups. (p<0.05, Tukey-Kramer).

Inflammation in Subcutaneous Fat.

As expected, db/db +/− demonstrated less inflammation in SQ fat than all Collagen/ORC treated groups (p<0.05, Tukey-Kramer).

Granulation Tissue in Wound Bed.

As expected, the db/db +/− group demonstrated statistically more granulation tissue in the wound bed than all other groups (p<0.05, Tukey-Kramer).

Summarized Qualitative Histology Data

Results of qualitative histology assessment are provided in Table 25-3.

TABLE 25-3

Summary of qualitative histological scoring - 14 Days Post Wounding

|  | Animal No. | Treatment Code | Scaffold Visible? | Was Adipose Tissue Near Wound Surface? | SQ Fat Necrosis | Inflammation in Superficial Wound Bed | Inflammation in SQ Fat | Granulation Tissue in Wound Bed |
|---|---|---|---|---|---|---|---|---|
| db/db +/− saline control | 1 | A | CE | CE | CE | CE | CE | CE |
|  | 2 | A | N | N | 0 | 1 | 0 | 4 |
|  | 3 | A | N | N | 0 | 1.5 | 1 | 4 |
|  | 4 | A | CE | CE | CE | CE | CE | CE |
|  | 5 | A | N | N | 0 | 1 | 0 | 4 |

TABLE 25-3-continued

Summary of qualitative histological scoring - 14 Days Post Wounding

|  | Animal No. | Treatment Code | Scaffold Visible? | Was Adipose Tissue Near Wound Surface? | SQ Fat Necrosis | Inflammation in Superficial Wound Bed | Inflammation in SQ Fat | Granulation Tissue in Wound Bed |
|---|---|---|---|---|---|---|---|---|
|  | 6 | A | N | N | 0 | 1 | 0 | 4 |
|  | 7 | A | N | N | 0 | 1 | 1 | 4 |
| db/db saline control | 8 | B | N | N | 2 | 1 | 2 | 3 with ares of LQ |
|  | 9 | B | N | Y | 0.5 | 1 | 0.5 | 1 |
|  | 10 | B | N | Y | 1.5 | 1 | 2 | 1 |
|  | 11 | B | N | Y-minor | 2 | 1 | 2 | 2 with areas of LQ |
|  | 12 | B | N | Y | 1 | Empty WB | 1 | 0.5 |
|  | 13 | B | N | N | 1 | 1 | 1 | 1.5 LQ |
|  | 14 | B | N | N | 1 | 1 | 1 | 1 LQ |
| Collagen/ ORC | 15 | C | S | Y | 2 | 2 | 2 | 1 to 2.5 with areas of rel-lq |
|  | 16 | C | S | Y | 2 | 1.5 | 2 | 1.5 rel-LQ |
|  | 17 | C | N | Y | 2 | 2 | 2 | 1.5 |
|  | 18 | C | S | Y | 0.5 | 2 | 1 | 1.5 rel-LQ |
|  | 19 | C | S | Y-minor | 0.5 | 1 | 1 | 1.5 rel-LQ |
|  | 20 | C | S | Y | 1.5 | 2.5 | 2 | 1 |
|  | 21 | C | N | Y | 1 | 2 | 2 | 1.5 LQ |
| Collagen/ORC + 30 ug lysate | 22 | D | N | N | 1 | 1 | 1 | 1.5 rel-LQ |
|  | 23 | D | S | N | 0 | 1 | 0.5 | 1 LQ |
|  | 24 | D | S | Y | 2.5 | 3 | 2.5 | 2 with areas LQ |
|  | 25 | D | S | Y | 2 | 2 | 2 | 1 lq |
|  | 26 | D | S | Y | 2 | 2 | 2 | 1.5 LQ |
|  | 27 | D | S | Y | 2 | 2 | 2 | 1.5 LQ |
|  | 28 | D | S | Y | 2.5 | 2 | 2 | 1 LQ |
| Collagen/ORC + 90 ug lysate | 29 | E | S | Y-rel minor | 2.5 | 2.5 | 2.5 | 2 with areas LQ |
|  | 30 | E | S | Y | 2.5 | 2 | 2.5 | 1.5 with areas LQ |
|  | 31 | E | Partial S | Y-rel minor | 1 | 1 | 1 | 1 LQ |
|  | 32 | E | S | Y-rel minor | 1-PF | 2 | 2-PF | 3* |
|  | 33 | E | S | N | 1.5-PF | 2 | 1.5-PF | 1 LQ |
|  | 34 | E | S | N | 1.5-PF | 2 | 1.5-PF | 1.5 mainly LQ |
|  | 35 | E | N | Y | 2.5 | 2 | 2.5 | 1.5 mainly LQ |

Table Key -
S = sloughing,
N = no,
NN = not notable (NN = 0 for mean calculations)

Summary.

The purpose of this study was to evaluate the biological effect of UDC lysate lyophilized onto and released from a natural scaffold consisting of collagen/ORC in a recognized model of delayed healing, the db/db mouse wound healing model. The primary endpoint considered in this evaluation was the effect on the increase in the healing rate (time to complete wound closure) in this impaired model since this is the key requirement set forth from the FDA Guidance for Industry for Development of products for treatment in cutaneous ulcers.

Quantitative analysis of clinical wound images shows that at days 7, 10 and 14, Collagen/ORC scaffolds containing 90 microgram cell lysate protein demonstrated statistically significant greater wound closure than the Collagen/ORC scaffold alone. In addition, at day 14, Collagen/ORC containing 30 microgram cell lysate protein demonstrated statistically significant greater wound closure than Collagen/ORC ($p<0.05$, Tukey-Kramer for all).

These results demonstrate the ability of UDC lysate, lyophilized onto and released from a natural biomaterial of collagen/ORC, to increase the rate of closure in a db/db mouse full thickness wound healing model.

Example 26

Evaluation of Potential Utility of Cells Derived from Postpartum Tissue and their Derivatives, and Growth Factors, for Meniscal Avascular Repair Following Implantation in SCID Mice The purpose of this study was to evaluate the utility of PPDCs, PPDC products, and recombinant human growth factors, following their loading on bioresorbable scaffolds and implantation in SCID mice, in meniscal avascular repair.

UDCs and human fibroblasts at passage 10-11 were evaluated in this study. UDC-conditioned medium and cell lysates obtained from umbilicus-derived cells and human fibroblasts also were evaluated in this study. Also included in this study were recombinant human basic fibroblast growth factor (bFGF) and recombinant human platelet derived growth factor-BB (PDGF-BB). The utility of these treatments was assessed following cell seeding or loading of the growth factor and cell derivatives on scaffolds. Treatments were placed between two discs made from the avascular region of the bovine meniscus. Constructs were held together with fibrin glue and implanted into SCID mice. Scaffolds without cells or growth factor were also implanted into SCID mice as controls.

Results showed that repair tissue filled the synthetic bioresorbable scaffolds without growth factor and cells or cell derivatives. Repair tissue appeared to be fibrous with collagen matrix that stained positive with trichrome but did not stain positive with Safranin O. No striking differences were observed in scaffolds containing cells, cell derivatives, or the growth factors bFGF and PDGF-BB in terms of the quality of repair tissue and intensity of the matrix staining with trichrome compared to scaffold alone at the cell densities and growth factor concentrations tested. Also no positive staining was observed with Safranin O in these samples. Marginal differences in intensity of trichrome staining were noted in scaffolds loaded with conditioned medium derived from umbilicus-derived cells compared to scaffolds loaded with medium alone. Scaffolds loaded with 100 ng of bFGF showed marginally higher intensity of staining with trichrome than scaffolds loaded with 10 ng of bFGF.

Methods & Materials

Reagents.

Dulbecco's Modified Essential Media (DMEM), Penicillin and Streptomycin, were obtained from Invitrogen, Carlsbad, Calif. Fetal calf serum (FCS) was obtained from HyClone (Logan, Utah). Recombinant human bFGF and PDGF-BB were obtained from R&D Systems, Minneapolis, Minn. Chondrocyte growth medium comprised DMEM-High glucose, supplemented with 10% fetal calf serum (FCS), 10 mM HEPES, 0.1 mM nonessential amino acids, 20 micrograms/milliliter of L-proline, 50 micrograms/milliliter ascorbic acid, 100 Units/milliliter penicillin, 100 micrograms/milliliter of streptomycin and 0.25 micrograms/milliliter of amphotericin B. TISSEEL fibrin sealant was obtained from Baxter (Deerfield, Ill.).

Cells and Cell Products.

Human adult fibroblasts were obtained from American Type Culture Collection (ATCC), Manassas, Va. and cultured in growth medium (Dulbecco's Modified Essential supplemented with 15% (v/v) fetal bovine serum, penicillin/streptomycin (100 U/100 mg, respectively) and 0.001% (v/v) 2-mercaptoethanol (Sigma, St. Louis, Mo.) on gelatin-coated tissue culture plastic flasks. UDCs were obtained from CBAT Lot# Umb120304. Cells were cultured in growth media similar to fibroblasts. The cell cultures were incubated at 37° C. with 5% $CO_2$. Cells used for experiments were at passage 11.

Cell lysates were prepared as described in Example 17. Briefly, human UDCs were thawed from cryopreserved stocks and seeded into gelatin-coated flasks at 5,000 cell/$cm^2$. Expanded cells, at 25,000 cell/$cm^2$ (passage 10), were harvested with trypsin and counted. Cells were distributed into siliconized microcentrifuge tubes at 1.0E+07, pelleted by centrifugation, and frozen at −80° C. Tubes containing the frozen cell pellets were placed in a 37° C. water bath, thawed, and then promptly placed in a liquid nitrogen bath. This freeze-thaw process was repeated two additional times. Upon the last thaw, the cell pellets were centrifuged at 13,000 g, 4° C. for 10 minutes. The total protein content of the collected supernatant fluid was assessed by Bradford assay. The cell lysate was applied to tested materials at 30 micrograms total protein per individual scaffold.

Conditioned medium from UDCs was prepared. UDCs Lot Umb022803 P12 cells were thawed and seeded at 5,000 cells/$cm^2$ on gelatin-coated flasks. Cells were cultured in Knockout Growth Medium (Knockout DMEM (Gibco) with 15% (v/v) Knockout serum (Gibson), penicillin/streptomycin (Invitrogen, Carlsbad, Calif.) and 0.001% (v/v) 2-mercaptoethanol (Sigma, St. Louis, Mo.) for 4 days. At the end of 4th day, medium was collected and filtered through a 0.2 micron filter. Medium was concentrated using the Ultra Centrifuge filter devices 5000 MWCO from Millipore (Billerica, Mass.) following the manufacturer's specifications.

Scaffolds.

Nonwoven scaffold made of 50:50 Polyglactin 910 and Polydioxanone, 3 mm in diameter, 1 mm thick, Ethylene Oxide (ETO) sterilized, were obtained from Center for Biomaterials and Advanced Technologies (CBAT, Somerville, N.J.). Duraform scaffolds (Codman, Raynham, Mass.), 3 mm diameter, ~1 mm thick were also evaluated.

Scaffold-Loading with Cells, Cell Products, and Growth Factors.

3.0 mm punches made from scaffolds were loaded with the following growth factors: bFGF, 10 nanograms/scaffold; bFGF, 100 nanograms/scaffold; PDGF-BB, 10 nanograms/scaffold; PDGF-BB, 100 nanograms/scaffold. Loaded scaffolds were lyophilized overnight. Control scaffolds received equivalent volume of vehicle. For cell lysates, scaffolds were loaded with lysate of UDCs (UDC120304 p10, scaffold containing the lysate from 1 million cells, 30 micrograms/scaffold) or Fibroblasts (NHDF IF 1122, scaffold containing the lysate from 1 million cells, 30 micrograms/scaffold). Cell- and lysate-loaded scaffolds were lyophilized overnight. For conditioned medium, scaffolds were loaded with 10 microliters of UDC-conditioned medium or 10 microliters of control medium alone and lyophilized. For cell loading, scaffolds were loaded with UDCs (Umb 120304 p11), at $1\times10^6$ cells per scaffold or Fibroblasts (NHDF IF1122, p11) at $1\times10^6$ cells per scaffold. Cells were seeded onto scaffolds prior to the day of the experiment. The cell-seeded scaffolds were incubated in a cell culture incubator (37° C., 5% $CO_2$) for one day prior to placement between meniscal discs.

Bovine Meniscal Explants.

Meniscal explants 3 mm in diameter were made from menisci obtained from bovine knees of 1 to 1½ year-old animals. 3 mm punches were excised from the central avascular portion of the meniscus. The excised 3 mm punch was trimmed to make discs of approximately 1 mm in thickness. Scaffolds with cells, cell products, or growth factors were placed between two meniscal avascular discs and held together using fibrin glue (50 microliters of TISSEEL). Samples were maintained in chondrocyte growth medium overnight, rinsed in phosphate buffered saline the following day, and implanted into SCID mice.

SCID Implantation.

Each SCID mouse received 2 treatments that were placed in pockets created in each hemithorax through one skin incision. Tacking sutures of 5-0 ETHIBOND* EXCEL (polyester) were used to tack the skin to musculature around each scaffold to prevent subcutaneous migration. Scaffolds were implanted for 6 weeks and then harvested. The various treatment groups implanted are outlined below.

Test Material (N=3 Per Treatment)
A. MBD+PDS/VNW
B. MBD+Duraform
C. MBD+PDS/VNW+PDGF, 10 ng
D. MBD+PDS/VNW+PDGF, 100 ng
E. MBD+PDS/VNW+bFGF, 10 ng
F. MBD+PDS/VNW+bFGF, 100 ng
G. MBD+PDS/VNW+UDC lysate
H. MBD+PDS/VNW+Fibroblast lysate
I. MBD+PDS/VNW+UDC CM
J. MBD+PDS/VNW+control medium
K. MBD+PDS/VNW+UDC
L. MBD+PDS/VNW+Fibroblasts
M. MBD+fibrin glue MBD=Meniscal Bilayer Disc, CM=Conditioned Medium; PDS=Polydioxanone Histology.

At necropsy, samples were fixed in 10% buffered formalin. Each implant was bisected in half and one half was sent to Paragon Bioservices (Baltimore, Md.) for paraffin embedding, sectioning, and staining with Hematoxylin/Eosin (H/E), Trichrome (Tri) and Safranin O (SO).

Results

New repair tissue formation was observed in the majority of the 50/50 Polyglactin 910/Polydioxanone (50:50 PDS/VNW) samples including scaffold alone, scaffolds loaded with growth factor, cell-seeded scaffolds, and cell derivative-loaded scaffolds. The repair tissue was predominantly fibrous in nature and stained positive with trichrome. Collagen fiber bundles were observed in most cases.

50/50 PDS/VNW scaffolds loaded with cells, lysates, or conditioned medium at the concentrations tested did not appear to be strikingly different than control scaffolds. Scaffolds loaded with cells as expected appeared to be more cellular than control scaffolds. A marginal increase in intensity of trichrome staining was noted in scaffolds loaded with UDC CM when compared to scaffolds loaded with control medium.

50/50 PDS/VNW scaffolds loaded with 100 ng bFGF showed marginally higher intensity of staining with trichrome than scaffolds loaded with 10 ng of bFGF. No striking differences were noted between the scaffolds treated with 10 ng and 100 ng of PDGF-BB.

DURAFORM Collagen control scaffolds were not observed in any of the samples indicating that they may have been resorbed before cells could migrate into and lay down new matrix.

Example 27

Cell Proliferation in Response to Basal Medium Supplemented with Expanded Human Umbilicus-Derived Cell (hUDC) Lysate Expanded hUDCs are being developed as a potential cell therapy for the treatment of a number of degenerative diseases. One of the mechanisms of action by which these cells can act is through trophic factor support. Trophic factors are the proteins and other materials (such as lipids and glycosaminoglycans) that cells produce to stimulate a biological effect. It is speculated that hUDC trophic factors could be beneficial in the treatment of a number of diseases, including chronic wounds.

To assess the potency of hUDC lysate, increasing concentrations were dissolved in culture medium and applied to mouse fibroblasts and human endothelial cells. The increases in proliferation above basal media indicate lysate potency.

New repair tissue formation was observed in the majority of the 50/50 Polyglactin 910/Polydioxanone (50:50 PDS/VNW) samples including scaffold alone, scaffolds loaded with growth factor, cell-seeded scaffolds, and cell product-loaded scaffolds. The repair tissue was predominantly fibrous in nature and stained positive with trichrome. Collagen fiber bundles were observed in most cases.

Methods & Materials

Proliferation with NIH/3T3 Cells.

To measure the potency of expanded hUDC lysate, mouse NIH/3T3 fibroblasts were cultured in medium containing hUDC lysate and assayed for increases in cell proliferation over basal media. Mouse NIH/3T3 cells were obtained from American Type Culture Collection and cultured in Fibroblast Growth Medium (DMEM:Hg (Invitrogen, Carlsbad, Calif.), 10% Newborn Calf Serum (Invitrogen, Carlsbad, Calif.), penicillin/streptomycin (Invitrogen, Carlsbad, Calif.) (1 mL per 100 mL (10,000 Units per mL)), at 37° C. in a humidified 5% $CO_2$ environment. Upon reaching 85% confluence, cells were trypsinized, counted and seeded in a 96-well plate at 3500 cell/$cm^2$ (1120 cells/well) in DMEM (low glucose, Invitrogen, Carlsbad, Calif.) supplemented with 2% Fetal Bovine Serum (FBS) (Hyclone, Logan, Utah) and 1% Penicillin/Streptomycin overnight. The following day, the media was removed by aspiration and experimental media were applied for three days. Control media included DMEM (low glucose), DMEM supplemented with 2% FBS, and DMEM supplemented with 10% FBS; experimental media were DMEM (low glucose) supplemented with 2% FBS and increasing concentrations of hUTC lysate (31 micrograms/ml-250 micrograms/ml). After three days, proliferation was measured using a CELLTITER 96 AqueousOne Solution Proliferation Assay kit (Promega, Madison, Wis.) according to the manufacturer's instructions.

Proliferation with CAECs.

To measure the potency of expanded hUDC lysate, human coronary artery endothelial cells (HCAEC) were cultured in medium containing hUDC lysate and assayed for increases in cell proliferation over basal media. Human CAE cells were obtained from Cambrex (Cat # CC-2585, East Rutherford, N.J.) and cultured in EGM-2MV (Endothelial cell Growth Medium formulated for Microvascular systems, Cambrex, East Rutherford, N.J.) at 37° C. in a humidified 5% $CO_2$ environment. Upon reaching 85% confluence, cells were trypsinized, counted and seeded in a 96-well plate at 5000 cell/$cm^2$ (1600 cells/well) in EGM-2MV overnight.

The following day, the media was removed by aspiration and experimental media were applied for three days. Control media included EBM (Endothelial cell Basal Medium, Cambrex, East Rutherford, N.J.) and EGM-2MV; experimental media were EBM supplemented with hUDC lysate (15.6-250 micrograms/ml). After five days, proliferation was measured using a CELLTITER 96 AqueousOne Solution Proliferation Assay kit (Promega, Madison, Wis.) according to the manufacturer instructions.

Results
Proliferation with NIH/3T3 Cells
The results are shown on Table 27-1.

TABLE 27-1

Response of NIH/3T3 cells to hUDC Lysate

| Media | Cells/Well | Standard Error |
|---|---|---|
| DMEM | 0* | 60 |
| DMEM + 2% FBS | 2590 | 300 |
| DMEM + 10% FBA | 15960 | 1480 |
| DMEM + 2% FBS + 31 micrograms/ml hUDC lysate | 13370 | 580 |
| DMEM + 2% FBS + 62 micrograms/ml hUDC lysate | 19240 | 1010 |
| DMEM + 2% FBS + 125 micrograms/ml hUDC lysate | 23690 | 1630 |
| DMEM + 2% FBS + 250 micrograms/ml hUDC lysate | 33140 | 2790 |

*denotes value below detection limits of assay

Expanded hUDC lysate added as a supplement to basal medium (DMEM with 2% FBS) resulted in increased proliferation of NIH/3T3 cells at all concentrations (31.25, 62.5, 125, and 250 micrograms/ml) in a dose dependent manner. Additionally, the two highest concentrations of hUDC lysate showed increased proliferation above the positive control, Complete Medium (DMEM with 10% FBS). These results indicate that hUDC lysate increased fibroblast proliferation, which can be quantitatively measured in vitro.

Proliferation with CAECs
The results are shown on Table 27-2.

TABLE 27-2

Response of Human Coronary Artery Endothelial cells to hUDC Lysate.

| Media | Cells/Well | Standard Deviation |
|---|---|---|
| EBM | 820 | 260 |
| EGM-2MV | 3470 | 80 |
| DMEM + 2% FBS + 15 micrograms/ml hUDC lysate | 3810 | 170 |
| DMEM + 2% FBS + 31 micrograms/ml hUDC lysate | 4300 | 210 |
| DMEM + 2% FBS + 62 micrograms/ml hUDC lysate | 4770 | 460 |

TABLE 27-2-continued

Response of Human Coronary Artery Endothelial cells to hUDC Lysate.

| Media | Cells/Well | Standard Deviation |
|---|---|---|
| DMEM + 2% FBS + 125 micrograms/ml hUDC lysate | 5890 | 30 |
| DMEM + 2% FBS + 250 micrograms/ml hUDC lysate | 6780 | 180 |

Expanded hUDC lysate added as a supplement to EBM resulted in increased proliferation of HCAE cells at all concentrations tested (15.6, 31.25, 62.5, 125, and 250 micrograms/ml) in a dose dependent manner. Additionally, all concentrations of hUDC lysate showed proliferation equal to or greater than the positive control, EGM-2MV. These results indicate that hUDC lysate increased human endothelial proliferation, which can be quantitatively measured in vitro.

Summary.

Expanded hUDCs are being developed as a potential cell therapy for the treatment of a number of degenerative diseases. In addition, the proteins and other materials cells produce, referred to as trophic factors, can be used as bioactives to augment cellular response.

A process has been developed to generate lysate from human umbilical tissue derived cells. To characterize potency, lysate was assayed for the ability to stimulate proliferation of either mouse fibroblast or human endothelial cells. Fibroblasts and endothelial cells are known to be key cell types involved in a wound healing response.

hUDC lysate increased proliferation of mouse fibroblasts (NIH/3T3) and human endothelial cells at all concentrations tested. For both cell types, the highest concentration of cell lysate stimulated proliferation above the level of complete growth media containing 10% serum. This assay system can be utilized for testing biological activity of lysate.

While the present invention has been particularly shown and described with reference to the presently preferred embodiments, it is understood that the invention is not limited to the embodiments specifically disclosed and exemplified herein. Numerous changes and modifications may be made to the preferred embodiment of the invention, and such changes and modifications may be made without departing from the scope and spirit of the invention as set forth in the appended claims.

What is claimed:

1. A method of making a cell lysate comprising lysing cells of a homogeneous umbilical cord cell population isolated from human umbilical cord tissue substantially free of blood, wherein said cell population self-renews and expands in culture, provides trophic support to a soft tissue cell, and has the following characteristics:
   a) secretes MCP-1, IL-6, IL-8, GCP-2, HGF, KGF, FGF, HB-EGF, BDNF, TPO, MIP1b, RANTES, and TIMP1;
   b) production of CD10, CD13, CD44, CD73, CD90, PDGFr-alpha, PD-L2 and HLA-A,B,C;
   c) lacks production of CD31, CD34, CD45, CD80, CD86, CD 117, CD141, CD178, B7-H2, HLA-G, and HLA-DR,DP,DQ;
   d) has increased expression, relative to a human cell that is a fibroblast, a mesenchymal stem cell, or an iliac crest bone marrow cell, of interleukin 8, reticulon 1 and chemokine (C-X-C motif) ligand 3; and
   e) has the ability to undergo at least 40 population doublings in culture,
   wherein a cell lysate is produced.

2. The method of claim 1 further comprising adding one or more bioactive factors.

3. The method of claim 2 wherein said bioactive factor is at least one of a differentiation-inducing factor, an anti-apoptotic agent, an anti-inflammatory agent, an immunosupressive/immunomodulatory agent, an anti-proliferative agent, a corticosteroid, an antibody, an anti-thrombogenic agent, an anti-oxidant, and scar inhibitory factor.

4. The method of claim 1, further comprising adding a pharmaceutically acceptable carrier.

5. The method of claim 1, wherein said cell population lacks secretion of SDF-1alpha, TGF-beta2, ANG2, PDGFbb, MIP1a, and VEGF.

6. The method of claim 1, further comprising lyophilizing the cell lysate.

7. The method of claim 1, wherein the cell lysing comprises disrupting the cells using freeze-thaw disruption, osmotic disruption, mechanical disruption, ultrasonic disruption, enzymatic disruption or chemical disruption.

8. A method of making a lyophilized cell lysate comprising lysing cells of a homogeneous umbilical cord cell population isolated from human umbilical cord tissue substantially free of blood, wherein said cell population self-renews and expands in culture, provides trophic support to a soft tissue cell, and has the following characteristics:
   a) secretes MCP-1, IL-6, IL-8, GCP-2, HGF, KGF, FGF, HB-EGF, BDNF, TPO, MIP1b, RANTES, and TIMP1;
   b) production of CD10, CD13, CD44, CD73, CD90, PDGFr-alpha, PD-L2 and HLA-A,B,C;
   c) lacks production of CD31, CD34, CD45, CD80, CD86, CD 117, CD141, CD178, B7-H2, HLA-G, and HLA-DR,DP,DQ;
   d) has increased expression, relative to a human cell that is a fibroblast, a mesenchymal stem cell, or an iliac crest bone marrow cell, of interleukin 8, reticulon 1 and chemokine (C-X-C motif) ligand 3; and
   e) has the ability to undergo at least 40 population doublings in culture
   wherein a cell lysate is produced, and
   lyophilizing the cell lysate.

9. The method of claim 8, wherein said cell population lacks secretion of SDF-1alpha, TGF-beta2, ANG2, PDGFbb, MIP1a, and VEGF.

10. The method of claim 8, wherein the lysate comprises HGF, FGF, IL-8, TIMP1 and BDNF.

11. The method of claim 10, wherein the lysate further comprises ANG2, HB-EGF, KGF, PDGFbb, VEGF, IL-6, MCP1 TGFa, TIMP2, and HGH.

12. The method of claim 8 further comprising adding one or more bioactive factors.

13. The method of claim 12, wherein said bioactive factor is at least one of a differentiation-inducing factor, an anti-apoptotic agent, an anti-inflammatory agent, an immunosupressive/immunomodulatory agent, an anti-proliferative agent, a corticosteroid, an antibody, an anti-thrombogenic agent, an anti-oxidant, and scar inhibitory factor.

14. A method of making a cell lysate matrix complex comprising lysing cells of a homogeneous umbilical cord cell population isolated from human umbilical cord tissue substantially free of blood, wherein said cell population self-renews and expands in culture, provides trophic support to a soft tissue cell, and has the following characteristics:
   a) secretes MCP-1, IL-6, IL-8, GCP-2, HGF, KGF, FGF, HB-EGF, BDNF, TPO, MIP1b, RANTES, and TIMP1;
   b) production of CD10, CD13, CD44, CD73, CD90, PDGFr-alpha, PD-L2 and HLA-A,B,C;

c) lacks production of CD31, CD34, CD45, CD80, CD86, CD117, CD141, CD178, B7-H2, HLA-G, and HLA-DR,DP,DQ;

d) has increased expression, relative to a human cell that is a fibroblast, a mesenchymal stem cell, or an iliac crest bone marrow cell, of interleukin 8, reticulon 1 and chemokine (C-X-C motif) ligand 3; and e) has the ability to undergo at least 40 population doublings in culture;

wherein a cell lysate is formed, and
adding a matrix to the cell lysate to form a complex.

* * * * *

UNITED STATES PATENT AND TRADEMARK OFFICE
CERTIFICATE OF CORRECTION

PATENT NO. : 9,504,719 B2
APPLICATION NO. : 11/316104
DATED : November 29, 2016
INVENTOR(S) : Laura Brown et al.

Page 1 of 1

It is certified that error appears in the above-identified patent and that said Letters Patent is hereby corrected as shown below:

In the Specification

On Column 170, Line 48, "MCP1 TGFa" should read --MCP1, TGFa--.

Signed and Sealed this
Eleventh Day of February, 2020

Andrei Iancu
*Director of the United States Patent and Trademark Office*

SEQUENCE LISTING

<160> NUMBER OF SEQ ID NOS: 10

<210> SEQ ID NO 1
<211> LENGTH: 22
<212> TYPE: DNA
<213> ORGANISM: Artificial Sequence
<220> FEATURE:
<223> OTHER INFORMATION: Synthetic Construct

<400> SEQUENCE: 1
gagaaatcca aagagcaaat gg                                                  22

<210> SEQ ID NO 2
<211> LENGTH: 21
<212> TYPE: DNA
<213> ORGANISM: Artificial Sequence
<220> FEATURE:

<223> OTHER INFORMATION: Synthetic Construct

<400> SEQUENCE: 2
agaatggaaa actggaatag g                                          21

<210> SEQ ID NO 3
<211> LENGTH: 20
<212> TYPE: DNA
<213> ORGANISM: Artificial Sequence
<220> FEATURE:
<223> OTHER INFORMATION: Synthetic Construct

<400> SEQUENCE: 3
tcttcgatgc ttcggattcc                                            20

<210> SEQ ID NO 4
<211> LENGTH: 21
<212> TYPE: DNA
<213> ORGANISM: Artificial Sequence
<220> FEATURE:
<223> OTHER INFORMATION: Synthetic Construct

<400> SEQUENCE: 4
gaattctcgg aatctctgtt g                                          21

<210> SEQ ID NO 5
<211> LENGTH: 21
<212> TYPE: DNA
<213> ORGANISM: Artificial Sequence
<220> FEATURE:
<223> OTHER INFORMATION: Synthetic Construct

<400> SEQUENCE: 5
ttacaagcag tgcagaaaac c                                          21

<210> SEQ ID NO 6
<211> LENGTH: 22
<212> TYPE: DNA
<213> ORGANISM: Artificial Sequence
<220> FEATURE:
<223> OTHER INFORMATION: Synthetic Construct

<400> SEQUENCE: 6
agtaaacatt gaaaccacag cc                                         22

<210> SEQ ID NO 7
<211> LENGTH: 20
<212> TYPE: DNA
<213> ORGANISM: Artificial Sequence
<220> FEATURE:
<223> OTHER INFORMATION: Synthetic Construct

<400> SEQUENCE: 7
tctgcagctc tgtgtgaagg                                            20

<210> SEQ ID NO 8
<211> LENGTH: 22
<212> TYPE: DNA
<213> ORGANISM: Artificial Sequence
<220> FEATURE:
<223> OTHER INFORMATION: Synthetic Construct

<400> SEQUENCE: 8
cttcaaaaac ttctccacaa cc                                         22

```
<210> SEQ ID NO 9
<211> LENGTH: 17
<212> TYPE: DNA
<213> ORGANISM: Artificial Sequence
<220> FEATURE:
<223> OTHER INFORMATION: Synthetic Construct

<400> SEQUENCE: 9
cccacgccac gctctcc                                                17

<210> SEQ ID NO 10
<211> LENGTH: 19
<212> TYPE: DNA
<213> ORGANISM: Artificial Sequence
<220> FEATURE:
<223> OTHER INFORMATION: Synthetic Construct

<400> SEQUENCE: 10
tcctgtcagt tggtgctcc                                              19
```